(12) United States Patent
Wada et al.

(10) Patent No.: US 7,674,807 B2
(45) Date of Patent: Mar. 9, 2010

(54) HETEROCYCLE-SUBSTITUTED N-PHENYL-PHTHALAMIDE DERIVATIVES, RELATED COMPOUNDS AND THEIR USE AS INSECTICIDES

(75) Inventors: Katsuaki Wada, Tochigi (JP); Takuya Gombuchi, Ibaraki (JP); Yasushi Yoneta, Saitama (JP); Yuichi Otsu, Tochigi (JP); Katsuhiko Shibuya, Tochigi (JP); Norihiko Nakakura, Tochigi (JP); Rüdiger Fischer, Pulheim (DE); Tetsuya Murata, Tochigi (JP); Eiichi Shimojo, Tochigi (JP)

(73) Assignee: Bayer CropScience AG, Monheim (DE)

( * ) Notice: Subject to any disclaimer, the term of this patent is extended or adjusted under 35 U.S.C. 154(b) by 187 days.

(21) Appl. No.: 10/592,361

(22) PCT Filed: Mar. 1, 2005

(86) PCT No.: PCT/EP2005/002130
§ 371 (c)(1),
(2), (4) Date: May 24, 2007

(87) PCT Pub. No.: WO2005/095351
PCT Pub. Date: Oct. 13, 2005

(65) Prior Publication Data
US 2007/0299085 A1   Dec. 27, 2007

(30) Foreign Application Priority Data
Mar. 12, 2004 (JP) .............. 2004-070976
Aug. 12, 2004 (JP) .............. 2004-235553
Dec. 20, 2004 (JP) .............. 2004-367994

(51) Int. Cl.
| | |
|---|---|
| A61K 31/40 | (2006.01) |
| A61K 31/415 | (2006.01) |
| A61K 31/4192 | (2006.01) |
| A61K 31/4196 | (2006.01) |
| C07D 211/06 | (2006.01) |
| C07D 241/10 | (2006.01) |
| C07D 249/04 | (2006.01) |
| C07D 249/08 | (2006.01) |
| C07D 233/96 | (2006.01) |
| C07D 207/32 | (2006.01) |
| C07D 335/02 | (2006.01) |
| C07D 333/02 | (2006.01) |
| C07D 307/02 | (2006.01) |
| C07D 309/02 | (2006.01) |
| C07D 309/32 | (2006.01) |

(52) U.S. Cl. .............. 514/351; 514/616; 544/336; 546/329; 548/255; 548/262.2; 548/300.1; 548/400; 549/13; 549/74; 549/426; 549/429

(58) Field of Classification Search ............. 564/164; 514/616, 351; 546/329; 548/198, 214, 240
See application file for complete search history.

(56) References Cited

U.S. PATENT DOCUMENTS 2,785,115 A   8/1956   Lorenzo et al.

(Continued)

FOREIGN PATENT DOCUMENTS

DE   26 41 343 A1   9/1976

(Continued)

OTHER PUBLICATIONS

RN 126951-92-6, retrieved from CAPLUS on Mar. 9, 2009.*

(Continued)

*Primary Examiner*—Rebecca L Anderson
*Assistant Examiner*—Shawquia Young
(74) *Attorney, Agent, or Firm*—Sterne, Kessler, Goldstein & Fox P.L.L.C.

(57) ABSTRACT

Novel benzenedicarboxamides of the formula (I) wherein X represents hydrogen, halogen atom, nitro, $C_{1-6}$alkylsulfonyloxy, $C_{1-6}$alkylsulfinyl, $C_{1-6}$alkylsulfenyl or $C_{1-6}$alkylsulfonyl, $R^1$ represents $C_{1-6}$alkyl, $C_{1-6}$alkylthio-$C_{1-6}$alkyl, or $C_{1-6}$alkyl, m represents 0 or 1, A represents O, S, SO, $SO_2$, $CH_2$ or $CH(CH_3)$, and Q represents a 5- or 6-membered heterocyclic group that contains at least one hetero atom selected from the group consisting of N, O and S and can be optionally substituted; processes for their preparation, their intermediates and their use as insecticides.

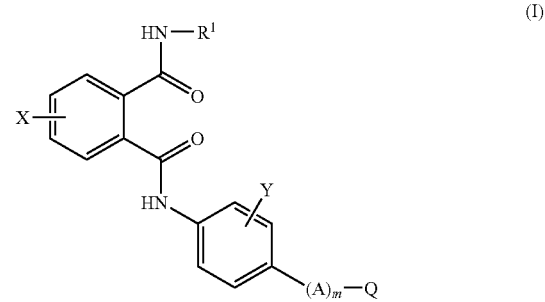

5 Claims, No Drawings

U.S. PATENT DOCUMENTS

| | | | |
|---|---|---|---|
| 3,264,177 A | 8/1966 | Kenaga et al. | |
| 3,309,266 A | 3/1967 | Magee et al. | |
| 4,053,608 A | 10/1977 | Morisawa et al. | |
| 4,181,800 A | 1/1980 | Kamiya et al. | |
| 4,808,430 A | 2/1989 | Kouno | |
| 5,416,103 A | 5/1995 | Eicken et al. | |
| 5,438,070 A | 8/1995 | Eicken et al. | |
| 5,556,988 A | 9/1996 | Eicken et al. | |
| 5,876,739 A | 3/1999 | Turnblad et al. | |
| 6,362,369 B2 * | 3/2002 | Tohnishi et al. | 564/156 |
| 6,559,341 B2 | 5/2003 | Tohnishi et al. | |
| 6,603,044 B1 | 8/2003 | Tohnishi et al. | |
| 6,639,109 B1 | 10/2003 | Sanpei et al. | |
| 6,642,379 B1 | 11/2003 | Furuya et al. | |
| 6,747,041 B1 | 6/2004 | Katsuhira et al. | |
| 6,864,289 B1 | 3/2005 | Tohnishi et al. | |
| 2001/0041814 A1 | 11/2001 | Tohnishi et al. | |
| 2003/0119670 A1 | 6/2003 | Arakai et al. | |
| 2003/0176428 A1 | 9/2003 | Schneidersmann et al. | |

FOREIGN PATENT DOCUMENTS

| | | |
|---|---|---|
| DE | 103 03 589 A1 | 8/2004 |
| EP | 0 119 428 A2 | 9/1984 |
| EP | 0 119 428 A3 | 9/1984 |
| EP | 0 234 045 A2 | 12/1986 |
| EP | 0 347 488 A1 | 8/1988 |
| EP | 0 545 099 A2 | 11/1992 |
| EP | 0 589 301 B1 | 9/1993 |
| EP | 0 589 313 A1 | 9/1993 |
| EP | 0 824 099 A1 | 8/1997 |
| EP | 1 006 107 A2 | 6/2000 |
| EP | 1 193 254 A1 | 4/2002 |
| EP | 1 389 612 A1 | 2/2004 |
| EP | 1 215 200 B1 | 3/2005 |
| EP | 1 538 138 A1 | 6/2005 |
| EP | 0 919 542 B1 | 8/2006 |
| JP | 59-163353 A | 9/1984 |
| JP | 61-246161 | 11/1986 |
| JP | 2001/64258 | 3/2001 |
| JP | 2001/64268 | 3/2001 |
| JP | 2003/40864 | 2/2003 |
| WO | WO 93/10083 A1 | 5/1993 |
| WO | WO 93/11117 A1 | 6/1993 |
| WO | WO 96/37494 A1 | 11/1996 |
| WO | WO 98/25923 A1 | 6/1998 |
| WO | WO 02/080675 A1 | 10/2002 |
| WO | WO 03/010149 A1 | 2/2003 |
| WO | WO 03/011028 A1 | 2/2003 |
| WO | WO 2004/080984 A1 | 9/2004 |
| WO | WO 2006/053643 A1 | 5/2006 |
| WO | WO 2006/092291 A2 | 9/2006 |
| WO | WO 2006/114212 A2 | 11/2006 |

OTHER PUBLICATIONS

RN 47662-35-6, retrieved from CAPLUS on Mar. 7, 2009.*
Dialog File 351, Accession No. 1284894, Derwent WPI English language abstract for DE 26 41 343A1 (listed as document FP1 on accompanying form PTO/SB/08A).
Dialog File 351, Accession No. 14392687, Derwent WPI English language abstract for DE 103 03 589 A1 (listed as document FP13 on accompanying form PTO/SB/08A).
Dialog File 351, Accession No. 3119554, Derwent WPI English language abstract for JP 59163353 A (listed as document FP16 on accompanying form PTO/SB/08A).
Dialog File 351, Accession No. 3119554, Derwent WPI English language abstract for EP 0 119 428 A2 & A3 (listed as document FP17 on accompanying form PTO/SB/08A).
Dialog File 351, Accession No. 3870718, Derwent WPI English language abstract for JP 61-246161 A (listed as document FP18 on accompanying form PTO/SB/08A).
Dialog File 351, Accession No. 10511120, Derwent WPI English language abstract for JP 2001/064268 A (listed as document FP22 on accompanying form PTO/SB/08A).
Dialog File 351, Accession No. 10535423, Derwent WPI English language abstract for JP 2001/064258 A (listed as document FP23 on accompanying form PTO/SB/08A).
Dialog File 351, Accession No. 13757425, Derwent WPI English language abstract for JP 2003/040864 A (listed as document FP25 on accompanying form PTO/SB/08A).
U.S. Patent Application No. 576,072, filed at the U.S. Patent and Trademark Office on Feb. 1, 1984.

* cited by examiner

HETEROCYCLE-SUBSTITUTED N-PHENYL-PHTHALAMIDE DERIVATIVES, RELATED COMPOUNDS AND THEIR USE AS INSECTICIDES

This application is a 35 U.S.C. §371 U.S. National Phase filing of International Application No. PCT/EP2005/002130, filed Mar. 1, 2005, which claims the benefit of Japanese Patent Application Nos. 2004-70976, filed Mar. 12, 2004; 2004-235553, filed Aug. 12, 2004; and 2004-367994, filed Dec. 20, 2004.

The present invention relates to novel benzenedicarboxamides, processes for the preparation thereof, their intermediates and their use as insecticides.

It was already known that phthalamide derivatives are useful as insecticides [see JP-A 11-240857 (1999), JP-A 2001-64258, JP-A 2001-64269, JP-A 2001-131141, JP-A 2003-40864, WO 01/21576 and WO 03/11028], and also that they show medicinal function [see JP-A 59-163353 (1984)].

There have now been found novel benzenedicarboxamides of the formula (I)

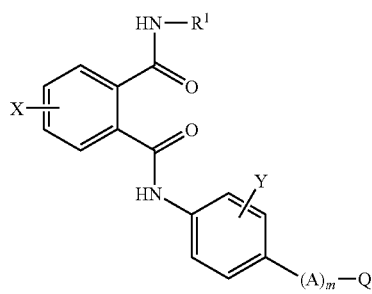

wherein
X represents hydrogen, halogen atom, nitro, $C_{1-6}$alkylsulfonyloxy, $C_{1-6}$alkylsulfinyl, $C_{1-6}$alkylsulfenyl or $C_{1-6}$alkylsulfonyl,
$R^1$ represents $C_{1-6}$alkyl, $C_{1-6}$alkylthio-$C_{1-6}$alkyl, $C_{1-6}$alkylsulfinyl-$C_{1-6}$alkyl or $C_{1-6}$alkylsulfonyl-$C_{1-6}$alkyl,
Y represents halogen or $C_{1-6}$alkyl,
m represents 0 or 1,
A represents O, S, SO, $SO_2$, $CH_2$ or $CH(CH_3)$, and
Q represents a 5- or 6-membered heterocyclic group that contains at least one hetero atom selected from the group consisting of N, O and S and can be optionally substituted.

The compounds of the formula (I), according to the invention, can be obtained by
(a) reacting compounds of the formula (II)

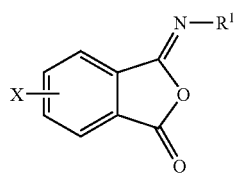

wherein $R^1$ and X have the same definitions as aforementioned,
with compounds of the formula (III)

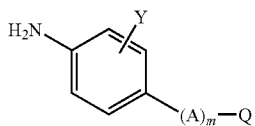

wherein Y, A, m and Q have the same definitions as aforementioned,
in the presence of inert solvents, and if appropriate in the presence of an acid catalyst, or
(b) reacting compounds of the formula (IV)

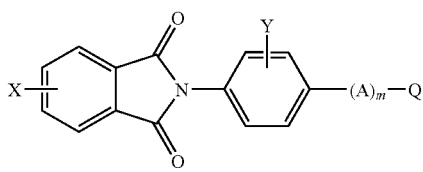

wherein X, Y, A, m and Q have the same definitions as aforementioned,
with compounds of the formula (V)

$$H_2N—R^1 \quad (V)$$

wherein $R^1$ has the same definitions as aforementioned,
in the presence of inert solvents, and if appropriate in the presence of an acid catalyst, or
(c) reacting compounds of the formula (VI)

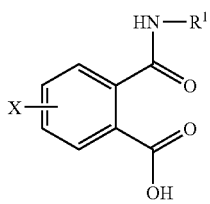

wherein X and $R^1$ have the same definitions as aforementioned,
with the compounds of the formula (III),

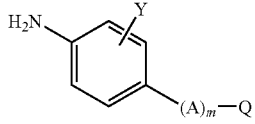

wherein Y, A, m and Q have the same definitions as aforementioned,
in the presence of inert solvents, and if appropriate in the presence of an acid catalyst, or
(d) reacting compounds of the formula (VII)

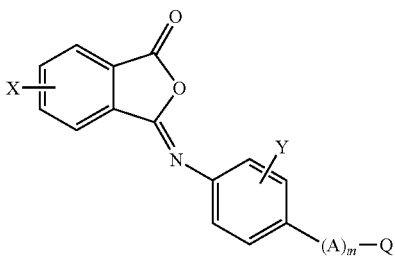

(VII)

wherein X, Y, A, m and Q have the same definitions as aforementioned,
with the compounds of the formula (V), $H_2N-R^1$ (V)

wherein $R^1$ has the same definitions as aforementioned,
in the presence of inert solvents, and if appropriate in the presence of an acid catalyst, or (e) compounds of the formula (VIII)

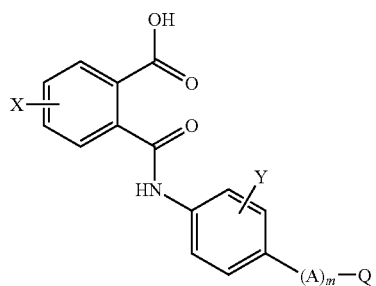

(VIII)

wherein X, Y, A, m and Q have the same definitions as aforementioned,
are reacted with the compounds of the formula (V), $H_2N-R^1$ (V)

wherein $R^1$ has the same definitions as aforementioned,
in the presence of inert solvents, and if appropriate in the presence of an acid catalyst, or (f) in the case that $R^1$ represents $C_{1-6}$alkylsulfinyl-$C_{1-6}$alkyl or $C_{1-6}$alkylsulfonyl-$C_{1-6}$alkyl in the formula (I), reacting compounds of the formula (If)

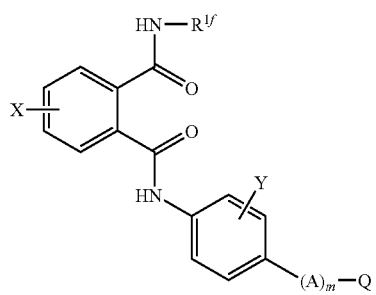

(If)

wherein
$R^{1f}$ represents $C_{1-6}$alkylthio-$C_{1-6}$alkyl, and
X, Y, A, m and Q have the same definitions as aforementioned,
with an oxidizing agent in the presence of inert solvents.

According to the present invention, the benzenedicarboxamides of the formula (I) show a strong insecticidal action.

The compounds of the formula (I) are conceptually embraced in the general formula described in the aforementioned JP-A 11-240857 (1999). But they are not specifically disclosed at all in it and new compounds. Surprisingly, they show particularly remarkable insecticidal action compared with similar compounds described in the known prior art.

In the present specification:

"Halogen" represents fluorine, chlorine, bromine and iodine, and preferably represents fluorine, chlorine and bromine.

"Alkyl" represents straight chain or branched chain $C_{1-12}$alkyl, for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, etc. and preferably represents $C_{1-6}$alkyl.

As each alkyl part in "alkylsulfonyloxy", "alkylsulfenyl", "alkylthioalkyl", "alkylsulfinylalkyl", "alkylsulfonylalkyl", "alkoxy", "alkylthio", "alkylsulfinyl", "alkylsulfonyl", "haloalkyl", "haloalkoxy", "haloalkylthio", "haloalkylsulfinyl", "haloalkylsulfonyl" and "haloalkylcarbonyl", there can be mentioned the same as described in the above-mentioned "alkyl" as examples.

As each halogen part in "haloalkyl", "haloalkoxy", "haloalkylthio", "haloalkylsulfinyl", "haloalkylsulfonyl" and "haloalkylcarbonyl", there can be mentioned the same as described in the above-mentioned "halogen" as examples.

"5- or 6-membered heterocyclic group" contains at least one hetero atom selected from the group consisting of N, O and S, and preferably represents a heterocyclic group containing "one to three N atoms", or "one O atom", or "one S atom", or "both one S atom and one to two N atoms", or "both one O atom and one to two N atoms", and as specific examples thereof, pyrazolyl, triazolyl, pyrazolinyl, imidazolyl, thiazolyl, pyrrolyl, furyl, thienyl, oxadiazolyl and pyrimidinyl, and moreover as most preferable examples thereof, pyrazolyl, triazolyl, pyrazolinyl, imidazolyl, thiazolyl, pyrrolyl, oxadiazolyl and pyrimidinyl are exemplified.

In the compounds of the formula (I), according to the invention, the compounds in case that X represents hydrogen, fluorine, chlorine, bromine, iodine, nitro, $C_{1-4}$ alkylsulfonyloxy, $C_{1-4}$alkylsulfinyl, $C_{1-4}$ alkylsulfenyl or $C_{1-4}$ alkylsulfonyl, $R^1$ represents $C_{1-4}$alkyl, $C_{1-4}$alkylthio-$C_{1-4}$alkyl, $C_{1-4}$alkylsulfinyl-$C_{1-4}$alkyl or $C_{1-4}$alkylsulfonyl-$C_{1-4}$alkyl, Y represents fluorine, chlorine, bromine or $C_{1-4}$alkyl, m represents 0 or 1, A represents O, S, SO, $SO_2$, $CH_2$ or $CH(CH_3)$, and Q represents 5-membered or 6-membered heterocyclic group that contains at least one hetero atom selected from a group consisting of N, O and S and can be optionally substituted by at least one selected from a group consisting of $C_{1-6}$alkyl, $C_{1-6}$alkoxy, $C_{1-6}$alkylthio, $C_{1-6}$alkylsulfinyl, $C_{1-6}$alkylsulfonyl, $C_{1-10}$haloalkyl, $C_{1-6}$haloalkoxy, $C_{1-6}$haloalkylthio, $C_{1-6}$haloalkylsulfinyl, $C_{1-6}$haloalkylsulfonyl, $C_{1-6}$haloalkylcarbonyl, halogen, oxo and hydroxy group, can be mentioned as preferable.

Above all, in the compounds of the formula (I), the compounds in case that

X represents hydrogen, fluorine, chlorine, bromine, iodine, nitro, methanesulfonyloxy, $C_{1-2}$alkylsulfinyl, $C_{1-2}$ alkylsulfenyl or $C_{1-2}$ alkylsulfonyl, $R^1$ represents isopropyl, $C_{1-2}$alkylthio-$C_{3-4}$alkyl, $C_{1-2}$alkylsulfinyl-$C_{3-4}$alkyl or $C_{1-2}$alkylsulfonyl-$C_{3-4}$alkyl, Y represents fluorine, chlorine or methyl, m represents 0 or 1, A represents O, S, SO, $SO_2$, $CH_2$ or $CH(CH_3)$, and Q represents heterocyclic group, selected from a group consisting of pyrazolyl, triazolyl, pyrazolinyl, imidazolyl, thiazolyl, pyrrolyl, oxadiazolyl and pyrimidinyl, that can be optionally substituted by at least one selected from the group consisting of $C_{1-4}$alkyl, $C_{1-4}$alkoxy, $C_{1-4}$alkylthio, $C_{1-4}$alkylsulfinyl, $C_{1-4}$alkylsulfonyl, $C_{1-8}$haloalkyl, $C_{1-4}$haloalkoxy, $C_{1-4}$haloalkylthio, $C_{1-4}$haloalkylsulfinyl, $C_{1-4}$haloalkylsulfonyl, $C_{1-4}$haloalkylcarbonyl, fluorine, chlorine, bromine, iodine, oxo and hydroxy group, are particularly preferable.

The compounds of the formula (I), according to the present invention, include stereo isomers (R/S configuration) in case that the group $R^1$ has an asymmetric carbon.

The aforementioned process (a) can be illustrated by the following reaction scheme in case that, for example, 3-(1,1-dimethyl-2-methylthioethylimino)-4-iodo-3H-isobenzofuran-1-one and 1-(4-amino-3-methylbenzyl)-3,5-bis(trifluoromethyl)-1H-pyrazole are used as starting materials.

The aforementioned preparation process (b) can be illustrated by the following reaction scheme in case that, for example, 2-{4-[3,5-bis(trifluoromethyl)pyrazole-1-ylmethyl]-2-methylphenyl}-4-fluoroisoindole-1,3-dione and (S)-1-methyl-2-methylthioethylamine are used as starting materials.

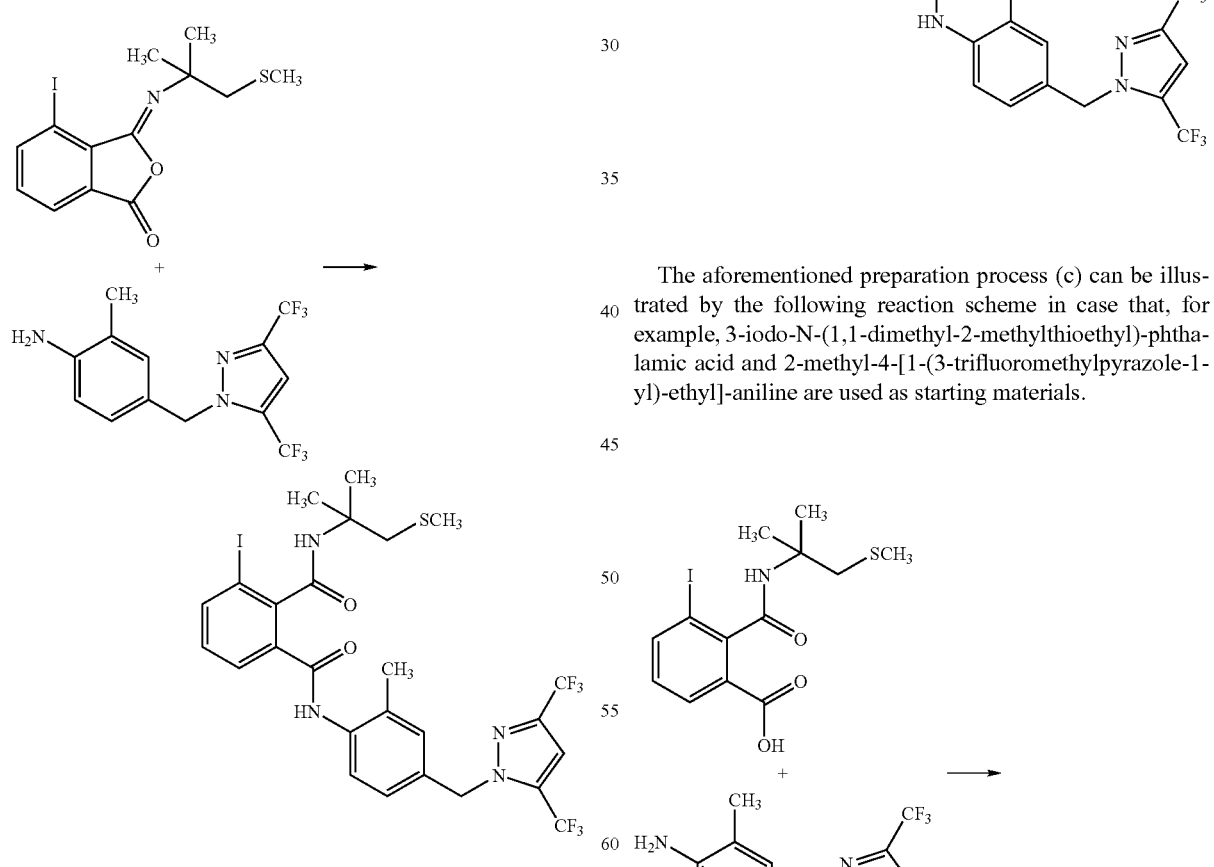

The aforementioned preparation process (c) can be illustrated by the following reaction scheme in case that, for example, 3-iodo-N-(1,1-dimethyl-2-methylthioethyl)-phthalamic acid and 2-methyl-4-[1-(3-trifluoromethylpyrazole-1-yl)-ethyl]-aniline are used as starting materials.

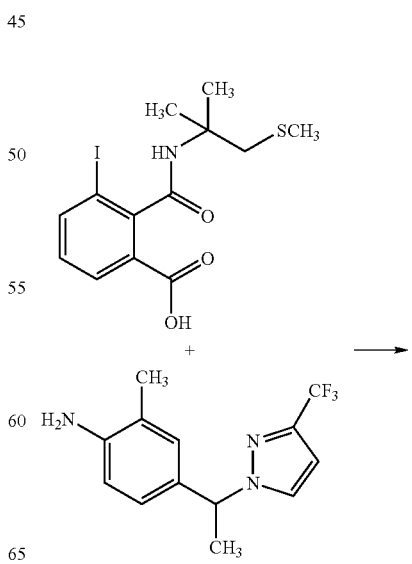

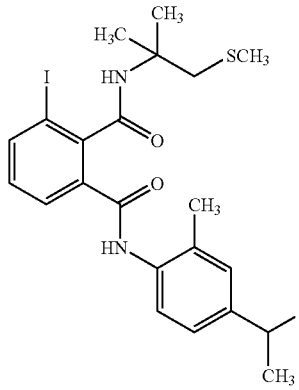

The aforementioned preparation process (d) can be illustrated by the following reaction scheme in case that, for example, 1-[4-(4-iodo-3-oxo-3H-isobenzofuran-1-ylidene-amino)-3-methyl-benzyl]-3,5-bis(trifluoromethyl)-(1,2,4)-triazol and 1-methyl-2-methylthioethylamine are used as starting materials.

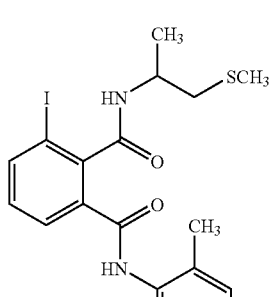

The aforementioned preparation process (e) can be illustrated by the following reaction scheme in case that, for example, N-{4-[3,5-bis(trifluoromethyl)-1H-pyrazol-1-ylmethyl]-2-methyl-phenyl}-6-iodo-phthalamic acid and 1-methyl-2-methylthioethylamine are used as starting materials.

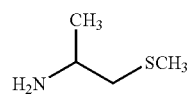
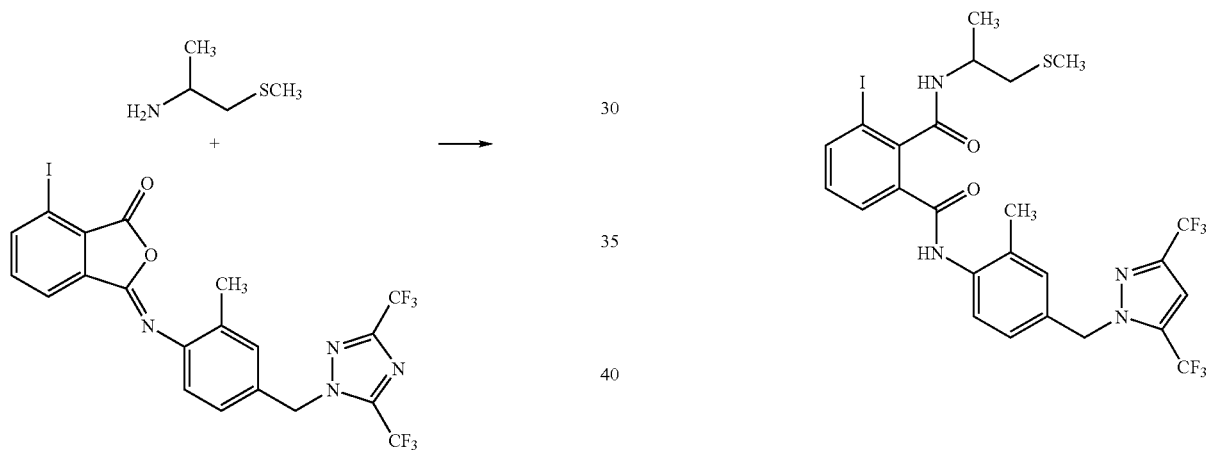

The aforementioned process (f) can be illustrated by the following reaction scheme in case that, for example, N²-(1-methyl-2-methylthioethyl)-3-iodo-N¹-{2-methyl-4-[3,5-bis(trifluoromethyl)-1H-pyrazol-1-ylmethyl] phenyl}phthalamide and m-chloroperbenzoic acid are used as starting materials.

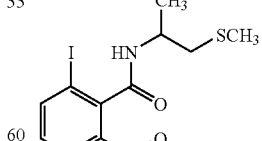
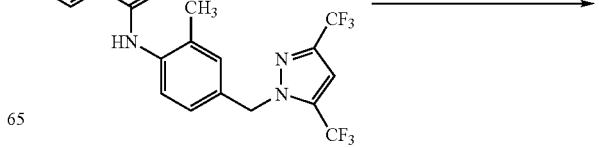

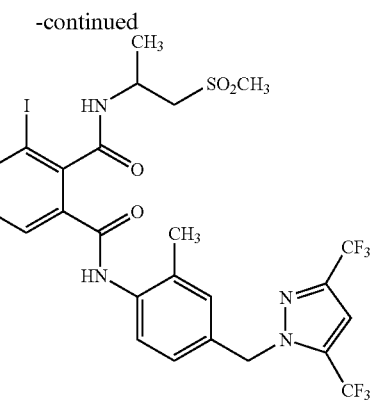

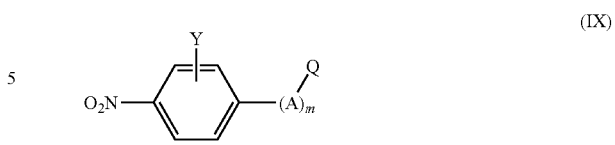

wherein Y, A, m and Q have the same definitions as aforementioned, according to the catalytic hydrogen reduction process, a well-known process in the field of organic chemistry, with hydrogen in the presence of a catalytic reduction catalyst, for example, palladium carbon, Raney nickel, platinum oxide, etc.

The above-mentioned catalytic hydrogen reduction process can be conducted in an adequate diluent.

As examples of the diluent used in that case there can be mentioned ethers, for example, ethyl ether, methyl ethyl ether, isopropyl ether, butyl ether, dioxane, tetrahydrofuran (THF), etc.; alcohols, for example, methanol, ethanol, isopropanol, butanol, ethylene glycol, etc. and as catalytic reduction catalyst there can be mentioned, palladium carbon, Raney nickel, platinum oxide, etc.

The reaction can be conducted at the temperatures generally from about 0 to about 100° C., preferably from room temperature (20° C.) to about 80° C.

Said reaction can be conducted usually under normal pressure but can be operated optionally also under elevated pressure.

For example, a compound of the formula (III) can be obtained by hydrogenating the compounds of the formula (IX) in a diluent, for example, ethanol, in the presence of 0.1-10% (w/w) palladium carbon.

Also by a reduction reaction using metals etc. instead of catalytic hydrogen reduction, the compounds of the formula (III) can be obtained from the compounds of the formula (IX).

As a reduction process using metals etc., there can be mentioned, for example, a process of reacting iron powder in acetic acid, a process of reacting zinc dust under neutral condition (Organic Syntheses Collective Vol. II, p. 447), a process of reacting stannic chloride under acidic condition (Organic Syntheses Collective Vol. II, p. 254), a process of reacting titanium trichloride under neutral condition, etc.

The compounds of the formula (IX) are novel compounds and can be obtained by reacting the compounds of the formula (IX) wherein A represents other than oxygen atom, for example, compounds of the formula (X)

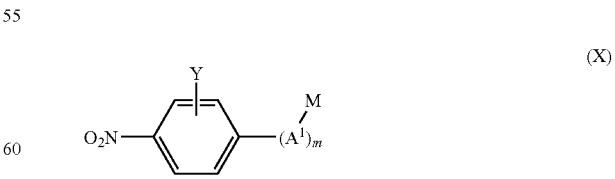

wherein

Y and m have the same definitions as aforementioned, $A^1$ represents S, SO, $SO_2$, $CH_2$ or $CH(CH_3)$, and The compounds of the formula (II), used as starting materials in the above-mentioned preparation process (a), are per se known compounds and can be easily prepared according to the process described in, for example, JP-A 11-240857 (1999), JP-A 2001-131141.

As specific examples of the compounds of the formula (II), used as starting materials in the preparation process (a), there can be mentioned the following:

3-isopropylimino-3H-isobenzofuran-1-one,
4-fluoro-3-isopropylimino-3H-isobenzofuran-1-one,
4-chloro-3-isopropylimino-3H-isobenzofuran-1-one,
4-bromo-3-isopropylimino-3H-isobenzofuran-1-one,
4-iodo-3-isopropylimino-3H-isobenzofuran-1-one,
3-(1-methyl-2-methylsulfanyl-ethylimino)-3H-isobenzofuran-1-one,
4-fluoro-3-(1-methyl-2-methylsulfanyl-ethylimino)-3H-isobenzofuran-1-one,
4-chloro-3-(1-methyl-2-methylsulfanyl-ethylimino)-3H-isobenzofuran-1-one,
4-bromo-3-(1-methyl-2-methylsulfanyl-ethylimino)-3H-isobenzofuran-1-one,
4-iodo-3-(1-methyl-2-methylsulfanyl-ethylimino)-3H-isobenzofuran-1-one,
3-(1,1-dimethyl-2-methylsulfanyl-ethylimino)-3H-isobenzofuran-1-one,
3-(1,1-dimethyl-2-methylsulfanyl-ethylimino)-4-fluoro-3H-isobenzofuran-1-one,
4-chloro-3-(1,1-dimethyl-2-methylsulfanyl-ethylimino)-3H-isobenzofuran-1-one,
4-bromo-3-(1,1-dimethyl-2-methylsulfanyl-ethylimino)-3H-isobenzofuran-1-one,
3-(1,1-dimethyl-2-methylsulfanyl-ethylimino)-4-iodo-3H-isobenzofuran-1-one,
3-isopropylimino-1-oxo-1,3-dihydro-isobenzofuran-4-yl methanesulfonate
3-(1-methyl-2-methylsulfanyl-ethylimino)-1-oxo-1,3-dihydro-isobenzofuran-4-yl methanesulfonate
3-(1,1-dimethyl-2-methylsulfanyl-ethylimino)-1-oxo-1,3-dihydro-isobenzofuran-4-yl methanesulfonate and so on.

The compounds of the formula (III), used as starting materials in the above-mentioned preparation process (a), which are partly novel compounds that are not described in the existing literature yet, can be obtained, for example, by reducing compounds of the formula (IX)

M represents chlorine, bromine or methanesulfonyloxy, with compounds of the formula (XI)

H-Q  (XI)

wherein Q has the same definition as aforementioned.

The compounds of the formula (X), are well known in the field of organic chemistry and described in publications, for example, Chem. Abstr., Vol. 58, 3444e (1963); Bull. Soc. Chim. Fr. (1934), p. 539-545; J. Chem. Res. Miniprint, Vol. 8 (1987), p. 2133-2139; J. Chem. Soc. B (1967), p. 1154-1158; J. Chem. Soc. (1961), p. 221-222; J. Amer. Chem. Soc., Vol. 111 (1989), p. 5880-5886; J. Amer. Chem. Soc., Vol. 96 (1974), p. 7770-7781; Can. J. Chem., Vol. 68 (1990), p. 1450-1455, Tetrahedron Letter, vol. 35 (1994), p. 7391-7394.

As specific examples of the compounds of the formula (X), there can be mentioned specifically
2-methyl-4-nitrobenzyl chloride,
3-methyl-4-nitrobenzyl chloride
4-nitrobenzyl methanesulfonate
2-methyl-4-nitrobenzyl methanesulfonate
3-methyl-4-nitrobenzyl methanesulfonate,
4-nitrobenzenesulfenyl chloride,
4-nitrobenzenesulfinyl chloride,
4-nitrobenzenesulfonyl chloride,
4-nitro-3-methylbenzenesulfonyl chloride,
3-fluoro-4-nitrobenzyl bromide,
3-chloro-4-nitrobenzyl chloride and so on.

The nitro-substituted benzoic acids and their esters, starting materials of the compounds of the formula (X), are known compounds described in, for example, Chem. Ber., Vol. 52 (1919), p. 1083; Bull. Soc. Chim. Fr. (1962), p. 2255-2261; Tetrahedron (1985), p. 115-118; Chem. Pharm. Bull., Vol. 41 (1993), p. 894-906; WO 2001/042227.

The compounds of the formula (XI) include known compounds and as their specific examples, there can be mentioned:
3,5-bis(trifluoromethyl)-1H-pyrazole,
5-difluoromethoxy-3-trifluoromethyl-1H-pyrazole,
4-pentafluoroethyl-1H-pyrazole,
5-hexafluoro-n-propyl-1H-pyrazole,
3,5-bis(trifluoromethyl)-1H-(1,2,4)-triazole,
5-pentafluoroethyl-3-trifluoromethyl-1H-(1,2,4)-triazole,
5-difluoromethyl-3-trifluoromethyl-1H-(1,2,4)-triazole,
5-hydroxy-3,5-bis(trifluoromethyl)-1H-4,5-dihydropyrazole,
2,4-bis(trifluoromethyl)-1H-imidazole,
3-(2,2,2-trifluoroethyl)-5-trifluoromethyl-1,2-dihydro-(1,3,4)-triazol-2-one,
2,5-bis(trifluoromethyl)-(1,3,4)-triazole,
5-pentafluoroethyl-1H-pyrazole,
3-pentafluoroethyl-1H-pyrazole,
4-bromo-3-trifluoromethyl-1H-pyrazole,
3-trifluoromethyl-1H-pyrazole,
5-(difluoromethyl)-1,2-dihydro-2-methyl-3H-(1,2,4)-triazol-3-one,
4-(trifluoromethyl)-2H-1,2,3-triazole,
4-iodo-3-pentafluoroethyl-1H-pyrazole,
3-pentafluoroethyl-4-(1,1,2,2-tetrafluoroethyl)-1H-pyrazole,
3,4-bis-pentafluoroethyl-1H-pyrazole,
3,5-diiodo-4-methyl-1H-pyrazole,
3-Heptafluoropropylsulfanyl-5-trifluoromethyl-1H-(1,2,4)-triazole,
3,5-bis(pentafluoroethyl)-1H-(1,2,4)-triazole and so on.

The above-mentioned reaction of the compounds of the formula (X) with the compounds of the formula (XI) can be conducted in an adequate diluent.

As examples of the diluent used in that case there can be mentioned, for example, aliphatic, alicyclic and aromatic hydrocarbons (may be optionally chlorinated), for example, pentane, hexane, cyclohexane, petroleum ether, ligroine, benzene, toluene, xylene, dichloromethane, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; ketones, for example, acetone, methyl ethyl ketone (MEK), methyl isopropyl ketone, methyl isobutyl ketone (MIBK), etc.; nitriles, for example, acetonitrile, propionitrile, acrylonitrile, etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethyl phosphoric triamide (HMPA), etc.

The reaction can be conducted in the presence of an acid binder and as said acid binder there can be mentioned, for example, as inorganic base, hydrides, hydroxides, carbonates, bicarbonates, etc. of alkali metals or alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide, etc.; inorganic alkali metal amides, for example, lithium amide, sodium amide, potassium amide, etc.; as organic base, alcoholates, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[5,4,0]undec-7-ene (DBU), etc.

The above-mentioned reaction can also be conducted by a process using a phase transfer catalyst in the presence of a diluent. As examples of the diluent used in that case there can be mentioned water; aliphatic, alicyclic and aromatic hydrocarbons (may be optionally chlorinated), for example, pentane, hexane, cyclohexane, petroleum ether, ligroine, benzene, toluene, xylene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc. As examples of the phase transfer catalyst, quaternary ions, for example, tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide, benzyltriethylammonium chloride, etc.; crown ethers, for example, dibenzo-18-crown-6, dicyclohexyl-18-crown-6, 18-crown-6, etc.; cryptands, for example, [2.2.2]-cryptate, [2.1.1]-cryptate, [2.2.1]-cryptate, [2.2.B]-cryptate, [3.2.2]-cryptate, etc.

The above-mentioned reaction can be conducted in a substantially wide range of temperature. It is adequate to conduct it at the temperatures in a range of generally from about 0 to about 200° C., preferably from room temperature (20° C.) to about 150° C.

Although said reaction is conducted desirably under normal pressure, it can be operated also under elevated pressure or under reduced pressure.

In conducting the above-mentioned reaction, the aimed compounds of the formula (IX) can be obtained, for example, by reacting 1 mole to a little excess mole amount of the compounds of the formula (XI) to 1 mole of the compounds of the formula (X) in a diluent, for example, DMF, in the presence of potassium carbonate.

As the compounds of the formula (IX) obtained according to the above-mentioned process, there can be mentioned, for example, the corresponding 4-nitrobenzyl derivatives to the 4-aminobenzyl derivatives of the formula (III) mentioned hereinafter. And, as one typical example, 1-(3-methyl-4-nitrobenzyl)-3,5-bis-(trifluoromethyl)-1H-pyrazole can be mentioned.

Furthermore, in a case where Q represents 2-thiazolyl in the formula (IX), as a specific example, 2-(3-methyl-4-nitrobenzyl)-4-pentafluoroethyl-thiazole can be prepared by the following way in which a known compound, 3-methyl-4-nitrobenzylcyanide (see J. Chem. Soc., vol. 97 (1910), p. 2260) is reacted with hydrogen sulfide, and then the product, 3-methyl-4-nitro-benzylthioamide is reacted with a commercial product, 1-bromo-3,3,4,4,4-pentafluoro-2-butanone and then cyclized, according to a method described in J. Heterocycl. Chem., vol. 28 (1991) p. 907 to 911.

In a case where Q represents 1,3,4-oxadiazol-2-yl in the formula (IX), as a specific example, 2-(3-methyl-4-nitrophenyl)-5-trifluoromethyl-1,3,4-oxazole can easily be obtained, according to a method described in Heterocycles, (1994) vol. 38, p. 981 to 990, from the corresponding aldoxime as a starting material which can be prepared by a method described in Justus Liebigs Ann. Chem., (1927) vol. 45, p. 166.

And, as another specific example, 2-(3-methyl-4-nitrobenzyl)-5-trifluoromethyl-1,3,4-oxazole can easily be obtained, according to a method described in Heterocycles, (1994) vol. 38, p. 981 to 990, from the corresponding 3-methyl-4-nitrobenzaldehyde oxime. In the above preparation, the oxime can be obtained from a known 3-methyl-4-nitrobenzaldehyde [see J. Chem. Soc. B, (1967) p. 1154 to 1158] as a starting material, according to methods described in J. Chem. Soc. C, (1969) p. 986 to 990 and then Tetrahedron Letter, vol. 35 (1994) p. 9099 to 9100.

In a case where Q represents 2H-1,2,3-triazol-2-yl in the formula (IX), as a specific example, 2-(3-methyl-4-nitrobenzyl)-2H-4-trifluoromethyl-1,2,3-triazole can easily be prepared by a reaction of a known 3-methyl-4-nitrobenzyl chloride with a known 2H-4-trifluoromethyl-1,2,3-triazole described in J. Chem. Soc., Perkin Transaction 2, vol. 10 (1989) p. 1355 to 1375.

In a case where Q represents 1H-1,2,4-triazol-1-yl in the formula (IX), as a specific example, 5-(3-methyl-4-nitrophenylsulfanyl)-1-methyl-3-trifluoromethyl-1H-1,2,4-triazole can easily be prepared by a reaction of 1-fluoro-3-methyl-4-nitrobenzene with a known 5-mercapto-1-methyl-3-trifluoromethyl-1H-1,2,4-triazole described in J. Med. Chem., vol. 35 (1992) p. 2103 to 2112, according to the same preparation as Synthesis Example 47 hereinafter.

In a case where Q represents 1,2,4-oxazol-3-yl in the formula (IX), as a specific example, 3-(3-methyl-4-nitrophenyl)-5-trifluoromethyl-1,2,4-oxazole can easily be obtained from 3-methyl-4-nitrobenzamideoxime, according to a method described in J. Org. Chem., vol. 68(2), 2003, p. 605-608. And, 3-methyl-4-nitrobenzamideoxime can be prepared by a reaction of a commercial 3-methyl-4-nitrobenzonitrile with hydroxylamine, according to a method described in Chem. Ber., vol. 22 (1889), p. 2428.

And, as another specific example, 3-(3-methyl-4-nitrobenzyl)-5-trifluoromethyl-1,2,4-oxazole can easily be obtained from 2-(3-methyl-4-nitrophenyl)-acetamideoxime as well, according to a method described in J. Org. Chem., vol. 68(2), 2003, p. 605-608. And, 2-(3-methyl-4-nitrophenyl)acetamideoxime can be prepared by a reaction of 3-methyl-4-nitrophenyl-acetonitrile with hydroxylamine, according to a method described in Chem. Ber., vol. 22 (1889), p. 2428.

In a case where Q represents 1H-1,2,4-triazol-3-yl in the formula (IX), as specific examples, 1-methyl-3-(3-methyl-4-nitrophenyl)-5-trifluoromethyl-1H-1,2,4-triazole can easily be prepared by a reaction of the above 3-(3-methyl-4-nitrophenyl)-5-trifluoromethyl-1,2,4-oxazole with methylhydrazine, according to a method described in J. Org. Chem., vol. 68(2), 2003, p. 605-608, and also 1-methyl-3-(3-methyl-4-nitrobenzyl)-5-trifluoromethyl-1H-1,2,4-triazole can be done by a reaction of the above 3-(3-methyl-4-nitrobenzyl)-5-trifluoromethyl-1,2,4-oxazole with methylhydrazine as well.

The compounds of the formula (IX) can be prepared, besides the above-mentioned preparation process, also by the process to be mentioned later in Examples as an alternative.

As specific examples of the compounds of the formula (III) there can be mentioned, for example, the following:

1-(4-amino-3-methylbenzyl)-3,5-bis(trifluoromethyl)-1H-pyrazole,
1-(4-amino-3-methylbenzyl)-5-difluoromethoxy-3-trifluoromethyl-1H-pyrazole,
1-(4-amino-3-methylbenzyl)-4-pentafluoroethyl-1H-pyrazole,
1-(4-amino-3-methylbenzyl)-5-hexafluoro-n-propyl-1H-pyrazole,
1-(4-amino-3-methylbenzyl)-3,5-bis(trifluoromethyl)-1H-(1,2,4)-triazole,
1-(4-amino-3-methylbenzyl)-5-pentafluoroethyl-3-trifluoromethyl-1H-(1,2,4)-triazole,
1-(4-amino-3-methylbenzyl)-5-difluoromethyl-3-trifluoromethyl-1H-(1,2,4)-triazole,
4-(4-amino-3-methylbenzyl)-5-difluoromethoxy-1-difluoromethyl-3-trifluoromethyl-1H-pyrazole,
4-(4-amino-3-methylbenzyl)-3-difluoromethoxy-1-difluoromethyl-5-trifluoromethyl-1H-pyrazole,
1-(4-amino-3-methylbenzyl)-5-hydroxy-3,5-bis(trifluoromethyl)-1H-4,5-dihydropyrazole,
1-(4-amino-3-methylbenzyl)-2,4-bis(trifluoromethyl)-1H-imidazole,
4-(4-amino-3-methylbenzyl)-2-(2,2,2-trifluoroethyl)-5-trifluoromethyl-2,4-dihydro-3H-(1,2,4)-triazol-3-one,
2-(4-amino-3-methylbenzyl)-4-(2,2,2-trifluoroethyl)-5-trifluoromethyl-2,4-dihydro-3H-(1,2,4)-triazol-3-one,
1-(4-amino-3-methylbenzyl)-2,5-bis(trifluoromethyl)-1,3,4-triazole,
2-(4-amino-3-methylbenzyl)-4,6-bis(trifluoromethyl)-pyrimidine,
2-(4-amino-3-methylphenoxy)-4,6-bis(trifluoromethyl)-pyrimidine,
1-(4-amino-3-methylphenyl)-3,5-bis(trifluoromethyl)-1H-pyrazole,
1-(4-amino-3-methylphenyl)-5-pentafluoroethyl-1H-pyrazole,
1-(4-amino-3-methylphenyl)-3-pentafluoroethyl-1H-pyrazole,
1-(4-amino-3-methylphenyl)-4-pentafluoroethyl-1H-pyrazole,
1-(4-amino-3-methylphenyl)-3-methyl-5-trifluoromethyl-1H-pyrazole,
1-(4-amino-3-methylphenyl)-5-methyl-3-trifluoromethyl-1H-pyrazole,
1-(4-amino-3-methylphenyl)-3-pentafluoroethyl-5-trifluoromethyl-1H-pyrazole,
1-(4-amino-3-methylphenyl)-4-bromo-3-trifluoromethyl-1H-pyrazole, 1-(4-amino-3-methylphenyl)-3-trifluoromethyl-1H-pyrazole, 1-(4-amino-3-methylphenyl)-5-hydroxy-3-(2,2,2-trifluoroethyl)-5-trifluoromethyl-1H-4,5-dihydropyrazole, 5-(4-amino-3-methylphenyl)-1-(2,2,2-trifluoroethyl)-3-trifluoromethyl-pyrazole, 5-(4-amino-3-methylphenyl)-1-difluoromethyl-3-trifluoromethyl-pyrazole, 3-(4-amino-3-methylphenyl)-1-difluoromethyl-3-difluoromethoxy-pyrazole, 1-(4-amino-3-methylbenzyl)-3,4-bis(pentafluoroethyl)-1H-pyrazole, 1-(4-amino-3-methylbenzyl)-3,5-bis(pentafluoroethyl)-1H-pyrazole, 1-(4-amino-3-methylbenzyl)-3,4-bis(pentafluoropropyl)-1H-pyrazole, 1-(4-amino-3-methylbenzyl)-3,5-bis(pentafluoropropyl)-1H-pyrazole, 1-(4-amino-3-methylbenzyl)-3,5-bis(pentafluoroethyl)-1H-(1,2,4)-triazole, 1-(4-amino-3-methylbenzyl)-2,5-bis(pentafluoroethyl)-1H-(1,3,4)-triazole, 2-(4-amino-3-methylphenyl)-5-(trifluoromethyl)-1,3,4-oxadiazole, 2-(4-amino-3-methylphenyl)-5-(pentafluoroethyl)-1,3,4-oxadiazole, 2-(4-amino-3-methylphenyl)-5-(heptafluoropropyl)-1,3,4-oxadiazole, 2-(4-amino-3-methylbenzyl)-5-(trifluoromethyl)-1,3,4-oxadiazole, 2-(4-amino-3-methylbenzyl)-4-(trifluoromethyl)-2H-1,2,3-triazole, 2-(4-amino-3-methylbenzyl)-4-(pentafluoroethyl)-thiazole, 5-(4-amino-3-methylphenyl)sulfanyl-1-methyl-3-(trifluoromethyl)-1H-1,2,4-triazole, 3-(4-amino-3-methylphenyl)-5-(trifluoromethyl)-1,2,4-oxadiazole, 3-(4-amino-3-methylphenyl)-1-methyl-5-(trifluoromethyl)-1H-1,2,4-triazole, 1-(4-amino-3-chlorobenzyl)-3,5-bis(trifluoromethyl)-1H-pyrazole, 1-(4-amino-3-fluorobenzyl)-3,5-bis(trifluoromethyl)-1H-pyrazole and so on.

The compounds of the formula (IV), used as starting materials in the above-mentioned preparation process (b), are novel compounds and can be easily obtained according to the process described in Japanese Laid-open Patent Publication No. 61-246161 (1986), for example, by reacting compounds of the formula (XII)

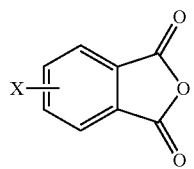

(XII)

wherein X has the same definition as aforementioned, with the compounds of the formula (III).

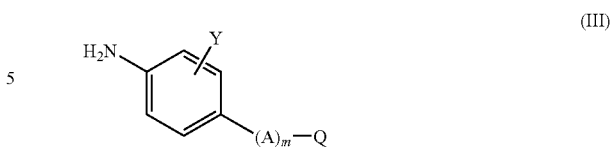

(III)

wherein Y, A, m and Q have the same definitions as aforementioned,

The reaction can be conducted in an adequate diluent. As the diluent used in that case there can be mentioned, for example, aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethyl phosphoric triamide (HMPA), etc.; acids, for example, acetic acid etc.

The reaction can be conducted in a substantially wide range of temperature. It is adequate to conduct it at the temperatures in a range of generally from room temperature (20° C.) to about 200° C., preferably from room temperature to 150° C.

Although said reaction is conducted desirably under normal pressure, it can be operated also under elevated pressure or under reduced pressure.

In conducting the reaction, the aimed compounds of the formula (IV) can be obtained, for example, by reacting equimolar to a little excess mole amount of the compounds of the formula (III) to 1 mole of the compounds of the formula (XII) in a diluent, for example, acetic acid.

Many of the compounds of the above-mentioned formula (XII) are publicly known, and as their specific examples there can be mentioned, phthalic anhydride, 3-fluorophthalic anhydride, 3-chlorophthalic anhydride, 3-bromophthalic anhydride, 3-iodophthalic anhydride, 3-methanesulfonyloxyphthalic anhydride, etc.

Among the above-mentioned compounds, 3-methanesulfonyloxyphthalic anhydride can be easily obtained from 3-hydroxyphthalic anhydride and methanesulfonyl chloride according to the process described in Tetrahedron Letters Vol. 29, p. 5595-8 (1988).

As specific examples of the compounds of the formula (IV), used as starting materials in the preparation process (b), there can be mentioned the following:

4-chloro-2-{2-methyl-4-[3,5-bis(trifluoromethyl)-1H-pyrazol-1-ylmethyl]phenyl}-isoindole-1,3-dione, 2-{2-methyl-4-[3,5-bis(trifluoromethyl)-1H-pyrazol-1-ylmethyl]-phenyl}-isoindole-1,3-dione, 4-chloro-2-[2-methyl-4-(5-difluoromethoxy-3-trifluoromethyl-1H-pyrazol-1-yl-methyl)-phenyl]-isoindole-1,3-dione, 4-chloro-2-[2-methyl-4-(4-pentafluoroethyl-1H-pyrazol-1-yl-methyl)-phenyl]-isoindole-1,3-dione, 4-bromo-2-{2-methyl-4-[3,5-bis(trifluoromethyl)-1H-pyrazol-1-yl-methyl]-phenyl}-isoindole-1,3-dione, 4-bromo-2-[2-methyl-4-(5-difluoromethoxy-3-trifluoromethyl-1H-pyrazol-1-yl-methyl)-phenyl]-isoindole-1,3-dione,
4-bromo-2-[2-methyl-4-(4-pentafluoroethyl-1H-pyrazol-1-yl-methyl)-phenyl]-isoindole-1,3-dione,
4-iodo-2-{2-methyl-4-[3,5-bis(trifluoromethyl)-1H-pyrazol-1-yl-methyl]-phenyl}-isoindole-1,3-dione,
4-iodo-2-[2-methyl-4-(5-difluoromethoxy-3-trifluoromethyl-1H-pyrazol-1-yl-methyl)-phenyl]-isoindole-1,3-dione,
4-iodo-2-[2-methyl-4-(4-pentafluoroethyl-1H-pyrazol-1-yl-methyl)-phenyl-]isoindole-1,3-dione,
4-iodo-2-[2-methyl-4-(5-hexafluoro-n-propyl-1H-pyrazol-1-yl-methyl)-phenyl]-isoindole-1,3-dione,
4-methanesulfonyloxy-2-{2-methyl-4-[3,5-bis(trifluoromethyl)-1H-pyrazol-1-yl-methyl]-phenyl}-isoindole-1,3-dione,
4-chloro-2-{2-methyl-4-[3,5-bis(trifluoromethyl)-1H-(1,2,4)-triazol-1-yl-methyl]-phenyl}-isoindole-1,3-dione,
4-chloro-2-{2-methyl-4-[5-pentafluoroethyl-3-trifluoromethyl-1H-(1,2,4)-triazol-1-yl-methyl]-phenyl} isoindole-1,3-dione,
4-chloro-2-{2-methyl-4-[5-difluoromethoxy-1-difluoromethyl-1H-(1,2,4)-triazol-1-yl-methyl]-phenyl}-isoindole-1,3-dione,
4-iodo-2-{2-methyl-4-[3,5-bis(trifluoromethyl)-1H-(1,2,4)-triazol-1-yl-methyl]-phenyl}-isoindole-1,3-dione,
4-iodo-2-{2-methyl-4-[5-pentafluoroethyl-3-trifluoromethyl-1H-(1,2,4)-triazol-1-yl-methyl]-phenyl}-isoindole-1,3-dione,
4-iodo-2-{2-methyl-4-[5-difluoromethyl-3-trifluoromethyl-1H-(1,2,4)-triazol-1-yl-methyl]-phenyl}-isoindole-1,3-dione,
4-methanesulfonyloxy-2-{2-methyl-4-[3,5-bis(trifluoromethyl)-1H-(1,2,4)-triazol-1-yl-methyl]-phenyl}-isoindole-1,3-dione,
4-iodo-2-[2-methyl-4-(5-difluoromethoxy-1-difluoromethyl-3-trifluoromethyl-1H-pyrazol-4-yl-methyl)-phenyl]-isoindole-1,3-dione,
4-iodo-2-[2-methyl-4-(5-hydroxy-3,5-bis(trifluoromethyl)-1H-4,5-dihydropyrazol-1-yl-methyl)-phenyl]-isoindole-1,3-dione,
4-iodo-2-{2-methyl-4-[2,4-bis(trifluoromethyl)-1H-imidazol-1-yl-methyl]-phenyl}-isoindole-1,3-dione,
4-iodo-2-{2-methyl-4-[3-(2,2,2-trifluoroethyl)-5-trifluoromethyl-1,2-dihydro-(1,3,4)-triazol-2-on-1-yl-methyl]-phenyl}-isoindole-1,3-dione,
4-iodo-2-{2-methyl-4-[4-(2,2,2-trifluoroethyl)-3-trifluoromethyl-4,5-dihydro-(1,2,4)-triazol-5-on-1-yl-methyl]-phenyl}-isoindole-1,3-dione,
4-iodo-2-{2-methyl-4-[2,5-bis(trifluoromethyl)-(1,3,4)-triazol-1-yl-methyl]-phenyl}-isoindole-1,3-dione,
4-iodo-2-{2-methyl-4-[4,6-bis(trifluoromethyl)pyrimidin-2-yl-methyl]-phenyl}-isoindole-1,3-dione,
4-iodo-2-{2-methyl-4-[4,6-bis(trifluoromethyl)pyrimidin-2-yloxy]-phenyl}-isoindole-1,3-dione,
4-chloro-2-{2-methyl-4-[3,5-bis(trifluoromethyl)-1H-pyrazol-1-yl]-phenyl}-isoindole-1,3-dione,
4-chloro-2-[2-methyl-4-(5-pentafluoroethyl-1H-pyrazol-1-yl)-phenyl]-isoindole-1,3-dione,
4-chloro-2-[2-methyl-4-(3-pentafluoroethyl-1H-pyrazol-1-yl)-phenyl]-isoindole-1,3-dione,
4-chloro-2-[2-methyl-4-(4-pentafluoroethyl-1H-pyrazol-1-yl)-phenyl]-isoindole-1,3-dione,
4-iodo-2-[2-methyl-4-[3-methyl-5-trifluoromethyl-1H-pyrazol-1-yl]-phenyl]-isoindole-1,3-dione,
4-iodo-2-[2-methyl-4-(5-methyl-3-trifluoromethyl-1H-pyrazol-1-yl)-phenyl]-isoindole-1,3-dione,
4-iodo-2-[2-methyl-4-(3-pentafluoroethyl-5-trifluoromethyl-1H-pyrazol-1-yl)-phenyl]-isoindole-1,3-dione,
4-iodo-2-[2-methyl-4-(4-bromo-3-trifluoromethyl-1H-pyrazol-1-yl)phenyl]isoindole-1,3-dione,
4-iodo-2-[2-methyl-4-(3-trifluoromethyl-1H-pyrazol-1-yl)-phenyl]-isoindole-1,3-dione,
4-iodo-2-{2-methyl-4-[5-hydroxy-3-(2,2,2-trifluoroethyl)-5-trifluoromethyl-1H-4,5-dihydropyrazol-1-yl]-phenyl}-isoindole-1,3-dione,
4-iodo-2-{2-methyl-4-[1-(2,2,2-trifluoroethyl)-3-trifluoromethyl-pyrazol-5-yl]-phenyl}-isoindole-1,3-dione,
4-iodo-2-[2-methyl-4-(1-difluoromethyl-3-trifluoromethyl-pyrazol-5-yl)-phenyl]-isoindole-1,3-dione,
4-iodo-2-[2-methyl-4-(1-difluoromethyl-3-difluoromethoxy-pyrazol-3-yl)-phenyl]-isoindole-1,3-dione,
4-iodo-2-{2-methyl-4-[3,5-bis(trifluoromethyl)-1H-pyrazol-1-yl]-phenyl}-isoindole-1,3-dione,
4-iodo-2-[2-methyl-4-(5-pentafluoroethyl-1H-pyrazol-1-yl)-phenyl]-isoindole-1,3-dione,
4-iodo-2-[2-methyl-4-(3-pentafluoroethyl-1H-pyrazol-1-yl)-phenyl]-isoindole-1,3-dione,
4-iodo-2-[2-methyl-4-(4-pentafluoroethyl-1H-pyrazol-1-yl)-phenyl]-isoindole-1,3-dione,
4-bromo-2-{2-methyl-4-[3,5-bis(trifluoromethyl)-1H-pyrazol-1-yl]-phenyl}-isoindole-1,3-dione,
4-bromo-2-[2-methyl-4-(5-pentafluoroethyl-1H-pyrazol-1-yl)-phenyl-isoindole-1,3-dione,
4-bromo-2-[2-methyl-4-(3-pentafluoroethyl-1H-pyrazol-1-yl)-phenyl]-isoindole-1,3-dione,
4-bromo-2-[2-methyl-4-(4-pentafluoroethyl-1H-pyrazol-1-yl)-phenyl]-isoindole-1,3-dione,
4-chloro-2-{2-methyl-4-[3,4-bis(pentafluoroethyl)-1H-pyrazol-1-ylmethyl]-phenyl}-isoindole-1,3-dione,
4-chloro-2-{2-methyl-4-[3,5-bis(pentafluoroethyl)-1H-pyrazol-1-ylmethyl]-phenyl}-isoindole-1,3-dione,
4-chloro-2-{2-methyl-4-[3,4-bis(heptafluoropropyl)-1H-pyrazol-1-ylmethyl]-phenyl}-isoindole-1,3-dione,
4-chloro-2-{2-methyl-4-[3,5-bis(heptafluoropropyl)-1H-pyrazol-1-ylmethyl]-phenyl}-isoindole-1,3-dione,
4-chloro-2-[2-methyl-4-(5-trifluoromethyl-1,3,4-oxadiazol-2-yl)-phenyl]-isoindole-1,3-dione,
4-chloro-2-[2-methyl-4-(5-pentafluoroethyl-1,3,4-oxadiazol-2-yl)-phenyl]-isoindole-1,3-dione,
4-chloro-2-[2-methyl-4-(5-heptafluoropropyl-1,3,4-oxadiazol-2-yl)-phenyl]-isoindole-1,3-dione,
4-chloro-2-[2-methyl-4-(5-trifluoromethyl-1,3,4-oxadiazol-2-yl-methyl)-phenyl]-isoindole-1,3-dione,
4-chloro-2-[2-methyl-4-(4-trifluoromethyl-2H-1,2,3-triazol-2-yl-methyl)-phenyl]-isoindole-1,3-dione,
4-chloro-2-[2-methyl-4-(4-(pentafluoroethyl)-thiazol-2-yl-methyl)-phenyl]-isoindole-1,3-dione,
4-chloro-2-{2-methyl-4-[1-methyl-3-(trifluoromethyl)-1H-1,2,4-triazol-5-yl-sulfanyl]-phenyl}-isoindole-1,3-dione,
4-chloro-2-[2-methyl-4-(5-trifluoromethyl-1,2,4-oxadiazol-3-yl)-phenyl]-isoindole-1,3-dione,
4-chloro-2-[2-methyl-4-(1-methyl-5-trifluoromethyl-1H-1,2,4-triazol-3-yl)-phenyl]-isoindole-1,3-dione,
4-iodo-2-[2-methyl-4-(5-trifluoromethyl-1,3,4-oxadiazol-2-yl)-phenyl]-isoindole-1,3-dione and so on.

The compounds of the formula (V), used as starting materials in the preparation process (b), are either compounds well known in the field of organic chemistry or can be synthesized according to the process described in DE-A 20 45 905, WO 01/23350.

As their specific examples there can be mentioned ethylamine, diethylamine, n-propylamine, isopropylamine, n-butylamine, sec-butylamine, isobutylamine, t-butylamine, t-amylamine, 2-(methyl thio)-ethylamine, 2-(ethylthio)-ethylamine, 1-methyl-2-(methylthio)-ethylamine, 1,1-dimethyl-2-(methylthio)-ethylamine and so on.

The compounds of the formula (VI), used as starting materials in the preparation process (c), include publicly known compounds and can be easily prepared according to the process described in JP-A 11-240857 (1999), JP-A 2001-131141, etc.

As their specific examples there can be mentioned the following:
N-isopropyl-phthalamic acid,
3-fluoro-N-isopropyl-phthalamic acid,
3-chloro-N-isopropyl-phthalamic acid,
3-bromo-N-isopropyl-phthalamic acid,
3-iodo-N-isopropyl-phthalamic acid,
N-(1-methyl-2-methylsulfanyl-ethyl)-phthalamic acid,
3-fluoro-N-(1-methyl-2-methylsulfanyl-ethyl)-phthalamic acid,
3-chloro-N-(1-methyl-2-methylsulfanyl-ethyl)-phthalamic acid,
3-bromo-N-(1-methyl-2-methylsulfanyl-ethyl)-phthalamic acid,
3-iodo-N-(1-methyl-2-methylsulfanyl-ethyl)-phthalamic acid,
N-(1,1-dimethyl-2-methylsulfanyl-ethyl)-phthalamic acid,
N-(1,1-dimethyl-2-methylsulfanyl-ethyl)-3-fluoro-phthalamic acid,
3-chloro-N-(1,1-dimethyl-2-methylsulfanyl-ethyl)-phthalamic acid,
3-bromo-N-(1,1-dimethyl-2-methylsulfanyl-ethyl)-phthalamic acid,
N-(1,1-dimethyl-2-methylsulfanyl-ethyl)-3-iodo-phthalamic acid,
N-isopropyl-3-methanesulfonyloxy-phthalamic acid,
N-(1-methyl-2-methylsulfanyl-ethyl)-3-methanesulfonyloxy-phthalamic acid,
N-(1-methyl-2-methylsulfanyl-ethyl)-3-nitro-phthalamic acid,
3-chloro-N-(2-ethylsulfanyl-1-methyl-ethyl)-phthalamic acid,
3-bromo-N-(2-ethylsulfanyl-1-methyl-ethyl)-phthalamic acid,
N-(2-ethylsulfanyl-1-methyl-ethyl)-3-iodo-phthalamic acid,
N-(2-ethylsulfanyl-1-methyl-ethyl)-3-nitro-phthalamic acid,
N-(2-ethylsulfanyl-1-methyl-ethyl)-3-methanesulfonyloxy-phthalamic acid,
N-(1,1-dimethyl-2-methylsulfanyl-ethyl)-3-methanesulfonyloxy-phthalamic acid and so on.

The above-mentioned compounds of the formula (VI) can be easily obtained generally by reacting phthalic anhydrides of the aforementioned formula (XII)

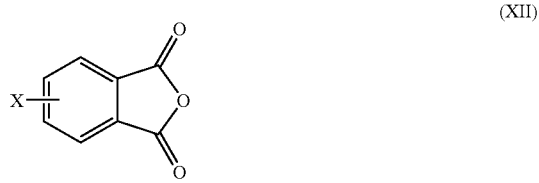

(XII)

wherein X has the same definition as aforementioned, with amines of the formula $$H_2N-R^1$$ (XIII)

wherein $R^1$ has the same definitions as aforementioned,

The compounds of the above-mentioned formula (II) are well known in the field of organic chemistry and there can be specifically mentioned, for example, ethylamine, n-propylamine, isopropylamine, n-butylamine, sec-butylamine, isobutylamine, t-butylamine, t-amylamine, 2-(methylthio)ethylamine, 2-(ethylthio)ethylamine, 1-methyl-2-(methylthio)ethylamine, 1,1-dimethyl-2-(methylthio)ethylamine, etc.

These amines can be easily obtained also by the process described in DE-A 20 45 905, WO 01/23350, etc.

The above-mentioned reaction of the compounds of the formula (XII) with the amines of the formula (XIII) can be conducted according to the process described in, for example, J. Org. Chem., Vol. 46, p. 175 (1981) etc.

Said reaction can be conducted in an adequate diluent, and as examples of the diluent used in that case there can be mentioned aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether DGM), etc.; ketones, for example, acetone, methyl ethyl ketone (MEK), methyl isopropyl ketone, methyl isobutyl ketone (MIBK), etc.; nitriles, for example, acetonitrile, propionitrile, acrylonitrile, etc.; esters, for example, ethyl acetate, amyl acetate, etc.

The above-mentioned reaction can be conducted in the presence of a base, and as said base there can be mentioned, for example, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[5,4,0]undec-7-ene (DBU), etc.

The above-mentioned reaction can be conducted in a substantially wide range of temperature. It is adequate to conduct it at the temperatures in a range of generally from about −70 to about 100° C., preferably from about −50 to about 80° C.

Although said reaction is conducted desirably under normal pressure, it can be operated also under elevated pressure or under reduced pressure.

In conducting the above-mentioned reaction, the aimed compounds of the formula (VI) can be obtained, for example, by reacting 1-4 moles of the compounds of the formula (XIII) to 1 mole of the compounds of the formula (XII) in a diluent, for example, acetonitrile.

The compounds of the formula (VII), used as starting materials in the preparation process (d), are novel compounds and can be easily obtained, for example, by reacting the compounds of the formula (VIII), starting materials in the belowmentioned preparation process (e), according to the process described in J. Med. Chem., Vol. 10, p. 982 (1967) etc. in the presence of a condensing agent.

As specific examples of the compounds of the formula (VII), there can be mentioned the following:
1-[4-(4-iodo-3-oxo-3H-isobenzofuran-1-ylideneamino)-3-methyl-benzyl]-3,5-bis(trifluoromethyl)-1H-pyrazole,
1-[4-(4-chloro-3-oxo-3H-isobenzofuran-1-ylideneamino)-3-methyl-benzyl]-3,5-bis(trifluoromethyl)-1H-pyrazole, 1-[4-(4-iodo-3-oxo-3H-isobenzofuran-1-ylideneamino)-3-methyl-benzyl]-3,5-bis(trifluoromethyl)-1,2,4-triazole,
1-[4-(4-iodo-3-oxo-3H-isobenzofuran-1-ylideneamino)-3-methylphenyl]-3,5-bis(trifluoromethyl)-1H-pyrazole,
1-[4-(4-chloro-3-oxo-3H-isobenzofuran-1-ylideneamino)-3-methyl-benzyl]-3,4-bis(pentafluoroethyl)-1H-pyrazole,
1-[4-(4-chloro-3-oxo-3H-isobenzofuran-1-ylideneamino)-3-methyl-benzyl]-3,5-bis(pentafluoroethyl)-1H-pyrazole,
1-[4-(4-chloro-3-oxo-3H-isobenzofuran-1-ylideneamino)-3-methyl-benzyl]-3,4-bis(heptafluoropropyl)-1H-pyrazole,
1-[4-(4-chloro-3-oxo-3H-isobenzofuran-1-ylideneamino)-3-methyl-benzyl]-3,5-bis(heptafluoropropyl)-1H-pyrazole,
2-[4-(4-chloro-3-oxo-3H-isobenzofuran-1-ylideneamino)-3-methylphenyl]-5-(trifluoromethyl)-1,3,4-oxadiazole,
2-[4-(4-chloro-3-oxo-3H-isobenzofuran-1-ylideneamino)-3-methylphenyl]-5-(pentafluoroethyl)-1,3,4-oxadiazole,
2-[4-(4-chloro-3-oxo-3H-isobenzofuran-1-ylideneamino)-3-methylphenyl]-5-(heptafluoropropyl)-1,3,4-oxadiazole,
2-[4-(4-chloro-3-oxo-3H-isobenzofuran-1-ylideneamino)-3-methylbenzyl]-5-(trifluoromethyl)-1,3,4-oxadiazole,
2-[4-(4-chloro-3-oxo-3H-isobenzofuran-1-ylideneamino)-3-methylbenzyl]-4-(trifluoromethyl)-2H-1,2,3-triazole,
2-[4-(4-chloro-3-oxo-3H-isobenzofuran-1-ylideneamino)-3-methylbenzyl]-4-(pentafluoroethyl)thiazole,
5-[4-(4-chloro-3-oxo-3H-isobenzofuran-1-ylideneamino)-3-methylphenyl]sulfanyl-1-methyl-3-(trifluoromethyl)-1H-1,2,4-triazole,
3-[4-(4-chloro-3-oxo-3H-isobenzofuran-1-ylideneamino)-3-methylphenyl]-5-(trifluoromethyl)-1,2,4-oxadiazole,
3-[4-(4-chloro-3-oxo-3H-isobenzofuran-1-ylideneamino)-3-methylphenyl]-1-methyl-5-(trifluoromethyl)-1H-1,2,4-triazole,
2-[4-(4-iodo-3-oxo-3H-isobenzofuran-1-ylideneamino)-3-methylphenyl]-5-(trifluoromethyl)-1,3,4-oxadiazole and so on.

The compounds of the formula (V), similarly used as starting materials in the preparation process (d), are the same as explained in the aforementioned preparation process (b).

The compounds of the formula (VIII), used as starting materials in the preparation process (e), are novel compounds and can be easily obtained, for example, by reacting phthalic anhydrides of the aforementioned formula (XII) with the compounds of the aforementioned formula (III).

The above-mentioned reaction can be conducted in an adequate diluent, and as examples of the diluent used in that case there can be mentioned aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; ketones, for example, acetone, methyl ethyl ketone (MEK), methyl isopropyl ketone, methyl isobutyl ketone (MIBK), etc.; nitriles, for example, acetonitrile, propionitrile, acrylonitrile, etc.; esters, for example, ethyl acetate, amyl acetate, etc.

The above-mentioned reaction can be conducted in the presence of a base, and as said base there can be mentioned tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU), etc.

The above-mentioned reaction can be conducted in a substantially wide range of temperature. It is adequate to conduct it at the temperatures in a range of generally from about −70 to about 100° C., preferably from about −50 to about 80° C.

Although said reaction is conducted desirably under normal pressure, it can be operated also under elevated pressure or under reduced pressure.

As specific examples of the compounds of the formula (VIII), there can be mentioned the following:
N-{4-[3,5-bis(trifluoromethyl)-1H-pyrazol-1-yl-methyl]-2-methyl-phenyl}-6-iodo-phthalamic acid,
N-{4-[3,5-bis(trifluoromethyl)-1H-pyrazol-1-yl-methyl]-2-methyl-phenyl}-6-chloro-phthalamic acid,
N-{4-[3,5-bis(trifluoromethyl)-(1,2,4)-triazol-1-yl-methyl]-2-methyl-phenyl}-6-iodo-phthalamic acid,
N-{4-[3,5-bis(trifluoromethyl)-1H-pyrazol-1-yl]-2-methyl-phenyl}-6-iodo-phthalamic acid,
N-{4-[3,4-bis(pentafluoroethyl)-1H-pyrazol-1-yl-methyl]-phenyl}-6-chloro-phthalamic acid,
N-{4-[3,5-bis(pentafluoroethyl)-1H-pyrazol-1-yl-methyl]-phenyl}-6-chloro-phthalamic acid,
N-{4-[3,4-bis(heptafluoropropyl)-1H-pyrazol-1-yl-methyl]-phenyl}-6-chloro-phthalamic acid,
N-{4-[3,5-bis(heptafluoropropyl)-1H-pyrazol-1-yl-methyl]-phenyl}-6-chloro-phthalamic acid,
N-[2-methyl-4-(5-trifluoromethyl-1,3,4-oxadiazol-2-yl)-phenyl]-6-chloro-phthalamic acid,
N-[2-methyl-4-(5-pentafluoroethyl-1,3,4-oxadiazol-2-yl)-phenyl]-6-chloro-phthalamic acid,
N-[2-methyl-4-(5-heptafluoropropyl-1,3,4-oxadiazol-2-yl)-phenyl]-6-chloro-phthalamic acid,
N-[2-methyl-4-(5-trifluoromethyl-1,3,4-oxadiazol-2-yl-methyl)-phenyl]-6-chloro-phthalamic acid,
N-[2-methyl-4-(4-trifluoromethyl-2H-1,2,3-triazol-2-yl-methyl)-phenyl]-6-chloro-phthalamic acid,
N-[2-methyl-4-(4-pentafluoroethyl-thiazol-2-yl-methyl)-phenyl]-6-chloro-phthalamic acid,
N-{2-methyl-4-[1-methyl-3-(trifluoromethyl)-1H-1,2,4-triazol-5-yl-sulfanyl]-phenyl}-6-chloro-phthalamic acid,
N-[2-methyl-4-(5-trifluoromethyl-1,2,4-oxadiazol-3-yl)-phenyl]-6-chloro-phthalamic acid,
N-[2-methyl-4-(1-methyl-5-trifluoromethyl-1H-1,2,4-triazol-3-yl)-phenyl]-6-chloro-phthalamic acid,
N-[2-methyl-4-(5-trifluoromethyl-1,3,4-oxadiazol-2-yl)-phenyl]-6-iodo-phthalamic acid and so on.

The compounds of the formula (V), similarly used as starting materials in the preparation process (e), can be the same as ones used in the aforementioned preparation processes (b) and (d).

The compounds of the formula (If), used as starting materials in the preparation process (f), are compounds included in the formula (I) of the present invention.

By oxidizing the group $R^{ff}$ in the compounds of the formula (If), namely, $C_{1-6}$alkylthio-$C_{1-6}$alkyl, the compounds of the formula (I), in which the group $R^{ff}$ corresponds to $C_{1-6}$ alkylsulfinyl-$C_{1-6}$alkyl or $C_{1-6}$alkylsulfonyl-$C_{1-6}$alkyl, can be obtained.

The compounds of the formula (If) can be prepared by the processes of the aforementioned preparation processes (a), (b), (c), (d) and/or (e).

As specific examples of the compounds of the formula (If), there can be mentioned the following:

3-iodo-$N^2$-(1-methyl-2-methylsulfanyl-ethyl)-$N^1$-{2-methyl-4-[3,5-bis(trifluoromethyl)-1H-pyrazol-1-ylmethyl]-phenyl}phthalamide, $N^2$-(1,1-dimethyl-2-methylsulfanyl-ethyl)-3-iodo-$N^1$-{2-methyl-4-[3,5-bis(trifluoro-methyl)-1H-pyrazol-1-ylmethyl]-phenyl}phthalamide, 3-iodo-$N^2$-(1-methyl-2-methylsulfanyl-ethyl)-$N^1$-{2-methyl-4-[3,5-bis(trifluoromethyl)(1,2,4)-triazol-1-ylmethyl]-phenyl}phthalamide, 3-chloro-$N^2$-(1-methyl-2-methylsulfanyl-ethyl)-$N^1$-{2-methyl-4-[3,5-bis(trifluoromethyl)-1H-pyrazol-1-ylmethyl]-phenyl}phthalamide, 3-chloro-$N^2$-(1-methyl-2-methylsulfanyl-ethyl)-$N^1$-{2-methyl-4-[3,4-bis(pentafluoro-ethyl)-1H-pyrazol-1-ylmethyl]-phenyl}phthalamide, 3-chloro-$N^2$-(1-methyl-2-methylsulfanyl-ethyl)-$N^1$-{2-methyl-4-[3,5-bis(pentafluoro-ethyl)-1H-pyrazol-1-ylmethyl]-phenyl}phthalamide, 3-chloro-$N^2$-(1-methyl-2-methylsulfanyl-ethyl)-$N^1$-{2-methyl-4-[3,4-bis(heptafluoro-propyl)-1H-pyrazol-1-ylmethyl]-phenyl}phthalamide, 3-chloro-$N^2$-(1-methyl-2-methylsulfanyl-ethyl)-$N^1$-{2-methyl-4-[3,5-bis(heptafluoro-propyl)-1H-pyrazol-1-ylmethyl]-phenyl}phthalamide and so on The reaction of the aforementioned preparation process (a) can be conducted in an adequate diluent singly or mixed. As examples of the diluent used in that case there can be mentioned water; aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; nitriles, for example, acetonitrile, propionitrile, acrylonitrile, etc.; esters, for example, ethyl acetate, amyl acetate, etc.

The preparation process (a) can be conducted in the presence of an acid catalyst, and as examples of said acid catalyst there can be mentioned mineral acids, for example, hydrochloric acid and sulfuric acid; organic acids, for example, acetic acid, trifluoroacetic acid, propionic acid, methanesulfonic acid, benzenesulfonic acid, p-toluenesulfonic acid, etc.

The preparation process (a) can be conducted in a substantially wide range of temperature. It is adequate to conduct it at the temperatures in a range of generally from about −20 to about 100° C., preferably from about 0 to about 100° C.

Although said reaction is conducted desirably under normal pressure, it can be operated also under elevated pressure or under reduced pressure.

In conducting the preparation process (a), the aimed compounds of the formula (I) can be obtained, for example, by reacting 1 to a little excess mole amount of the compounds of the formula (III) to 1 mole of the compounds of the formula (II) in a diluent, for example, 1,2-dichloroethane in the presence of 0.01-0.1 mole amount of p-toluenesulfonic acid.

The reaction of the aforementioned preparation process (b) can be conducted in an adequate diluent. As examples of the diluent used in that case there can be mentioned aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethyl phosphoric triamide (HMPA), etc.

The preparation process (b) can be conducted in the presence of an acid catalyst and as examples of said acid catalyst there can be mentioned mineral acids, for example, hydrochloric acid and sulfuric acid; organic acids, for example, acetic acid, trifluoroacetic acid, propionic acid, methanesulfonic acid, p-toluenesulfonic acid, etc.

The preparation process (b) can be conducted in a substantially wide range of temperature. It is adequate to conduct it at the temperatures in a range of generally from about −20 to about 150° C., preferably from room temperature (20° C.) to about 100° C.

Although said reaction is conducted desirably under normal pressure, it can be operated also under elevated pressure or under reduced pressure.

In conducting the preparation process (b), the aimed compounds of the formula (I) can be obtained, for example, by reacting 1-25 moles of the compounds of the formula (V) to 1 mole of the compounds of the formula (IV) in a diluent, for example, dioxane in the presence of 0.01-0.5 mole amount of acetic acid.

The aforementioned preparation processes (c), (d) and (e) can be conducted under the similar condition as the abovementioned preparation process (a).

The reaction of the aforementioned preparation process (f) can be conducted in an adequate diluent. As examples of the diluent used in that case there can be mentioned aliphatic, alicyclic and aromatic hydrocarbons (may be optionally chlorinated), for example, benzene, toluene, xylene, dichloromethane, chloroform, carbon tetrachloride, 1,2-dichloroethane, chlorobenzene, dichlorobenzene, etc.; alcohols, for example, methanol, ethanol, isopropanol and butanol; acids; formic acid, acetic acid, etc.

As the oxidizing agents usable in the aforementioned preparation process (f) there can be mentioned, for example, m-chloroperbenzoic acid, peracetic acid, potassium metaperiodate, potassium hydrogen persulfate (oxon), hydrogen peroxide, etc.

The preparation process (f) can be conducted in a substantially wide range of temperature. It is adequate to conduct it at the temperatures in a range of generally from about −50 to about 150° C., preferably from about −10 to about 100° C.

Although said reaction is conducted desirably under normal pressure, it can be operated also under elevated pressure or under reduced pressure.

In conducting the preparation process (f), the aimed compounds of the corresponding formula (I) can be obtained, for example, by reacting 1-5 moles of an oxidizing agent to 1 mole of the compounds of the formula (If) in a diluent, for example, dichloromethane.

The reaction of the aforementioned preparation process (f) can be conducted, for example, according to the process described in JIKKEN KAGAKU KOZA (Lecture on experimental chemistry) edited by the Chemical Society of Japan, 4$^{th}$, ed., Vol. 24, p. 350 (1992) published by MARUZEN or ibid. p. 365.

The compounds of the formula (I) of the present invention show strong insecticidal action. The compounds of the formula (I), according to the present invention can, therefore, be used as insecticidal agents. And the active compounds of the formula (I) of the present invention exhibit exact controlling effect against harmful insects without giving phytotoxicity on cultured plants. And the compounds of the present invention can be used for controlling a wide variety of pests, for example, harmful sucking insects, biting insects and other plant-parasitic pests, stored grain pests, hygienic pests, etc. and applied for their extermination.

As examples of such pests there can be mentioned the following pests:

As insects, there can be mentioned:

Coleoptera pests, for example,

*Callosobruchus Chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus;*

Lepidoptera pests, for example,

*Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens, Phyllocnistis citrella;*

Hemiptera pests, for example,

*Nephotettix cincticeps, Nilaparvata lugens, Pseudococcus comstocki, Unaspis yanonensis, Myzus persicae, Aphis pomi, Aphis gossypii, Rhopalosiphum pseudobrassicas, Stephanitis nashi, Nazara* spp., *Trialeurodes vaporariorum, Psylla* spp.;

Thysanoptera pests, for example,

*Thrips palmni, Frankliniella occidental;*

Orthoptera pests, for example,

*Blatella germanica, Periplaneta americana, Gryllotalpa africana, Locusta migratoria migratoriodes;*

Homoptera pests, for example,

*Reticulitermes speratus, Coptotermes formosanus;*

Diptera pests, for example,

*Musca domestica, Aedes aegypti, Hylemia platura, Culex pipiens, Anopheles slnensis, Culex tritaeniorhynchus, Liriomyzae trifolii* etc.

Moreover, as mites there can be mentioned, for example,

*Tetranychus cinnabarinus, Tetranychus urticae, Panonychus citri, Aculops pelekassi, Tarsonemus* spp., etc.

Furthermore, as nematodes there can be mentioned, for example,

*Meloidogyne incognita, Bursaphelenchus lignicolus Mamiya et Kiyohara, Aphelenchoides besseyi, Heterodera glycines, Pratylenchus* spp., etc.

In addition, in the field of veterinary medicine, the novel compounds of the present invention can be effectively used against various harmful animal-parasitic pests (endoparasites and ectoparasites), for example, insects and helminthes. As examples of such animal-parasitic pests there can be mentioned the following pests:

As insects there can be mentioned, for example,

*Gastrophilus* spp., *Stomoxys* spp., *Trichodectes* spp., *Rhodnius* spp., *Ctenocephalides canis, Cimex lectularius* etc.

As mites there can be mentioned, for example,

*Ornithodoros* spp., *Ixodes* spp., *Boophilus* spp., etc.

In the present invention, substances having insecticidal action against pests, which include all of them, are in some cases called as insecticides.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds, according to the present invention, can be converted into the customary formulation forms, when they are used as insecticides. As formulation forms there can be mentioned, for example, solutions, emulsions, wettable powders, water dispersible granules, suspensions, powders, foams, pastes, tablets, granules, aerosols, natural and synthetic materials impregnated with active compound, microcapsules, seed coating agents, formulations used with burning equipment (as burning equipment, for example, fumigation and smoking cartridges, cans, coils, etc.), ULV [cold mist, warm mist], etc.

These formulations can be produced according to per se known methods, for example, by mixing the active compounds with extenders, namely liquid diluents or carriers; liquefied gas diluents or carriers; solid diluents or carriers, and optionally with surface-active agents, namely emulsifiers and/or dispersants and/or foam-forming agents.

In case that water is used as extender, for example, organic solvents can also be used as auxiliary solvents.

As liquid diluents or carriers there can be mentioned, for example, aromatic hydrocarbons (for example, xylene, toluene, alkylnaphthalene, etc.), chlorinated aromatic or chlorinated aliphatic hydrocarbons (for example, chlorobenzenes, ethylene chlorides, methylene chloride, etc.), aliphatic hydrocarbons [for example, cyclohexane etc. or paraffins (for example, mineral oil fractions etc.)], alcohols (for example, butanol, glycols and their ethers, esters, etc.), ketones (for example, acetone, methyl ethyl ketone, methyl isobutyl ketone, cyclohexanone, etc.), strongly polar solvents (for example, dimethylformamide, dimethyl sulfoxide, etc.), and water.

Liquefied gas diluents or carriers are substances that are gases at normal temperature and pressure and there can be mentioned, for example, aerosol propellants such as butane, propane, nitrogen gas, carbon dioxide, halogenated hydrocarbons.

As solid diluents there can be mentioned, for example, ground natural minerals (for example, kaolin, clay, talc, chalk quartz, attapulgite, montmorillonite, diatomaceous earth, etc.), ground synthetic minerals (for example, highly dispersed silicic acid, alumina, silicates, etc.).

As solid carriers for granules there can be mentioned, for example, crushed and fractionated rocks (for example, calcite, marble, pumice, sepiolite, dolomite, etc.), synthetic granules of inorganic or organic meals, particles of organic materials (for example, saw dust, coconut shells, maize cobs, tobacco stalks, etc.), etc.

As emulsifiers and/or foam-forming agents, there can be mentioned, for example, nonionic and anionic emulsifiers [for example, polyoxyethylene fatty acid esters, polyoxyethylene fatty acid alcohol ethers (for example, alkylaryl polyglycol ethers), alkylsulfonates, alkylsulfates, arylsulfonates, etc.], albumin hydrolysis products, etc.

Dispersants include, for example, lignin sulfite waste liquor and methyl cellulose.

Tackifiers can also be used in formulations (powders, granules, emulsifiable concentrates). As said tackifiers, there can be mentioned, for example, carboxymethyl cellulose, natural or synthetic polymers (for example, gum Arabic, polyvinyl alcohol, polyvinyl acetate, etc.).

Colorants can also be used. As said colorants there can be mentioned, for example, inorganic pigments (for example, iron oxide, titanium oxide, Prussian Blue, etc.), organic dyestuffs such as alizarin dyestuffs, azo dyestuffs or metal phthalocyanine dyestuffs, and further trace nutrients such as salts of iron, manganese, boron, copper, cobalt, molybdenum and zinc.

Said formulations can contain the aforementioned active component of the amount in the range of generally 0.1-95% by weight, preferably 0.5-90% by weight.

The active compounds of the formula (I) of the present invention can exist also as a mixed agent with other active compounds, for example, insecticides, poisonous baits, bactericides, miticides, nematicides, fungicides, growth regulators or herbicides in the form of their commercially useful formulations and in the application forms prepared from such formulations. Here, as the above-mentioned insecticides, there can be mentioned, for example, organophosphorous agents, carbamate agents, carboxylate type chemicals, chlorinated hydrocarbon type chemicals, insecticidal substances produced by microorganisms, etc.

Further, the active compounds of the formula (I) of the present invention can exist also as a mixed agent with a synergist, and such formulations and application forms can be mentioned as commercially useful. Said synergist itself must not be active, but is a compound that enhances the action of the active compound.

Particularly favourable mixing components are, for example, the following compounds:

Fungicides:

2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benalaxyl-M; benodanil; benomyl; benthiavalicarb-isopropyl; benzamacril; benzamacril-isobutyl; bilanafos; binapacryl; biphenyl; bitertanol; blasticidin-S; boscalid; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulfonyl)amino]-butanamide; 1-(1-naphthalenyl)-1H-pyrrol-2,5-dione; 2,3,5,6-tetrachloro-4-(methylsulfonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)-cycloheptanol;

methyl 1-(2,3-dihydro-2,2-dimethyl-1H-inden-1-yl)-1H-imidazole-5-carboxylate; mono potassium carbonate; N-(6-methoxy-3-pyridinyl)-cyclopropanecarboxamide; N-butyl-8-(1,1-dimethylethyl)-1-oxaspiro[4,5]decan-3-amine;

sodium tetrathiocarbonate; and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholinesterase (AChE) inhibitors 1.1 Carbamates (e.g. alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, cloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 Organophosphates (e.g. acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-s-methyl, demeton-s-methylsulphon, dialifos, diazinon, dichlofenthion, dichlorvos/ddvp, dicrotophos, dimethoate, dimethylvinphos, dioxabenzofos, disulfoton, epn, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium channel modulators/voltage dependant sodium channel blockers 2.1 Pyrethroids (e.g. acrinathrin, allethrin (d-cis-trans, d-trans), beta-cyfluthrin, bifenthrin, bioallethrin, bioallethrin-s-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum))

2.2 Oxadiazine (e.g. indoxacarb)

3. Acetylcholine receptor agonists/-antagonists 3.1 Chloronicotinyls/neonicotinoids (e.g. acetamiprid, clothianidin, dinotefuran, imidacloprid, nitenpyram, nithiazine, thiacloprid, thiamethoxam)

3.2 nicotine, bensultap, cartap

4. Acetylcholine receptor modulators 4.1 Spinosyns (e.g. spinosad)

5. GABA gated chloride channel antagonists 5.1 Cyclodiene organochlorines (e.g. camphechlor, chlordane, endosulfan, gamma-HCH, HCH, heptachlor, lindane, methoxychlor 5.2 Fiproles (e.g. acetoprole, ethiprole, fipronil, vaniliprole)

6. Chloride channel activators 6.1 Mectins (e.g. abamectin, avermectin, emamectin, emamectin-benzoate, ivermectin, milbemectin, milbemycin)

7. Juvenile hormone mimics (e.g. diofenolan, epofenonane, fenoxycarb, hydroprene, kinoprene, methoprene, pyriproxifen, triprene)

8. Ecdysone agonists/disruptors 8.1 Diacylhydrazines (e.g. chromafenozide, halofenozide, methoxyfenozide, tebufenozide)

9. Inhibitors of chitin biosynthesis 9.1 Benzoylureas (e.g. bistrifluron, chlofluazuron, diflubenzuron, fluazuron, flucycloxuron, flufenoxuron, hexaflumuron, lufenuron, novaluron, noviflumuron, penfluron, teflubenzuron, triflumuron)

9.2 buprofezin 9.3 cyromazine

10. Inhibitors of oxidative phosphorylation, ATP-disruptors 10.1 diafenthiuron 10.2 Organotins (e.g. azocyclotin, cyhexatin, fenbutatin-oxide)

11. Decoupler of oxidative phosphorylation by disruption of H proton gradient 11.1 Pyrroles (e.g. chlorfenapyr)

11.2 Dinitrophenoles (e.g. binapacyrl, dinobuton, dinocap, DNOC)

12. Site I electron transport inhibitors 12.1 METI's (e.g. fenazaquin, fenpyroximate, pyrimidifen, pyridaben, tebufenpyrad, tolfenpyrad)

12.2 hydramethylnone 12.3 dicofol

13. Site II electron transport inhibitors 13.1 rotenone

14. Site III electron transport inhibitors 14.1 acequinocyl, fluacrypyrim

15. Microbial disruptors of insect midgut membranes

*Bacillus thuringiensis* strains

16. Inhibitors of lipid synthesis 16.1 Tetronic acid insecticides (e.g. spirodiclofen, spiromesifen)

16.2 Tetramic acid insecticides [e.g. 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]-dec-3-en-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1)]

17. Carboxamides (e.g. flonicamid)

18. Octopaminergic agonists (e.g. amitraz)

19. Inhibitors of magnesium stimulated ATPase (e.g. propargite)

20. Phthalamides (e.g. $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide (CAS-Reg.-No.: 272451-65-7, flubendiamide))

21. Nereistoxin analogues (e.g. thiocyclam hydrogen oxalate, thiosultap-sodium)

22. Biologica, hormones or pheromones (e.g. azadirachtin, *Bacillus* spec., *Beauveria* spec., codlemone, *Metarrhizium* spec., *Paecilomyces* spec., thuringiensin, *Verticillium* spec.)

23. Compounds of unknown or non-specific mode of action 23.1 Fumigants (e.g. aluminium phosphide, methyl bromide, sulfuryl fluoride)

23.2 Selective feeding blockers (e.g. cryolite, flonicamid, pymetrozine)

23.3 Mite growth inhibitors (e.g. clofentezine, etoxazole, hexythiazox)

23.4 amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin further the compound 3-methyl-phenyl-propylcarbamate (Tsumacide Z), the compound 3-(5-chloro-3-pyridinyl)-8-(2,2,2-trifluoroethyl)-8-azabicyclo[3.2.1]octan-3-carbonitrile (CAS-Reg.-Nr. 185982-80-3) and the corresponding 3-endo isomer (CAS-Reg.-Nr. 185984-60-5) (cf. WO 96/37494, WO 98/25923), and preparations comprising insecticidal active plant extracts, nematodes, fungi or viruses.

A mixture with other known active compounds, such as herbicides, fertilizers, growth regulators, safeners and/or semiochemicals is also possible.

When used as insecticides, the active compounds according to the invention can furthermore be present in their commercially available formulations and in the use forms, prepared from these formulations, as a mixture with synergistic agents. Synergistic agents are compounds, which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the vicinity of the plant, on the surface of parts of plants or in plant tissues.

The content of the active compounds of the formula (I) of the present invention in a commercially useful application form can be varied in a wide range.

The concentration of the active compounds of the formula (I) of the present invention at the time of actual usage can be, for example, in the range of 0.0000001-100% by weight, preferably 0.00001-1% by weight.

The compounds of the formula (I) of the present invention can be applied by usual methods suitable to the application forms.

In case of application against hygiene pests and pests of stored products, the active compounds of the present invention have a good stability against alkali on limed substrates and further show an excellent residual effectiveness on wood and soil.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and worms by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defense of the plants against fungi, bacteria and viruses by systemic acquired resistance (SAR), systemin, phytoalexius, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

Then the present invention will be described more specifically by examples. The present invention, however, should not be restricted only to them in any way.

SYNTHESIS EXAMPLES

Synthesis Example 1

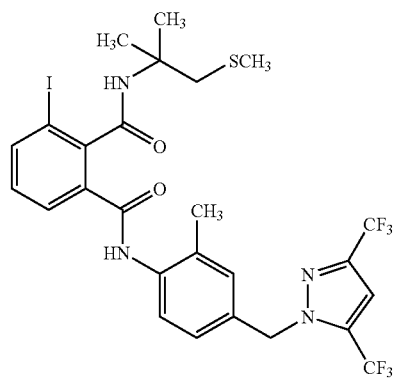

3-(1,1-Dimethyl-2-methylsulfanyl-ethylimino)-4-iodo-3H-isobenzofuran-1-one (0.53 g) and 1-(3-methyl-4-aminobenzyl)-3,5-bis(trifluoromethyl)-1H-pyrazole (0.45 g) were dissolved in acetonitrile (15 ml), to which p-toluenesulfonic acid monohydrate (0.01 g) was added and the mixture was stirred at 60° C. for 3 hours. After finishing the reaction, the solvent was distilled off under reduced pressure and the residue was purified by silica gel column chromatography to obtain $N^1$-[4-(3,5-bistrifluoromethylpyrazol-1-ylmethyl)-2-methylphenyl]-$N^2$-(1,1-dimethyl-2-methylsulfanylethyl)-3-iodophthalamide (0.91 g). mp. 83-87° C.

Synthesis Example 2

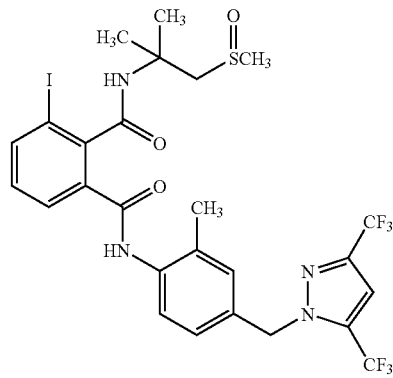

$N^1$-{4-[3,5-Bis(trifluoromethyl)-1H-pyrazol-1-ylmethyl]-2-methlylphenyl}-$N^2$-(1,1-dimethyl-2-methylsulfanylethyl)-3-iodophthalamide (0.5 g) was dissolved in dichloromethane, to which m-chloroperbenzoic acid (0.26 g) was added and the mixture was stirred for 5 hours under ice cooling. After finishing the reaction, the mixture was washed successively with aqueous solution of sodium thiosulfate, saturated aqueous solution of sodium bicarbonate and saturated aqueous solution of sodium chloride, and dried with anhydrous magnesium sulfate. After distilling off the solvent, the obtained residue was purified by silica gel column chromatography to obtain N¹-{4-[3,5-bis(trifluoromethyl)-1H-pyrazol-1-ylmethyl]-2-methylphenyl}-N²-(2-methanesulfinyl-1,1-dimethylethyl)-3-iodophthalamide (0.30 g).

¹H-NMR (CDCl₃, ppm): 1.57 (3H, s), 1.60 (3H, s), 2.20 (3H, s), 2.30 (3H, s), 2.93 (2H, dd), 5.43 (2H, s), 6.57 (1H, s), 6.90 (1H, s), 7.0-8.2 (7H, m).

Synthesis Example 3

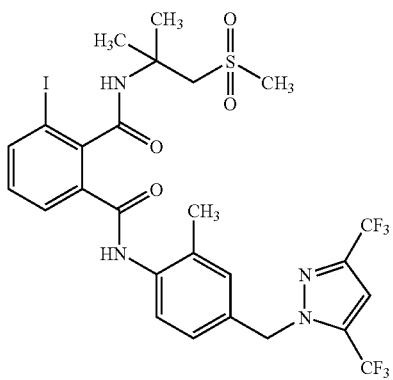

N¹-{4-[3,5-Bis(trifluoromethyl)-1H-pyrazol-1-ylmethyl]-2-methylphenyl}-N²-(1,1-dimethyl-2-methylsulfanylethyl)-3-iodophthalamide (0.30 g) was dissolved in dichloromethane, to which m-chloroperbenzoic acid (0.26 g) was added and the mixture was stirred at room temperature for 5 hours. After finishing the reaction, the mixture was washed successively with aqueous solution of sodium thiosulfate, saturated aqueous solution of sodium bicarbonate and saturated aqueous solution of sodium chloride, and dried with anhydrous magnesium sulfate. After distilling off the solvent, the obtained crude crystals were washed with petroleum ether to obtain N¹-{4-[3,5-bis(trifluoromethyl)-1H-pyrazol-1-ylmethyl]-2-methylphenyl}-3-iodo-N²-(2-methanesulfonyl-1,1-dimethylethyl)phthalamide (0.25 g). mp. 104-107° C.

Synthesis Example 4

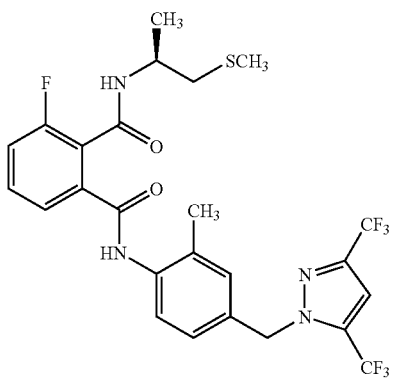

A dioxane solution (15 ml) of 2-{4-[3,5-bis(trifluoromethyl)-1H-pyrazol-1-ylmethyl]-2-methylphenyl}-4-fluoroisoindole-1,3-dione (0.94 g), (S)-1-methyl-2-methylsulfanylethylamine (0.63 g) and acetic acid (0.12 g) was refluxed for 18 hours. After cooling to room temperature, the solvent was distilled off and the obtained residue was purified by silica gel column chromatography to obtain N¹-{4-[3,5-bis(trifluoromethyl)-1H-pyrazol-1-ylmethyl]-2-methylphenyl}-3-fluoro-N²-[1-(S)-1-methyl-2-methylsulfanyl-ethyl]-phthalamide (0.19 g) (compound No. 549). mp. 66-68° C.

Synthesis Example 5

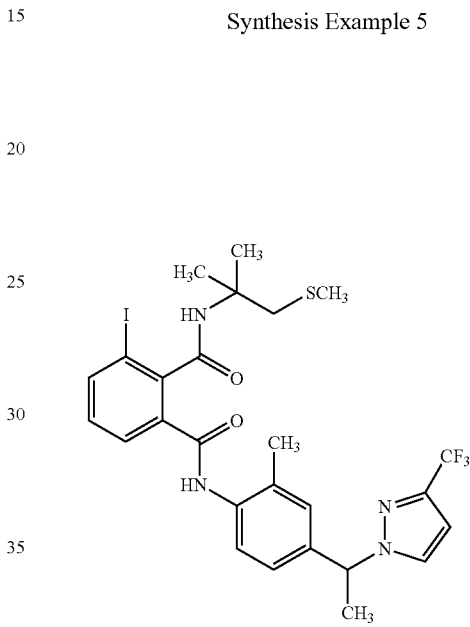

3-Iodo-N-(1,1-dimethyl-2-methylsulfanyl-ethyl)-phthalamic acid (0.39 g) and N-(3-dimethylaminopropyl)-N¹-ethylcarbonyl diimidazole hydrochloride (0.19 g) were stirred in dichloromethane (10 ml) at room temperature for 30 minutes. Then, 2-methyl-4-[1-(3-trifluoromethyl-1H-pyrazol-1-yl)-ethyl]-aniline (0.30 g) and p-toluenesulphonic acid monohydrate (0.02 g) were added thereto and the mixture was stirred at room temperature for 3 hours. After distilling off the solvent under reduced pressure, the obtained residue was purified by silica gel column chromatography to obtain N²-(1,1-dimethyl-2-methylsulfanyl-ethyl)-3-iodo-N¹-{2-methyl-4-[1-(3-trifluoromethyl-1H-pyrazol-1-yl)-ethyl]-phenyl}-phthalamide (0.38 g) (compound No. 558). mp. 79-86° C.

The compounds of the formula (I), according to the present invention, which can be obtained in the same manner as the above-mentioned Synthesis Examples 1 to 5 are shown in Table 1, together with the compounds obtained in the above-mentioned Synthesis Examples 1 to 5.

NMR data of the compounds, whose mp. column is marked as ***, are collectively shown in Table 2, separately from Table 1.

TABLE 1

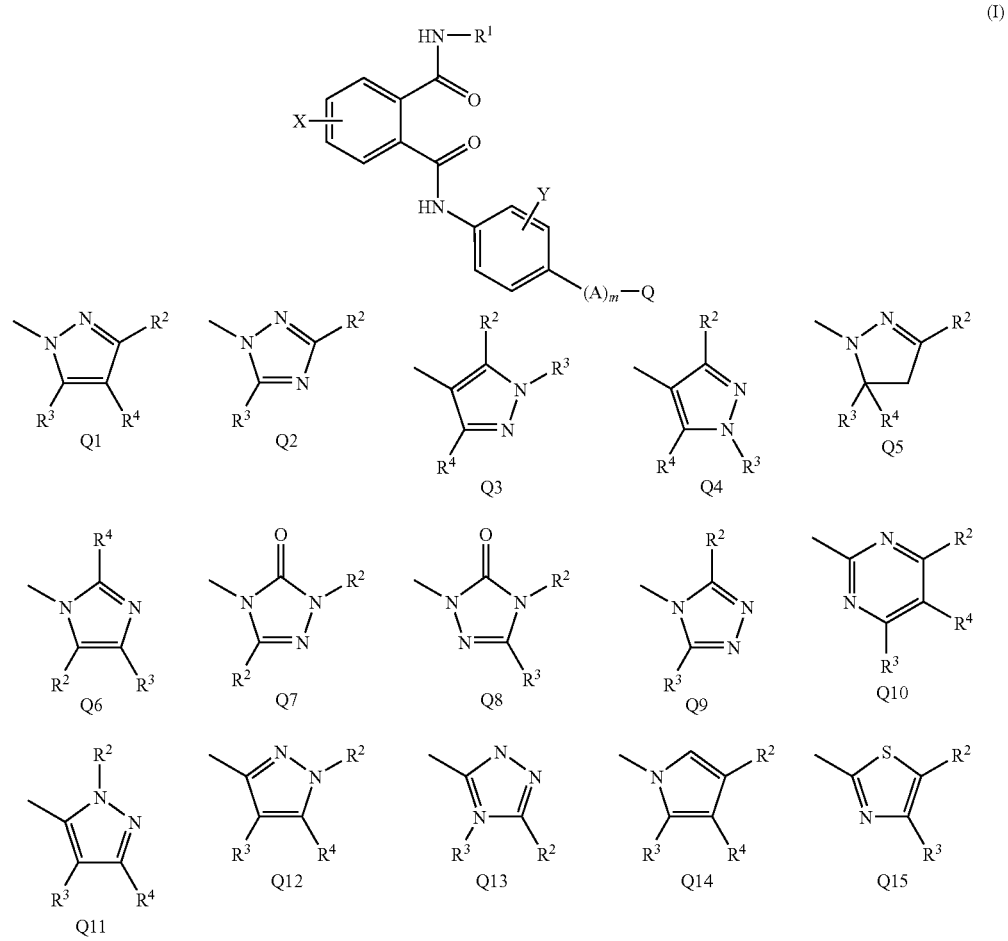

| No. | R¹ | X | Y | A | m | Q | R² | R³ | R⁴ | mp |
|---|---|---|---|---|---|---|---|---|---|---|
| 1 | C(CH₃)₂CH₂SCH₃ | 3-H | 2-CH₃ | CH₂ | 1 | Q1 | CF₃ | CF₃ | H | *** |
| 2 | C(CH₃)₂CH₂SOCH₃ | 3-H | 2-CH₃ | CH₂ | 1 | Q1 | CF₃ | CF₃ | H | |
| 3 | C(CH₃)₂CH₂SO₂CH₃ | 3-H | 2-CH₃ | CH₂ | 1 | Q1 | CF₃ | CF₃ | H | *** |
| 4 | CH(CH₃)CH₂SCH₃ | 3-H | 2-CH₃ | CH₂ | 1 | Q1 | CF₃ | CF₃ | H | |
| 5 | CH(CH₃)CH₂SOCH₃ | 3-H | 2-CH₃ | CH₂ | 1 | Q1 | CF₃ | CF₃ | H | |
| 6 | CH(CH₃)CH₂SO₂CH₃ | 3-H | 2-CH₃ | CH₂ | 1 | Q1 | CF₃ | CF₃ | H | |
| 7 | CH(CH₃)₂ | 3-Cl | 2-CH₃ | CH₂ | 1 | Q1 | CF₃ | CF₃ | H | |
| 8 | C(CH₃)₂CH₂SCH₃ | 3-Cl | 2-CH₃ | CH₂ | 1 | Q1 | CF₃ | CF₃ | H | *** |
| 9 | C(CH₃)₂CH₂SOCH₃ | 3-Cl | 2-CH₃ | CH₂ | 1 | Q1 | CF₃ | CF₃ | H | 80-84 |
| 10 | C(CH₃)₂CH₂SO₂CH₃ | 3-Cl | 2-CH₃ | CH₂ | 1 | Q1 | CF₃ | CF₃ | H | 183-186 |
| 11 | CH(CH₃)CH₂SCH₃ | 3-Cl | 2-CH₃ | CH₂ | 1 | Q1 | CF₃ | CF₃ | H | *** |
| 12 | CH(CH₃)CH₂SCH₃ (S)-isomer | 3-Cl | 2-CH₃ | CH₂ | 1 | Q1 | CF₃ | CF₃ | H | 76-81 |
| 13 | CH(CH₃)CH₂SOCH₃ | 3-Cl | 2-CH₃ | CH₂ | 1 | Q1 | CF₃ | CF₃ | H | 185-193 |
| 14 | CH(CH₃)CH₂SOCH₃ (S)-isomer | 3-Cl | 2-CH₃ | CH₂ | 1 | Q1 | CF₃ | CF₃ | H | 192-194 |
| 15 | CH(CH₃)CH₂SO₂CH₃ | 3-Cl | 2-CH₃ | CH₂ | 1 | Q1 | CF₃ | CF₃ | H | *** |
| 16 | CH(CH₃)CH₂SO₂CH₃ (S)-isomer | 3-Cl | 2-CH₃ | CH₂ | 1 | Q1 | CF₃ | CF₃ | H | 88-93 |
| 17 | CH(CH₃)CH₂SC₂H₅ (S)-isomer | 3-Cl | 2-CH₃ | CH₂ | 1 | Q1 | CF₃ | CF₃ | H | |
| 18 | CH(CH₃)CH₂SOC₂H₅ (S)-isomer | 3-Cl | 2-CH₃ | CH₂ | 1 | Q1 | CF₃ | CF₃ | H | |
| 19 | CH(CH₃)CH₂SO₂C₂H₅ (S)-isomer | 3-Cl | 2-CH₃ | CH₂ | 1 | Q1 | CF₃ | CF₃ | H | |
| 20 | C(CH₃)₂CH₂SCH₃ | 3-Cl | 2-CH₃ | CH₂ | 1 | Q1 | CF₃ | OCHF₂ | H | |
| 21 | C(CH₃)₂CH₂SOCH₃ | 3-Cl | 2-CH₃ | CH₂ | 1 | Q1 | CF₃ | OCHF₂ | H | |
| 22 | C(CH₃)₂CH₂SO₂CH₃ | 3-Cl | 2-CH₃ | CH₂ | 1 | Q1 | CF₃ | OCHF₂ | H | |
| 23 | CH(CH₃)CH₂SCH₃ | 3-Cl | 2-CH₃ | CH₂ | 1 | Q1 | CF₃ | OCHF₂ | H | |

TABLE 1-continued

| | | | | | | | | | | |
|---|---|---|---|---|---|---|---|---|---|---|
| 24 | CH(CH$_3$)CH$_2$SCH$_3$ (S)-isomer | 3-Cl | 2-CH$_3$ | CH$_2$ | 1 | Q1 | CF$_3$ | OCHF$_2$ | H | |
| 25 | CH(CH$_3$)CH$_2$SOCH$_3$ | 3-Cl | 2-CH$_3$ | CH$_2$ | 1 | Q1 | CF$_3$ | OCHF$_2$ | H | |
| 26 | CH(CH$_3$)CH$_2$SOCH$_3$ (S)-isomer | 3-Cl | 2-CH$_3$ | CH$_2$ | 1 | Q1 | CF$_3$ | OCHF$_2$ | H | |
| 27 | CH(CH$_3$)CH$_2$SO$_2$CH$_3$ | 3-Cl | 2-CH$_3$ | CH$_2$ | 1 | Q1 | CF$_3$ | OCHF$_2$ | H | |
| 28 | CH(CH$_3$)CH$_2$SO$_2$CH$_3$ (S)-isomer | 3-Cl | 2-CH$_3$ | CH$_2$ | 1 | Q1 | CF$_3$ | OCHF$_2$ | H | |
| 29 | CH(CH$_3$)CH$_2$SC$_2$H$_5$ (S)-isomer | 3-Cl | 2-CH$_3$ | CH$_2$ | 1 | Q1 | CF$_3$ | OCHF$_2$ | H | |
| 30 | CH(CH$_3$)CH$_2$SOC$_2$H$_5$ (S)-isomer | 3-Cl | 2-CH$_3$ | CH$_2$ | 1 | Q1 | CF$_3$ | OCHF$_2$ | H | |
| 31 | CH(CH$_3$)CH$_2$SO$_2$C$_2$H$_5$ (S)-isomer | 3-Cl | 2-CH$_3$ | CH$_2$ | 1 | Q1 | CF$_3$ | OCHF$_2$ | H | |
| 32 | C(CH$_3$)$_2$CH$_2$SCH$_3$ | 3-Cl | 2-CH$_3$ | CH$_2$ | 1 | Q1 | H | H | C$_2$F$_5$ | |
| 33 | C(CH$_3$)$_2$CH$_2$SOCH$_3$ | 3-Cl | 2-CH$_3$ | CH$_2$ | 1 | Q1 | H | H | C$_2$F$_5$ | |
| 34 | C(CH$_3$)$_2$CH$_2$SO$_2$CH$_3$ | 3-Cl | 2-CH$_3$ | CH$_2$ | 1 | Q1 | H | H | C$_2$F$_5$ | |
| 35 | CH(CH$_3$)CH$_2$SCH$_3$ | 3-Cl | 2-CH$_3$ | CH$_2$ | 1 | Q1 | H | H | C$_2$F$_5$ | |
| 36 | CH(CH$_3$)CH$_2$SCH$_3$ (S)-isomer | 3-Cl | 2-CH$_3$ | CH$_2$ | 1 | Q1 | H | H | C$_2$F$_5$ | |
| 37 | CH(CH$_3$)CH$_2$SOCH$_3$ | 3-Cl | 2-CH$_3$ | CH$_2$ | 1 | Q1 | H | H | C$_2$F$_5$ | |
| 38 | CH(CH$_3$)CH$_2$SOCH$_3$ (S)-isomer | 3-Cl | 2-CH$_3$ | CH$_2$ | 1 | Q1 | H | H | C$_2$F$_5$ | |
| 39 | CH(CH$_3$)CH$_2$SO$_2$CH$_3$ | 3-Cl | 2-CH$_3$ | CH$_2$ | 1 | Q1 | H | H | C$_2$F$_5$ | |
| 40 | CH(CH$_3$)CH$_2$SO$_2$CH$_3$ (S)-isomer | 3-Cl | 2-CH$_3$ | CH$_2$ | 1 | Q1 | H | H | C$_2$F$_5$ | |
| 41 | CH(CH$_3$)CH$_2$SC$_2$H$_5$ (S)-isomer | 3-Cl | 2-CH$_3$ | CH$_2$ | 1 | Q1 | H | H | C$_2$F$_5$ | |
| 42 | CH(CH$_3$)CH$_2$SOC$_2$H$_5$ (S)-isomer | 3-Cl | 2-CH$_3$ | CH$_2$ | 1 | Q1 | H | H | C$_2$F$_5$ | |
| 43 | CH(CH$_3$)CH$_2$SO$_2$C$_2$H$_5$ (S)-isomer | 3-Cl | 2-CH$_3$ | CH$_2$ | 1 | Q1 | H | H | C$_2$F$_5$ | |
| 44 | CH(CH$_3$)$_2$ | 3-Br | 2-CH$_3$ | CH$_2$ | 1 | Q1 | CF$_3$ | CF$_3$ | H | |
| 45 | C(CH$_3$)$_2$CH$_2$SCH$_3$ | 3-Br | 2-CH$_3$ | CH$_2$ | 1 | Q1 | CF$_3$ | CF$_3$ | H | 154-160 |
| 46 | C(CH$_3$)$_2$CH$_2$SOCH$_3$ | 3-Br | 2-CH$_3$ | CH$_2$ | 1 | Q1 | CF$_3$ | CF$_3$ | H | |
| 47 | C(CH$_3$)$_2$CH$_2$SO$_2$CH$_3$ | 3-Br | 2-CH$_3$ | CH$_2$ | 1 | Q1 | CF$_3$ | CF$_3$ | H | *** |
| 48 | CH(CH$_3$)CH$_2$SCH$_3$ | 3-Br | 2-CH$_3$ | CH$_2$ | 1 | Q1 | CF$_3$ | CF$_3$ | H | 147-155 |
| 49 | CH(CH$_3$)CH$_2$SCH$_3$ (S)-isomer | 3-Br | 2-CH$_3$ | CH$_2$ | 1 | Q1 | CF$_3$ | CF$_3$ | H | 80-86 |
| 50 | CH(CH$_3$)CH$_2$SOCH$_3$ | 3-Br | 2-CH$_3$ | CH$_2$ | 1 | Q1 | CF$_3$ | CF$_3$ | H | |
| 51 | CH(CH$_3$)CH$_2$SOCH$_3$ (S)-isomer | 3-Br | 2-CH$_3$ | CH$_2$ | 1 | Q1 | CF$_3$ | CF$_3$ | H | 207-209 |
| 52 | CH(CH$_3$)CH$_2$SO$_2$CH$_3$ | 3-Br | 2-CH$_3$ | CH$_2$ | 1 | Q1 | CF$_3$ | CF$_3$ | H | *** |
| 53 | CH(CH$_3$)CH$_2$SO$_2$CH$_3$ (S)-isomer | 3-Br | 2-CH$_3$ | CH$_2$ | 1 | Q1 | CF$_3$ | CF$_3$ | H | 77-85 |
| 54 | CH(CH$_3$)CH$_2$SC$_2$H$_5$ (S)-isomer | 3-Br | 2-CH$_3$ | CH$_2$ | 1 | Q1 | CF$_3$ | CF$_3$ | H | |
| 55 | CH(CH$_3$)CH$_2$SOC$_2$H$_5$ (S)-isomer | 3-Br | 2-CH$_3$ | CH$_2$ | 1 | Q1 | CF$_3$ | CF$_3$ | H | |
| 56 | CH(CH$_3$)CH$_2$SO$_2$C$_2$H$_5$ (S)-isomer | 3-Br | 2-CH$_3$ | CH$_2$ | 1 | Q1 | CF$_3$ | CF$_3$ | H | |
| 57 | C(CH$_3$)$_2$CH$_2$SCH$_3$ | 3-Br | 2-CH$_3$ | CH$_2$ | 1 | Q1 | CF$_3$ | OCHF$_2$ | H | |
| 58 | C(CH$_3$)$_2$CH$_2$SOCH$_3$ | 3-Br | 2-CH$_3$ | CH$_2$ | 1 | Q1 | CF$_3$ | OCHF$_2$ | H | |
| 59 | C(CH$_3$)$_2$CH$_2$SO$_2$CH$_3$ | 3-Br | 2-CH$_3$ | CH$_2$ | 1 | Q1 | CF$_3$ | OCHF$_2$ | H | |
| 60 | CH(CH$_3$)CH$_2$SCH$_3$ | 3-Br | 2-CH$_3$ | CH$_2$ | 1 | Q1 | CF$_3$ | OCHF$_2$ | H | |
| 61 | CH(CH$_3$)CH$_2$SCH$_3$ (S)-isomer | 3-Br | 2-CH$_3$ | CH$_2$ | 1 | Q1 | CF$_3$ | OCHF$_2$ | H | |
| 62 | CH(CH$_3$)CH$_2$SOCH$_3$ | 3-Br | 2-CH$_3$ | CH$_2$ | 1 | Q1 | CF$_3$ | OCHF$_2$ | H | |
| 63 | CH(CH$_3$)CH$_2$SOCH$_3$ (S)-isomer | 3-Br | 2-CH$_3$ | CH$_2$ | 1 | Q1 | CF$_3$ | OCHF$_2$ | H | |
| 64 | CH(CH$_3$)CH$_2$SO$_2$CH$_3$ | 3-Br | 2-CH$_3$ | CH$_2$ | 1 | Q1 | CF$_3$ | OCHF$_2$ | H | |
| 65 | CH(CH$_3$)CH$_2$SO$_2$CH$_3$ (S)-isomer | 3-Br | 2-CH$_3$ | CH$_2$ | 1 | Q1 | CF$_3$ | OCHF$_2$ | H | |
| 66 | CH(CH$_3$)CH$_2$SC$_2$H$_5$ (S)-isomer | 3-Br | 2-CH$_3$ | CH$_2$ | 1 | Q1 | CF$_3$ | OCHF$_2$ | H | |
| 67 | CH(CH$_3$)CH$_2$SOC$_2$H$_5$ (S)-isomer | 3-Br | 2-CH$_3$ | CH$_2$ | 1 | Q1 | CF$_3$ | OCHF$_2$ | H | |
| 68 | CH(CH$_3$)CH$_2$SO$_2$C$_2$H$_5$ (S)-isomer | 3-Br | 2-CH$_3$ | CH$_2$ | 1 | Q1 | CF$_3$ | OCHF$_2$ | H | |
| 69 | C(CH$_3$)$_2$CH$_2$SCH$_3$ | 3-Br | 2-CH$_3$ | CH$_2$ | 1 | Q1 | H | H | C$_2$F$_5$ | |
| 70 | C(CH$_3$)$_2$CH$_2$SOCH$_3$ | 3-Br | 2-CH$_3$ | CH$_2$ | 1 | Q1 | H | H | C$_2$F$_5$ | |
| 71 | C(CH$_3$)$_2$CH$_2$SO$_2$CH$_3$ | 3-Br | 2-CH$_3$ | CH$_2$ | 1 | Q1 | H | H | C$_2$F$_5$ | |
| 72 | CH(CH$_3$)CH$_2$SCH$_3$ | 3-Br | 2-CH$_3$ | CH$_2$ | 1 | Q1 | H | H | C$_2$F$_5$ | |
| 73 | CH(CH$_3$)CH$_2$SCH$_3$ (S)-isomer | 3-Br | 2-CH$_3$ | CH$_2$ | 1 | Q1 | H | H | C$_2$F$_5$ | |
| 74 | CH(CH$_3$)CH$_2$SOCH$_3$ | 3-Br | 2-CH$_3$ | CH$_2$ | 1 | Q1 | H | H | C$_2$F$_5$ | |
| 75 | CH(CH$_3$)CH$_2$SOCH$_3$ (S)-isomer | 3-Br | 2-CH$_3$ | CH$_2$ | 1 | Q1 | H | H | C$_2$F$_5$ | |
| 76 | CH(CH$_3$)CH$_2$SO$_2$CH$_3$ | 3-Br | 2-CH$_3$ | CH$_2$ | 1 | Q1 | H | H | C$_2$F$_5$ | |

TABLE 1-continued

| | | | | | | | | | | |
|---|---|---|---|---|---|---|---|---|---|---|
| 77 | CH(CH₃)CH₂SO₂CH₃ (S)-isomer | 3-Br | 2-CH₃ | CH₂ | 1 | Q1 | H | H | C₂F₅ | |
| 78 | CH(CH₃)CH₂SC₂H₅ (S)-isomer | 3-Br | 2-CH₃ | CH₂ | 1 | Q1 | H | H | C₂F₅ | |
| 79 | CH(CH₃)CH₂SOC₂H₅ (S)-isomer | 3-Br | 2-CH₃ | CH₂ | 1 | Q1 | H | H | C₂F₅ | |
| 80 | CH(CH₃)CH₂SO₂C₂H₅ (S)-isomer | 3-Br | 2-CH₃ | CH₂ | 1 | Q1 | H | H | C₂F₅ | |
| 81 | CH(CH₃)₂ | 3-I | 2-CH₃ | CH₂ | 1 | Q1 | CF₃ | CF₃ | H | *** |
| 82 | C(CH₃)₂CH₂SCH₃ | 3-I | 2-CH₃ | CH₂ | 1 | Q1 | CF₃ | CF₃ | H | 83-87 |
| 83 | C(CH₃)₂CH₂SOCH₃ | 3-I | 2-CH₃ | CH₂ | 1 | Q1 | CF₃ | CF₃ | H | *** |
| 84 | C(CH₃)₂CH₂SO₂CH₃ | 3-I | 2-CH₃ | CH₂ | 1 | Q1 | CF₃ | CF₃ | H | 104-107 |
| 85 | CH(CH₃)CH₂SCH₃ | 3-I | 2-CH₃ | CH₂ | 1 | Q1 | CF₃ | CF₃ | H | *** |
| 86 | CH(CH₃)CH₂SCH₃ (S)-isomer | 3-I | 2-CH₃ | CH₂ | 1 | Q1 | CF₃ | CF₃ | H | 85-93 |
| 87 | CH(CH₃)CH₂SOCH₃ | 3-I | 2-CH₃ | CH₂ | 1 | Q1 | CF₃ | CF₃ | H | 213-215 |
| 88 | CH(CH₃)CH₂SOCH₃ (S)-isomer | 3-I | 2-CH₃ | CH₂ | 1 | Q1 | CF₃ | CF₃ | H | 193-195 |
| 89 | CH(CH₃)CH₂SO₂CH₃ | 3-I | 2-CH₃ | CH₂ | 1 | Q1 | CF₃ | CF₃ | H | *** |
| 90 | CH(CH₃)CH₂SO₂CH₃ (S)-isomer | 3-I | 2-CH₃ | CH₂ | 1 | Q1 | CF₃ | CF₃ | H | 87-93 |
| 91 | CH(CH₃)CH₂SC₂H₅ (S)-isomer | 3-I | 2-CH₃ | CH₂ | 1 | Q1 | CF₃ | CF₃ | H | 79-83 |
| 92 | CH(CH₃)CH₂SOC₂H₅ (S)-isomer | 3-I | 2-CH₃ | CH₂ | 1 | Q1 | CF₃ | CF₃ | H | |
| 93 | CH(CH₃)CH₂SO₂C₂H₅ (S)-isomer | 3-I | 2-CH₃ | CH₂ | 1 | Q1 | CF₃ | CF₃ | H | 79-91 |
| 94 | C(CH₃)₂CH₂SCH₃ | 3-I | 2-CH₃ | CH₂ | 1 | Q1 | H | C₃F₇-n | H | *** |
| 95 | C(CH₃)₂CH₂SOCH₃ | 3-I | 2-CH₃ | CH₂ | 1 | Q1 | H | C₃F₇-n | H | |
| 96 | C(CH₃)₂CH₂SO₂CH₃ | 3-I | 2-CH₃ | CH₂ | 1 | Q1 | H | C₃F₇-n | H | *** |
| 97 | CH(CH₃)CH₂SCH₃ | 3-I | 2-CH₃ | CH₂ | 1 | Q1 | H | C₃F₇-n | H | *** |
| 98 | CH(CH₃)CH₂SOCH₃ | 3-I | 2-CH₃ | CH₂ | 1 | Q1 | H | C₃F₇-n | H | |
| 99 | CH(CH₃)CH₂SO₂CH₃ | 3-I | 2-CH₃ | CH₂ | 1 | Q1 | H | C₃F₇-n | H | *** |
| 100 | C(CH₃)₂CH₂SCH₃ | 3-I | 2-CH₃ | CH₂ | 1 | Q1 | CF₃ | OCHF₂ | H | |
| 101 | C(CH₃)₂CH₂SOCH₃ | 3-I | 2-CH₃ | CH₂ | 1 | Q1 | CF₃ | OCHF₂ | H | |
| 102 | C(CH₃)₂CH₂SO₂CH₃ | 3-I | 2-CH₃ | CH₂ | 1 | Q1 | CF₃ | OCHF₂ | H | |
| 103 | CH(CH₃)CH₂SCH₃ | 3-I | 2-CH₃ | CH₂ | 1 | Q1 | CF₃ | OCHF₂ | H | *** |
| 104 | CH(CH₃)CH₂SCH₃ (S)-isomer | 3-I | 2-CH₃ | CH₂ | 1 | Q1 | CF₃ | OCHF₂ | H | |
| 105 | CH(CH₃)CH₂SOCH₃ | 3-I | 2-CH₃ | CH₂ | 1 | Q1 | CF₃ | OCHF₂ | H | |
| 106 | CH(CH₃)CH₂SOCH₃ (S)-isomer | 3-I | 2-CH₃ | CH₂ | 1 | Q1 | CF₃ | OCHF₂ | H | |
| 107 | CH(CH₃)CH₂SO₂CH₃ | 3-I | 2-CH₃ | CH₂ | 1 | Q1 | CF₃ | OCHF₂ | H | *** |
| 108 | CH(CH₃)CH₂SO₂CH₃ (S)-isomer | 3-I | 2-CH₃ | CH₂ | 1 | Q1 | CF₃ | OCHF₂ | H | |
| 109 | CH(CH₃)CH₂SC₂H₅ (S)-isomer | 3-I | 2-CH₃ | CH₂ | 1 | Q1 | CF₃ | OCHF₂ | H | |
| 110 | CH(CH₃)CH₂SOC₂H₅ (S)-isomer | 3-I | 2-CH₃ | CH₂ | 1 | Q1 | CF₃ | OCHF₂ | H | |
| 111 | CH(CH₃)CH₂SO₂C₂H₅ (S)-isomer | 3-I | 2-CH₃ | CH₂ | 1 | Q1 | CF₃ | OCHF₂ | H | |
| 112 | C(CH₃)₂CH₂SCH₃ | 3-I | 2-CH₃ | CH₂ | 1 | Q1 | H | H | C₂F₅ | |
| 113 | C(CH₃)₂CH₂SOCH₃ | 3-I | 2-CH₃ | CH₂ | 1 | Q1 | H | H | C₂F₅ | |
| 114 | C(CH₃)₂CH₂SO₂CH₃ | 3-I | 2-CH₃ | CH₂ | 1 | Q1 | H | H | C₂F₅ | |
| 115 | CH(CH₃)CH₂SCH₃ | 3-I | 2-CH₃ | CH₂ | 1 | Q1 | H | H | C₂F₅ | |
| 116 | CH(CH₃)CH₂SCH₃ (S)-isomer | 3-I | 2-CH₃ | CH₂ | 1 | Q1 | H | H | C₂F₅ | *** |
| 117 | CH(CH₃)CH₂SOCH₃ | 3-I | 2-CH₃ | CH₂ | 1 | Q1 | H | H | C₂F₅ | |
| 118 | CH(CH₃)CH₂SOCH₃ (S)-isomer | 3-I | 2-CH₃ | CH₂ | 1 | Q1 | H | H | C₂F₅ | |
| 119 | CH(CH₃)CH₂SO₂CH₃ | 3-I | 2-CH₃ | CH₂ | 1 | Q1 | H | H | C₂F₅ | |
| 120 | CH(CH₃)CH₂SO₂CH₃ (S)-isomer | 3-I | 2-CH₃ | CH₂ | 1 | Q1 | H | H | C₂F₅ | |
| 121 | CH(CH₃)CH₂SC₂H₅ (S)-isomer | 3-I | 2-CH₃ | CH₂ | 1 | Q1 | H | H | C₂F₅ | |
| 122 | CH(CH₃)CH₂SOC₂H₅ (S)-isomer | 3-I | 2-CH₃ | CH₂ | 1 | Q1 | H | H | C₂F₅ | |
| 123 | CH(CH₃)CH₂SO₂C₂H₅ (S)-isomer | 3-I | 2-CH₃ | CH₂ | 1 | Q1 | H | H | C₂F₅ | |
| 124 | C(CH₃)₂CH₂SCH₃ | 3-OSO2CH3 | 2-CH₃ | CH₂ | 1 | Q1 | CF₃ | CF₃ | H | |
| 125 | C(CH₃)₂CH₂SOCH₃ | 3-OSO2CH3 | 2-CH₃ | CH₂ | 1 | Q1 | CF₃ | CF₃ | H | |
| 126 | C(CH₃)₂CH₂SO₂CH₃ | 3-OSO2CH3 | 2-CH₃ | CH₂ | 1 | Q1 | CF₃ | CF₃ | H | |
| 127 | CH(CH₃)CH₂SCH₃ | 3-OSO2CH3 | 2-CH₃ | CH₂ | 1 | Q1 | CF₃ | CF₃ | H | |
| 128 | CH(CH₃)CH₂SCH₃ (S)-isomer | 3-OSO2CH3 | 2-CH₃ | CH₂ | 1 | Q1 | CF₃ | CF₃ | H | 177-180 |
| 129 | CH(CH₃)CH₂SOCH₃ | 3-OSO2CH3 | 2-CH₃ | CH₂ | 1 | Q1 | CF₃ | CF₃ | H | |
| 130 | CH(CH₃)CH₂SOCH₃ (S)-isomer | 3-OSO2CH3 | 2-CH₃ | CH₂ | 1 | Q1 | CF₃ | CF₃ | H | |
| 131 | CH(CH₃)CH₂SO₂CH₃ | 3-OSO2CH3 | 2-CH₃ | CH₂ | 1 | Q1 | CF₃ | CF₃ | H | |

TABLE 1-continued

| | | | | | | | | | |
|---|---|---|---|---|---|---|---|---|---|
| 132 | CH(CH$_3$)CH$_2$SO$_2$CH$_3$ (S)-isomer | 3-OSO2CH3 | 2-CH$_3$ | CH$_2$ | 1 | Q1 | CF$_3$ | CF$_3$ | H | 85-93 |
| 133 | CH(CH$_3$)CH$_2$SC$_2$H$_5$ (S)-isomer | 3-OSO2CH3 | 2-CH$_3$ | CH$_2$ | 1 | Q1 | CF$_3$ | CF$_3$ | H | |
| 134 | CH(CH$_3$)CH$_2$SOC$_2$H$_5$ (S)-isomer | 3-OSO2CH3 | 2-CH$_3$ | CH$_2$ | 1 | Q1 | CF$_3$ | CF$_3$ | H | |
| 135 | CH(CH$_3$)CH$_2$SO$_2$C$_2$H$_5$ (S)-isomer | 3-OSO2CH3 | 2-CH$_3$ | CH$_2$ | 1 | Q1 | CF$_3$ | CF$_3$ | H | |
| 136 | CH(CH$_3$)$_2$ | 3-Cl | 2-CH$_3$ | CH$_2$ | 1 | Q2 | CF$_3$ | CF$_3$ | — | |
| 137 | C(CH$_3$)$_2$CH$_2$SCH$_3$ | 3-Cl | 2-CH$_3$ | CH$_2$ | 1 | Q2 | CF$_3$ | CF$_3$ | — | 70-72 |
| 138 | C(CH$_3$)$_2$CH$_2$SOCH$_3$ | 3-Cl | 2-CH$_3$ | CH$_2$ | 1 | Q2 | CF$_3$ | CF$_3$ | — | 84-90 |
| 139 | C(CH$_3$)$_2$CH$_2$SO$_2$CH$_3$ | 3-Cl | 2-CH$_3$ | CH$_2$ | 1 | Q2 | CF$_3$ | CF$_3$ | — | 88-95 |
| 140 | CH(CH$_3$)CH$_2$SCH$_3$ | 3-Cl | 2-CH$_3$ | CH$_2$ | 1 | Q2 | CF$_3$ | CF$_3$ | — | 76-80 |
| 141 | CH(CH$_3$)CH$_2$SCH$_3$ (S)-isomer | 3-Cl | 2-CH$_3$ | CH$_2$ | 1 | Q2 | CF$_3$ | CF$_3$ | — | 72-81 |
| 142 | CH(CH$_3$)CH$_2$SOCH$_3$ | 3-Cl | 2-CH$_3$ | CH$_2$ | 1 | Q2 | CF$_3$ | CF$_3$ | — | 186-188 |
| 143 | CH(CH$_3$)CH$_2$SOCH$_3$ (S)-isomer | 3-Cl | 2-CH$_3$ | CH$_2$ | 1 | Q2 | CF$_3$ | CF$_3$ | — | 195-198 |
| 144 | CH(CH$_3$)CH$_2$SO$_2$CH$_3$ | 3-Cl | 2-CH$_3$ | CH$_2$ | 1 | Q2 | CF$_3$ | CF$_3$ | — | 116-118 |
| 145 | CH(CH$_3$)CH$_2$SO$_2$CH$_3$ (S)-isomer | 3-Cl | 2-CH$_3$ | CH$_2$ | 1 | Q2 | CF$_3$ | CF$_3$ | — | 95-99 |
| 146 | CH(CH$_3$)CH$_2$SC$_2$H$_5$ (S)-isomer | 3-Cl | 2-CH$_3$ | CH$_2$ | 1 | Q2 | CF$_3$ | CF$_3$ | — | 73-76 |
| 147 | CH(CH$_3$)CH$_2$SOC$_2$H$_5$ (S)-isomer | 3-Cl | 2-CH$_3$ | CH$_2$ | 1 | Q2 | CF$_3$ | CF$_3$ | — | 180-183 |
| 148 | CH(CH$_3$)CH$_2$SO$_2$C$_2$H$_5$ (S)-isomer | 3-Cl | 2-CH$_3$ | CH$_2$ | 1 | Q2 | CF$_3$ | CF$_3$ | — | 66-72 |
| 149 | C(CH$_3$)$_2$CH$_2$SCH$_3$ | 3-Cl | 2-CH$_3$ | CH$_2$ | 1 | Q2 | C$_2$F$_5$ | CF$_3$ | — | *** |
| 150 | C(CH$_3$)$_2$CH$_2$SOCH$_3$ | 3-Cl | 2-CH$_3$ | CH$_2$ | 1 | Q2 | C$_2$F$_5$ | CF$_3$ | — | 59-64 |
| 151 | C(CH$_3$)$_2$CH$_2$SO$_2$CH$_3$ | 3-Cl | 2-CH$_3$ | CH$_2$ | 1 | Q2 | C$_2$F$_5$ | CF$_3$ | — | 82-87 |
| 152 | CH(CH$_3$)CH$_2$SCH$_3$ | 3-Cl | 2-CH$_3$ | CH$_2$ | 1 | Q2 | C$_2$F$_5$ | CF$_3$ | — | |
| 153 | CH(CH$_3$)CH$_2$SCH$_3$ (S)-isomer | 3-Cl | 2-CH$_3$ | CH$_2$ | 1 | Q2 | C$_2$F$_5$ | CF$_3$ | — | *** |
| 154 | CH(CH$_3$)CH$_2$SOCH$_3$ | 3-Cl | 2-CH$_3$ | CH$_2$ | 1 | Q2 | C$_2$F$_5$ | CF$_3$ | — | |
| 155 | CH(CH$_3$)CH$_2$SOCH$_3$ (S)-isomer | 3-Cl | 2-CH$_3$ | CH$_2$ | 1 | Q2 | C$_2$F$_5$ | CF$_3$ | — | 175-176 |
| 156 | CH(CH$_3$)CH$_2$SO$_2$CH$_3$ | 3-Cl | 2-CH$_3$ | CH$_2$ | 1 | Q2 | C$_2$F$_5$ | CF$_3$ | — | |
| 157 | CH(CH$_3$)CH$_2$SO$_2$CH$_3$ (S)-isomer | 3-Cl | 2-CH$_3$ | CH$_2$ | 1 | Q2 | C$_2$F$_5$ | CF$_3$ | — | 82-90 |
| 158 | CH(CH$_3$)CH$_2$SC$_2$H$_5$ (S)-isomer | 3-Cl | 2-CH$_3$ | CH$_2$ | 1 | Q2 | C$_2$F$_5$ | CF$_3$ | — | |
| 159 | CH(CH$_3$)CH$_2$SOC$_2$H$_5$ (S)-isomer | 3-Cl | 2-CH$_3$ | CH$_2$ | 1 | Q2 | C$_2$F$_5$ | CF$_3$ | — | |
| 160 | CH(CH$_3$)CH$_2$SO$_2$C$_2$H$_5$ (S)-isomer | 3-Cl | 2-CH$_3$ | CH$_2$ | 1 | Q2 | C$_2$F$_5$ | CF$_3$ | — | |
| 161 | C(CH$_3$)$_2$CH$_2$SCH$_3$ | 3-Cl | 2-CH$_3$ | CH$_2$ | 1 | Q2 | CF$_3$ | CHF$_2$ | — | |
| 162 | C(CH$_3$)$_2$CH$_2$SOCH$_3$ | 3-Cl | 2-CH$_3$ | CH$_2$ | 1 | Q2 | CF$_3$ | CHF$_2$ | — | |
| 163 | C(CH$_3$)$_2$CH$_2$SO$_2$CH$_3$ | 3-Cl | 2-CH$_3$ | CH$_2$ | 1 | Q2 | CF$_3$ | CHF$_2$ | — | |
| 164 | CH(CH$_3$)CH$_2$SCH$_3$ | 3-Cl | 2-CH$_3$ | CH$_2$ | 1 | Q2 | CF$_3$ | CHF$_2$ | — | |
| 165 | CH(CH$_3$)CH$_2$SCH$_3$ (S)-isomer | 3-Cl | 2-CH$_3$ | CH$_2$ | 1 | Q2 | CF$_3$ | CHF$_2$ | — | |
| 166 | CH(CH$_3$)CH$_2$SOCH$_3$ | 3-Cl | 2-CH$_3$ | CH$_2$ | 1 | Q2 | CF$_3$ | CHF$_2$ | — | |
| 167 | CH(CH$_3$)CH$_2$SOCH$_3$ (S)-isomer | 3-Cl | 2-CH$_3$ | CH$_2$ | 1 | Q2 | CF$_3$ | CHF$_2$ | — | |
| 168 | CH(CH$_3$)CH$_2$SO$_2$CH$_3$ | 3-Cl | 2-CH$_3$ | CH$_2$ | 1 | Q2 | CF$_3$ | CHF$_2$ | — | |
| 169 | CH(CH$_3$)CH$_2$SO$_2$CH$_3$ (S)-isomer | 3-Cl | 2-CH$_3$ | CH$_2$ | 1 | Q2 | CF$_3$ | CHF$_2$ | — | |
| 170 | CH(CH$_3$)CH$_2$SC$_2$H$_5$ (S)-isomer | 3-Cl | 2-CH$_3$ | CH$_2$ | 1 | Q2 | CF$_3$ | CHF$_2$ | — | |
| 171 | CH(CH$_3$)CH$_2$SOC$_2$H$_5$ (S)-isomer | 3-Cl | 2-CH$_3$ | CH$_2$ | 1 | Q2 | CF$_3$ | CHF$_2$ | — | |
| 172 | CH(CH$_3$)CH$_2$SO$_2$C$_2$H$_5$ (S)-isomer | 3-Cl | 2-CH$_3$ | CH$_2$ | 1 | Q2 | CF$_3$ | CHF$_2$ | — | |
| 173 | CH(CH$_3$)$_2$ | 3-Br | 2-CH$_3$ | CH$_2$ | 1 | Q2 | CF$_3$ | CF$_3$ | — | |
| 174 | C(CH$_3$)$_2$CH$_2$SCH$_3$ | 3-Br | 2-CH$_3$ | CH$_2$ | 1 | Q2 | CF$_3$ | CF$_3$ | — | 77-82 |
| 175 | C(CH$_3$)$_2$CH$_2$SOCH$_3$ | 3-Br | 2-CH$_3$ | CH$_2$ | 1 | Q2 | CF$_3$ | CF$_3$ | — | |
| 176 | C(CH$_3$)$_2$CH$_2$SO$_2$CH$_3$ | 3-Br | 2-CH$_3$ | CH$_2$ | 1 | Q2 | CF$_3$ | CF$_3$ | — | 151-155 |
| 177 | CH(CH$_3$)CH$_2$SCH$_3$ | 3-Br | 2-CH$_3$ | CH$_2$ | 1 | Q2 | CF$_3$ | CF$_3$ | — | 167-169 |
| 178 | CH(CH$_3$)CH$_2$SCH$_3$ (S)-isomer | 3-Br | 2-CH$_3$ | CH$_2$ | 1 | Q2 | CF$_3$ | CF$_3$ | — | 68-73 |
| 179 | CH(CH$_3$)CH$_2$SOCH$_3$ | 3-Br | 2-CH$_3$ | CH$_2$ | 1 | Q2 | CF$_3$ | CF$_3$ | — | |
| 180 | CH(CH$_3$)CH$_2$SOCH$_3$ (S)-isomer | 3-Br | 2-CH$_3$ | CH$_2$ | 1 | Q2 | CF$_3$ | CF$_3$ | — | *** |
| 181 | CH(CH$_3$)CH$_2$SO$_2$CH$_3$ | 3-Br | 2-CH$_3$ | CH$_2$ | 1 | Q2 | CF$_3$ | CF$_3$ | — | 90-98 |
| 182 | CH(CH$_3$)CH$_2$SO$_2$CH$_3$ (S)-isomer | 3-Br | 2-CH$_3$ | CH$_2$ | 1 | Q2 | CF$_3$ | CF$_3$ | — | 99-112 |
| 183 | CH(CH$_3$)CH$_2$SC$_2$H$_5$ (S)-isomer | 3-Br | 2-CH$_3$ | CH$_2$ | 1 | Q2 | CF$_3$ | CF$_3$ | — | |

TABLE 1-continued

| | | | | | | | | | |
|---|---|---|---|---|---|---|---|---|---|
| 184 | CH(CH$_3$)CH$_2$SOC$_2$H$_5$ (S)-isomer | 3-Br | 2-CH$_3$ | CH$_2$ | 1 | Q2 | CF$_3$ | CF$_3$ | — |
| 185 | CH(CH$_3$)CH$_2$SO$_2$C$_2$H$_5$ (S)-isomer | 3-Br | 2-CH$_3$ | CH$_2$ | 1 | Q2 | CF$_3$ | CF$_3$ | — |
| 186 | C(CH$_3$)$_2$CH$_2$SCH$_3$ | 3-Br | 2-CH$_3$ | CH$_2$ | 1 | Q2 | C$_2$F$_5$ | CF$_3$ | — |
| 187 | C(CH$_3$)$_2$CH$_2$SOCH$_3$ | 3-Br | 2-CH$_3$ | CH$_2$ | 1 | Q2 | C$_2$F$_5$ | CF$_3$ | — |
| 188 | C(CH$_3$)$_2$CH$_2$SO$_2$CH$_3$ | 3-Br | 2-CH$_3$ | CH$_2$ | 1 | Q2 | C$_2$F$_5$ | CF$_3$ | — |
| 189 | CH(CH$_3$)CH$_2$SCH$_3$ | 3-Br | 2-CH$_3$ | CH$_2$ | 1 | Q2 | C$_2$F$_5$ | CF$_3$ | — |
| 190 | CH(CH$_3$)CH$_2$SCH$_3$ (S)-isomer | 3-Br | 2-CH$_3$ | CH$_2$ | 1 | Q2 | C$_2$F$_5$ | CF$_3$ | — |
| 191 | CH(CH$_3$)CH$_2$SOCH$_3$ | 3-Br | 2-CH$_3$ | CH$_2$ | 1 | Q2 | C$_2$F$_5$ | CF$_3$ | — |
| 192 | CH(CH$_3$)CH$_2$SOCH$_3$ (S)-isomer | 3-Br | 2-CH$_3$ | CH$_2$ | 1 | Q2 | C$_2$F$_5$ | CF$_3$ | — |
| 193 | CH(CH$_3$)CH$_2$SO$_2$CH$_3$ | 3-Br | 2-CH$_3$ | CH$_2$ | 1 | Q2 | C$_2$F$_5$ | CF$_3$ | — |
| 194 | CH(CH$_3$)CH$_2$SO$_2$CH$_3$ (S)-isomer | 3-Br | 2-CH$_3$ | CH$_2$ | 1 | Q2 | C$_2$F$_5$ | CF$_3$ | — |
| 195 | CH(CH$_3$)CH$_2$SC$_2$H$_5$ (S)-isomer | 3-Br | 2-CH$_3$ | CH$_2$ | 1 | Q2 | C$_2$F$_5$ | CF$_3$ | — |
| 196 | CH(CH$_3$)CH$_2$SOC$_2$H$_5$ (S)-isomer | 3-Br | 2-CH$_3$ | CH$_2$ | 1 | Q2 | C$_2$F$_5$ | CF$_3$ | — |
| 197 | CH(CH$_3$)CH$_2$SO$_2$C$_2$H$_5$ (S)-isomer | 3-Br | 2-CH$_3$ | CH$_2$ | 1 | Q2 | C$_2$F$_5$ | CF$_3$ | — |
| 198 | C(CH$_3$)$_2$CH$_2$SCH$_3$ | 3-Br | 2-CH$_3$ | CH$_2$ | 1 | Q2 | CF$_3$ | CHF$_2$ | — |
| 199 | C(CH$_3$)$_2$CH$_2$SOCH$_3$ | 3-Br | 2-CH$_3$ | CH$_2$ | 1 | Q2 | CF$_3$ | CHF$_2$ | — |
| 200 | C(CH$_3$)$_2$CH$_2$SO$_2$CH$_3$ | 3-Br | 2-CH$_3$ | CH$_2$ | 1 | Q2 | CF$_3$ | CHF$_2$ | — |
| 201 | CH(CH$_3$)CH$_2$SCH$_3$ | 3-Br | 2-CH$_3$ | CH$_2$ | 1 | Q2 | CF$_3$ | CHF$_2$ | — |
| 202 | CH(CH$_3$)CH$_2$SCH$_3$ (S)-isomer | 3-Br | 2-CH$_3$ | CH$_2$ | 1 | Q2 | CF$_3$ | CHF$_2$ | — |
| 203 | CH(CH$_3$)CH$_2$SOCH$_3$ | 3-Br | 2-CH$_3$ | CH$_2$ | 1 | Q2 | CF$_3$ | CHF$_2$ | — |
| 204 | CH(CH$_3$)CH$_2$SOCH$_3$ (S)-isomer | 3-Br | 2-CH$_3$ | CH$_2$ | 1 | Q2 | CF$_3$ | CHF$_2$ | — |
| 205 | CH(CH$_3$)CH$_2$SO$_2$CH$_3$ | 3-Br | 2-CH$_3$ | CH$_2$ | 1 | Q2 | CF$_3$ | CHF$_2$ | — |
| 206 | CH(CH$_3$)CH$_2$SO$_2$CH$_3$ (S)-isomer | 3-Br | 2-CH$_3$ | CH$_2$ | 1 | Q2 | CF$_3$ | CHF$_2$ | — |
| 207 | CH(CH$_3$)CH$_2$SC$_2$H$_5$ (S)-isomer | 3-Br | 2-CH$_3$ | CH$_2$ | 1 | Q2 | CF$_3$ | CHF$_2$ | — |
| 208 | CH(CH$_3$)CH$_2$SOC$_2$H$_5$ (S)-isomer | 3-Br | 2-CH$_3$ | CH$_2$ | 1 | Q2 | CF$_3$ | CHF$_2$ | — |
| 209 | CH(CH$_3$)CH$_2$SO$_2$C$_2$H$_5$ (S)-isomer | 3-Br | 2-CH$_3$ | CH$_2$ | 1 | Q2 | CF$_3$ | CHF$_2$ | — |
| 210 | CH(CH$_3$)$_2$ | 3-I | 2-CH$_3$ | CH$_2$ | 1 | Q2 | CF$_3$ | CF$_3$ | — | 102-105 |
| 211 | C(CH$_3$)$_2$CH$_2$SCH$_3$ | 3-I | 2-CH$_3$ | CH$_2$ | 1 | Q2 | CF$_3$ | CF$_3$ | — | 93-97 |
| 212 | C(CH$_3$)$_2$CH$_2$SOCH$_3$ | 3-I | 2-CH$_3$ | CH$_2$ | 1 | Q2 | CF$_3$ | CF$_3$ | — | 92-93 |
| 213 | C(CH$_3$)$_2$CH$_2$SO$_2$CH$_3$ | 3-I | 2-CH$_3$ | CH$_2$ | 1 | Q2 | CF$_3$ | CF$_3$ | — | 104-107 |
| 214 | CH(CH$_3$)CH$_2$SCH$_3$ | 3-I | 2-CH$_3$ | CH$_2$ | 1 | Q2 | CF$_3$ | CF$_3$ | — | 92-95 |
| 215 | CH(CH$_3$)CH$_2$SCH$_3$ (S)-isomer | 3-I | 2-CH$_3$ | CH$_2$ | 1 | Q2 | CF$_3$ | CF$_3$ | — | 81-90 |
| 216 | CH(CH$_3$)CH$_2$SOCH$_3$ | 3-I | 2-CH$_3$ | CH$_2$ | 1 | Q2 | CF$_3$ | CF$_3$ | — | 192-195 |
| 217 | CH(CH$_3$)CH$_2$SOCH$_3$ (S)-isomer | 3-I | 2-CH$_3$ | CH$_2$ | 1 | Q2 | CF | CF$_3$ | — | 192-199 |
| 218 | CH(CH$_3$)CH$_2$SO$_2$CH$_3$ | 3-I | 2-CH$_3$ | CH$_2$ | 1 | Q2 | CF$_3$ | CF$_3$ | — | 99-104 |
| 219 | CH(CH$_3$)CH$_2$SO$_2$CH$_3$ (S)-isomer | 3-I | 2-CH$_3$ | CH$_2$ | 1 | Q2 | CF$_3$ | CF$_3$ | — | 164-167 |
| 220 | CH(CH$_3$)CH$_2$SC$_2$H$_5$ (S)-isomer | 3-I | 2-CH$_3$ | CH$_2$ | 1 | Q2 | CF$_3$ | CF$_3$ | — | 90-94 |
| 221 | CH(CH$_3$)CH$_2$SOC$_2$H$_5$ (S)-isomer | 3-I | 2-CH$_3$ | CH$_2$ | 1 | Q2 | CF$_3$ | CF$_3$ | — | 201-205 |
| 222 | CH(CH$_3$)CH$_2$SO$_2$C$_2$H$_5$ (S)-isomer | 3-I | 2-CH$_3$ | CH$_2$ | 1 | Q2 | CF$_3$ | CF$_3$ | — | 91-99 |
| 223 | C(CH$_3$)$_2$CH$_2$SCH$_3$ | 3-I | 2-CH$_3$ | CH$_2$ | 1 | Q2 | C$_2$F$_5$ | CF$_3$ | — | |
| 224 | C(CH$_3$)$_2$CH$_2$SOCH$_3$ | 3-I | 2-CH$_3$ | CH$_2$ | 1 | Q2 | C$_2$F$_5$ | CF$_3$ | — | |
| 225 | C(CH$_3$)$_2$CH$_2$SO$_2$CH$_3$ | 3-I | 2-CH$_3$ | CH$_2$ | 1 | Q2 | C$_2$F$_5$ | CF$_3$ | — | |
| 226 | CH(CH$_3$)CH$_2$SCH$_3$ | 3-I | 2-CH$_3$ | CH$_2$ | 1 | Q2 | C$_2$F$_5$ | CF$_3$ | — | 89-94 |
| 227 | CH(CH$_3$)CH$_2$SCH$_3$ (S)-isomer | 3-I | 2-CH$_3$ | CH$_2$ | 1 | Q2 | C$_2$F$_5$ | CF$_3$ | — | 91-104 |
| 228 | CH(CH$_3$)CH$_2$SOCH$_3$ | 3-I | 2-CH$_3$ | CH$_2$ | 1 | Q2 | C$_2$F$_5$ | CF$_3$ | — | |
| 229 | CH(CH$_3$)CH$_2$SOCH$_3$ (S)-isomer | 3-I | 2-CH$_3$ | CH$_2$ | 1 | Q2 | C$_2$F$_5$ | CF$_3$ | — | 190-193 |
| 230 | CH(CH$_3$)CH$_2$SO$_2$CH$_3$ | 3-I | 2-CH$_3$ | CH$_2$ | 1 | Q2 | C$_2$F$_5$ | CF$_3$ | — | 99-116 |
| 231 | CH(CH$_3$)CH$_2$SO$_2$CH$_3$ (S)-isomer | 3-I | 2-CH$_3$ | CH$_2$ | 1 | Q2 | C$_2$F$_5$ | CF$_3$ | — | 126-132 |
| 232 | CH(CH$_3$)CH$_2$SC$_2$H$_5$ (S)-isomer | 3-I | 2-CH$_3$ | CH$_2$ | 1 | Q2 | C$_2$F$_5$ | CF$_3$ | — | |
| 233 | CH(CH$_3$)CH$_2$SOC$_2$H$_5$ (S)-isomer | 3-I | 2-CH$_3$ | CH$_2$ | 1 | Q2 | C$_2$F$_5$ | CF$_3$ | — | |
| 234 | CH(CH$_3$)CH$_2$SO$_2$C$_2$H$_5$ (S)-isomer | 3-I | 2-CH$_3$ | CH$_2$ | 1 | Q2 | C$_2$F$_5$ | CF$_3$ | — | |
| 235 | C(CH$_3$)$_2$CH$_2$SCH$_3$ | 3-I | 2-CH$_3$ | CH$_2$ | 1 | Q2 | CF$_3$ | CHF$_2$ | — | |
| 236 | C(CH$_3$)$_2$CH$_2$SOCH$_3$ | 3-I | 2-CH$_3$ | CH$_2$ | 1 | Q2 | CF$_3$ | CHF$_2$ | — | |
| 237 | C(CH$_3$)$_2$CH$_2$SO$_2$CH$_3$ | 3-I | 2-CH$_3$ | CH$_2$ | 1 | Q2 | CF$_3$ | CHF$_2$ | — | |

TABLE 1-continued

| | | | | | | | | | | |
|---|---|---|---|---|---|---|---|---|---|---|
| 238 | CH(CH₃)CH₂SCH₃ | 3-I | 2-CH₃ | CH₂ | 1 | Q2 | CF₃ | CHF₂ | — | 85-88 |
| 239 | CH(CH₃)CH₂SCH₃ (S)-isomer | 3-I | 2-CH₃ | CH₂ | 1 | Q2 | CF₃ | CHF₂ | — | 160-161 |
| 240 | CH(CH₃)CH₂SOCH₃ | 3-I | 2-CH₃ | CH₂ | 1 | Q2 | CF₃ | CHF₂ | — | |
| 241 | CH(CH₃)CH₂SOCH₃ (S)-isomer | 3-I | 2-CH₃ | CH₂ | 1 | Q2 | CF₃ | CHF₂ | — | |
| 242 | CH(CH₃)CH₂SO₂CH₃ | 3-I | 2-CH₃ | CH₂ | 1 | Q2 | CF₃ | CHF₂ | — | *** |
| 243 | CH(CH₃)CH₂SO₂CH₃ (S)-isomer | 3-I | 2-CH₃ | CH₂ | 1 | Q2 | CF₃ | CHF₂ | — | 174-178 |
| 244 | CH(CH₃)CH₂SC₂H₅ (S)-isomer | 3-I | 2-CH₃ | CH₂ | 1 | Q2 | CF₃ | CHF₂ | — | |
| 245 | CH(CH₃)CH₂SOC₂H₅ (S)-isomer | 3-I | 2-CH₃ | CH₂ | 1 | Q2 | CF₃ | CHF₂ | — | |
| 246 | CH(CH₃)CH₂SO₂C₂H₅ (S)-isomer | 3-I | 2-CH₃ | CH₂ | 1 | Q2 | CF₃ | CHF₂ | — | |
| 247 | C(CH₃)₂CH₂SCH₃ | 3-OSO2CH3 | 2-CH₃ | CH₂ | 1 | Q2 | CF₃ | CF₃ | — | |
| 248 | C(CH₃)₂CH₂SOCH₃ | 3-OSO2CH3 | 2-CH₃ | CH₂ | 1 | Q2 | CF₃ | CF₃ | — | |
| 249 | C(CH₃)₂CH₂SO₂CH₃ | 3-OSO2CH3 | 2-CH₃ | CH₂ | 1 | Q2 | CF₃ | CF₃ | — | |
| 250 | CH(CH₃)CH₂SCH₃ | 3-OSO2CH3 | 2-CH₃ | CH₂ | 1 | Q2 | CF₃ | CF₃ | — | |
| 251 | CH(CH₃)CH₂SCH₃ (S)-isomer | 3-OSO2CH3 | 2-CH₃ | CH₂ | 1 | Q2 | CF₃ | CF₃ | — | *** |
| 252 | CH(CH₃)CH₂SOCH₃ | 3-OSO2CH3 | 2-CH₃ | CH₂ | 1 | Q2 | CF₃ | CF₃ | — | |
| 253 | CH(CH₃)CH₂SOCH₃ (S)-isomer | 3-OSO2CH3 | 2-CH₃ | CH₂ | 1 | Q2 | CF₃ | CF₃ | — | 207-208 |
| 254 | CH(CH₃)CH₂SO₂CH₃ | 3-OSO2CH3 | 2-CH₃ | CH₂ | 1 | Q2 | CF₃ | CF₃ | — | |
| 255 | CH(CH₃)CH₂SO₂CH₃ (S)-isomer | 3-OSO2CH3 | 2-CH₃ | CH₂ | 1 | Q2 | CF₃ | CF₃ | — | |
| 256 | CH(CH₃)CH₂SC₂H₅ (S)-isomer | 3-OSO2CH3 | 2-CH₃ | CH₂ | 1 | Q2 | CF₃ | CF₃ | — | |
| 257 | CH(CH₃)CH₂SOC₂H₅ (S)-isomer | 3-OSO2CH3 | 2-CH₃ | CH₂ | 1 | Q2 | CF₃ | CF₃ | — | |
| 258 | CH(CH₃)CH₂SO₂C₂H₅ (S)-isomer | 3-OSO2CH3 | 2-CH₃ | CH₂ | 1 | Q2 | CF₃ | CF₃ | — | |
| 259 | C(CH₃)₂CH₂SCH₃ | 3-I | 2-CH₃ | CH₂ | 1 | Q3 | OCHF₂ | CHF₂ | CF₃ | |
| 260 | C(CH₃)₂CH₂SOCH₃ | 3-I | 2-CH₃ | CH₂ | 1 | Q3 | OCHF₂ | CHF₂ | CF₃ | |
| 261 | C(CH₃)₂CH₂SO₂CH₃ | 3-I | 2-CH₃ | CH₂ | 1 | Q3 | OCHF₂ | CHF₂ | CF₃ | |
| 262 | CH(CH₃)CH₂SCH₃ | 3-I | 2-CH₃ | CH₂ | 1 | Q3 | OCHF₂ | CHF₂ | CF₃ | 82-90 |
| 263 | CH(CH₃)CH₂SOCH₃ | 3-I | 2-CH₃ | CH₂ | 1 | Q3 | OCHF₂ | CHF₂ | CF₃ | |
| 264 | CH(CH₃)CH₂SO₂CH₃ | 3-I | 2-CH₃ | CH₂ | 1 | Q3 | OCHF₂ | CHF₂ | CF₃ | 88-99 |
| 265 | C(CH₃)₂CH₂SCH₃ | 3-I | 2-CH₃ | CH₂ | 1 | Q4 | OCHF₂ | CHF₂ | CF₃ | |
| 266 | C(CH₃)₂CH₂SOCH₃ | 3-I | 2-CH₃ | CH₂ | 1 | Q4 | OCHF₂ | CHF₂ | CF₃ | |
| 267 | C(CH₃)₂CH₂SO₂CH₃ | 3-I | 2-CH₃ | CH₂ | 1 | Q4 | OCHF₂ | CHF₂ | CF₃ | |
| 268 | CH(CH₃)CH₂SCH₃ | 3-I | 2-CH₃ | CH₂ | 1 | Q4 | OCHF₂ | CHF₂ | CF₃ | 149-151 |
| 269 | CH(CH₃)CH₂SOCH₃ | 3-I | 2-CH₃ | CH₂ | 1 | Q4 | OCHF₂ | CHF₂ | CF₃ | |
| 270 | CH(CH₃)CH₂SO₂CH₃ | 3-I | 2-CH₃ | CH₂ | 1 | Q4 | OCHF₂ | CHF₂ | CF₃ | 81-90 |
| 271 | C(CH₃)₂CH₂SCH₃ | 3-I | 2-CH₃ | CH₂ | 1 | Q5 | CF₃ | CF₃ | OH | *** |
| 272 | C(CH₃)₂CH₂SOCH₃ | 3-I | 2-CH₃ | CH₂ | 1 | Q5 | CF₃ | CF₃ | OH | |
| 273 | C(CH₃)₂CH₂SO₂CH₃ | 3-I | 2-CH₃ | CH₂ | 1 | Q5 | CF₃ | CF₃ | OH | |
| 274 | CH(CH₃)CH₂SCH₃ | 3-I | 2-CH₃ | CH₂ | 1 | Q5 | CF₃ | CF₃ | OH | |
| 275 | CH(CH₃)CH₂SOCH₃ | 3-I | 2-CH₃ | CH₂ | 1 | Q5 | CF₃ | CF₃ | OH | |
| 276 | CH(CH₃)CH₂SO₂CH₃ | 3-I | 2-CH₃ | CH₂ | 1 | Q5 | CF₃ | CF₃ | OH | |
| 277 | CH(CH₃)₂ | 3-I | 2-CH₃ | CH₂ | 1 | Q6 | Cl | Cl | H | *** |
| 278 | C(CH₃)₂CH₂SCH₃ | 3-I | 2-CH₃ | CH₂ | 1 | Q6 | H | CF₃ | CF₃ | |
| 279 | C(CH₃)₂CH₂SOCH₃ | 3-I | 2-CH₃ | CH₂ | 1 | Q6 | H | CF₃ | CF₃ | |
| 280 | C(CH₃)₂CH₂SO₂CH₃ | 3-I | 2-CH₃ | CH₂ | 1 | Q6 | H | CF₃ | CF₃ | |
| 281 | CH(CH₃)CH₂SCH₃ (S)-isomer | 3-I | 2-CH₃ | CH₂ | 1 | Q6 | H | CF₃ | CF₃ | 149-158 |
| 282 | CH(CH₃)CH₂SOCH₃ | 3-I | 2-CH₃ | CH₂ | 1 | Q6 | H | CF₃ | CF₃ | |
| 283 | CH(CH₃)CH₂SO₂CH₃ | 3-I | 2-CH₃ | CH₂ | 1 | Q6 | H | CF₃ | CF₃ | |
| 284 | C(CH₃)₂CH₂SCH₃ | 3-I | 2-CH₃ | CH₂ | 1 | Q7 | CH₂CF₃ | CF₃ | — | |
| 285 | C(CH₃)₂CH₂SOCH₃ | 3-I | 2-CH₃ | CH₂ | 1 | Q7 | CH₂CF₃ | CF₃ | — | |
| 286 | C(CH₃)₂CH₂SO₂CH₃ | 3-I | 2-CH₃ | CH₂ | 1 | Q7 | CH₂CF₃ | CF₃ | — | |
| 287 | CH(CH₃)CH₂SCH₃ | 3-I | 2-CH₃ | CH₂ | 1 | Q7 | CH₂CF₃ | CF₃ | — | |
| 288 | CH(CH₃)CH₂SOCH₃ | 3-I | 2-CH₃ | CH₂ | 1 | Q7 | CH₂CF₃ | CF₃ | — | |
| 289 | CH(CH₃)CH₂SO₂CH₃ | 3-I | 2-CH₃ | CH₂ | 1 | Q7 | CH₂CF₃ | CF₃ | — | |
| 290 | C(CH₃)₂CH₂SCH₃ | 3-I | 2-CH₃ | CH₂ | 1 | Q8 | CH₂CF₃ | CF₃ | — | |
| 291 | C(CH₃)₂CH₂SOCH₃ | 3-I | 2-CH₃ | CH₂ | 1 | Q8 | CH₂CF₃ | CF₃ | — | |
| 292 | C(CH₃)₂CH₂SO₂CH₃ | 3-I | 2-CH₃ | CH₂ | 1 | Q8 | CH₂CF₃ | CF₃ | — | |
| 293 | CH(CH₃)CH₂SCH₃ | 3-I | 2-CH₃ | CH₂ | 1 | Q8 | CH₂CF₃ | CF₃ | — | |
| 294 | CH(CH₃)CH₂SOCH₃ | 3-I | 2-CH₃ | CH₂ | 1 | Q8 | CH₂CF₃ | CF₃ | — | |
| 295 | CH(CH₃)CH₂SO₂CH₃ | 3-I | 2-CH₃ | CH₂ | 1 | Q8 | CH₂CF₃ | CF₃ | — | |
| 296 | C(CH₃)₂CH₂SCH₃ | 3-I | 2-CH₃ | CH₂ | 1 | Q9 | CF₃ | CF₃ | — | |
| 297 | C(CH₃)₂CH₂SOCH₃ | 3-I | 2-CH₃ | CH₂ | 1 | Q9 | CF₃ | CF₃ | — | |
| 298 | C(CH₃)₂CH₂SO₂CH₃ | 3-I | 2-CH₃ | CH₂ | 1 | Q9 | CF₃ | CF₃ | — | |
| 299 | CH(CH₃)CH₂SCH₃ (S)-isomer | 3-I | 2-CH₃ | CH₂ | 1 | Q9 | CF₃ | CF₃ | — | 65-79 |
| 300 | CH(CH₃)CH₂SOCH₃ | 3-I | 2-CH₃ | CH₂ | 1 | Q9 | CF₃ | CF₃ | — | |
| 301 | CH(CH₃)CH₂SO₂CH₃ | 3-I | 2-CH₃ | CH₂ | 1 | Q9 | CF₃ | CF₃ | — | |
| 302 | C(CH₃)₂CH₂SCH₃ | 3-I | 2-CH₃ | CH₂ | 1 | Q10 | CF₃ | CF₃ | H | |

TABLE 1-continued

| | | | | | | | | | |
|---|---|---|---|---|---|---|---|---|---|
| 303 | C(CH$_3$)$_2$CH$_2$SOCH$_3$ | 3-I | 2-CH$_3$ | CH$_2$ | 1 | Q10 | CF$_3$ | CF$_3$ | H | |
| 304 | C(CH$_3$)$_2$CH$_2$SO$_2$CH$_3$ | 3-I | 2-CH$_3$ | CH$_2$ | 1 | Q10 | CF$_3$ | CF$_3$ | H | |
| 305 | CH(CH$_3$)CH$_2$SCH$_3$ | 3-I | 2-CH$_3$ | CH$_2$ | 1 | Q10 | CF$_3$ | CF$_3$ | H | |
| 306 | CH(CH$_3$)CH$_2$SOCH$_3$ | 3-I | 2-CH$_3$ | CH$_2$ | 1 | Q10 | CF$_3$ | CF$_3$ | H | |
| 307 | CH(CH$_3$)CH$_2$SO$_2$CH$_3$ | 3-I | 2-CH$_3$ | CH$_2$ | 1 | Q10 | CF$_3$ | CF$_3$ | H | |
| 308 | C(CH$_3$)$_2$CH$_2$SCH$_3$ | 3-I | 2-CH$_3$ | O | 1 | Q10 | CF$_3$ | CF$_3$ | H | 179-181 |
| 309 | C(CH$_3$)$_2$CH$_2$SOCH$_3$ | 3-I | 2-CH$_3$ | O | 1 | Q10 | CF$_3$ | CF$_3$ | H | |
| 310 | C(CH$_3$)$_2$CH$_2$SO$_2$CH$_3$ | 3-I | 2-CH$_3$ | O | 1 | Q10 | CF$_3$ | CF$_3$ | H | 148-153 |
| 311 | CH(CH$_3$)CH$_2$SCH$_3$ | 3-I | 2-CH$_3$ | O | 1 | Q10 | CF$_3$ | CF$_3$ | H | |
| 312 | CH(CH$_3$)CH$_2$SOCH$_3$ | 3-I | 2-CH$_3$ | O | 1 | Q10 | CF$_3$ | CF$_3$ | H | |
| 313 | CH(CH$_3$)CH$_2$SO$_2$CH$_3$ | 3-I | 2-CH$_3$ | O | 1 | Q10 | CF$_3$ | CF$_3$ | H | |
| 314 | C(CH$_3$)$_2$CH$_2$SCH$_3$ | 3-Cl | 2-CH$_3$ | — | 0 | Q1 | CF$_3$ | CF$_3$ | H | |
| 315 | C(CH$_3$)$_2$CH$_2$SOCH$_3$ | 3-Cl | 2-CH$_3$ | — | 0 | Q1 | CF$_3$ | CF$_3$ | H | |
| 316 | C(CH$_3$)$_2$CH$_2$SO$_2$CH$_3$ | 3-Cl | 2-CH$_3$ | — | 0 | Q1 | CF$_3$ | CF$_3$ | H | |
| 317 | CH(CH$_3$)CH$_2$SCH$_3$ | 3-Cl | 2-CH$_3$ | — | 0 | Q1 | CF$_3$ | CF$_3$ | H | |
| 318 | CH(CH$_3$)CH$_2$SCH$_3$ (S)-isomer | 3-Cl | 2-CH$_3$ | — | 0 | Q1 | CF$_3$ | CF$_3$ | H | 209-210 |
| 319 | CH(CH$_3$)CH$_2$SOCH$_3$ | 3-Cl | 2-CH$_3$ | — | 0 | Q1 | CF$_3$ | CF$_3$ | H | |
| 320 | CH(CH$_3$)CH$_2$SOCH$_3$ (S)-isomer | 3-Cl | 2-CH$_3$ | — | 0 | Q1 | CF$_3$ | CF$_3$ | H | |
| 321 | CH(CH$_3$)CH$_2$SO$_2$CH$_3$ | 3-Cl | 2-CH$_3$ | — | 0 | Q1 | CF$_3$ | CF$_3$ | H | |
| 322 | CH(CH$_3$)CH$_2$SO$_2$CH$_3$ (S)-isomer | 3-Cl | 2-CH$_3$ | — | 0 | Q1 | CF$_3$ | CF$_3$ | H | 218-219 |
| 323 | CH(CH$_3$)CH$_2$SC$_2$H$_5$ | 3-Cl | 2-CH$_3$ | — | 0 | Q1 | CF$_3$ | CF$_3$ | H | |
| 324 | CH(CH$_3$)CH$_2$SOC$_2$H$_5$ (S)-isomer | 3-Cl | 2-CH$_3$ | — | 0 | Q1 | CF$_3$ | CF$_3$ | H | |
| 325 | CH(CH$_3$)CH$_2$SO$_2$C$_2$H$_5$ (S)-isomer | 3-Cl | 2-CH$_3$ | — | 0 | Q1 | CF$_3$ | CF$_3$ | H | |
| 326 | C(CH$_3$)$_2$CH$_2$SCH$_3$ | 3-Cl | 2-CH$_3$ | — | 0 | Q1 | H | C$_2$F$_5$ | H | |
| 327 | C(CH$_3$)$_2$CH$_2$SOCH$_3$ | 3-Cl | 2-CH$_3$ | — | 0 | Q1 | H | C$_2$F$_5$ | H | |
| 328 | C(CH$_3$)$_2$CH$_2$SO$_2$CH$_3$ | 3-Cl | 2-CH$_3$ | — | 0 | Q1 | H | C$_2$F$_5$ | H | |
| 329 | CH(CH$_3$)CH$_2$SCH$_3$ | 3-Cl | 2-CH$_3$ | — | 0 | Q1 | H | C$_2$F$_5$ | H | |
| 330 | CH(CH$_3$)CH$_2$SCH$_3$ (S)-isomer | 3-Cl | 2-CH$_3$ | — | 0 | Q1 | H | C$_2$F$_5$ | H | |
| 331 | CH(CH$_3$)CH$_2$SOCH$_3$ | 3-Cl | 2-CH$_3$ | — | 0 | Q1 | H | C$_2$F$_5$ | H | |
| 332 | CH(CH$_3$)CH$_2$SOCH$_3$ (S)-isomer | 3-Cl | 2-CH$_3$ | — | 0 | Q1 | H | C$_2$F$_5$ | H | |
| 333 | CH(CH$_3$)CH$_2$SO$_2$CH$_3$ | 3-Cl | 2-CH$_3$ | — | 0 | Q1 | H | C$_2$F$_5$ | H | |
| 334 | CH(CH$_3$)CH$_2$SO$_2$CH$_3$ (S)-isomer | 3-Cl | 2-CH$_3$ | — | 0 | Q1 | H | C$_2$F$_5$ | H | |
| 335 | CH(CH$_3$)CH$_2$SC$_2$H$_5$ (S)-isomer | 3-Cl | 2-CH$_3$ | — | 0 | Q1 | H | C$_2$F$_5$ | H | |
| 336 | CH(CH$_3$)CH$_2$SOC$_2$H$_5$ (S)-isomer | 3-Cl | 2-CH$_3$ | — | 0 | Q1 | H | C$_2$F$_5$ | H | |
| 337 | CH(CH$_3$)CH$_2$SO$_2$C$_2$H$_5$ (S)-isomer | 3-Cl | 2-CH$_3$ | — | 0 | Q1 | H | C$_2$F$_5$ | H | |
| 338 | C(CH$_3$)$_2$CH$_2$SCH$_3$ | 3-Cl | 2-CH$_3$ | — | 0 | Q1 | C$_2$F$_5$ | H | H | |
| 339 | C(CH$_3$)$_2$CH$_2$SOCH$_3$ | 3-Cl | 2-CH$_3$ | — | 0 | Q1 | C$_2$F$_5$ | H | H | |
| 340 | C(CH$_3$)$_2$CH$_2$SO$_2$CH$_3$ | 3-Cl | 2-CH$_3$ | — | 0 | Q1 | C$_2$F$_5$ | H | H | |
| 341 | CH(CH$_3$)CH$_2$SCH$_3$ | 3-Cl | 2-CH$_3$ | — | 0 | Q1 | C$_2$F$_5$ | H | H | |
| 342 | CH(CH$_3$)CH$_2$SCH$_3$ (S)-isomer | 3-Cl | 2-CH$_3$ | — | 0 | Q1 | C$_2$F$_5$ | H | H | |
| 343 | CH(CH$_3$)CH$_2$SOCH$_3$ | 3-Cl | 2-CH$_3$ | — | 0 | Q1 | C$_2$F$_5$ | H | H | |
| 344 | CH(CH$_3$)CH$_2$SOCH$_3$ (S)-isomer | 3-Cl | 2-CH$_3$ | — | 0 | Q1 | C$_2$F$_5$ | H | H | |
| 345 | CH(CH$_3$)CH$_2$SO$_2$CH$_3$ | 3-Cl | 2-CH$_3$ | — | 0 | Q1 | C$_2$F$_5$ | H | H | |
| 346 | CH(CH$_3$)CH$_2$SO$_2$CH$_3$ (S)-isomer | 3-Cl | 2-CH$_3$ | — | 0 | Q1 | C$_2$F$_5$ | H | H | |
| 347 | CH(CH$_3$)CH$_2$SC$_2$H$_5$ (S)-isomer | 3-Cl | 2-CH$_3$ | — | 0 | Q1 | C$_2$F$_5$ | H | H | |
| 348 | CH(CH$_3$)CH$_2$SOC$_2$H$_5$ (S)-isomer | 3-Cl | 2-CH$_3$ | — | 0 | Q1 | C$_2$F$_5$ | H | H | |
| 349 | CH(CH$_3$)CH$_2$SO$_2$C$_2$H$_5$ (S)-isomer | 3-Cl | 2-CH$_3$ | — | 0 | Q1 | C$_2$F$_5$ | H | H | |
| 350 | C(CH$_3$)$_2$CH$_2$SCH$_3$ | 3-Cl | 2-CH$_3$ | — | 0 | Q1 | H | H | C$_2$F$_5$ | |
| 351 | C(CH$_3$)$_2$CH$_2$SOCH$_3$ | 3-Cl | 2-CH$_3$ | — | 0 | Q1 | H | H | C$_2$F$_5$ | |
| 352 | C(CH$_3$)$_2$CH$_2$SO$_2$CH$_3$ | 3-Cl | 2-CH$_3$ | — | 0 | Q1 | H | H | C$_2$F$_5$ | |
| 353 | CH(CH$_3$)CH$_2$SCH$_3$ | 3-Cl | 2-CH$_3$ | — | 0 | Q1 | H | H | C$_2$F$_5$ | |
| 354 | CH(CH$_3$)CH$_2$SCH$_3$ (S)-isomer | 3-Cl | 2-CH$_3$ | — | 0 | Q1 | H | H | C$_2$F$_5$ | |
| 355 | CH(CH$_3$)CH$_2$SOCH$_3$ | 3-Cl | 2-CH$_3$ | — | 0 | Q1 | H | H | C$_2$F$_5$ | |
| 356 | CH(CH$_3$)CH$_2$SOCH$_3$ (S)-isomer | 3-Cl | 2-CH$_3$ | — | 0 | Q1 | H | H | C$_2$F$_5$ | |
| 357 | CH(CH$_3$)CH$_2$SO$_2$CH$_3$ | 3-Cl | 2-CH$_3$ | — | 0 | Q1 | H | H | C$_2$F$_5$ | |
| 358 | CH(CH$_3$)CH$_2$SO$_2$CH$_3$ (S)-isomer | 3-Cl | 2-CH$_3$ | — | 0 | Q1 | H | H | C$_2$F$_5$ | |
| 359 | CH(CH$_3$)CH$_2$SC$_2$H$_5$ (S)-isomer | 3-Cl | 2-CH$_3$ | — | 0 | Q1 | H | H | C$_2$F$_5$ | |

TABLE 1-continued

| | | | | | | | | | |
|---|---|---|---|---|---|---|---|---|---|
| 360 | CH(CH$_3$)CH$_2$SOC$_2$H$_5$ (S)-isomer | 3-Cl | 2-CH$_3$ | — | 0 | Q1 | H | H | C$_2$F$_5$ |
| 361 | CH(CH$_3$)CH$_2$SO$_2$C$_2$H$_5$ (S)-isomer | 3-Cl | 2-CH$_3$ | — | 0 | Q1 | H | H | C$_2$F$_5$ |
| 362 | C(CH$_3$)$_2$CH$_2$SCH$_3$ | 3-Br | 2-CH$_3$ | — | 0 | Q1 | CF$_3$ | CF$_3$ | H |
| 363 | C(CH$_3$)$_2$CH$_2$SOCH$_3$ | 3-Br | 2-CH$_3$ | — | 0 | Q1 | CF$_3$ | CF$_3$ | H |
| 364 | C(CH$_3$)$_2$CH$_2$SO$_2$CH$_3$ | 3-Br | 2-CH$_3$ | — | 0 | Q1 | CF$_3$ | CF$_3$ | H |
| 365 | CH(CH$_3$)CH$_2$SCH$_3$ | 3-Br | 2-CH$_3$ | — | 0 | Q1 | CF$_3$ | CF$_3$ | H |
| 366 | CH(CH$_3$)CH$_2$SCH$_3$ (S)-isomer | 3-Br | 2-CH$_3$ | — | 0 | Q1 | CF$_3$ | CF$_3$ | H |
| 367 | CH(CH$_3$)CH$_2$SOCH$_3$ | 3-Br | 2-CH$_3$ | — | 0 | Q1 | CF$_3$ | CF$_3$ | H |
| 368 | CH(CH$_3$)CH$_2$SOCH$_3$ (S)-isomer | 3-Br | 2-CH$_3$ | — | 0 | Q1 | CF$_3$ | CF$_3$ | H |
| 369 | CH(CH$_3$)CH$_2$SO$_2$CH$_3$ | 3-Br | 2-CH$_3$ | — | 0 | Q1 | CF$_3$ | CF$_3$ | H |
| 370 | CH(CH$_3$)CH$_2$SO$_2$CH$_3$ (S)-isomer | 3-Br | 2-CH$_3$ | — | 0 | Q1 | CF$_3$ | CF$_3$ | H |
| 371 | CH(CH$_3$)CH$_2$SC$_2$H$_5$ (S)-isomer | 3-Br | 2-CH$_3$ | — | 0 | Q1 | CF$_3$ | CF$_3$ | H |
| 372 | CH(CH$_3$)CH$_2$SOC$_2$H$_5$ (S)-isomer | 3-Br | 2-CH$_3$ | — | 0 | Q1 | CF$_3$ | CF$_3$ | H |
| 373 | CH(CH$_3$)CH$_2$SO$_2$C$_2$H$_5$ (S)-isomer | 3-Br | 2-CH$_3$ | — | 0 | Q1 | CF$_3$ | CF$_3$ | H |
| 374 | C(CH$_3$)$_2$CH$_2$SCH$_3$ | 3-Br | 2-CH$_3$ | — | 0 | Q1 | H | C$_2$F$_5$ | H |
| 375 | C(CH$_3$)$_2$CH$_2$SOCH$_3$ | 3-Br | 2-CH$_3$ | — | 0 | Q1 | H | C$_2$F$_5$ | H |
| 376 | C(CH$_3$)$_2$CH$_2$SO$_2$CH$_3$ | 3-Br | 2-CH$_3$ | — | 0 | Q1 | H | C$_2$F$_5$ | H |
| 377 | CH(CH$_3$)CH$_2$SCH$_3$ | 3-Br | 2-CH$_3$ | — | 0 | Q1 | H | C$_2$F$_5$ | H |
| 378 | CH(CH$_3$)CH$_2$SCH$_3$ (S)-isomer | 3-Br | 2-CH$_3$ | — | 0 | Q1 | H | C$_2$F$_5$ | H |
| 379 | CH(CH$_3$)CH$_2$SOCH$_3$ | 3-Br | 2-CH$_3$ | — | 0 | Q1 | H | C$_2$F$_5$ | H |
| 380 | CH(CH$_3$)CH$_2$SOCH$_3$ (S)-isomer | 3-Br | 2-CH$_3$ | — | 0 | Q1 | H | C$_2$F$_5$ | H |
| 381 | CH(CH$_3$)CH$_2$SO$_2$CH$_3$ | 3-Br | 2-CH$_3$ | — | 0 | Q1 | H | C$_2$F$_5$ | H |
| 382 | CH(CH$_3$)CH$_2$SO$_2$CH$_3$ (S)-isomer | 3-Br | 2-CH$_3$ | — | 0 | Q1 | H | C$_2$F$_5$ | H |
| 383 | CH(CH$_3$)CH$_2$SC$_2$H$_5$ (S)-isomer | 3-Br | 2-CH$_3$ | — | 0 | Q1 | H | C$_2$F$_5$ | H |
| 384 | CH(CH$_3$)CH$_2$SOC$_2$H$_5$ (S)-isomer | 3-Br | 2-CH$_3$ | — | 0 | Q1 | H | C$_2$F$_5$ | H |
| 385 | CH(CH$_3$)CH$_2$SO$_2$C$_2$H$_5$ (S)-isomer | 3-Br | 2-CH$_3$ | — | 0 | Q1 | H | C$_2$F$_5$ | H |
| 386 | C(CH$_3$)$_2$CH$_2$SCH$_3$ | 3-Br | 2-CH$_3$ | — | 0 | Q1 | C$_2$F$_5$ | H | H |
| 387 | C(CH$_3$)$_2$CH$_2$SOCH$_3$ | 3-Br | 2-CH$_3$ | — | 0 | Q1 | C$_2$F$_5$ | H | H |
| 388 | C(CH$_3$)$_2$CH$_2$SO$_2$CH$_3$ | 3-Br | 2-CH$_3$ | — | 0 | Q1 | C$_2$F$_5$ | H | H |
| 389 | CH(CH$_3$)CH$_2$SCH$_3$ | 3-Br | 2-CH$_3$ | — | 0 | Q1 | C$_2$F$_5$ | H | H |
| 390 | CH(CH$_3$)CH$_2$SCH$_3$ (S)-isomer | 3-Br | 2-CH$_3$ | — | 0 | Q1 | C$_2$F$_5$ | H | H |
| 391 | CH(CH$_3$)CH$_2$SOCH$_3$ | 3-Br | 2-CH$_3$ | — | 0 | Q1 | C$_2$F$_5$ | H | H |
| 392 | CH(CH$_3$)CH$_2$SOCH$_3$ (S)-isomer | 3-Br | 2-CH$_3$ | — | 0 | Q1 | C$_2$F$_5$ | H | H |
| 393 | CH(CH$_3$)CH$_2$SO$_2$CH$_3$ | 3-Br | 2-CH$_3$ | — | 0 | Q1 | C$_2$F$_5$ | H | H |
| 394 | CH(CH$_3$)CH$_2$SO$_2$CH$_3$ (S)-isomer | 3-Br | 2-CH$_3$ | — | 0 | Q1 | C$_2$F$_5$ | H | H |
| 395 | CH(CH$_3$)CH$_2$SC$_2$H$_5$ (S)-isomer | 3-Br | 2-CH$_3$ | — | 0 | Q1 | C$_2$F$_5$ | H | H |
| 396 | CH(CH$_3$)CH$_2$SOC$_2$H$_5$ (S)-isomer | 3-Br | 2-CH$_3$ | — | 0 | Q1 | C$_2$F$_5$ | H | H |
| 397 | CH(CH$_3$)CH$_2$SO$_2$C$_2$H$_5$ (S)-isomer | 3-Br | 2-CH$_3$ | — | 0 | Q1 | C$_2$F$_5$ | H | H |
| 398 | C(CH$_3$)$_2$CH$_2$SCH$_3$ | 3-Br | 2-CH$_3$ | — | 0 | Q1 | H | H | C$_2$F$_5$ |
| 399 | C(CH$_3$)$_2$CH$_2$SOCH$_3$ | 3-Br | 2-CH$_3$ | — | 0 | Q1 | H | H | C$_2$F$_5$ |
| 400 | C(CH$_3$)$_2$CH$_2$SO$_2$CH$_3$ | 3-Br | 2-CH$_3$ | — | 0 | Q1 | H | H | C$_2$F$_5$ |
| 401 | CH(CH$_3$)CH$_2$SCH$_3$ | 3-Br | 2-CH$_3$ | — | 0 | Q1 | H | H | C$_2$F$_5$ |
| 402 | CH(CH$_3$)CH$_2$SCH$_3$ (S)-isomer | 3-Br | 2-CH$_3$ | — | 0 | Q1 | H | H | C$_2$F$_5$ |
| 403 | CH(CH$_3$)CH$_2$SOCH$_3$ | 3-Br | 2-CH$_3$ | — | 0 | Q1 | H | H | C$_2$F$_5$ |
| 404 | CH(CH$_3$)CH$_2$SOCH$_3$ (S)-isomer | 3-Br | 2-CH$_3$ | — | 0 | Q1 | H | H | C$_2$F$_5$ |
| 405 | CH(CH$_3$)CH$_2$SO$_2$CH$_3$ | 3-Br | 2-CH$_3$ | — | 0 | Q1 | H | H | C$_2$F$_5$ |
| 406 | CH(CH$_3$)CH$_2$SO$_2$CH$_3$ (S)-isomer | 3-Br | 2-CH$_3$ | — | 0 | Q1 | H | H | C$_2$F$_5$ |
| 407 | CH(CH$_3$)CH$_2$SC$_2$H$_5$ (S)-isomer | 3-Br | 2-CH$_3$ | — | 0 | Q1 | H | H | C$_2$F$_5$ |
| 408 | CH(CH$_3$)CH$_2$SOC$_2$H$_5$ (S)-isomer | 3-Br | 2-CH$_3$ | — | 0 | Q1 | H | H | C$_2$F$_5$ |
| 409 | CH(CH$_3$)CH$_2$SO$_2$C$_2$H$_5$ (S)-isomer | 3-Br | 2-CH$_3$ | — | 0 | Q1 | H | H | C$_2$F$_5$ |
| 410 | C(CH$_3$)$_2$CH$_2$SCH$_3$ | 3-I | 2-CH$_3$ | — | 0 | Q1 | CF$_3$ | CF$_3$ | H |
| 411 | C(CH$_3$)$_2$CH$_2$SOCH$_3$ | 3-I | 2-CH$_3$ | — | 0 | Q1 | CF$_3$ | CF$_3$ | H |
| 412 | C(CH$_3$)$_2$CH$_2$SO$_2$CH$_3$ | 3-I | 2-CH$_3$ | — | 0 | Q1 | CF$_3$ | CF$_3$ | H |

TABLE 1-continued

| | | | | | | | | | | |
|---|---|---|---|---|---|---|---|---|---|---|
| 413 | CH(CH₃)CH₂SCH₃ | 3-I | 2-CH₃ | — | 0 | Q1 | CF₃ | CF₃ | H | 201 |
| 414 | CH(CH₃)CH₂SCH₃ (S)-isomer | 3-I | 2-CH₃ | — | 0 | Q1 | CF₃ | CF₃ | H | 192-206 |
| 415 | CH(CH₃)CH₂SOCH₃ | 3-I | 2-CH₃ | — | 0 | Q1 | CF₃ | CF₃ | H | |
| 416 | CH(CH₃)CH₂SOCH₃ (S)-isomer | 3-I | 2-CH₃ | — | 0 | Q1 | CF₃ | CF₃ | H | |
| 417 | CH(CH₃)CH₂SO₂CH₃ | 3-I | 2-CH₃ | — | 0 | Q1 | CF₃ | CF₃ | H | *** |
| 418 | CH(CH₃)CH₂SO₂CH₃ (S)-isomer | 3-I | 2-CH₃ | — | 0 | Q1 | CF₃ | CF₃ | H | |
| 419 | CH(CH₃)CH₂SC₂H₅ (S)-isomer | 3-I | 2-CH₃ | — | 0 | Q1 | CF₃ | CF₃ | H | |
| 420 | CH(CH₃)CH₂SOC₂H₅ (S)-isomer | 3-I | 2-CH₃ | — | 0 | Q1 | CF₃ | CF₃ | H | |
| 421 | CH(CH₃)CH₂SO₂C₂H₅ (S)-isomer | 3-I | 2-CH₃ | — | 0 | Q1 | CF₃ | CF₃ | H | |
| 422 | C(CH₃)₂CH₂SCH₃ | 3-I | 2-CH₃ | — | 0 | Q1 | H | C₂F₅ | H | *** |
| 423 | C(CH₃)₂CH₂SOCH₃ | 3-I | 2-CH₃ | — | 0 | Q1 | H | C₂F₅ | H | |
| 424 | C(CH₃)₂CH₂SO₂CH₃ | 3-I | 2-CH₃ | — | 0 | Q1 | H | C₂F₅ | H | |
| 425 | CH(CH₃)CH₂SCH₃ | 3-I | 2-CH₃ | — | 0 | Q1 | H | C₂F₅ | H | |
| 426 | CH(CH₃)CH₂SCH₃ (S)-isomer | 3-I | 2-CH₃ | — | 0 | Q1 | H | C₂F₅ | H | |
| 427 | CH(CH₃)CH₂SOCH₃ | 3-I | 2-CH₃ | — | 0 | Q1 | H | C₂F₅ | H | |
| 428 | CH(CH₃)CH₂SOCH₃ (S)-isomer | 3-I | 2-CH₃ | — | 0 | Q1 | H | C₂F₅ | H | |
| 429 | CH(CH₃)CH₂SO₂CH₃ | 3-I | 2-CH₃ | — | 0 | Q1 | H | C₂F₅ | H | |
| 430 | CH(CH₃)CH₂SO₂CH₃ (S)-isomer | 3-I | 2-CH₃ | — | 0 | Q1 | H | C₂F₅ | H | |
| 431 | CH(CH₃)CH₂SC₂H₅ (S)-isomer | 3-I | 2-CH₃ | — | 0 | Q1 | H | C₂F₅ | H | |
| 432 | CH(CH₃)CH₂SOC₂H₅ (S)-isomer | 3-I | 2-CH₃ | — | 0 | Q1 | H | C₂F₅ | H | |
| 433 | CH(CH₃)CH₂SO₂C₂H₅ (S)-isomer | 3-I | 2-CH₃ | — | 0 | Q1 | H | C₂F₅ | H | |
| 434 | C(CH₃)₂CH₂SCH₃ | 3-I | 2-CH₃ | — | 0 | Q1 | C₂F₅ | H | H | *** |
| 435 | C(CH₃)₂CH₂SOCH₃ | 3-I | 2-CH₃ | — | 0 | Q1 | C₂F₅ | H | H | |
| 436 | C(CH₃)₂CH₂SO₂CH₃ | 3-I | 2-CH₃ | — | 0 | Q1 | C₂H₅ | H | H | |
| 437 | CH(CH₃)CH₂SCH₃ | 3-I | 2-CH₃ | — | 0 | Q1 | C₂F₅ | H | H | |
| 438 | CH(CH₃)CH₂SCH₃ (S)-isomer | 3-I | 2-CH₃ | — | 0 | Q1 | C₂F₅ | H | H | |
| 439 | CH(CH₃)CH₂SOCH₃ | 3-I | 2-CH₃ | — | 0 | Q1 | C₂F₅ | H | H | |
| 440 | CH(CH₃)CH₂SOCH₃ (S)-isomer | 3-I | 2-CH₃ | — | 0 | Q1 | C₂F₅ | H | H | |
| 441 | CH(CH₃)CH₂SO₂CH₃ | 3-I | 2-CH₃ | — | 0 | Q1 | C₂F₅ | H | H | |
| 442 | CH(CH₃)CH₂SO₂CH₃ (S)-isomer | 3-I | 2-CH₃ | — | 0 | Q1 | C₂F₅ | H | H | |
| 443 | CH(CH₃)CH₂SC₂H₅ (S)-isomer | 3-I | 2-CH₃ | — | 0 | Q1 | C₂F₅ | H | H | |
| 444 | CH(CH₃)CH₂SOC₂H₅ (S)-isomer | 3-I | 2-CH₃ | — | 0 | Q1 | C₂F₅ | H | H | |
| 445 | CH(CH₃)CH₂SO₂C₂H₅ (S)-isomer | 3-I | 2-CH₃ | — | 0 | Q1 | C₂F₅ | H | H | |
| 446 | C(CH₃)₂CH₂SCH₃ | 3-I | 2-CH₃ | — | 0 | Q1 | H | H | C₂F₅ | 155-157 |
| 447 | C(CH₃)₂CH₂SOCH₃ | 3-I | 2-CH₃ | — | 0 | Q1 | H | H | C₂F₅ | |
| 448 | C(CH₃)₂CH₂SO₂CH₃ | 3-I | 2-CH₃ | — | 0 | Q1 | H | H | C₂F₅ | 162-168 |
| 449 | CH(CH₃)CH₂SCH₃ | 3-I | 2-CH₃ | — | 0 | Q1 | H | H | C₂F₅ | |
| 450 | CH(CH₃)CH₂SCH₃ (S)-isomer | 3-I | 2-CH₃ | — | 0 | Q1 | H | H | C₂F₅ | |
| 451 | CH(CH₃)CH₂SOCH₃ | 3-I | 2-CH₃ | — | 0 | Q1 | H | H | C₂F₅ | |
| 452 | CH(CH₃)CH₂SOCH₃ (S)-isomer | 3-I | 2-CH₃ | — | 0 | Q1 | H | H | C₂F₅ | |
| 453 | CH(CH₃)CH₂SO₂CH₃ | 3-I | 2-CH₃ | — | 0 | Q1 | H | H | C₂F₅ | |
| 454 | CH(CH₃)CH₂SO₂CH₃ (S)-isomer | 3-I | 2-CH₃ | — | 0 | Q1 | H | H | C₂F₅ | |
| 455 | CH(CH₃)CH₂SC₂H₅ (S)-isomer | 3-I | 2-CH₃ | — | 0 | Q1 | H | H | C₂F₅ | |
| 456 | CH(CH₃)CH₂SOC₂H₅ (S)-isomer | 3-I | 2-CH₃ | — | 0 | Q1 | H | H | C₂F₅ | |
| 457 | CH(CH₃)CH₂SO₂C₂H₅ (S)-isomer | 3-I | 2-CH₃ | — | 0 | Q1 | H | H | C₂F₅ | |
| 458 | C(CH₃)₂CH₂SCH₃ | 3-I | 2-CH₃ | — | 0 | Q1 | CH₃ | CF₃ | H | |
| 459 | C(CH₃)₂CH₂SOCH₃ | 3-I | 2-CH₃ | — | 0 | Q1 | CH₃ | CF₃ | H | |
| 460 | C(CH₃)₂CH₂SO₂CH₃ | 3-I | 2-CH₃ | — | 0 | Q1 | CH₃ | CF₃ | H | |
| 461 | CH(CH₃)CH₂SCH₃ | 3-I | 2-CH₃ | — | 0 | Q1 | CH₃ | CF₃ | H | 178-180 |
| 462 | CH(CH₃)CH₂SOCH₃ | 3-I | 2-CH₃ | — | 0 | Q1 | CH₃ | CF₃ | H | |
| 463 | CH(CH₃)CH₂SO₂CH₃ | 3-I | 2-CH₃ | — | 0 | Q1 | CH₃ | CF₃ | H | 101-112 |
| 464 | C(CH₃)₂CH₂SCH₃ | 3-I | 2-CH₃ | — | 0 | Q1 | CF₃ | CH₃ | H | |
| 465 | C(CH₃)₂CH₂SOCH₃ | 3-I | 2-CH₃ | — | 0 | Q1 | CF₃ | CH₃ | H | |
| 466 | C(CH₃)₂CH₂SO₂CH₃ | 3-I | 2-CH₃ | — | 0 | Q1 | CF₃ | CH₃ | H | |
| 467 | CH(CH₃)CH₂SCH₃ | 3-I | 2-CH₃ | — | 0 | Q1 | CF₃ | CH₃ | H | 187-192 |

TABLE 1-continued

| | | | | | | | | | | |
|---|---|---|---|---|---|---|---|---|---|---|
| 468 | CH(CH₃)CH₂SOCH₃ | 3-I | 2-CH₃ | — | 0 | Q1 | CF₃ | CH₃ | H | |
| 469 | CH(CH₃)CH₂SO₂CH₃ | 3-I | 2-CH₃ | — | 0 | Q1 | CF₃ | CH₃ | H | 108-116 |
| 470 | C(CH₃)₂CH₂SCH₃ | 3-I | 2-CH₃ | — | 0 | Q1 | C₂F₅ | CF₃ | H | |
| 471 | C(CH₃)₂CH₂SOCH₃ | 3-I | 2-CH₃ | — | 0 | Q1 | C₂F₅ | CF₃ | H | |
| 472 | C(CH₃)₂CH₂SO₂CH₃ | 3-I | 2-CH₃ | — | 0 | Q1 | C₂F₅ | CF₃ | H | |
| 473 | CH(CH₃)CH₂SCH₃ | 3-I | 2-CH₃ | — | 0 | Q1 | C₂F₅ | CF₃ | H | 109-111 |
| 474 | CH(CH₃)CH₂SOCH₃ | 3-I | 2-CH₃ | — | 0 | Q1 | C₂F₅ | CF₃ | H | |
| 475 | CH(CH₃)CH₂SO₂CH₃ | 3-I | 2-CH₃ | — | 0 | Q1 | C₂F₅ | CF₃ | H | 103-115 |
| 476 | C(CH₃)₂CH₂SCH₃ | 3-I | 2-CH₃ | — | 0 | Q1 | CF₃ | H | Br | |
| 477 | C(CH₃)₂CH₂SOCH₃ | 3-I | 2-CH₃ | — | 0 | Q1 | CF₃ | H | Br | |
| 478 | C(CH₃)₂CH₂SO₂CH₃ | 3-I | 2-CH₃ | — | 0 | Q1 | CF₃ | H | Br | |
| 479 | CH(CH₃)CH₂SCH₃ | 3-I | 2-CH₃ | — | 0 | Q1 | CF₃ | H | Br | 235-237 |
| 480 | CH(CH₃)CH₂SOCH₃ | 3-I | 2-CH₃ | — | 0 | Q1 | CF₃ | H | Br | |
| 481 | CH(CH₃)CH₂SO₂CH₃ | 3-I | 2-CH₃ | — | 0 | Q1 | CF₃ | H | Br | 201-209 |
| 482 | C(CH₃)₂CH₂SCH₃ | 3-I | 2-CH₃ | — | 0 | Q1 | CF₃ | H | H | |
| 483 | C(CH₃)₂CH₂SOCH₃ | 3-I | 2-CH₃ | — | 0 | Q1 | CF₃ | H | H | |
| 484 | C(CH₃)₂CH₂SO₂CH₃ | 3-I | 2-CH₃ | — | 0 | Q1 | CF₃ | H | H | |
| 485 | CH(CH₃)CH₂SCH₃ | 3-I | 2-CH₃ | — | 0 | Q1 | CF₃ | H | H | 173-174 |
| 486 | CH(CH₃)CH₂SOCH₃ | 3-I | 2-CH₃ | — | 0 | Q1 | CF₃ | H | H | |
| 487 | CH(CH₃)CH₂SO₂CH₃ | 3-I | 2-CH₃ | — | 0 | Q1 | CF₃ | H | H | 107-109 |
| 488 | C(CH₃)₂CH₂SCH₃ | 3-OSO2CH3 | 2-CH₃ | — | 0 | Q1 | CF₃ | CF₃ | H | |
| 489 | C(CH₃)₂CH₂SOCH₃ | 3-OSO2CH3 | 2-CH₃ | — | 0 | Q1 | CF₃ | CF₃ | H | |
| 490 | C(CH₃)₂CH₂SO₂CH₃ | 3-OSO2CH3 | 2-CH₃ | — | 0 | Q1 | CF₃ | CF₃ | H | |
| 491 | CH(CH₃)CH₂SCH₃ | 3-OSO2CH3 | 2-CH₃ | — | 0 | Q1 | CF₃ | CF₃ | H | |
| 492 | CH(CH₃)CH₂SCH₃ (S)-isomer | 3-OSO2CH3 | 2-CH₃ | — | 0 | Q1 | CF₃ | CF₃ | H | 175-177 |
| 493 | CH(CH₃)CH₂SOCH₃ | 3-OSO2CH3 | 2-CH₃ | — | 0 | Q1 | CF₃ | CF₃ | H | |
| 494 | CH(CH₃)CH₂SOCH₃ (S)-isomer | 3-OSO2CH3 | 2-CH₃ | — | 0 | Q1 | CF₃ | CF₃ | H | |
| 495 | CH(CH₃)CH₂SO₂CH₃ | 3-OSO2CH3 | 2-CH₃ | — | 0 | Q1 | CF₃ | CF₃ | H | |
| 496 | CH(CH₃)CH₂SO₂CH₃ (S)-isomer | 3-OSO2CH3 | 2-CH₃ | — | 0 | Q1 | CF₃ | CF₃ | H | |
| 497 | C(CH₃)₂CH₂SCH₃ | 3-I | 2-CH₃ | — | 0 | Q5 | C₂F₅ | CF₃ | OH | |
| 498 | C(CH₃)₂CH₂SOCH₃ | 3-I | 2-CH₃ | — | 0 | Q5 | C₂F₅ | CF₃ | OH | |
| 499 | C(CH₃)₂CH₂SO₂CH₃ | 3-I | 2-CH₃ | — | 0 | Q5 | C₂F₅ | CF₃ | OH | |
| 500 | CH(CH₃)CH₂SCH₃ | 3-I | 2-CH₃ | — | 0 | Q5 | C₂F₅ | CF₃ | OH | 101-106 |
| 501 | CH(CH₃)CH₂SOCH₃ | 3-I | 2-CH₃ | — | 0 | Q5 | C₂F₅ | CF₃ | OH | |
| 502 | CH(CH₃)CH₂SO₂CH₃ | 3-I | 2-CH₃ | — | 0 | Q5 | C₂F₅ | CF₃ | OH | |
| 503 | C(CH₃)₂CH₂SCH₃ | 3-I | 2-CH₃ | — | 0 | Q11 | CH₂CF₃ | H | CF₃ | |
| 504 | C(CH₃)₂CH₂SOCH₃ | 3-I | 2-CH₃ | — | 0 | Q11 | CH₂CF₃ | H | CF₃ | |
| 505 | C(CH₃)₂CH₂SO₂CH₃ | 3-I | 2-CH₃ | — | 0 | Q11 | CH₂CF₃ | H | CF₃ | |
| 506 | CH(CH₃)CH₂SCH₃ | 3-I | 2-CH₃ | — | 0 | Q11 | CH₂CF₃ | H | CF₃ | 106-116 |
| 507 | CH(CH₃)CH₂SOCH₃ | 3-I | 2-CH₃ | — | 0 | Q11 | CH₂CF₃ | H | CF₃ | |
| 508 | CH(CH₃)CH₂SO₂CH₃ | 3-I | 2-CH₃ | — | 0 | Q11 | CH₂CF₃ | H | CF₃ | 127-139 |
| 509 | C(CH₃)₂CH₂SCH₃ | 3-I | 2-CH₃ | — | 0 | Q11 | CHF₂ | H | CF₃ | |
| 510 | C(CH₃)₂CH₂SOCH₃ | 3-I | 2-CH₃ | — | 0 | Q11 | CHF₂ | H | CF₃ | |
| 511 | C(CH₃)₂CH₂SO₂CH₃ | 3-I | 2-CH₃ | — | 0 | Q11 | CHF₂ | H | CF₃ | |
| 512 | CH(CH₃)CH₂SCH₃ | 3-I | 2-CH₃ | — | 0 | Q11 | CHF₂ | H | CF₃ | 138-144 |
| 513 | CH(CH₃)CH₂SOCH₃ | 3-I | 2-CH₃ | — | 0 | Q11 | CHF₂ | H | CF₃ | |
| 514 | CH(CH₃)CH₂SO₂CH₃ | 3-I | 2-CH₃ | — | 0 | Q11 | CHF₂ | H | CF₃ | |
| 515 | C(CH₃)₂CH₂SCH₃ | 3-I | 2-CH₃ | — | 0 | Q12 | CHF₂ | H | OCHF₂ | |
| 516 | C(CH₃)₂CH₂SOCH₃ | 3-I | 2-CH₃ | — | 0 | Q12 | CHF₂ | H | OCHF₂ | |
| 517 | C(CH₃)₂CH₂SO₂CH₃ | 3-I | 2-CH₃ | — | 0 | Q12 | CHF₂ | H | OCHF₂ | |
| 518 | CH(CH₃)CH₂SCH₃ | 3-I | 2-CH₃ | — | 0 | Q12 | CHF₂ | H | OCHF₂ | 83-89 |
| 519 | CH(CH₃)CH₂SOCH₃ | 3-I | 2-CH₃ | — | 0 | Q12 | CHF₂ | H | OCHF₂ | |
| 520 | CH(CH₃)CH₂SO₂CH₃ | 3-I | 2-CH₃ | — | 0 | Q12 | CHF₂ | H | OCHF₂ | 92-97 |
| 521 | CH(CH₃)CH₂SCH₃ | 3-I | 2-CH₃ | CH₂ | 1 | Q1 | H | C₂F₅ | H | *** |
| 522 | CH(CH₃)CH₂SO₂CH₃ | 3-I | 2-CH₃ | CH₂ | 1 | Q1 | H | C₂F₅ | H | *** |
| 523 | C(CH₃)₂CH₂SCH₃ | 3-I | 2-CH₃ | CH₂ | 1 | Q1 | H | C₂F₅ | H | *** |
| 524 | C(CH₃)₂CH₂SO₂CH₃ | 3-I | 2-CH₃ | CH₂ | 1 | Q1 | H | C₂F₅ | H | |
| 525 | CH(CH₃)CH₂SCH₃ | 3-Cl | 2-CH₃ | CH₂ | 1 | Q1 | C₂F₅ | H | H | |
| 526 | C(CH₃)₂CH₂SCH₃ | 3-Cl | 2-CH₃ | CH₂ | 1 | Q1 | C₂F₅ | H | H | |
| 527 | CH(CH₃)CH₂SCH₃ | 3-I | 2-CH₃ | CH₂ | 1 | Q1 | C₂F₅ | H | H | |
| 528 | CH(CH₃)CH₂SO₂CH₃ | 3-I | 2-CH₃ | CH₂ | 1 | Q1 | C₂F₅ | H | H | |
| 529 | C(CH₃)₂CH₂SCH₃ | 3-I | 2-CH₃ | CH₂ | 1 | Q1 | C₂F₅ | H | H | *** |
| 530 | C(CH₃)₂CH₂SO₂CH₃ | 3-I | 2-CH₃ | CH₂ | 1 | Q1 | C₂F₅ | H | H | *** |
| 531 | CH(CH₃)CH₂SCH₃ | 3-Cl | 2-CH₃ | CH₂ | 1 | Q1 | C₃F₇-n | H | H | |
| 532 | CH(CH₃)CH₂SCH₃ (S)-isomer | 3-Cl | 2-CH₃ | CH₂ | 1 | Q1 | C₃F₇-n | H | H | |
| 533 | C(CH₃)₂CH₂SCH₃ | 3-Cl | 2-CH₃ | CH₂ | 1 | Q1 | C₃F₇-n | H | H | |
| 534 | CH(CH₃)CH₂SCH₃ | 3-I | 2-CH₃ | CH₂ | 1 | Q1 | C₃F₇-n | H | H | *** |
| 535 | CH(CH₃)CH₂SCH₃ (S)-isomer | 3-I | 2-CH₃ | CH₂ | 1 | Q1 | C₃F₇-n | H | H | |
| 536 | CH(CH₃)CH₂SO₂CH₃ | 3-I | 2-CH₃ | CH₂ | 1 | Q1 | C₃F₇-n | H | H | *** |
| 537 | C(CH₃)₂CH₂SCH₃ | 3-I | 2-CH₃ | CH₂ | 1 | Q1 | C₃F₇-n | H | H | *** |
| 538 | C(CH₃)₂CH₂SO₂CH₃ | 3-I | 2-CH₃ | CH₂ | 1 | Q1 | C₃F₇-n | H | H | *** |
| 539 | CH(CH₃)CH₂SCH(CH₃)₂ (S)-isomer | 3-I | 2-CH₃ | CH₂ | 1 | Q1 | CF₃ | CF₃ | H | 81-83 |

TABLE 1-continued

| | | | | | | | | | |
|---|---|---|---|---|---|---|---|---|---|
| 540 | CH(CH$_3$)CH$_2$SOCH(CH$_3$)$_2$ (S)-isomer | 3-I | 2-CH$_3$ | CH$_2$ | 1 | Q1 | CF$_3$ | CF$_3$ | H | |
| 541 | CH(CH$_3$)CH$_2$SO$_2$CH(CH$_3$)$_2$ (S)-isomer | 3-I | 2-CH$_3$ | CH$_2$ | 1 | Q1 | CF$_3$ | CF$_3$ | H | |
| 542 | CH(CH$_3$)CH$_2$SCH(CH$_3$)$_2$ (S)-isomer | 3-Cl | 2-CH$_3$ | CH$_2$ | 1 | Q1 | CF$_3$ | CF$_3$ | H | |
| 543 | CH(CH$_3$)CH$_2$SCH$_3$ (S)-isomer | 3-NO$_2$ | 2-CH$_3$ | CH$_2$ | 1 | Q1 | CF$_3$ | CF$_3$ | H | 161-171 |
| 544 | CH(CH$_3$)CH$_2$SOCH$_3$ (S)-isomer | 3-NO$_2$ | 2-CH$_3$ | CH$_2$ | 1 | Q1 | CF$_3$ | CF$_3$ | H | 227-229 |
| 545 | CH(CH$_3$)CH$_2$SO$_2$CH$_3$ (S)-isomer | 3-NO$_2$ | 2-CH$_3$ | CH$_2$ | 1 | Q1 | CF$_3$ | CF$_3$ | H | 215-216 |
| 546 | CH(CH$_3$)CH$_2$SCH$_3$ (S)-isomer | 3-NO$_2$ | 2-CH$_3$ | CH$_2$ | 1 | Q2 | CF$_3$ | CF$_3$ | — | 175-179 |
| 547 | CH(CH$_3$)CH$_2$SOCH$_3$ (S)-isomer | 3-NO$_2$ | 2-CH$_3$ | CH$_2$ | 1 | Q2 | CF$_3$ | CF$_3$ | — | 225-228 |
| 548 | CH(CH$_3$)CH$_2$SO$_2$CH$_3$ (S)-isomer | 3-NO$_2$ | 2-CH$_3$ | CH$_2$ | 1 | Q2 | CF$_3$ | CF$_3$ | — | 206-208 |
| 549 | CH(CH$_3$)CH$_2$SCH$_3$ (S)-isomer | 3-F | 2-CH$_3$ | CH$_2$ | 1 | Q1 | CF$_3$ | CF$_3$ | H | 66-68 |
| 550 | CH(CH$_3$)$_2$ | 3-SCH$_3$ | 2-CH$_3$ | CH$_2$ | 1 | Q1 | CF$_3$ | CF$_3$ | H | *** |
| 551 | CH(CH$_3$)CH$_2$SCH$_3$ (S)-isomer | 3-SCH$_3$ | 2-CH$_3$ | CH$_2$ | 1 | Q1 | CF$_3$ | CF$_3$ | H | |
| 552 | CH(CH$_3$)CH$_2$SCH$_3$ (S)-isomer | 3-SO$_2$CH$_3$ | 2-CH$_3$ | CH$_2$ | 1 | Q1 | CF$_3$ | CF$_3$ | H | *** |
| 553 | CH(CH$_3$)CH$_2$SCH$_3$ (S)-isomer | 3-SCH$_2$CH$_3$ | 2-CH$_3$ | CH$_2$ | 1 | Q1 | CF$_3$ | CF$_3$ | H | *** |
| 554 | CH(CH$_3$)CH$_2$SCH$_3$ (S)-isomer | 3-I | 2-CH$_3$ | CH$_2$ | 1 | Q1 | CF$_3$ | CF$_3$ | I | *** |
| 555 | CH(CH$_3$)CH$_2$SCH$_3$ | 3-I | 2-CH$_3$ | CH(CH$_3$) | 1 | Q1 | CF$_3$ | H | H | |
| 556 | CH(CH$_3$)CH$_2$SCH$_3$ | 3-I | 2-CH$_3$ | CH(CH$_3$) | 1 | Q1 | CF$_3$ | H | H | 78-89 |
| 557 | CH(CH$_3$)CH$_2$SO$_2$CH$_3$ (S)-isomer | 3-I | 2-CH$_3$ | CH(CH$_3$) | 1 | Q1 | CF$_3$ | H | H | 150-152 |
| 558 | C(CH$_3$)$_2$CH$_2$SCH$_3$ | 3-I | 2-CH$_3$ | CH(CH$_3$) | 1 | Q1 | CF$_3$ | H | H | 79-86 |
| 559 | CH(CH$_3$)CH$_2$SCH$_3$ (S)-isomer | 3-Cl | 2-CH$_3$ | CH(CH$_3$) | 1 | Q1 | CF$_3$ | CF$_3$ | H | 80-91 |
| 560 | CH(CH$_3$)CH$_2$SOCH$_3$ (S)-isomer | 3-Cl | 2-CH$_3$ | CH(CH$_3$) | 1 | Q1 | CF$_3$ | CF$_3$ | H | |
| 561 | CH(CH$_3$)CH$_2$SO$_2$CH$_3$ (S)-isomer | 3-Cl | 2-CH$_3$ | CH(CH$_3$) | 1 | Q1 | CF$_3$ | CF$_3$ | H | 103-105 |
| 562 | CH(CH$_3$)CH$_2$SCH$_3$ (S)-isomer | 3-I | 2-CH$_3$ | CH(CH$_3$) | 1 | Q1 | CF$_3$ | CF$_3$ | H | 84-89 |
| 563 | CH(CH$_3$)CH$_2$SOCH$_3$ (S)-isomer | 3-I | 2-CH$_3$ | CH(CH$_3$) | 1 | Q1 | CF$_3$ | CF$_3$ | H | 177-179 |
| 564 | CH(CH$_3$)CH$_2$SO$_2$CH$_3$ (S)-isomer | 3-I | 2-CH$_3$ | CH(CH$_3$) | 1 | Q1 | CF$_3$ | CF$_3$ | H | 101-105 |
| 565 | C(CH$_3$)$_2$CH$_2$SCH$_3$ | 3-I | 2-CH$_3$ | CH(CH$_3$) | 1 | Q1 | CF$_3$ | CF$_3$ | H | 98-106 |
| 566 | C(CH$_3$)$_2$CH$_2$SOCH$_3$ | 3-I | 2-CH$_3$ | CH(CH$_3$) | 1 | Q1 | CF$_3$ | CF$_3$ | H | 132-136 |
| 567 | C(CH$_3$)$_2$CH$_2$SO$_2$CH$_3$ | 3-I | 2-CH$_3$ | CH(CH$_3$) | 1 | Q1 | CF$_3$ | CF$_3$ | H | 173-174 |
| 568 | CH(CH$_3$)CH$_2$SCH$_3$ (S)-isomer | 3-Cl | 2-CH$_3$ | CH(CH$_3$) | 1 | Q2 | CF$_3$ | CF$_3$ | — | 87-92 |
| 569 | CH(CH$_3$)CH$_2$SOCH$_3$ (S)-isomer | 3-Cl | 2-CH$_3$ | CH(CH$_3$) | 1 | Q2 | CF$_3$ | CF$_3$ | — | *** |
| 570 | CH(CH$_3$)CH$_2$SO$_2$CH$_3$ (S)-isomer | 3-Cl | 2-CH$_3$ | CH(CH$_3$) | 1 | Q2 | CF$_3$ | CF$_3$ | — | 91-95 |
| 571 | CH(CH$_3$)CH$_2$SCH$_3$ (S)-isomer | 3-I | 2-CH$_3$ | CH(CH$_3$) | 1 | Q2 | CF$_3$ | CF$_3$ | — | 98-105 |
| 572 | CH(CH$_3$)CH$_2$SOCH$_3$ (S)-isomer | 3-I | 2-CH$_3$ | CH(CH$_3$) | 1 | Q2 | CF$_3$ | CF$_3$ | — | 98-105 |
| 573 | CH(CH$_3$)CH$_2$SO$_2$CH$_3$ (S)-isomer | 3-I | 2-CH$_3$ | CH(CH$_3$) | 1 | Q2 | CF$_3$ | CF$_3$ | — | 103-106 |
| 574 | CH(CH$_3$)CH$_2$SCH$_3$ (S)-isomer | 3-Cl | 2-CH$_3$ | CH(CH$_3$) | 1 | Q2 | CF$_3$ | C$_2$F$_5$ | — | *** |
| 575 | CH(CH$_3$)CH$_2$SOCH$_3$ (S)-isomer | 3-Cl | 2-CH$_3$ | CH(CH$_3$) | 1 | Q2 | CF$_3$ | C$_2$F$_5$ | — | |
| 576 | CH(CH$_3$)CH$_2$SO$_2$CH$_3$ (S)-isomer | 3-Cl | 2-CH$_3$ | CH(CH$_3$) | 1 | Q2 | CF$_3$ | C$_2$F$_5$ | — | |
| 577 | CH(CH$_3$)CH$_2$SCH$_3$ (S)-isomer | 3-I | 2-CH$_3$ | CH(CH$_3$) | 1 | Q2 | CF$_3$ | C$_2$F$_5$ | — | |
| 578 | CH(CH$_3$)CH$_2$SCH$_3$ (S)-isomer | 3-Cl | 2-CH$_3$ | CH(CH$_3$) | 1 | Q2 | C$_2$F$_5$ | CF$_3$ | — | 83-85 |
| 579 | CH(CH$_3$)CH$_2$SOCH$_3$ (S)-isomer | 3-Cl | 2-CH$_3$ | CH(CH$_3$) | 1 | Q2 | C$_2$F$_5$ | CF$_3$ | — | 121-124 |
| 580 | CH(CH$_3$)CH$_2$SO$_2$CH$_3$ (S)-isomer | 3-Cl | 2-CH$_3$ | CH(CH$_3$) | 1 | Q2 | C$_2$F$_5$ | CF$_3$ | — | 87-94 |
| 581 | CH(CH$_3$)CH$_2$SCH$_3$ (S)-isomer | 3-Cl | 2-CH$_3$ | CH(CH$_3$) | 1 | Q2 | C$_2$F$_5$ | C$_2$F$_5$ | — | |
| 582 | CH(CH$_3$)CH$_2$SCH$_3$ (S)-isomer | 3-I | 2-CH$_3$ | CH(CH$_3$) | 1 | Q2 | C$_2$F$_5$ | C$_2$F$_5$ | — | |

TABLE 1-continued

| | | | | | | | | | | |
|---|---|---|---|---|---|---|---|---|---|---|
| 583 | CH(CH₃)CH₂SCH₃ (S)-isomer | 3-Cl | 2-CH₃ | S | 1 | Q10 | CF₃ | CF₃ | H | |
| 584 | CH(CH₃)CH₂SCH₃ (S)-isomer | 3-I | 2-CH₃ | S | 1 | Q10 | CF₃ | CF₃ | H | |
| 585 | CH(CH₃)CH₂SCH₃ (S)-isomer | 3-Cl | 2-CH₃ | S | 1 | Q10 | C₂F₅ | C₂F₅ | H | |
| 586 | CH(CH₃)CH₂SCH₃ (S)-isomer | 3-I | 2-CH₃ | S | 1 | Q10 | C₂F₅ | C₂F₅ | H | |
| 587 | CH(CH₃)CH₂SCH₃ (S)-isomer | 3-Cl | 2-CH₃ | S | 1 | Q13 | CF₃ | CF₃ | — | |
| 588 | CH(CH₃)CH₂SCH₃ (S)-isomer | 3-I | 2-CH₃ | S | 1 | Q13 | CF₃ | CF₃ | — | 223-225 |
| 589 | CH(CH₃)CH₂SCH₃ (S)-isomer | 3-I | 2-CH₃ | SO₂ | 1 | Q13 | CF₃ | CF₃ | — | |
| 590 | C(CH₃)₂CH₂SCH₃ | 3-Cl | 2-CH₃ | CH₂ | 1 | Q7 | CH₃ | CHF₂ | — | |
| 591 | C(CH₃)₂CH₂SO₂CH₃ | 3-Cl | 2-CH₃ | CH₂ | 1 | Q7 | CH₃ | CHF₂ | — | |
| 592 | C(CH₃)₂CH₂SCH₃ | 3-I | 2-CH₃ | CH₂ | 1 | Q7 | CH₃ | CHF₂ | — | 99-101 |
| 593 | C(CH₃)₂CH₂SO₂CH₃ | 3-I | 2-CH₃ | CH₂ | 1 | Q7 | CH₃ | CHF₂ | — | 83-94 |
| 594 | CH(CH₃)CH₂SCH₃ (S)-isomer | 3-I | 2-CH₃ | CH₂ | 1 | Q14 | H | COCF₃ | H | *** |
| 595 | CH(CH₃)CH₂SCH₃ (S)-isomer | 3-I | 2-CH₃ | CH₂ | 1 | Q14 | I | COCF₃ | H | *** |
| 596 | CH(CH₃)CH₂SCH₃ (S)-isomer | 3-I | 2-CH₃ | CH₂ | 1 | Q14 | C₂F₅ | COCF₃ | H | *** |
| 597 | C(CH₃)₂CH₂SCH₃ | 3-I | 2-CH₃ | — | 0 | Q1 | H | H | C₃F₇-n | |
| 598 | C(CH₃)₂CH₂SCH₃ | 3-I | 2-CH₃ | — | 0 | Q1 | H | H | C₄F₉-n | |
| 599 | C(CH₃)₂CH₂SCH₃ | 3-I | 2-CH₃ | — | 0 | Q1 | H | H | C₆F₁₃-n | |
| 600 | C(CH₃)₂CH₂SCH₃ | 3-I | 2-CH₃ | — | 0 | Q1 | H | H | C₈F₁₇-n | |
| 601 | CH(CH₃)CH₂SCH₃ (S)-isomer | 3-Cl | 2-CH₃ | CH₂ | 1 | Q1 | H | H | C₃F₇-n | |
| 602 | CH(CH₃)CH₂SCH₃ (S)-isomer | 3-Cl | 2-CH₃ | CH₂ | 1 | Q1 | H | H | C₄F₉-n | 69-72 |
| 603 | CH(CH₃)CH₂SCH₃ (S)-isomer | 3-Cl | 2-CH₃ | CH₂ | 1 | Q1 | H | H | C₆F₁₃-n | |
| 604 | CH(CH₃)CH₂SCH₃ (S)-isomer | 3-Cl | 2-CH₃ | CH₂ | 1 | Q1 | H | H | C₈F₁₇-n | |
| 605 | C(CH₃)₂CH₂SCH₃ | 3-I | 2-CH₃ | CH₂ | 1 | Q1 | CH₃ | H | C₃F₇-n | |
| 606 | C(CH₃)₂CH₂SCH₃ | 3-I | 2-CH₃ | CH₂ | 1 | Q1 | CH₃ | H | C₄F₉-n | |
| 607 | C(CH₃)₂CH₂SCH₃ | 3-I | 2-CH₃ | CH₂ | 1 | Q1 | CH₃ | H | C₆F₁₃-n | |
| 608 | CH(CH₃)CH₂SCH₃ (S)-isomer | 3-Cl | 2-CH₃ | CH₂ | 1 | Q1 | C₂F₅ | CF₃ | H | 74-78 |
| 609 | CH(CH₃)CH₂SOCH₃ (S)-isomer | 3-Cl | 2-CH₃ | CH₂ | 1 | Q1 | C₂F₅ | CF₃ | H | 176-177 |
| 610 | CH(CH₃)CH₂SO₂CH₃ (S)-isomer | 3-Cl | 2-CH₃ | CH₂ | 1 | Q1 | C₂F₅ | CF₃ | H | 81-87 |
| 611 | CH(CH₃)CH₂SCH₃ (S)-isomer | 3-I | 2-CH₃ | CH₂ | 1 | Q1 | C₂F₅ | CF₃ | H | |
| 612 | CH(CH₃)CH₂SOCH₃ (S)-isomer | 3-I | 2-CH₃ | CH₂ | 1 | Q1 | C₂F₅ | CF₃ | H | |
| 613 | CH(CH₃)CH₂SO₂CH₃ (S)-isomer | 3-I | 2-CH₃ | CH₂ | 1 | Q1 | C₂F₅ | CF₃ | H | |
| 614 | CH(CH₃)CH₂SCH₃ (S)-isomer | 3-Cl | 2-CH₃ | CH₂ | 1 | Q1 | C₃F₇-n | CF₃ | H | |
| 615 | CH(CH₃)CH₂SOCH₃ (S)-isomer | 3-Cl | 2-CH₃ | CH₂ | 1 | Q1 | C₃F₇-n | CF₃ | H | |
| 616 | CH(CH₃)CH₂SO₂CH₃ (S)-isomer | 3-Cl | 2-CH₃ | CH₂ | 1 | Q1 | C₃F₇-n | CF₃ | H | |
| 617 | CH(CH₃)CH₂SCH₃ (S)-isomer | 3-I | 2-CH₃ | CH₂ | 1 | Q1 | C₃F₇-n | CF₃ | H | |
| 618 | CH(CH₃)CH₂SOCH₃ (S)-isomer | 3-I | 2-CH₃ | CH₂ | 1 | Q1 | C₃F₇-n | CF₃ | H | |
| 619 | CH(CH₃)CH₂SO₂CH₃ (S)-isomer | 3-I | 2-CH₃ | CH₂ | 1 | Q1 | C₃F₇-n | CF₃ | H | |
| 620 | C(CH₃)₂CH₂SCH₃ | 3-Cl | 2-CH₃ | CH₂ | 1 | Q1 | C₂F₅ | C₂F₅ | H | |
| 621 | C(CH₃)₂CH₂SOCH₃ | 3-Cl | 2-CH₃ | CH₂ | 1 | Q1 | C₂F₅ | C₂F₅ | H | |
| 622 | C(CH₃)₂CH₂SO₂CH₃ | 3-Cl | 2-CH₃ | CH₂ | 1 | Q1 | C₂F₅ | C₂F₅ | H | |
| 623 | C(CH₃)₂CH₂SCH₃ | 3-I | 2-CH₃ | CH₂ | 1 | Q1 | C₂F₅ | C₂F₅ | H | |
| 624 | C(CH₃)₂CH₂SOCH₃ | 3-I | 2-CH₃ | CH₂ | 1 | Q1 | C₂F₅ | C₂F₅ | H | |
| 625 | C(CH₃)₂CH₂SO₂CH₃ | 3-I | 2-CH₃ | CH₂ | 1 | Q1 | C₂F₅ | C₂F₅ | H | |
| 626 | CH(CH₃)CH₂SCH₃ (S)-isomer | 3-Cl | 2-CH₃ | CH₂ | 1 | Q1 | C₂F₅ | C₂F₅ | H | *** |
| 627 | CH(CH₃)CH₂SOCH₃ (S)-isomer | 3-Cl | 2-CH₃ | CH₂ | 1 | Q1 | C₂F₅ | C₂F₅ | H | |
| 628 | CH(CH₃)CH₂SO₂CH₃ (S)-isomer | 3-Cl | 2-CH₃ | CH₂ | 1 | Q1 | C₂F₅ | C₂F₅ | H | |
| 629 | CH(CH₃)CH₂SCH₃ (S)-isomer | 3-I | 2-CH₃ | CH₂ | 1 | Q1 | C₂F₅ | C₂F₅ | H | |
| 630 | CH(CH₃)CH₂SOCH₃ (S)-isomer | 3-I | 2-CH₃ | CH₂ | 1 | Q1 | C₂F₅ | C₂F₅ | H | |

TABLE 1-continued

| | | | | | | | | | | |
|---|---|---|---|---|---|---|---|---|---|---|
| 631 | CH(CH$_3$)CH$_2$SO$_2$CH$_3$ (S)-isomer | 3-I | 2-CH$_3$ | CH$_2$ | 1 | Q1 | C$_2$F$_5$ | C$_2$F$_5$ | H | |
| 632 | CH(CH$_3$)CH$_2$SCH$_3$ (S)-isomer | 3-I | 2-CH$_3$ | CH$_2$ | 1 | Q1 | CF$_3$ | H | Cl | *** |
| 633 | CH(CH$_3$)CH$_2$SCH$_3$ (S)-isomer | 3-Cl | 2-CH$_3$ | CH$_2$ | 1 | Q1 | C$_2$F$_5$ | H | Cl | *** |
| 634 | CH(CH$_3$)CH$_2$SCH$_3$ (S)-isomer | 3-Cl | 2-CH$_3$ | CH$_2$ | 1 | Q1 | C$_3$F$_7$-n | H | Cl | *** |
| 635 | CH(CH$_3$)CH$_2$SCH$_3$ (S)-isomer | 3-Cl | 2-CH$_3$ | CH$_2$ | 1 | Q1 | CF$_3$ | H | Br | *** |
| 636 | CH(CH$_3$)CH$_2$SCH$_3$ (S)-isomer | 3-Cl | 2-CH$_3$ | CH$_2$ | 1 | Q1 | CF$_3$ | H | I | *** |
| 637 | CH(CH$_3$)CH$_2$SCH$_3$ (S)-isomer | 3-Cl | 2-CH$_3$ | CH$_2$ | 1 | Q1 | CF$_3$ | H | C$_2$F$_5$ | 73-78 |
| 638 | CH(CH$_3$)CH$_2$SOCH$_3$ (S)-isomer | 3-Cl | 2-CH$_3$ | CH$_2$ | 1 | Q1 | CF$_3$ | H | C$_2$F$_5$ | 81-84 |
| 639 | CH(CH$_3$)CH$_2$SO$_2$CH$_3$ (S)-isomer | 3-Cl | 2-CH$_3$ | CH$_2$ | 1 | Q1 | CF$_3$ | H | C$_2$F$_5$ | 87-90 |
| 640 | CH(CH$_3$)CH$_2$SCH$_3$ (S)-isomer | 3-I | 2-CH$_3$ | CH$_2$ | 1 | Q1 | CF$_3$ | H | C$_2$F$_5$ | *** |
| 641 | CH(CH$_3$)CH$_2$SOCH$_3$ (S)-isomer | 3-I | 2-CH$_3$ | CH$_2$ | 1 | Q1 | CF$_3$ | H | C$_2$F$_5$ | 164-166 |
| 642 | CH(CH$_3$)CH$_2$SO$_2$CH$_3$ (S)-isomer | 3-I | 2-CH$_3$ | CH$_2$ | 1 | Q1 | CF$_3$ | H | C$_2$F$_5$ | 75-85 |
| 643 | CH(CH$_3$)CH$_2$SCH$_3$ (S)-isomer | 3-Cl | 2-CH$_3$ | CH$_2$ | 1 | Q1 | CF$_3$ | H | C$_3$F$_7$-n | 73-75 |
| 644 | CH(CH$_3$)CH$_2$SCH$_3$ (S)-isomer | 3-I | 2-CH$_3$ | CH$_2$ | 1 | Q1 | CF$_3$ | H | C$_3$F$_7$-n | 86-88 |
| 645 | CH(CH$_3$)CH$_2$SCH$_3$ (S)-isomer | 3-Cl | 2-CH$_3$ | CH$_2$ | 1 | Q1 | CF$_3$ | H | C$_4$F$_9$-n | 79-82 |
| 646 | CH(CH$_3$)CH$_2$SOCH$_3$ (S)-isomer | 3-Cl | 2-CH$_3$ | CH$_2$ | 1 | Q1 | CF$_3$ | H | C$_4$F$_9$-n | 73-76 |
| 647 | CH(CH$_3$)CH$_2$SO$_2$CH$_3$ (S)-isomer | 3-Cl | 2-CH$_3$ | CH$_2$ | 1 | Q1 | CF$_3$ | H | C$_4$F$_9$-n | 83-88 |
| 648 | CH(CH$_3$)CH$_2$SCH$_3$ (S)-isomer | 3-I | 2-CH$_3$ | CH$_2$ | 1 | Q1 | CF$_3$ | H | C$_4$F$_9$-n | 88-92 |
| 649 | CH(CH$_3$)CH$_2$SOCH$_3$ (S)-isomer | 3-I | 2-CH$_3$ | CH$_2$ | 1 | Q1 | CF$_3$ | H | C$_4$F$_9$-n | 84-90 |
| 650 | CH(CH$_3$)CH$_2$SO$_2$CH$_3$ (S)-isomer | 3-I | 2-CH$_3$ | CH$_2$ | 1 | Q1 | CF$_3$ | H | C$_4$F$_9$-n | 75-78 |
| 651 | CH(CH$_3$)CH$_2$SCH$_3$ (S)-isomer | 3-Cl | 2-CH$_3$ | CH$_2$ | 1 | Q1 | C$_2$F$_5$ | H | C$_2$F$_5$ | *** |
| 652 | CH(CH$_3$)CH$_2$SOCH$_3$ (S)-isomer | 3-Cl | 2-CH$_3$ | CH$_2$ | 1 | Q1 | C$_2$F$_5$ | H | C$_2$F$_5$ | 124-125 |
| 653 | CH(CH$_3$)CH$_2$SO$_2$CH$_3$ (S)-isomer | 3-Cl | 2-CH$_3$ | CH$_2$ | 1 | Q1 | C$_2$F$_5$ | H | C$_2$F$_5$ | 88-91 |
| 654 | CH(CH$_3$)CH$_2$SCH$_3$ (S)-isomer | 3-I | 2-CH$_3$ | CH$_2$ | 1 | Q1 | C$_2$F$_5$ | H | C$_2$F$_5$ | *** |
| 655 | CH(CH$_3$)CH$_2$SOCH$_3$ (S)-isomer | 3-I | 2-CH$_3$ | CH$_2$ | 1 | Q1 | C$_2$F$_5$ | H | C$_2$F$_5$ | 87-92 |
| 656 | CH(CH$_3$)CH$_2$SO$_2$CH$_3$ (S)-isomer | 3-I | 2-CH$_3$ | CH$_2$ | 1 | Q1 | C$_2$F$_5$ | H | C$_2$F$_5$ | 100-107 |
| 657 | CH(CH$_3$)CH$_2$SCH$_3$ (S)-isomer | 3-Cl | 2-CH$_3$ | CH$_2$ | 1 | Q1 | C$_2$F$_5$ | H | C$_3$F$_7$-n | 64-65 |
| 658 | CH(CH$_3$)CH$_2$SOCH$_3$ (S)-isomer | 3-Cl | 2-CH$_3$ | CH$_2$ | 1 | Q1 | C$_2$F$_5$ | H | C$_3$F$_7$-n | *** |
| 659 | CH(CH$_3$)CH$_2$SO$_2$CH$_3$ (S)-isomer | 3-Cl | 2-CH$_3$ | CH$_2$ | 1 | Q1 | C$_2$F$_5$ | H | C$_3$F$_7$-n | 78-81 |
| 660 | CH(CH$_3$)CH$_2$SCH$_3$ (S)-isomer | 3-I | 2-CH$_3$ | CH$_2$ | 1 | Q1 | C$_2$F$_5$ | H | C$_3$F$_7$-n | *** |
| 661 | CH(CH$_3$)CH$_2$SOCH$_3$ (S)-isomer | 3-I | 2-CH$_3$ | CH$_2$ | 1 | Q1 | C$_2$F$_5$ | H | C$_3$F$_7$-n | 83-85 |
| 662 | CH(CH$_3$)CH$_2$SO$_2$CH$_3$ (S)-isomer | 3-I | 2-CH$_3$ | CH$_2$ | 1 | Q1 | C$_2$F$_5$ | H | C$_3$F$_7$-n | 92-96 |
| 663 | CH(CH$_3$)CH$_2$SCH$_3$ (S)-isomer | 3-Cl | 2-CH$_3$ | CH$_2$ | 1 | Q1 | C$_2$F$_5$ | H | C$_4$F$_9$-n | 72-74 |
| 664 | CH(CH$_3$)CH$_2$SCH$_3$ (S)-isomer | 3-I | 2-CH$_3$ | CH$_2$ | 1 | Q1 | C$_2$F$_5$ | H | C$_4$F$_9$-n | 84-88 |
| 665 | CH(CH$_3$)CH$_2$SCH$_3$ (S)-isomer | 3-Cl | 2-CH$_3$ | CH$_2$ | 1 | Q1 | C$_3$F$_7$-n | H | C$_2$F$_5$ | 78-85 |
| 666 | CH(CH$_3$)CH$_2$SCH$_3$ (S)-isomer | 3-I | 2-CH$_3$ | CH$_2$ | 1 | Q1 | C$_3$F$_7$-n | H | C$_2$F$_5$ | 78-85 |
| 667 | CH(CH$_3$)CH$_2$SCH$_3$ (S)-isomer | 3-Cl | 2-CH$_3$ | CH$_2$ | 1 | Q1 | C$_3$F$_7$-n | H | C$_3$F$_7$-n | 70-74 |
| 668 | CH(CH$_3$)CH$_2$SOCH$_3$ (S)-isomer | 3-Cl | 2-CH$_3$ | CH$_2$ | 1 | Q1 | C$_3$F$_7$-n | H | C$_3$F$_7$-n | 73-77 |
| 669 | CH(CH$_3$)CH$_2$SO$_2$CH$_3$ (S)-isomer | 3-Cl | 2-CH$_3$ | CH$_2$ | 1 | Q1 | C$_3$F$_7$-n | H | C$_3$F$_7$-n | 77-82 |

TABLE 1-continued

| | | | | | | | | | | |
|---|---|---|---|---|---|---|---|---|---|---|
| 670 | CH(CH₃)CH₂SCH₃ (S)-isomer | 3-I | 2-CH₃ | CH₂ | 1 | Q1 | C₃F₇-n | H | C₃F₇-n | 86-90 |
| 671 | CH(CH₃)CH₂SOCH₃ (S)-isomer | 3-I | 2-CH₃ | CH₂ | 1 | Q1 | C₃F₇-n | H | C₃F₇-n | 81-84 |
| 672 | CH(CH₃)CH₂SO₂CH₃ (S)-isomer | 3-I | 2-CH₃ | CH₂ | 1 | Q1 | C₃F₇-n | H | C₃F₇-n | 147-148 |
| 673 | CH(CH₃)CH₂SCH₃ (S)-isomer | 3-Cl | 2-CH₃ | CH₂ | 1 | Q1 | H | C₂F₅ | CF₃ | |
| 674 | CH(CH₃)CH₂SCH₃ (S)-isomer | 3-I | 2-CH₃ | CH₂ | 1 | Q1 | H | C₂F₅ | CF₃ | |
| 675 | CH(CH₃)CH₂SCH₃ (S)-isomer | 3-Cl | 2-CH₃ | CH₂ | 1 | Q1 | H | C₂F₅ | C₂F₅ | *** |
| 676 | CH(CH₃)CH₂SCH₃ (S)-isomer | 3-I | 2-CH₃ | CH₂ | 1 | Q1 | H | C₂F₅ | C₂F₅ | |
| 677 | C(CH₃)₂CH₂SCH₃ | 3-Cl | 2-CH₃ | CH₂ | 1 | Q2 | C₂F₅ | C₂F₅ | — | |
| 678 | C(CH₃)₂CH₂SOCH₃ | 3-Cl | 2-CH₃ | CH₂ | 1 | Q2 | C₂F₅ | C₂F₅ | — | |
| 679 | C(CH₃)₂CH₂SO₂CH₃ | 3-Cl | 2-CH₃ | CH₂ | 1 | Q2 | C₂F₅ | C₂F₅ | — | |
| 680 | CH(CH₃)CH₂SCH₃ | 3-Cl | 2-CH₃ | CH₂ | 1 | Q2 | C₂F₅ | C₂F₅ | — | |
| 681 | CH(CH₃)CH₂SCH₃ (S)-isomer | 3-Cl | 2-CH₃ | CH₂ | 1 | Q2 | C₂F₅ | C₂F₅ | — | *** |
| 682 | CH(CH₃)CH₂SOCH₃ | 3-Cl | 2-CH₃ | CH₂ | 1 | Q2 | C₂F₅ | C₂F₅ | — | |
| 683 | CH(CH₃)CH₂SOCH₃ (S)-isomer | 3-Cl | 2-CH₃ | CH₂ | 1 | Q2 | C₂F₅ | C₂F₅ | — | 162-164 |
| 684 | CH(CH₃)CH₂SO₂CH₃ | 3-Cl | 2-CH₃ | CH₂ | 1 | Q2 | C₂F₅ | C₂F₅ | — | |
| 685 | CH(CH₃)CH₂SO₂CH₃ (S)-isomer | 3-Cl | 2-CH₃ | CH₂ | 1 | Q2 | C₂F₅ | C₂F₅ | — | 103-106 |
| 686 | CH(CH₃)CH₂SC₂H₅ (S)-isomer | 3-Cl | 2-CH₃ | CH₂ | 1 | Q2 | C₂F₅ | C₂F₅ | — | |
| 687 | CH(CH₃)CH₂SOC₂H₅ (S)-isomer | 3-Cl | 2-CH₃ | CH₂ | 1 | Q2 | C₂F₅ | C₂F₅ | — | |
| 688 | CH(CH₃)CH₂SO₂C₂H₅ (S)-isomer | 3-Cl | 2-CH₃ | CH₂ | 1 | Q2 | C₂F₅ | C₂F₅ | — | |
| 689 | C(CH₃)₂CH₂SCH₃ | 3-Br | 2-CH₃ | CH₂ | 1 | Q2 | C₂F₅ | C₂F₅ | — | |
| 690 | C(CH₃)₂CH₂SOCH₃ | 3-Br | 2-CH₃ | CH₂ | 1 | Q2 | C₂F₅ | C₂F₅ | — | |
| 691 | C(CH₃)₂CH₂SO₂CH₃ | 3-Br | 2-CH₃ | CH₂ | 1 | Q2 | C₂F₅ | C₂F₅ | — | |
| 692 | CH(CH₃)CH₂SCH₃ | 3-Br | 2-CH₃ | CH₂ | 1 | Q2 | C₂F₅ | C₂F₅ | — | |
| 693 | CH(CH₃)CH₂SCH₃ (S)-isomer | 3-Br | 2-CH₃ | CH₂ | 1 | Q2 | C₂F₅ | C₂F₅ | — | |
| 694 | CH(CH₃)CH₂SOCH₃ | 3-Br | 2-CH₃ | CH₂ | 1 | Q2 | C₂F₅ | C₂F₅ | — | |
| 695 | CH(CH₃)CH₂SOCH₃ (S)-isomer | 3-Br | 2-CH₃ | CH₂ | 1 | Q2 | C₂F₅ | C₂F₅ | — | |
| 696 | CH(CH₃)CH₂SO₂CH₃ | 3-Br | 2-CH₃ | CH₂ | 1 | Q2 | C₂F₅ | C₂F₅ | — | |
| 697 | CH(CH₃)CH₂SO₂CH₃ (S)-isomer | 3-Br | 2-CH₃ | HC₂ | 1 | Q2 | C₂F₅ | C₂F₅ | — | |
| 698 | CH(CH₃)CH₂SC₂H₅ (S)-isomer | 3-Br | 2-CH₃ | CH₂ | 1 | Q2 | C₂F₅ | C₂F₅ | — | |
| 699 | CH(CH₃)CH₂SOC₂H₅ (S)-isomer | 3-Br | 2-CH₃ | CH₂ | 1 | Q2 | C₂F₅ | C₂F₅ | — | |
| 700 | CH(CH₃)CH₂SO₂C₂H₅ (S)-isomer | 3-Br | 2-CH₃ | CH₂ | 1 | Q2 | C₂F₅ | C₂F₅ | — | |
| 701 | C(CH₃)₂CH₂SCH₃ | 3-I | 2-CH₃ | CH₂ | 1 | Q2 | C₂F₅ | C₂F₅ | — | |
| 702 | C(CH₃)₂CH₂SOCH₃ | 3-I | 2-CH₃ | CH₂ | 1 | Q2 | C₂F₅ | C₂F₅ | — | |
| 703 | C(CH₃)₂CH₂SO₂CH₃ | 3-I | 2-CH₃ | CH₂ | 1 | Q2 | C₂F₅ | C₂F₅ | — | |
| 704 | CH(CH₃)CH₂SCH₃ | 3-I | 2-CH₃ | CH₂ | 1 | Q2 | C₂F₅ | C₂F₅ | — | |
| 705 | CH(CH₃)CH₂SCH₃ (S)-isomer | 3-I | 2-CH₃ | CH₂ | 1 | Q2 | C₂F₅ | C₂F₅ | — | |
| 706 | CH(CH₃)CH₂SOCH₃ | 3-I | 2-CH₃ | CH₂ | 1 | Q2 | C₂F₅ | C₂F₅ | — | |
| 707 | CH(CH₃)CH₂SOCH₃ (S)-isomer | 3-I | 2-CH₃ | CH₂ | 1 | Q2 | C₂F₅ | C₂F₅ | — | |
| 708 | CH(CH₃)CH₂SO₂CH₃ | 3-I | 2-CH₃ | CH₂ | 1 | Q2 | C₂F₅ | C₂F₅ | — | |
| 709 | CH(CH₃)CH₂SO₂CH₃ (S)-isomer | 3-I | 2-CH₃ | CH₂ | 1 | Q2 | C₂F₅ | C₂F₅ | — | |
| 710 | CH(CH₃)CH₂SC₂H₅ (S)-isomer | 3-I | 2-CH₃ | CH₂ | 1 | Q2 | C₂F₅ | C₂F₅ | — | |
| 711 | CH(CH₃)CH₂SOC₂H₅ (S)-isomer | 3-I | 2-CH₃ | CH₂ | 1 | Q2 | C₂F₅ | C₂F₅ | — | |
| 712 | CH(CH₃)CH₂SO₂C₂H₅ (S)-isomer | 3-I | 2-CH₃ | CH₂ | 1 | Q2 | C₂F₅ | C₂F₅ | — | |
| 713 | C(CH₃)₂CH₂SCH₃ | 3-Cl | 2-CH₃ | CH₂ | 1 | Q2 | C₃F₇-n | CF₃ | — | |
| 714 | CH(CH₃)CH₂SCH₃ | 3-Cl | 2-CH₃ | CH₂ | 1 | Q2 | C₃F₇-n | CF₃ | — | *** |
| 715 | CH(CH₃)CH₂SCH₃ (S)-isomer | 3-I | 2-CH₃ | CH₂ | 1 | Q2 | C₃F₇-n | CF₃ | — | |
| 716 | CH(CH₃)CH₂SCH₃ | 3-Cl | 2-CH₃ | CH₂ | 1 | Q2 | C₃F₇-n | C₂F₅ | — | |
| 717 | CH(CH₃)CH₂SCH₃ (S)-isomer | 3-I | 2-CH₃ | CH₂ | 1 | Q2 | C₃F₇-n | C₂F₅ | — | |
| 718 | C(CH₃)₂CH₂SCH₃ | 3-F | 2-CH₃ | CH₂ | 1 | Q1 | CF₃ | CF₃ | H | |
| 719 | C(CH₃)₂CH₂SOCH₃ | 3-F | 2-CH₃ | CH₂ | 1 | Q1 | CF₃ | CF₃ | H | |

TABLE 1-continued

| | | | | | | | | | |
|---|---|---|---|---|---|---|---|---|---|
| 720 | C(CH$_3$)$_2$CH$_2$SO$_2$CH$_3$ | 3-F | 2-CH$_3$ | CH$_2$ | 1 | Q1 | CF$_3$ | CF$_3$ | H | |
| 721 | CH(CH$_3$)CH$_2$SOCH$_3$ (S)-isomer | 3-F | 2-CH$_3$ | CH$_2$ | 1 | Q1 | CF$_3$ | CF$_3$ | H | |
| 722 | CH(CH$_3$)CH$_2$SO$_2$CH$_3$ (S)-isomer | 3-F | 2-CH$_3$ | CH$_2$ | 1 | Q1 | CF$_3$ | CF$_3$ | H | |
| 723 | CH(CH$_3$)CH$_2$SOCH$_3$ (S)-isomer | 3-Cl | 2-CH$_3$ | CH$_2$ | 1 | Q1 | H | H | C$_4$F$_9$-n | 63-69 |
| 724 | CH(CH$_3$)CH$_2$SO$_2$CH$_3$ (S)-isomer | 3-Cl | 2-CH$_3$ | CH$_2$ | 1 | Q1 | H | H | C$_4$F$_9$-n | 95-97 |
| 725 | CH(CH$_3$)CH$_2$SCH$_3$ (S)-isomer | 3-Cl | 2-CH$_3$ | CH$_2$ | 1 | Q1 | H | CF$_3$ | C$_3$F$_7$-n | 76-81 |
| 726 | CH(CH$_3$)CH$_2$SOCH$_3$ (S)-isomer | 3-Cl | 2-CH$_3$ | CH$_2$ | 1 | Q1 | H | CF$_3$ | C$_3$F$_7$-n | *** |
| 727 | CH(CH$_3$)CH$_2$SO$_2$CH$_3$ (S)-isomer | 3-Cl | 2-CH$_3$ | CH$_2$ | 1 | Q1 | H | CF$_3$ | C$_3$F$_7$-n | *** |
| 728 | CH(CH$_3$)CH$_2$SOCH$_3$ (S)-isomer | 3-Cl | 2-CH$_3$ | CH$_2$ | 1 | Q1 | H | C$_2$F$_5$ | C$_2$F$_5$ | 68-72 |
| 729 | CH(CH$_3$)CH$_2$SO$_2$CH$_3$ (S)-isomer | 3-Cl | 2-CH$_3$ | CH$_2$ | 1 | Q1 | H | C$_2$F$_5$ | C$_2$F$_5$ | *** |
| 730 | CH(CH$_3$)CH$_2$SCH$_3$ (S)-isomer | 3-Cl | 2-CH$_3$ | CH$_2$ | 1 | Q1 | CHF$_2$ | CHF$_2$ | H | *** |
| 731 | C(CH$_3$)$_2$CH$_2$SCH$_3$ | 3-Cl | 2-CH$_3$ | CH$_2$ | 1 | Q1 | CF$_3$ | H | CF$_3$ | |
| 732 | CH(CH$_3$)CH$_2$SCH$_3$ (S)-isomer | 3-Cl | 2-CH$_3$ | CH$_2$ | 1 | Q1 | CF$_3$ | H | CF$_3$ | |
| 733 | C(CH$_3$)$_2$CH$_2$SCH$_3$ | 3-Cl | 2-CH$_3$ | CH$_2$ | 1 | Q1 | CF$_3$ | H | CF$_2$CHF$_2$ | |
| 734 | CH(CH$_3$)CH$_2$SCH$_3$ (S)-isomer | 3-Cl | 2-CH$_3$ | CH$_2$ | 1 | Q1 | CF$_3$ | H | CF$_2$CHF$_2$ | |
| 735 | C(CH$_3$)$_2$CH$_2$SCH$_3$ | 3-Cl | 2-CH$_3$ | CH$_2$ | 1 | Q1 | CF$_3$ | H | C$_4$F$_9$-n | |
| 736 | CH(CH$_3$)CH$_2$SCH$_3$ | 3-Cl | 2-CH$_3$ | CH$_2$ | 1 | Q1 | CF$_3$ | H | C$_4$F$_9$-n | |
| 737 | CH(CH$_3$)CH$_2$SCH$_3$ (S)-isomer | 3-Cl | 2-CH$_3$ | CH$_2$ | 1 | Q1 | CF$_3$ | H | C$_6$F$_{13}$-n | 78-82 |
| 738 | CH(CH$_3$)CH$_2$SCH$_3$ (S)-isomer | 3-Cl | 2-CH$_3$ | CH$_2$ | 1 | Q1 | CF$_3$ | H | C$_8$F$_{17}$-n | 79-82 |
| 739 | CH(CH$_3$)CH$_2$SCH$_3$ (S)-isomer | 3-Cl | 2-CH$_3$ | CH$_2$ | 1 | Q1 | CF$_3$ | CF$_3$ | CF$_3$ | |
| 740 | C(CH$_3$)$_2$CH$_2$SCH$_3$ | 3-Cl | 2-CH$_3$ | CH$_2$ | 1 | Q1 | CF$_2$CHF$_2$ | H | C$_2$F$_5$ | |
| 741 | CH(CH$_3$)CH$_2$SCH$_3$ (S)-isomer | 3-Cl | 2-CH$_3$ | CH$_2$ | 1 | Q1 | CF$_2$CHF$_2$ | H | C$_2$F$_5$ | *** |
| 742 | CH(CH$_3$)CH$_2$SOCH$_3$ (S)-isomer | 3-Cl | 2-CH$_3$ | CH$_2$ | 1 | Q1 | CF$_2$CHF$_2$ | H | C$_2$F$_5$ | 64-67 |
| 743 | CH(CH$_3$)CH$_2$SO$_2$CH$_3$ (S)-isomer | 3-Cl | 2-CH$_3$ | CH$_2$ | 1 | Q1 | CF$_2$CHF$_2$ | H | C$_2$F$_5$ | 83-89 |
| 744 | C(CH$_3$)$_2$CH$_2$SCH$_3$ | 3-Cl | 2-CH$_3$ | CH$_2$ | 1 | Q1 | C$_2$F$_5$ | H | CF$_3$ | |
| 745 | CH(CH$_3$)CH$_2$SCH$_3$ (S)-isomer | 3-Cl | 2-CH$_3$ | CH$_2$ | 1 | Q1 | C$_2$F$_5$ | H | CF$_3$ | 75-80 |
| 746 | CH(CH$_3$)CH$_2$SCH$_3$ (S)-isomer | 3-Cl | 2-CH$_3$ | CH$_2$ | 1 | Q1 | C$_2$F$_5$ | H | CF$_2$CHF$_2$ | |
| 747 | CH(CH$_3$)CH$_2$SOCH$_3$ (S)-isomer | 3-Cl | 2-CH$_3$ | CH$_2$ | 1 | Q1 | C$_2$F$_5$ | H | CF$_2$CHF$_2$ | |
| 748 | CH(CH$_3$)CH$_2$SO$_2$CH$_3$ (S)-isomer | 3-Cl | 2-CH$_3$ | CH$_2$ | 1 | Q1 | C$_2$F$_5$ | H | CF$_2$CHF$_2$ | |
| 749 | C(CH$_3$)$_2$CH$_2$SCH$_3$ | 3-Cl | 2-CH$_3$ | CH$_2$ | 1 | Q1 | C$_2$F$_5$ | H | C$_2$F$_5$ | |
| 750 | C(CH$_3$)$_2$CH$_2$SOCH$_3$ | 3-Cl | 2-CH$_3$ | CH$_2$ | 1 | Q1 | C$_2$F$_5$ | H | C$_2$F$_5$ | |
| 751 | C(CH$_3$)$_2$CH$_2$SO$_2$CH$_3$ | 3-Cl | 2-CH$_3$ | CH$_2$ | 1 | Q1 | C$_2$F$_5$ | H | C$_2$F$_5$ | |
| 752 | CH(CH$_3$)CH$_2$SCH$_3$ | 3-Cl | 2-CH$_3$ | CH$_2$ | 1 | Q1 | C$_2$F$_5$ | H | C$_2$F$_5$ | |
| 753 | CH(CH$_3$)CH$_2$SOCH$_3$ | 3-Cl | 2-CH$_3$ | CH$_2$ | 1 | Q1 | C$_2$F$_5$ | H | C$_2$F$_5$ | |
| 754 | CH(CH$_3$)CH$_2$SO$_2$CH$_3$ | 3-Cl | 2-CH$_3$ | CH$_2$ | 1 | Q1 | C$_2$F$_5$ | H | C$_2$F$_5$ | |
| 755 | CH(CH$_3$)CH$_2$SCH$_3$ (S)-isomer | 3-Cl | 2-CH$_3$ | — | 0 | Q1 | C$_2$F$_5$ | H | C$_2$F$_5$ | 95-100 |
| 756 | CH(CH$_3$)CH$_2$SCH$_3$ (S)-isomer | 3-Cl | 2-CH$_3$ | CH(CH$_3$) | 1 | Q1 | C$_2$F$_5$ | H | C$_2$F$_5$ | |
| 757 | CH(CH$_3$)CH$_2$SOCH$_3$ (S)-isomer | 3-Cl | 2-CH$_3$ | — | 0 | Q1 | C$_2$F$_5$ | H | C$_2$F$_5$ | 89-94 |
| 758 | CH(CH$_3$)CH$_2$SOCH$_3$ (S)-isomer | 3-Cl | 2-CH$_3$ | CH(CH$_3$) | 1 | Q1 | C$_2$F$_5$ | H | C$_2$F$_5$ | |
| 759 | CH(CH$_3$)CH$_2$SO$_2$CH$_3$ (S)-isomer | 3-Cl | 2-CH$_3$ | — | 0 | Q1 | C$_2$F$_5$ | H | C$_2$F$_5$ | 195-195 |
| 760 | CH(CH$_3$)CH$_2$SO$_2$CH$_3$ (S)-isomer | 3-Cl | 2-CH$_3$ | CH(CH$_3$) | 1 | Q1 | C$_2$F$_5$ | H | C$_2$F$_5$ | |
| 761 | CH(CH$_3$)CH$_2$SC$_2$H$_5$ (S)-isomer | 3-Cl | 2-CH$_3$ | CH$_2$ | 1 | Q1 | C$_2$F$_5$ | H | C$_2$F$_5$ | 70-74 |
| 762 | CH(CH$_3$)CH$_2$SOC$_2$H$_5$ (S)-isomer | 3-Cl | 2-CH$_3$ | CH$_2$ | 1 | Q1 | C$_2$F$_5$ | H | C$_2$F$_5$ | 79-84 |
| 763 | CH(CH$_3$)CH$_2$SO$_2$C$_2$H$_5$ (S)-isomer | 3-Cl | 2-CH$_3$ | CH$_2$ | 1 | Q1 | C$_2$F$_5$ | H | C$_2$F$_5$ | 185-188 |
| 764 | C(CH$_3$)$_2$CH$_2$SCH$_3$ | 3-Cl | 2-CH$_3$ | CH(CH$_3$) | 1 | Q1 | C$_2$F$_5$ | H | C$_3$F$_7$-n | |
| 765 | C(CH$_3$)$_2$CH$_2$SCH$_3$ | 3-Cl | 2-CH$_3$ | CH$_2$ | 1 | Q1 | C$_2$F$_5$ | H | C$_3$F$_7$-n | |
| 766 | C(CH$_3$)$_2$CH$_2$SOCH$_3$ | 3-Cl | 2-CH$_3$ | CH$_2$ | 1 | Q1 | C$_2$F$_5$ | H | C$_3$F$_7$-n | |
| 767 | C(CH$_3$)$_2$CH$_2$SO$_2$CH$_3$ | 3-Cl | 2-CH$_3$ | CH$_2$ | 1 | Q1 | C$_2$F$_5$ | H | C$_3$F$_7$-n | |

TABLE 1-continued

| | | | | | | | | | |
|---|---|---|---|---|---|---|---|---|---|
| 768 | CH(CH₃)CH₂SCH₃ | 3-Cl | 2-CH₃ | CH₂ | 1 | Q1 | C₂F₅ | H | C₃F₇-n | |
| 769 | C(CH₃)₂CH₂SCH₃ | 3-Cl | 2-CH₃ | CH₂ | 1 | Q1 | C₂F₅ | H | C₄F₉-n | |
| 770 | CH(CH₃)CH₂SCH₃ | 3-Cl | 2-CH₃ | CH₂ | 1 | Q1 | C₂F₅ | H | C₄F₉-n | |
| 771 | CH(CH₃)CH₂SOCH₃ (S)-isomer | 3-Cl | 2-CH₃ | CH₂ | 1 | Q1 | C₂F₅ | H | C₄F₉-n | 81-85 |
| 772 | CH(CH₃)CH₂SO₂CH₃ (S)-isomer | 3-Cl | 2-CH₃ | CH₂ | 1 | Q1 | C₂F₅ | H | C₄F₉-n | |
| 773 | C(CH₃)₂CH₂SCH₃ | 3-Cl | 2-CH₃ | CH₂ | 1 | Q1 | C₂F₅ | F | CF₃ | |
| 774 | CH(CH₃)CH₂SCH₃ | 3-Cl | 2-CH₃ | CH₂ | 1 | Q1 | C₂F₅ | F | CF₃ | |
| 775 | CH(CH₃)CH₂SCH₃ (S)-isomer | 3-Cl | 2-CH₃ | CH₂ | 1 | Q1 | C₂F₅ | F | CF₃ | 142-146 |
| 776 | CH(CH₃)CH₂SOCH₃ (S)-isomer | 3-Cl | 2-CH₃ | CH₂ | 1 | Q1 | C₂F₅ | F | CF₃ | |
| 777 | CH(CH₃)CH₂SO₂CH₃ (S)-isomer | 3-Cl | 2-CH₃ | CH₂ | 1 | Q1 | C₂F₅ | F | CF₃ | |
| 778 | CH(CH₃)CH₂SCH₃ (S)-isomer | 3-Cl | 2-CH₃ | CH₂ | 1 | Q1 | C₂F₅ | CH₃ | C₂F₅ | *** |
| 779 | CH(CH₃)CH₂SCH₃ (S)-isomer | 3-Cl | 2-CH₃ | CH₂ | 1 | Q1 | C₂F₅ | C₂F₅ | C₂F₅ | |
| 780 | C(CH₃)₂CH₂SCH₃ | 3-Cl | 2-CH₃ | CH₂ | 1 | Q1 | C₃F₇-n | H | C₂F₅ | |
| 781 | C(CH₃)₂CH₂SOCH₃ | 3-Cl | 2-CH₃ | CH₂ | 1 | Q1 | C₃F₇-n | H | C₂F₅ | |
| 782 | C(CH₃)₂CH₂SO₂CH₃ | 3-Cl | 2-CH₃ | CH₂ | 1 | Q1 | C₃F₇-n | H | C₂F₅ | |
| 783 | CH(CH₃)CH₂SCH₃ | 3-Cl | 2-CH₃ | CH₂ | 1 | Q1 | C₃F₇-n | H | C₂F₅ | |
| 784 | CH(CH₃)CH₂SOCH₃ (S)-isomer | 3-Cl | 2-CH₃ | CH₂ | 1 | Q1 | C₃F₇-n | H | C₂F₅ | 81-83 |
| 785 | CH(CH₃)CH₂SO₂CH₃ (S)-isomer | 3-Cl | 2-CH₃ | CH₂ | 1 | Q1 | C₃F₇-n | H | C₂F₅ | 85-90 |
| 786 | C(CH₃)₂CH₂SCH₃ | 3-Cl | 2-CH₃ | CH(CH₃) | 1 | Q1 | C₃F₇-n | H | C₃F₇-n | |
| 787 | CH(CH₃)CH₂SCH₃ | 3-Cl | 2-CH₃ | CH₂ | 1 | Q1 | C₃F₇-n | H | C₃F₇-n | |
| 788 | C(CH₃)₂CH₂SOCH₃ | 3-Cl | 2-CH₃ | CH₂ | 1 | Q1 | C₃F₇-n | H | C₃F₇-n | |
| 789 | C(CH₃)₂CH₂SO₂CH₃ | 3-Cl | 2-CH₃ | CH₂ | 1 | Q1 | C₃F₇-n | H | C₃F₇-n | |
| 790 | CH(CH₃)CH₂SCH₃ | 3-Cl | 2-CH₃ | CH₂ | 1 | Q1 | C₃F₇-n | H | C₃F₇-n | |
| 791 | CH(CH₃)CH₂SOCH₃ | 3-Cl | 2-CH₃ | CH₂ | 1 | Q1 | C₃F₇-n | H | C₃F₇-n | |
| 792 | CH(CH₃)CH₂SO₂CH₃ | 3-Cl | 2-CH₃ | CH₂ | 1 | Q1 | C₃F₇-n | H | C₃F₇-n | |
| 793 | CH(CH₃)CH₂SCH₃ (S)-isomer | 3-Cl | 2-CH₃ | CH₂ | 1 | Q1 | C₃F₇-n | C₃F₇-n | H | 74-78 |
| 794 | CH(CH₃)CH₂SOCH₃ (S)-isomer | 3-Cl | 2-CH₃ | CH₂ | 1 | Q1 | C₃F₇-n | C₃F₇-n | H | 72-76 |
| 795 | CH(CH₃)CH₂SO₂CH₃ (S)-isomer | 3-Cl | 2-CH₃ | CH₂ | 1 | Q1 | C₃F₇-n | C₃F₇-n | H | 149-150 |
| 796 | CH(CH₃)CH₂SCH₃ (S)-isomer | 3-Cl | 2-CH₃ | CH₂ | 1 | Q2 | CHFCF₃ | CF₃ | — | 66-69 |
| 797 | CH(CH₃)CH₂SOCH₃ (S)-isomer | 3-Cl | 2-CH₃ | CH₂ | 1 | Q2 | CHFCF₃ | CF₃ | — | 80-85 |
| 798 | CH(CH₃)CH₂SO₂CH₃ (S)-isomer | 3-Cl | 2-CH₃ | CH₂ | 1 | Q2 | CHFCF₃ | CF₃ | — | 81-86 |
| 799 | CH(CH₃)CH₂SCH₃ (S)-isomer | 3-Cl | 2-CH₃ | CH₂ | 1 | Q2 | CF₂CHF₂ | CF₂CHF₂ | — | *** |
| 800 | CH(CH₃)CH₂SOCH₃ (S)-isomer | 3-Cl | 2-CH₃ | CH₂ | 1 | Q2 | CF₂CHF₂ | CF₂CHF₂ | — | 159-163 |
| 801 | CH(CH₃)CH₂SO₂CH₃ (S)-isomer | 3-Cl | 2-CH₃ | CH₂ | 1 | Q2 | CF₂CHF₂ | CF₂CHF₂ | — | 77-83 |
| 802 | C(CH₃)₂CH₂SCH₃ | 3-Cl | 2-CH₃ | CH₂ | 1 | Q2 | C₃F₇-n | C₃F₇-n | — | |
| 803 | CH(CH₃)CH₂SCH₃ (S)-isomer | 3-Cl | 2-CH₃ | CH₂ | 1 | Q2 | C₄F₉-n | H | — | 218-210 |
| 804 | CH(CH₃)CH₂SCH₃ (S)-isomer | 3-Cl | 2-CH₃ | CH₂ | 1 | Q2 | SC₃F₇-n | CF₃ | — | 73-76 |
| 805 | CH(CH₃)CH₂SCH₃ (S)-isomer | 3-Cl | 2-CH₃ | CH₂ | 1 | Q6 | CF₃ | CF₃ | CF₃ | |
| 806 | CH(CH₃)CH₂SOCH₃ (S)-isomer | 3-Cl | 2-CH₃ | CH₂ | 1 | Q6 | CF₃ | CF₃ | CF₃ | |
| 807 | CH(CH₃)CH₂SO₂CH₃ (S)-isomer | 3-Cl | 2-CH₃ | CH₂ | 1 | Q6 | CF₃ | CF₃ | CF₃ | |
| 808 | C(CH₃)₂CH₂SCH₃ | 3-Cl | 2-CH₃ | CH₂ | 1 | Q9 | CF₃ | CF₃ | — | |
| 809 | C(CH₃)₂CH₂SOCH₃ | 3-Cl | 2-CH₃ | CH₂ | 1 | Q9 | CF₃ | CF₃ | — | |
| 810 | C(CH₃)₂CH₂SO₂CH₃ | 3-Cl | 2-CH₃ | CH₂ | 1 | Q9 | CF₃ | CF₃ | — | |
| 811 | CH(CH₃)CH₂SCH₃ | 3-Cl | 2-CH₃ | CH₂ | 1 | Q9 | CF₃ | CF₃ | — | |
| 812 | CH(CH₃)CH₂SOCH₃ | 3-Cl | 2-CH₃ | CH₂ | 1 | Q9 | CF₃ | CF₃ | — | |
| 813 | CH(CH₃)CH₂SO₂CH₃ | 3-Cl | 2-CH₃ | CH₂ | 1 | Q9 | CF₃ | CF₃ | — | |
| 814 | CH(CH₃)CH₂SOCH₃ (S)-isomer | 3-Cl | 2-CH₃ | CH₂ | 1 | Q9 | CF₃ | CF₃ | — | |
| 815 | CH(CH₃)CH₂SO₂CH₃ (S)-isomer | 3-Cl | 2-CH₃ | CH₂ | 1 | Q9 | CF₃ | CF₃ | — | |
| 816 | CH(CH₃)CH₂SC₂H₅ (S)-isomer | 3-Cl | 2-CH₃ | CH₂ | 1 | Q9 | CF₃ | CF₃ | — | |
| 817 | CH(CH₃)CH₂SOC₂H₅ (S)-isomer | 3-Cl | 2-CH₃ | CH₂ | 1 | Q9 | CF₃ | CF₃ | — | |
| 818 | CH(CH₃)CH₂SO₂C₂H₅ (S)-isomer | 3-Cl | 2-CH₃ | CH₂ | 1 | Q9 | CF₃ | CF₃ | — | |

TABLE 1-continued

| | | | | | | | | | | |
|---|---|---|---|---|---|---|---|---|---|---|
| 819 | C(CH$_3$)$_2$CH$_2$SCH$_3$ | 3-Cl | 2-CH$_3$ | CH$_2$ | 1 | Q9 | C$_2$F$_5$ | CF$_3$ | — | |
| 820 | C(CH$_3$)$_2$CH$_2$SOCH$_3$ | 3-Cl | 2-CH$_3$ | CH$_2$ | 1 | Q9 | C$_2$F$_5$ | CF$_3$ | — | |
| 821 | C(CH$_3$)$_2$CH$_2$SO$_2$CH$_3$ | 3-Cl | 2-CH$_3$ | CH$_2$ | 1 | Q9 | C$_2$F$_5$ | CF$_3$ | — | |
| 822 | CH(CH$_3$)CH$_2$SCH$_3$ | 3-Cl | 2-CH$_3$ | CH$_2$ | 1 | Q9 | C$_2$F$_5$ | CF$_3$ | — | |
| 823 | CH(CH$_3$)CH$_2$SOCH$_3$ | 3-Cl | 2-CH$_3$ | CH$_2$ | 1 | Q9 | C$_2$F$_5$ | CF$_3$ | — | |
| 824 | CH(CH$_3$)CH$_2$SO$_2$CH$_3$ | 3-Cl | 2-CH$_3$ | CH$_2$ | 1 | Q9 | C$_2$F$_5$ | CF$_3$ | — | |
| 825 | CH(CH$_3$)CH$_2$SCH$_3$ (S)-isomer | 3-Cl | 2-CH$_3$ | CH$_2$ | 1 | Q9 | C$_2$F$_5$ | CF$_3$ | — | |
| 826 | CH(CH$_3$)CH$_2$SOCH$_3$ (S)-isomer | 3-Cl | 2-CH$_3$ | CH$_2$ | 1 | Q9 | C$_2$F$_5$ | CF$_3$ | — | |
| 827 | CH(CH$_3$)CH$_2$SO$_2$CH$_3$ (S)-isomer | 3-Cl | 2-CH$_3$ | CH$_2$ | 1 | Q9 | C$_2$F$_5$ | CF$_3$ | — | |
| 828 | CH(CH$_3$)CH$_2$SC$_2$H$_5$ (S)-isomer | 3-Cl | 2-CH$_3$ | CH$_2$ | 1 | Q9 | C$_2$F$_5$ | CF$_3$ | — | |
| 829 | CH(CH$_3$)CH$_2$SOC$_2$H$_5$ (S)-isomer | 3-Cl | 2-CH$_3$ | CH$_2$ | 1 | Q9 | C$_2$F$_5$ | CF$_3$ | — | |
| 830 | CH(CH$_3$)CH$_2$SO$_2$C$_2$H$_5$ (S)-isomer | 3-Cl | 2-CH$_3$ | CH$_2$ | 1 | Q9 | C$_2$F$_5$ | CF$_3$ | — | |
| 831 | C(CH$_3$)$_2$CH$_2$SCH$_3$ | 3-Cl | 2-CH$_3$ | CH$_2$ | 1 | Q9 | C$_2$F$_5$ | C$_2$F$_5$ | — | |
| 832 | CH(CH$_3$)CH$_2$SCH$_3$ | 3-Cl | 2-CH$_3$ | CH$_2$ | 1 | Q9 | C$_2$F$_5$ | C$_2$F$_5$ | — | |
| 833 | CH(CH$_3$)CH$_2$SCH$_3$ (S)-isomer | 3-Cl | 2-CH$_3$ | CH$_2$ | 1 | Q9 | C$_2$F$_5$ | C$_2$F$_5$ | — | |
| 834 | C(CH$_3$)$_2$CH$_2$SCH$_3$ | 3-Cl | 2-CH$_3$ | CH$_2$ | 1 | Q9 | C$_3$F$_7$-n | CF$_3$ | — | |
| 835 | CH(CH$_3$)CH$_2$SCH$_3$ (S)-isomer | 3-Cl | 2-CH$_3$ | CH$_2$ | 1 | Q9 | C$_3$F$_7$-n | CF$_3$ | — | |
| 836 | CH(CH$_3$)CH$_2$SCH$_3$ (S)-isomer | 3-Cl | 2-CH$_3$ | S | 1 | Q18 | CF$_3$ | CH$_3$ | — | |
| 837 | CH(CH$_3$)CH$_2$SCH$_3$ (S)-isomer | 3-Cl | 2-CH$_3$ | — | 0 | Q19 | CF$_3$ | CH$_3$ | — | |
| 838 | CH(CH$_3$)CH$_2$SCH$_3$ | 3-Cl | 2-CH$_3$ | CH$_2$ | 1 | Q17 | CF$_3$ | H | — | |
| 839 | CH(CH$_3$)CH$_2$SCH$_3$ | 3-Cl | 2-CH$_3$ | CH$_2$ | 1 | Q15 | H | C$_2$F$_5$ | — | |
| 840 | CH(CH$_3$)CH$_2$SCH$_3$ (S)-isomer | 3-Cl | 2-CH$_3$ | CH$_2$ | 1 | Q15 | H | C$_2$F$_5$ | — | 71-75 |
| 841 | CH(CH$_3$)CH$_2$SCH$_3$ (S)-isomer | 3-Cl | 2-CH$_3$ | — | 0 | Q20 | CF$_3$ | — | — | |
| 842 | CH(CH$_3$)CH$_2$SCH$_3$ | 3-Cl | 2-CH$_3$ | — | 0 | Q16 | C$_2$F$_5$ | — | — | |
| 843 | CH(CH$_3$)CH$_2$SCH$_3$ | 3-Cl | 2-CH$_3$ | — | 0 | Q16 | C$_3$F$_7$-n | — | — | |
| 844 | C(CH$_3$)$_2$CH$_2$SCH$_3$ | 3-Br | 2-CH$_3$ | CH$_2$ | 1 | Q1 | CF$_3$ | H | C$_2$F$_5$ | |
| 845 | C(CH$_3$)$_2$CH$_2$SCH$_3$ | 3-Br | 2-CH$_3$ | CH$_2$ | 1 | Q1 | CF$_3$ | H | C$_4$F$_9$-n | |
| 846 | CH(CH$_3$)CH$_2$SCH$_3$ | 3-Br | 2-CH$_3$ | CH$_2$ | 1 | Q1 | CF$_3$ | H | C$_4$F$_9$-n | |
| 847 | CH(CH$_3$)CH$_2$SCH$_3$ | 3-Br | 2-CH$_3$ | CH$_2$ | 1 | Q1 | CF$_2$CHF$_2$ | H | C$_2$F$_5$ | |
| 848 | C(CH$_3$)$_2$CH$_2$SCH$_3$ | 3-Br | 2-CH$_3$ | CH$_2$ | 1 | Q1 | C$_2$F$_5$ | H | C$_2$F$_5$ | |
| 849 | C(CH$_3$)$_2$CH$_2$SOCH$_3$ | 3-Br | 2-CH$_3$ | CH$_2$ | 1 | Q1 | C$_2$F$_5$ | H | C$_2$F$_5$ | |
| 850 | C(CH$_3$)$_2$CH$_2$SO$_2$CH$_3$ | 3-Br | 2-CH$_3$ | CH$_2$ | 1 | Q1 | C$_2$F$_5$ | H | C$_2$F$_5$ | |
| 851 | CH(CH$_3$)CH$_2$SCH$_3$ | 3-Br | 2-CH$_3$ | CH$_2$ | 1 | Q1 | C$_2$F$_5$ | H | C$_2$F$_5$ | |
| 852 | CH(CH$_3$)CH$_2$SOCH$_3$ | 3-Br | 2-CH$_3$ | CH$_2$ | 1 | Q1 | C$_2$F$_5$ | H | C$_2$F$_5$ | |
| 853 | CH(CH$_3$)CH$_2$SO$_2$CH$_3$ | 3-Br | 2-CH$_3$ | CH$_2$ | 1 | Q1 | C$_2$F$_5$ | H | C$_2$F$_5$ | |
| 854 | C(CH$_3$)$_2$CH$_2$SCH$_3$ | 3-Br | 2-CH$_3$ | CH$_2$ | 1 | Q1 | C$_2$F$_5$ | H | C$_4$F$_9$-n | |
| 855 | CH(CH$_3$)CH$_2$SCH$_3$ | 3-Br | 2-CH$_3$ | CH$_2$ | 1 | Q1 | C$_2$F$_5$ | H | C$_4$F$_9$-n | |
| 856 | CH(CH$_3$)CH$_2$SCH$_3$ | 3-Br | 2-CH$_3$ | CH$_2$ | 1 | Q1 | C$_3$F$_7$-n | H | C$_2$F$_5$ | |
| 857 | C(CH$_3$)$_2$CH$_2$SCH$_3$ | 3-Br | 2-CH$_3$ | CH$_2$ | 1 | Q1 | C$_3$F$_7$-n | H | C$_3$F$_7$-n | |
| 858 | C(CH$_3$)$_2$CH$_2$SOCH$_3$ | 3-Br | 2-CH$_3$ | CH$_2$ | 1 | Q1 | C$_3$F$_7$-n | H | C$_3$F$_7$-n | |
| 859 | C(CH$_3$)$_2$CH$_2$SO$_2$CH$_3$ | 3-Br | 2-CH$_3$ | CH$_2$ | 1 | Q1 | C$_3$F$_7$-n | H | C$_3$F$_7$-n | |
| 860 | CH(CH$_3$)CH$_2$SCH$_3$ | 3-Br | 2-CH$_3$ | CH$_2$ | 1 | Q1 | C$_3$F$_7$-n | H | C$_3$F$_7$-n | |
| 861 | CH(CH$_3$)CH$_2$SOCH$_3$ | 3-Br | 2-CH$_3$ | CH$_2$ | 1 | Q1 | C$_3$F$_7$-n | H | C$_3$F$_7$-n | |
| 862 | CH(CH$_3$)CH$_2$SO$_2$CH$_3$ | 3-Br | 2-CH$_3$ | CH$_2$ | 1 | Q1 | C$_3$F$_7$-n | H | C$_3$F$_7$-n | |
| 863 | C(CH$_3$)$_2$CH$_2$SCH$_3$ | 3-Br | 2-CH$_3$ | CH$_2$ | 1 | Q9 | CF$_3$ | CF$_3$ | — | |
| 864 | C(CH$_3$)$_2$CH$_2$SOCH$_3$ | 3-Br | 2-CH$_3$ | CH$_2$ | 1 | Q9 | CF$_3$ | CF$_3$ | — | |
| 865 | C(CH$_3$)$_2$CH$_2$SO$_2$CH$_3$ | 3-Br | 2-CH$_3$ | CH$_2$ | 1 | Q9 | CF$_3$ | CF$_3$ | — | |
| 866 | CH(CH$_3$)CH$_2$SCH$_3$ | 3-Br | 2-CH$_3$ | CH$_2$ | 1 | Q9 | CF$_3$ | CF$_3$ | — | |
| 867 | CH(CH$_3$)CH$_2$SOCH$_3$ | 3-Br | 2-CH$_3$ | CH$_2$ | 1 | Q9 | CF$_3$ | CF$_3$ | — | |
| 868 | CH(CH$_3$)CH$_2$SO$_2$CH$_3$ | 3-Br | 2-CH$_3$ | CH$_2$ | 1 | Q9 | CF$_3$ | CF$_3$ | — | |
| 869 | C(CH$_3$)$_2$CH$_2$SCH$_3$ | 3-Br | 2-CH$_3$ | CH$_2$ | 1 | Q9 | C$_2$F$_5$ | CF$_3$ | — | |
| 870 | C(CH$_3$)$_2$CH$_2$SOCH$_3$ | 3-Br | 2-CH$_3$ | CH$_2$ | 1 | Q9 | C$_2$F$_5$ | CF$_3$ | — | |
| 871 | C(CH$_3$)$_2$CH$_2$SO$_2$CH$_3$ | 3-Br | 2-CH$_3$ | CH$_2$ | 1 | Q9 | C$_2$F$_5$ | CF$_3$ | — | |
| 872 | CH(CH$_3$)CH$_2$SCH$_3$ | 3-Br | 2-CH$_3$ | CH$_2$ | 1 | Q9 | C$_2$F$_5$ | CF$_3$ | — | |
| 873 | CH(CH$_3$)CH$_2$SOCH$_3$ | 3-Br | 2-CH$_3$ | CH$_2$ | 1 | Q9 | C$_2$F$_5$ | CF$_3$ | — | |
| 874 | CH(CH$_3$)CH$_2$SO$_2$CH$_3$ | 3-Br | 2-CH$_3$ | CH$_2$ | 1 | Q9 | C$_2$F$_5$ | CF$_3$ | — | |
| 875 | CH(CH$_3$)CH$_2$SCH$_3$ (S)-isomer | 3-I | 2-CH$_3$ | CH$_2$ | 1 | Q1 | H | H | C$_4$F$_9$-n | 80-85 |
| 876 | CH(CH$_3$)CH$_2$SOCH$_3$ (S)-isomer | 3-I | 2-CH$_3$ | CH$_2$ | 1 | Q1 | H | H | C$_4$F$_9$-n | 160-162 |
| 877 | CH(CH$_3$)CH$_2$SO$_2$CH$_3$ (S)-isomer | 3-I | 2-CH$_3$ | CH$_2$ | 1 | Q1 | H | H | C$_4$F$_9$-n | 85-89 |
| 878 | CH(CH$_3$)CH$_2$SCH$_3$ (S)-isomer | 3-I | 2-CH$_3$ | CH$_2$ | 1 | Q1 | CHF$_2$ | CHF$_2$ | H | *** |
| 879 | C(CH$_3$)$_2$CH$_2$SCH$_3$ | 3-I | 2-CH$_3$ | CH$_2$ | 1 | Q1 | CF$_3$ | H | CF$_3$ | |
| 880 | C(CH$_3$)$_2$CH$_2$SCH$_3$ | 3-I | 2-CH$_3$ | CH$_2$ | 1 | Q1 | CF$_3$ | H | CF$_2$CHF$_2$ | |

TABLE 1-continued

| | | | | | | | | | | |
|---|---|---|---|---|---|---|---|---|---|---|
| 881 | CH(CH₃)CH₂SCH₃ (S)-isomer | 3-I | 2-CH₃ | CH₂ | 1 | Q1 | CF₃ | H | CF₂CHF₂ | |
| 882 | C(CH₃)₂CH₂SCH₃ | 3-I | 2-CH₃ | CH₂ | 1 | Q1 | CF₃ | H | C₂F₅ | |
| 883 | CH(CH₃)CH₂SCH₃ | 3-I | 2-CH₃ | CH₂ | 1 | Q1 | CF₃ | H | C₂F₅ | |
| 884 | C(CH₃)₂CH₂SCH₃ | 3-I | 2-CH₃ | CH₂ | 1 | Q1 | CF₃ | H | C₄F₉-n | |
| 885 | CH(CH₃)CH₂SCH₃ | 3-I | 2-CH₃ | CH₂ | 1 | Q1 | CF₃ | H | C₄F₉-n | |
| 886 | C(CH₃)₂CH₂SCH₃ | 3-I | 2-CH₃ | CH₂ | 1 | Q1 | CF₃ | CF₃ | CF₃ | |
| 887 | CH(CH₃)CH₂SCH₃ | 3-I | 2-CH₃ | CH₂ | 1 | Q1 | CF₃ | CF₃ | CF₃ | |
| 888 | C(CH₃)₂CH₂SCH₃ | 3-I | 2-CH₃ | CH(CH₃) | 1 | Q1 | CF₂CHF₂ | H | C₂F₅ | |
| 889 | C(CH₃)₂CH₂SCH₃ | 3-I | 2-CH₃ | CH₂ | 1 | Q1 | CF₂CHF₂ | H | C₂F₅ | |
| 890 | CH(CH₃)CH₂SCH₃ (S)-isomer | 3-I | 2-CH₃ | CH₂ | 1 | Q1 | CF₂CHF₂ | H | C₂F₅ | |
| 891 | CH(CH₃)CH₂SOCH₃ (S)-isomer | 3-I | 2-CH₃ | CH₂ | 1 | Q1 | CF₂CHF₂ | H | C₂F₅ | |
| 892 | CH(CH₃)CH₂SO₂CH₃ (S)-isomer | 3-I | 2-CH₃ | CH₂ | 1 | Q1 | CF₂CHF₂ | H | C₂F₅ | |
| 893 | C(CH₃)₂CH₂SCH₃ | 3-I | 2-CH₃ | CH₂ | 1 | Q1 | C₂F₅ | H | CF₃ | |
| 894 | CH(CH₃)CH₂SCH₃ (S)-isomer | 3-I | 2-CH₃ | CH₂ | 1 | Q1 | C₂F₅ | H | CF₂CHF₂ | |
| 895 | CH(CH₃)CH₂SOCH₃ (S)-isomer | 3-I | 2-CH₃ | CH₂ | 1 | Q1 | C₂F₅ | H | CF₂CHF₂ | |
| 896 | CH(CH₃)CH₂SO₂CH₃ (S)-isomer | 3-I | 2-CH₃ | CH₂ | 1 | Q1 | C₂F₅ | H | CF₂CHF₂ | |
| 897 | C(CH₃)₂CH₂SCH₃ | 3-I | 2-CH₃ | CH(CH₃) | 1 | Q1 | C₂F₅ | H | C₂F₅ | |
| 898 | C(CH₃)₂CH₂SCH₃ | 3-I | 2-CH₃ | CH₂ | 1 | Q1 | C₂F₅ | H | C₂F₅ | |
| 899 | C(CH₃)₂CH₂SOCH₃ | 3-I | 2-CH₃ | CH₂ | 1 | Q1 | C₂F₅ | H | C₂F₅ | |
| 900 | C(CH₃)₂CH₂SO₂CH₃ | 3-I | 2-CH₃ | CH₂ | 1 | Q1 | C₂F₅ | H | C₂F₅ | |
| 901 | CH(CH₃)CH₂SCH₃ | 3-I | 2-CH₃ | CH₂ | 1 | Q1 | C₂F₅ | H | C₂F₅ | |
| 902 | CH(CH₃)CH₂SOCH₃ | 3-I | 2-CH₃ | CH₂ | 1 | Q1 | C₂F₅ | H | C₂F₅ | |
| 903 | CH(CH₃)CH₂SO₂CH₃ | 3-I | 2-CH₃ | CH₂ | 1 | Q1 | C₂F₅ | H | C₂F₅ | |
| 904 | CH(CH₃)CH₂SC₂H₅ (S)-isomer | 3-I | 2-CH₃ | CH₂ | 1 | Q1 | C₂F₅ | H | C₂F₅ | |
| 905 | CH(CH₃)CH₂SOC₂H₅ (S)-isomer | 3-I | 2-CH₃ | CH₂ | 1 | Q1 | C₂F₅ | H | C₂F₅ | |
| 906 | CH(CH₃)CH₂SO₂C₂H₅ (S)-isomer | 3-I | 2-CH₃ | CH₂ | 1 | Q1 | C₂F₅ | H | C₂F₅ | |
| 907 | C(CH₃)₂CH₂SCH₃ | 3-I | 2-CH₃ | CH₂ | 1 | Q1 | C₂F₅ | H | C₃F₇-n | |
| 908 | C(CH₃)₂CH₂SOCH₃ | 3-I | 2-CH₃ | CH₂ | 1 | Q1 | C₂F₅ | H | C₃F₇-n | |
| 909 | C(CH₃)₂CH₂SO₂CH₃ | 3-I | 2-CH₃ | CH₂ | 1 | Q1 | C₂F₅ | H | C₃F₇-n | |
| 910 | CH(CH₃)CH₂SCH₃ | 3-I | 2-CH₃ | CH₂ | 1 | Q1 | C₂F₅ | H | C₃F₇-n | |
| 911 | C(CH₃)₂CH₂SCH₃ | 3-I | 2-CH₃ | CH₂ | 1 | Q1 | C₂F₅ | H | C₄F₉-n | |
| 912 | CH(CH₃)CH₂SCH₃ | 3-I | 2-CH₃ | CH₂ | 1 | Q1 | C₂F₅ | H | C₄F₉-n | |
| 913 | CH(CH₃)CH₂SOCH₃ (S)-isomer | 3-I | 2-CH₃ | CH₂ | 1 | Q1 | C₂F₅ | H | C₄F₉-n | 90-96 |
| 914 | CH(CH₃)CH₂SO₂CH₃ (S)-isomer | 3-I | 2-CH₃ | CH₂ | 1 | Q1 | C₂F₅ | H | C₄F₉-n | 92-97 |
| 915 | C(CH₃)₂CH₂SCH₃ | 3-I | 2-CH₃ | CH₂ | 1 | Q1 | C₂F₅ | F | CF₃ | |
| 916 | C(CH₃)₂CH₂SCH₃ | 3-I | 2-CH₃ | CH₂ | 1 | Q1 | C₃F₇-n | H | C₂F₅ | |
| 917 | CH(CH₃)CH₂SCH₃ | 3-I | 2-CH₃ | CH₂ | 1 | Q1 | C₃F₇-n | H | C₂F₅ | |
| 918 | CH(CH₃)CH₂SOCH₃ | 3-I | 2-CH₃ | CH₂ | 1 | Q1 | C₃F₇-n | H | C₂F₅ | |
| 919 | CH(CH₃)CH₂SO₂CH₃ | 3-I | 2-CH₃ | CH₂ | 1 | Q1 | C₃F₇-n | H | C₂F₅ | |
| 920 | CH(CH₃)CH₂SOCH₃ (S)-isomer | 3-I | 2-CH | CH₂ | 1 | Q1 | C₃F₇-n | H | C₂F₅ | 89-96 |
| 921 | CH(CH₃)CH₂SO₂CH₃ (S)-isomer | 3-I | 2-CH₃ | CH₂ | 1 | Q1 | C₃F₇-n | H | C₂F₅ | 92-96 |
| 922 | C(CH₃)₂CH₂SCH₃ | 3-I | 2-CH₃ | CH₂ | 1 | Q1 | C₃F₇-n | H | C₃F₇-n | |
| 923 | C(CH₃)₂CH₂SOCH₃ | 3-I | 2-CH₃ | CH₂ | 1 | Q1 | C₃F₇-n | H | C₃F₇-n | |
| 924 | C(CH₃)₂CH₂SO₂CH₃ | 3-I | 2-CH₃ | CH₂ | 1 | Q1 | C₃F₇-n | H | C₃F₇-n | |
| 925 | CH(CH₃)CH₂SCH₃ | 3-I | 2-CH₃ | CH₂ | 1 | Q1 | C₃F₇-n | H | C₃F₇-n | |
| 926 | CH(CH₃)CH₂SOCH₃ | 3-I | 2-CH₃ | CH₂ | 1 | Q1 | C₃F₇-n | H | C₃F₇-n | |
| 927 | CH(CH₃)CH₂SO₂CH₃ | 3-I | 2-CH₃ | CH₂ | 1 | Q1 | C₃F₇-n | H | C₃F₇-n | |
| 928 | C(CH₃)₂CH₂SCH₃ | 3-I | 2-CH₃ | CH₂ | 1 | Q2 | C₃F₇-n | C₃F₇-n | — | |
| 929 | CH(CH₃)CH₂SCH₃ (S)-isomer | 3-I | 2-CH₃ | CH₂ | 1 | Q6 | CF₃ | CF₃ | CF₃ | |
| 930 | CH(CH₃)CH₂SOCH₃ (S)-isomer | 3-I | 2-CH₃ | CH₂ | 1 | Q6 | CF₃ | CF₃ | CF₃ | |
| 931 | CH(CH₃)CH₂SO₂CH₃ (S)-isomer | 3-I | 2-CH₃ | CH₂ | 1 | Q6 | CF₃ | CF₃ | CF₃ | |
| 932 | C(CH₃)₂CH₂SCH₃ | 3-I | 2-CH₃ | CH(CH₃) | 1 | Q9 | CF₃ | CF₃ | — | |
| 933 | CH(CH₃)CH₂SCH₃ | 3-I | 2-CH₃ | CH₂ | 1 | Q9 | CF₃ | CF₃ | — | |
| 934 | CH(CH₃)CH₂SOCH₃ | 3-I | 2-CH₃ | CH₂ | 1 | Q9 | CF₃ | CF₃ | — | |
| 935 | CH(CH₃)CH₂SO₂CH₃ | 3-I | 2-CH₃ | CH₂ | 1 | Q9 | CF₃ | CF₃ | — | |
| 936 | CH(CH₃)CH₂SOCH₃ (S)-isomer | 3-I | 2-CH₃ | CH₂ | 1 | Q9 | CF₃ | CF₃ | — | |
| 937 | CH(CH₃)CH₂SO₂CH₃ (S)-isomer | 3-I | 2-CH₃ | CH₂ | 1 | Q9 | CF₃ | CF₃ | — | |
| 938 | CH(CH₃)CH₂SC₂H₅ (S)-isomer | 3-I | 2-CH₃ | CH₂ | 1 | Q9 | CF₃ | CF₃ | — | |

TABLE 1-continued

| | | | | | | | | | |
|---|---|---|---|---|---|---|---|---|---|
| 939 | CH(CH₃)CH₂SOC₂H₅ (S)-isomer | 3-I | 2-CH₃ | CH₂ | 1 | Q9 | CF₃ | CF₃ | — |
| 940 | CH(CH₃)CH₂SO₂C₂H₅ (S)-isomer | 3-I | 2-CH₃ | CH₂ | 1 | Q9 | CF₃ | CF₃ | — |
| 941 | C(CH₃)₂CH₂SCH₃ | 3-I | 2-CH₃ | CH(CH₃) | 1 | Q9 | C₂F₅ | CF₃ | — |
| 942 | C(CH₃)₂CH₂SCH₃ | 3-I | 2-CH₃ | CH₂ | 1 | Q9 | C₂F₅ | CF₃ | — |
| 943 | C(CH₃)₂CH₂SOCH₃ | 3-I | 2-CH₃ | CH₂ | 1 | Q9 | C₂F₅ | CF₃ | — |
| 944 | C(CH₃)₂CH₂SO₂CH₃ | 3-I | 2-CH₃ | CH₂ | 1 | Q9 | C₂F₅ | CF₃ | — |
| 945 | CH(CH₃)CH₂SCH₃ | 3-I | 2-CH₃ | CH₂ | 1 | Q9 | C₂F₅ | CF₃ | — |
| 946 | CH(CH₃)CH₂SOCH₃ | 3-I | 2-CH₃ | CH₂ | 1 | Q9 | C₂F₅ | CF₃ | — |
| 947 | CH(CH₃)CH₂SO₂CH₃ | 3-I | 2-CH₃ | CH₂ | 1 | Q9 | C₂F₅ | CF₃ | — |
| 948 | CH(CH₃)CH₂SCH₃ (S)-isomer | 3-I | 2-CH₃ | CH₂ | 1 | Q9 | C₂F₅ | CF₃ | — |
| 949 | CH(CH₃)CH₂SOCH₃ (S)-isomer | 3-I | 2-CH₃ | CH₂ | 1 | Q9 | C₂F₅ | CF₃ | — |
| 950 | CH(CH₃)CH₂SO₂CH₃ (S)-isomer | 3-I | 2-CH₃ | CH₂ | 1 | Q9 | C₂F₅ | CF₃ | — |
| 951 | CH(CH₃)CH₂SC₂H₅ (S)-isomer | 3-I | 2-CH₃ | CH₂ | 1 | Q9 | C₂F₅ | CF₃ | — |
| 952 | CH(CH₃)CH₂SOC₂H₅ (S)-isomer | 3-I | 2-CH₃ | CH₂ | 1 | Q9 | C₂F₅ | CF₃ | — |
| 953 | CH(CH₃)CH₂SO₂C₂H₅ (S)-isomer | 3-I | 2-CH₃ | CH₂ | 1 | Q9 | C₂F₅ | CF₃ | — |
| 954 | C(CH₃)₂CH₂SCH₃ | 3-I | 2-CH₃ | CH(CH₃) | 1 | Q9 | C₂F₅ | C₂F₅ | — |
| 955 | C(CH₃)₂CH₂SCH₃ | 3-I | 2-CH₃ | CH₂ | 1 | Q9 | C₂F₅ | C₂F₅ | — |
| 956 | CH(CH₃)CH₂SCH₃ | 3-I | 2-CH₃ | CH₂ | 1 | Q9 | C₂F₅ | C₂F₅ | — |
| 957 | CH(CH₃)CH₂SCH₃ (S)-isomer | 3-I | 2-CH₃ | CH₂ | 1 | Q9 | C₂F₅ | C₂F₅ | — |
| 958 | C(CH₃)₂CH₂SCH₃ | 3-I | 2-CH₃ | CH₂ | 1 | Q9 | C₃F₇-n | CF₃ | — |
| 959 | CH(CH₃)CH₂SCH₃ (S)-isomer | 3-I | 2-CH₃ | CH₂ | 1 | Q9 | C₃F₇-n | CF₃ | — |
| 960 | C(CH₃)₂CH₂SCH₃ | 3-I | 2-CH₃ | S | 1 | Q18 | CF₃ | CH₃ | — |
| 961 | C(CH₃)₂CH₂SCH₃ | 3-I | 2-CH₃ | — | 0 | Q19 | CF₃ | CH₃ | — |
| 962 | C(CH₃)₂CH₂SCH₃ | 3-I | 2-CH₃ | CH₂ | 1 | Q17 | CF₃ | H | — |
| 963 | C(CH₃)₂CH₂SCH₃ | 3-I | 2-CH₃ | CH₂ | 1 | Q15 | H | C₂F₅ | — |
| 964 | C(CH₃)₂CH₂SCH₃ | 3-I | 2-CH₃ | — | 0 | Q20 | CF₃ | — | — |
| 965 | C(CH₃)₂CH₂SCH₃ | 3-I | 2-CH₃ | — | 0 | Q16 | CF₃ | — | — |
| 966 | C(CH₃)₂CH₂SCH₃ | 3-Cl | 2-F | CH₂ | 1 | Q1 | CF₃ | CF₃ | H |
| 967 | C(CH₃)₂CH₂SOCH₃ | 3-Cl | 2-F | CH₂ | 1 | Q1 | CF₃ | CF₃ | H |
| 968 | C(CH₃)₂CH₂SO₂CH₃ | 3-Cl | 2-F | CH₂ | 1 | Q1 | CF₃ | CF₃ | H |
| 969 | C(CH₃)₂CH₂SCH₃ | 3-Cl | 2-Cl | CH₂ | 1 | Q1 | CF₃ | CF₃ | H |
| 970 | C(CH₃)₂CH₂SOCH₃ | 3-Cl | 2-Cl | CH₂ | 1 | Q1 | CF₃ | CF₃ | H |
| 971 | C(CH₃)₂CH₂SO₂CH₃ | 3-Cl | 2-Cl | CH₂ | 1 | Q1 | CF₃ | CF₃ | H |
| 972 | CH(CH₃)₂SCH₃ | 3-Cl | 2-Cl | CH₂ | 1 | Q1 | CF₃ | CF₃ | H |
| 973 | CH(CH₃)CH₂SOCH₃ | 3-Cl | 2-Cl | CH₂ | 1 | Q1 | CF₃ | CF₃ | H |
| 974 | CH(CH₃)CH₂SO₂CH₃ | 3-Cl | 2-Cl | CH₂ | 1 | Q1 | CF₃ | CF₃ | H |
| 975 | CH(CH₃)CH₂SCH₃ (S)-isomer | 3-Cl | 2-Cl | CH₂ | 1 | Q1 | CF₃ | CF₃ | H |
| 976 | CH(CH₃)CH₂SOCH₃ (S)-isomer | 3-Cl | 2-Cl | CH₂ | 1 | Q1 | CF₃ | CF₃ | H |
| 977 | CH(CH₃)CH₂SO₂CH₃ (S)-isomer | 3-Cl | 2-Cl | CH₂ | 1 | Q1 | CF₃ | CF₃ | H |
| 978 | CH(CH₃)CH₂SCH₃ (S)-isomer | 3-Cl | 2-Cl | CH₂ | 1 | Q1 | C₂F₅ | CF₃ | H |
| 979 | CH(CH₃)CH₂SOCH₃ (S)-isomer | 3-Cl | 2-Cl | CH₂ | 1 | Q1 | C₂F₅ | CF₃ | H |
| 980 | CH(CH₃)CH₂SO₂CH₃ (S)-isomer | 3-Cl | 2-Cl | CH₂ | 1 | Q1 | C₂F₅ | CF₃ | H |
| 981 | C(CH₃)₂CH₂SCH₃ | 3-Cl | 2-Cl | CH₂ | 1 | Q1 | CF₃ | H | C₂F₅ |
| 982 | C(CH₃)₂CH₂SCH₃ | 3-Cl | 2-Cl | CH₂ | 1 | Q1 | CF₃ | H | C₃F₇-n |
| 983 | C(CH₃)₂CH₂SCH₃ | 3-Cl | 2-Cl | CH₂ | 1 | Q1 | CF₃ | H | C₄F₉-n |
| 984 | C(CH₃)₂CH₂SCH₃ | 3-Cl | 2-Cl | CH₂ | 1 | Q1 | CF₃ | H | C₆F₁₃-n |
| 985 | CH(CH₃)CH₂SCH₃ (S)-isomer | 3-Cl | 2-Cl | CH₂ | 1 | Q1 | C₂F₅ | H | C₂F₅ |
| 986 | CH(CH₃)CH₂SOCH₃ (S)-isomer | 3-Cl | 2-Cl | CH₂ | 1 | Q1 | C₂F₅ | H | C₂F₅ |
| 987 | CH(CH₃)CH₂SO₂CH₃ (S)-isomer | 3-Cl | 2-Cl | CH₂ | 1 | Q1 | C₂F₅ | H | C₂F₅ |
| 988 | CH(CH₃)CH₂SCH₃ (S)-isomer | 3-Cl | 2-Cl | CH₂ | 1 | Q1 | C₂F₅ | H | C₃F₇-n |
| 989 | CH(CH₃)CH₂SOCH₃ (S)-isomer | 3-Cl | 2-Cl | CH₂ | 1 | Q1 | C₂F₅ | H | C₃F₇-n |
| 990 | CH(CH₃)CH₂SO₂CH₃ (S)-isomer | 3-Cl | 2-Cl | CH₂ | 1 | Q1 | C₂F₅ | H | C₃F₇-n |
| 991 | CH(CH₃)CH₂SCH₃ (S)-isomer | 3-Cl | 2-Cl | CH₂ | 1 | Q2 | CF₃ | CF₃ | — |
| 992 | CH(CH₃)CH₂SCH₃ (S)-isomer | 3-Cl | 2-Cl | CH₂ | 1 | Q2 | C₂F₅ | CF₃ | — |

TABLE 1-continued

| | | | | | | | | | |
|---|---|---|---|---|---|---|---|---|---|
| 993 | CH(CH₃)CH₂SCH₃ (S)-isomer | 3-Cl | 2-Cl | CH₂ | 1 | Q9 | CF₃ | CF₃ | — |
| 994 | CH(CH₃)CH₂SCH₃ (S)-isomer | 3-Cl | 2-Cl | CH₂ | 1 | Q9 | C₂F₅ | CF₃ | — |
| 995 | C(CH₃)₂CH₂SCH₃ | 3-I | 2-F | CH₂ | 1 | Q1 | CF₃ | CF₃ | H | *** |
| 996 | C(CH₃)₂CH₂SOCH₃ | 3-I | 2-F | CH₂ | 1 | Q1 | CF₃ | CF₃ | H | |
| 997 | C(CH₃)₂CH₂SO₂CH₃ | 3-I | 2-F | CH₂ | 1 | Q1 | CF₃ | CF₃ | H | 113-115 |
| 998 | C(CH₃)₂CH₂SCH₃ | 3-I | 2-Cl | CH₂ | 1 | Q1 | CF₃ | CF₃ | H | 157-159 |
| 999 | C(CH₃)₂CH₂SOCH₃ | 3-I | 2-Cl | CH₂ | 1 | Q1 | CF₃ | CF₃ | H | |
| 1000 | C(CH₃)₂CH₂SO₂CH₃ | 3-I | 2-Cl | CH₂ | 1 | Q1 | CF₃ | CF₃ | H | 129-134 |
| 1001 | C(CH₃)₂CH₂SCH₃ | 3-I | 2-Cl | CH₂ | 1 | Q1 | C₂F₅ | CF₃ | H | |
| 1002 | C(CH₃)₂CH₂SOCH₃ | 3-I | 2-Cl | CH₂ | 1 | Q1 | C₂F₅ | CF₃ | H | |
| 1003 | C(CH₃)₂CH₂SO₂CH₃ | 3-I | 2-Cl | CH₂ | 1 | Q1 | C₂F₅ | CF₃ | H | |
| 1004 | C(CH₃)₂CH₂SCH₃ | 3-I | 2-Cl | CH₂ | 1 | Q1 | C₂F₅ | C₂F₅ | H | |
| 1005 | C(CH₃)₂CH₂SOCH₃ | 3-I | 2-Cl | CH₂ | 1 | Q1 | C₂F₅ | C₂F₅ | H | |
| 1006 | C(CH₃)₂CH₂SO₂CH₃ | 3-I | 2-Cl | CH₂ | 1 | Q1 | C₂F₅ | C₂F₅ | H | |
| 1007 | CH(CH₃)CH₂SCH₃ (S)-isomer | 3-I | 2-Cl | CH₂ | 1 | Q1 | C₂F₅ | H | C₂F₅ | |
| 1008 | CH(CH₃)CH₂SCH₃ (S)-isomer | 3-I | 2-Cl | CH₂ | 1 | Q1 | C₂F₅ | H | C₃F₇-n | |
| 1009 | CH(CH₃)CH₂SCH₃ (S)-isomer | 3-I | 2-Cl | CH₂ | 1 | Q1 | C₂F₅ | H | C₄F₉-n | |
| 1010 | CH(CH₃)CH₂SCH₃ (S)-isomer | 3-I | 2-Cl | CH₂ | 1 | Q1 | C₂F₅ | H | C₆F₁₃-n | |
| 1011 | CH(CH₃)CH₂SCH₃ (S)-isomer | 3-I | 2-Cl | CH₂ | 1 | Q2 | CF₃ | CF₃ | — | |
| 1012 | CH(CH₃)CH₂SCH₃ (S)-isomer | 3-I | 2-Cl | CH₂ | 1 | Q2 | C₂F₅ | CF₃ | — | |
| 1013 | CH(CH₃)CH₂SCH₃ (S)-isomer | 3-I | 2-Cl | CH₂ | 1 | Q2 | C₂F₅ | C₂F₅ | — | |
| 1014 | CH(CH₃)CH₂SCH₃ (S)-isomer | 3-I | 2-Cl | CH₂ | 1 | Q2 | C₃F₇-n | CF₃ | — | |

TABLE 2

| No. | | |
|---|---|---|
| 1 | 1H-NMR | (CDCl3, ppm): 1.4 (6H, s), 2.0 (3H, s), 2.3 (3H, s), 2.9 (2H, s), 5.4 (2H, s), 6.2 (1H, s), 6.9 (1H, s), 7.3-8.7 (8H, m) |
| 3 | 1H-NMR | (CDCl3, ppm): 1.5 (6H, s), 2.2 (3H, s), 2.6 (3H, s), 3.7 (2H, s), 5.4 (2H, s), 6.4 (1H, s), 6.9 (1H, s), 7.3-8.2 (8H, m) |
| 8 | 1H-NMR | (CDCl3, ppm): 1.4 (6H, s), 2.0 (3H, s), 2.3 (3H, s), 2.9 (2H, s), 5.4 (2H, s), 6.1 (1H, s), 6.9 (1H, s), 7.3-8.4 (7H, m) |
| 11 | 1H-NMR | (CDCl3, ppm): 1.2 (3H, d), 1.9 (3H, s), 2.3 (3H, s), 2.7 (2H, dd), 4.2 (1H, m), 5.4 (2H, s), 6.4 (1H, d), 6.9 (1H, s), 7.3-8.4 (7H, m) |
| 15 | 1H-NMR | (CDCl3, ppm): 1.3 (3H, d), 2.2 (3H, s), 2.8 (3H, s), 3.2 (2H, m), 4.6 (1H, m), 5.4 (2H, s), 6.4 (1H, d), 6.9-8.4 (8H, m) |
| 47 | 1H-NMR | (CDCl3, ppm): 1.6 (6H, s), 2.3 (3H, s), 2.5 (3H, s), 3.5 (2H, s), 5.4 (2H, s), 6.6 (1H, s), 6.9 (1H, s), 7.3-8.2 (7H, m) |
| 52 | 1H-NMR | (CDCl3, ppm): 1.4 (3H, d), 2.2 (3H, s), 2.7 (3H, s), 3.2 (2H, m), 4.4 (1H, m), 5.4 (2H, s), 6.9-8.2 (9H, m) |
| 81 | 1H-NMR | (CDCl3, ppm): 1.1 (6H, d), 2.2 (3H, s), 4.2 (1H, m), 5.3 (2H, s), 5.9 (1H, d), 6.9-8.2 (8H, m) |
| 83 | 1H-NMR | (CDCl3, ppm): 1.57 (3H, s), 1.60 (3H, s), 2.20 (3H, s), 2.30 (3H, s), 2.93 (2H, dd), 5.43 (2H, s), 6.57 (1H, s), 6.90 (1H, s), 7.0-8.2 (7H, m) |
| 85 | 1H-NMR | (CDCl3, ppm): 1.2 (3H, d), 1.8 (3H, s), 2.2 (3H, s), 2.6 (2H, dd), 4.2 (1H, m), 5.3 (2H, s), 6.5 (1H, d), 6.9 (1H, s), 7.3-8.4 (7H, m) |
| 89 | 1H-NMR | (CDCl3, ppm): 1.4 (3H, d), 2.2 (3H, s), 2.7 (3H, s), 3.2 (2H, m), 4.5 (1H, m), 5.3 (2H, s), 6.6 (1H, d), 6.9-7.9 (8H, m) |
| 94 | 1H-NMR | (CDCl3, ppm): 1.57 (3H, s), 1.60 (3H, s), 2.20 (3H, s), 2.30 (3H, s), 2.93 (2H, dd), 5.43 (2H, s), 6.57 (1H, s), 6.90 (1H, s), 7.0-8.2 (7H, m) |
| 96 | 1H-NMR | (CDCl3, ppm): 1.63 (6H, s), 2.27 (3H, s), 2.50 (3H, s), 3.47 (2H, s), 5.30 (2H, s), 6.23 (1H, s), 6.57 (1H, s), 7.0-8.1 (8H, m) |
| 97 | 1H-NMR | (CDCl3, ppm): 1.27 (3H, d), 1.93 (3H, s), 2.30 (3H, s), 2.63 (2H, m), 4.33 (1H, m), 5.37 (2H, s), 6.07 (1H, m), 6.60 (1H, s), 6.9-8.2 (8H, m) |
| 99 | 1H-NMR | (CDCl3, ppm): 1.50 (3H, d), 2.27 (3H, s), 2.70 (3H, s), 3.0-3.5 (2H, m), 4.60 (1H, m), 5.37 (2H, s), 6.5-8.0 (10H, m) |
| 103 | 1H-NMR | (CDCl3, ppm): 1.27 (3H, d), 1.93 (3H, s), 2.30 (3H, s), 2.60 (2H, m), 4.33 (1H, m), 5.20 (2H, s), 6.17 (1H, s), 6.47 (1H, t), 7.1-8.3 (8H, m) |
| 107 | 1H-NMR | (CDCl3, ppm): 1.50 (3H, d), 1.93 (3H, s), 2.30 (3H, s), 2.60 (2H, m), 4.33 (1H, m), 5.20 (2H, s), 6.17 (1H, s), 6.47 (1H, t), 6.67 (1H, s), 7.0-8.1 (7H, m) |
| 116 | 1H-NMR | (CDCl3, ppm): 1.2 (3H, d), 1.9 (3H, s), 2.2 (3H, s), 2.6 (2H, dd), 4.2 (1H, m), 5.2 (2H, s), 6.4 (1H, d), 7.0-8.3 (9H, m) |
| 149 | 1H-NMR | (CDCl3, ppm): 1.34 (6H, s), 1.95 (3H, s), 2.33 (3H, s), 2.86 (2H, s), 5.48 (2H, s), 6.11 (1H, s), 7.56-7.00 (4H, m), 7.84-7.72 (1H, m), 8.23 (1H, d), 8.49 (1H, s) |
| 153 | 1H-NMR | (CDCl3, ppm): 1.22 (3H, d), 2.05 (3H, s), 2.30 (3H, s), 2.61-2.53 (2H, m), 4.40-4.29 (1H, m), 5.44 (2H, s), 6.19 (1H, s), 7.17 (2H, t), 7.54-7.48 (2H, m), 7.73 (1H, d), 8.15 (1H, d), 8.44 (1H, s) |

TABLE 2-continued

| No. | | |
|---|---|---|
| 180 | 1H-NMR | (CDCl3, ppm): 1.3 (3H, d), 2.2 (3H, s), 2.3 (3H, s), 2.8 (2H, d), 4.5 (1H, m), 5.4 (2H, s), 7.1-8.3 (8H, m) |
| 242 | 1H-NMR | (CDCl3, ppm): 1.4 (3H, d), 2.2 (3H, s), 2.8 (3H, s), 3.2 (2H, m), 4.6 (1H, m), 5.5 (2H, s), 6.2-8.2 (9H, m) |
| 251 | 1H-NMR | (CDCl3, ppm): 1.25 (3H, d), 1.95 (3H, s), 2.28 (3H, s), 2.63-2.51 (2H, m), 3.28 (3H, s), 4.36-4.26 (1H, m), 5.43 (2H, s), 6.38 (1H, d, J = 9.3 Hz), 7.39-7.16 (2H, m), 7.62-7.53 (2H, m), 7.81-7.74 (1H, m), 8.38 (1H, s) |
| 271 | 1H-NMR | (CDCl3, ppm): 1.47 (6H, s), 2.00 (3H, s), 2.30 (3H, s), 2.83 (2H, s), 3.30 (1H, m), 4.2-4.6 (4H, m), 6.07 (1H, s), 7.1-8.2 (7H, m) |
| 277 | 1H-NMR | (CDCl3, ppm): 1.1 (6H, d), 2.2 (3H, s), 4.1 (1H, m), 5.0 (2H, s), 6.0 (1H, d), 7.0-8.4 (8H, m) |
| 417 | 1H-NMR | (CDCl3, ppm): 1.5 (3H, d), 2.3 (3H, s), 2.8 (3H, s), 3.2 (2H, dd), 4.7 (1H, m), 6.5 (1H, m), 7.0 (1H, s), 7.3-8.3 (6H, m) |
| 422 | 1H-NMR | (CDCl3, ppm): 1.47 (6H, s), 2.03 (3H, s), 2.40 (3H, s), 2.87 (2H, s), 6.03 (1H, s), 6.80 (1H, m), 7.1-8.6 (8H, m) |
| 434 | 1H-NMR | (CDCl3, ppm): 1.40 (6H, s), 2.03 (3H, s), 2.40 (3H, s), 2.87 (2H, s), 6.07 (1H, s), 6.77 (1H, m), 7.2-8.5 (8H, m) |
| 521 | 1H-NMR | (CDCl3, ppm): 1.23 (3H, d), 1.90 (3H, s), 2.26 (3H, s), 2.50-2.67 (2H, m), 4.10-4.50 (1H, m), 5.37 (2H, s), 6.15 (1H, d), 6.60 (1H, bs), 6.90-7.20 (3H, m), 7.57 (1H, bs), 7.70 (1H, d), 7.80-8.23 (3H, m) |
| 522 | 1H-NMR | (CDCl3, ppm): 1.50 (3H, d), 2.30 (3H, s), 2.70 (3H, s), 2.97-3.50 (2H, m), 4.56 (1H, m), 5.43 (2H, s), 6.60-8.03(10H, m) |
| 523 | 1H-NMR | (CDCl3, ppm): 1.40 (6H, s), 1.98 (3H, s), 2.30 (3H, s), 2.73 (2H, s), 5.40 (2H, s), 6.03 (1H, bs), 6.60-7.20 (4H, m), 7.50-8.20 (5H, m) |
| 529 | 1H-NMR | (CDCl3, ppm): 1.42 (6H, s), 1.98 (3H, s), 2.30 (3H, s), 2.71 (2H, s), 5.30 (2H, s), 6.03 (1H, bs), 6.52 (1H, d), 7.03-7.35 (4H, m), 7.73 (1H, d), 7.93 (1H, d), 8.10-8.40 (2H, m) |
| 530 | 1H-NMR | (CDCl3, ppm): 1.63 (6H, s), 2.30 (3H, s), 2.57 (3H, s), 3.47 (2H, s), 5.30 (2H, s), 6.40 (1H, bs), 6.57 (1H, d), 7.03-8.1 7 (8H, m) |
| 532 | 1H-NMR | (CDCl3, ppm): 1.30 (4H, dd), 1.97 (3H, s), 2.28 (3H, s), 2.73-2.42 (2H, m), 4.37-4.28 (1H, m), 5.28 (2H, s), 6.42 (1H, d), 6.55 (1H, d), 7.09 (2H, t), 7.42-7.39 (2H, m), 7.51 (1H, d), 7.70 (1H, t), 8.02 (1H, d), 8.49 (1H, d) |
| 534 | 1H-NMR | (CDCl3, ppm): 1.24 (3H, d), 1.93 (3H, s), 2.30 (3H, s), 2.50-2.66 (2H, m), 4.23-4.40 (1H, m), 5.32 (2H, s), 6.16 (1H, d), 6.54 (1H, d), 7.06 (1H, bs), 7.11 (1H, d), 7.22 (1H, t), 7.40 (1H, d), 7.78 (1H, d), 7.97 (1H, d), 8.17 (1H, d), 8.30 (1H, bs) |
| 536 | 1H-NMR | (CDCl3, ppm): 1.50 (3H, d), 2.28 (3H, s), 2.73 (3H, s), 2.97-3.50 (2H, m), 4.60 (1H, m), 5.30 (2H, s), 6.53 (1H, d), 6.73 (1H, d), 7.00-8.07(8H, m) |
| 537 | 1H-NMR | (CDCl3, ppm): 1.40(6H, s), 1.98 (3H, s), 2.31 (3H, s), 2.81 (2H, s), 5.32 (2H, s), 6.08 (1H, bs), 6.54 (1H, d), 7.04 (1H, bs) 7.11 (1H, d), 7.20 (1H, t), 7.38 (1H, d), 7.79 (1H, d), 7.96 (1H, d), 8.22 (1H, d), 8.38 (1H, bs) |
| 538 | 1H-NMR | (CDCl3, ppm): 1.66(6H, s), 2.30 (3H, s), 2.60 (3H, s), 3.52 (2H, s), 5.30 (2H, s), 6.47 (1H, bs), 6.57 (1H, d), 7.03-8.23 (8H, m) |
| 550 | 1H-NMR | (CDCl3, ppm): 1.48 (6H, d), 2.21 (3H, s), 2.48 (3H, s), 4.13 (1H, m), 5.42 (2H, s), 6.18(1H, d), 6.91 (1H, s), 7.1-7,6 (6H, m), 8.08 (1H, d) |
| 552 | 1H-NMR | (CDCl3, ppm): 1.17 (3H, d), 1.89 (3H, s), 2.29 (3H, s), 2.42 (1H, dd), 2.60 (1H, dd), 3.29 (3H, s), 4.24 (1H, m), 5.42 (2H, s), 6.41 (1H, d), 6.92 (1H, s), 7.1-7.2 (2H, m), 7.6-8.2 (5H, m) |
| 553 | 1H-NMR | (CDCl3, ppm): 1.21 (3H, d), 1.32 (3H, t), 1.95 (3H, s), 2.29 (3H, s), 2.51 (1H, dd), 2.60 (1H, dd), 3.00 (2H, q), 4.31 (1H, m), 5.41 (2H, s), 6.28 (1H, d), 6.91 (1H, s), 7.1-7.2 (2H, m), 7.4-7.6 (3H, m), 8.09 (1H, d), 8.34 (1H, s) |
| 554 | 1H-NMR | (CDCl3, ppm): 1.25 (5H, dd), 1.91 (3H, s), 2.29 (3H, s), 2.60-2.54 (2H, m), 4.32-4.27 (1H, m), 5.44 (2H, s), 6.40 (1H, d), 7.06 (2H, d, J = 7.5 Hz), 7.19-7.12 (1H, m), 7.71 (1H, d), 7.94-7.91 (1H, m), 8.08 (1H, d), 8.36 (1H, s) |
| 569 | 1H-NMR | (CDCl3, ppm): 8.50 (1H, m), 7.95 (1H, m), 7.79-7.49 (4H, m), 7.44-7.38 (1H, m), 7.22 (1H, m), 5.75 (1H, q), 4.38 (1H, m), 2.79 (2H, m), 2.29 (3H, s), 2.20 (3H, s), 2.00 (3H, d), 1.43-1.18 (3H, d) |
| 574 | 1H-NMR | (CDCl3, ppm): 1.31 (3H, d), 1.95 (3H, s), 2.30 (3H, s), 2.61-2.57 (2H, m), 4.37-4.27 (1H, m), 5.79-5.73 (1H, m), 6.48 (1H, d), 7.02 (1H, s), 7.25-7.21 (2H, m), 7.52-7.36 (3H, m), 7.84-7.69 (2H, m), 8.04 (1H, d), 8.50 (1H, s) |
| 594 | 1H-NMR | (CDCl3, ppm): 1.22 (3H, d), 1.93 (3H, s), 2.26 (3H, s), 2.61-2.55 (2H, m), 4.36-4.27 (1H, m), 5.49 (2H, s), 6.07 (1H, d), 6.34-6.30 (1H, m), 6.98 (2H, d), 7.13 (1H, t), 7.27-7.22 (3H, m), 7.79 (1H, d), 7.97 (1H, dd), 8.08 (1H, d), 8.23 (1H, s) |
| 595 | 1H-NMR | (CDCl3, ppm): 1.25 (3H, d), 1.94 (3H, s), 2.27 (3H, s), 2.60-2.54 (2H, m), 4.34-4.25 (1H, m), 5.49 (2H, d), 6.42 (1H, d), 7.04-6.99 (2H, m), 7.21-7.14 (2H, m), 7.35-7.32 (1H, m), 7.72 (1H, d), 7.93 (1H, dd), 8.05 (1H, d), 8.36 (1H, s) |
| 596 | 1H-NMR | (CDCl3, ppm): 1.24 (3H, d), 1.97 (3H, s), 2.33 (3H, s), 2.63-2.54 (2H, m), 4.35-4.30 (1H, m), 5.52 (2H, s), 6.05 (1H, d), 7.02-7.00 (2H, m), 7.26-7.21 (1H, m), 7.35-7.32 (1H, m), 7.42-7.39 (1H, m), 7.80 (1H, t), 7.98 (1H, d), 8.18 (1H, t), 8.32 (1H, d) |
| 626 | 1H-NMR | (CDCl3, ppm): 1.22 (3H, d), 1.92 (3H, s), 2.30 (3H, s), 2.54 (1H, dd), 2.61 (1H, dd), 4.32 (1H, m), 5.46 (2H, s), 6.23 (1H, m), 6.94 (1H, s), 7.0-7.1 (2H, m), 7.45 (1H, m), 7.54 (1H, d), 7.72 (1H, d), 8.07 (1H, d), 8.38 (1H, bs) |
| 632 | 1H-NMR | (CDCl3, ppm): 1.26 (3H, dd), 1.96 (3H, s), 2.32 (3H, s), 2.61-2.55 (2H, m), 4.34-4.29 (1H, m), 5.22 (2H, s), 6.22 (1H, d), 7.21-7.13 (3H, m), 7.36 (1H, d), 7.78 (1H, d), 7.97 (1H, dd), 8.16 (1H, d), 8.35 (1H, s) |
| 633 | 1H-NMR | (CDCl3, ppm): 1.23 (3H, dd), 1.97 (3H, s), 2.31 (3H, s), 2.61-2.56 (2H, m), 4.37-4.32 (1H, m), 5.25 (2H, s), 6.13 (1H, d), 7.11 (2H, dd), 7.37 (1H, t), 7.48 (1H, dd), 7.61-7.53 (1H, m), 7.79 (1H, dt), 8.15 (1H, d), 8.43 (1H, d) |

TABLE 2-continued

| No. | | |
|---|---|---|
| 634 | 1H-NMR | (CDCl3, ppm): 1.25 (4H, dd), 1.98 (3H, s), 2.33 (3H, s), 2.61-2.56 (2H, m), 8.41 (1H, s), 4.38-4.31 (1H, m), 5.24 (2H, s), 6.17 (1H, d), 7.13-7.11 (2H, m), 7.38 (1H, s), 7.46 (1H, t), 7.56 (1H, dd), 7.79 (1H, t), 8.14 (1H, d) |
| 635 | 1H-NMR | (CDCl3, ppm): 1.26 (3H, dd), 1.94 (3H, s), 2.31 (3H, s), 2.61-2.52 (2H, m), 4.33-4.29 (1H, m), 5.24 (2H, s), 6.34 (1H, d), 7.21-7.11 (3H, m), 7.39 (1H, d), 7.75 (1H, d), 7.95 (1H, dd), 8.13 (1H, d, )8.38 (1H, s) |
| 636 | 1H-NMR | (CDCl3, ppm): 1.25 (3H, dd), 1.93 (2H, s), 2.31 (3H, s), 2.65-2.52 (2H, m), 4.32-4.29 (1H, m), 5.26 (2H, s), 6.40 (1H, d), 7.21-7.11 (3H, m), 8.39 (1H, s), 7.42 (1H, s), 7.74 (1H, d), 7.94 (1H, d), 8.11 (1H, d) |
| 640 | 1H-NMR | (CDCl3, ppm): 1.29 (3H, dd), 1.95 (3H, s), 2.32 (3H, s), 2.62-2.54 (2H, m), 4.34-4.27 (1H, m), 5.31 (2H, s), 6.21 (1H, d), 7.96 (1H, d), 8.19 (1H, t), 7.21-7.13 (3H, m), 7.62 (1H, s), 7.78 (1H, d), 8.37 (1H, d) |
| 651 | 1H-NMR | (CDCl3, ppm): 1.24 (3H, dd), 1.96 (3H, s), 2.31 (3H, s), 2.60-2.55 (2H, m), 4.36-4.31 (1H, m), 5.31 (2H, s), 6.34 (1H, d), 7.16-7.14 (2H, m), 7.43 (1H, t), 7.53 (1H, dd), 7.64 (1H, s), 7.71 (1H, d), 8.12 (1H, d), 8.50 (1H, s) |
| 654 | 1H-NMR | (CDCl3, ppm): 1.26 (3H, dd), 1.93 (3H, s), 2.34 (3H, s), 2.62-2.55 (2H, m), 4.34-4.29 (1H, m), 5.31 (2H, s), 6.23 (1H, d), 7.24-7.14 (3H, m), 7.63 (1H, s), 7.78 (1H, d), 7.97 (1H, dd), 8.20 (1H, d), 8.37 (1H, s) |
| 658 | 1H-NMR | (CDCl3, ppm): 1.44-1.38 (3H, m), 2.35-2.30 (6H, m), 2.90-2.77 (2H, m), 4.56-4.48 (1H, m), 5.32 (2H, s), 7.18-7.14 (3H, m), 7.44-7.37 (1H, m), 7.56-7.52 (1H, m), 7.67-7.64 (2H, m), 8.10-8.07 (1H, m), 8.44-8.39 (1H, m) |
| 660 | 1H-NMR | (CDCl3, ppm): 1.25 (4H, dd), 1.90 (3H, s), 2.31 (3H, s), 2.63-2.55 (2H, m), 4.37-4.28 (1H, m), 5.34 (2H, s), 6.12 (1H, d), 7.22-7.15 (2H, m), 7.63 (1H, d), 7.83 (1H, t), 7.98 (1H, dt), 8.25 (1H, t), 8.34 (1H, s) |
| 675 | 1H-NMR | (CDCl3, ppm): 1.23 (3H, d), 1.97 (3H, s), 2.33 (3H, s), 2.63-2.54 (2H, m), 4.38-4.29 (1H, m), 5.41 (2H, s), 6.21 (1H, d), 7.09 (2H, d), 7.44 (1H, t), 7.54 (1H, d), 7.73 (1H, d), 7.84 (1H, s), 8.07 (1H, d), 8.38 (1H, s) |
| 681 | 1H-NMR | (CDCl3, ppm): 1.25 (3H, d), 1.95 (3H, s), 2.32 (3H, s), 2.62-2.54 (2H, m), 4.36-4.32 (1H, m), 5.52 (2H, s), 6.13 (1H, d), 7.18-7.16 (2H, m), 7.57-7.47 (2H, m), 7.76 (1H, d), 8.17 (1H, d), 8.41 (1H, s) |
| 714 | 1H-NMR | (CDCl3, ppm): 1.24 (3H, d), 1.99 (3H, s), 2.30 (3H, s), 2.64-2.52 (2H, m), 4.38-4.29 (1H, m), 5.49 (2H, s), 6.15 (1H, d), 7.17-7.15 (2H, m), 7.57-7.43 (2H, m), 7.75 (1H, d), 8.17 (1H, d), 8.41 (1H, s) |
| 726 | 1H-NMR | (CDCl3, ppm): 1.45-1.37 (3H, m), 2.32-2.30 (6H, m), 2.87-2.83 (2H, m), 4.61-4.46 (1H, m), 5.44 (2H, s), 6.90-6.88 (1H, m), 7.12-7.09 (2H, m), 7.45-7.42 (1H, m), 7.55-7.52 (1H, m), 7.68-7.66 (1H, m), 7.79-7.77 (1H, m), 8.06-8.04 (1H, m), 8.32-8.24 (1H, m) |
| 727 | 1H-NMR | (CDCl3, ppm): 1.44 (3H, d), 2.30 (3H, s), 2.75 (3H, s), 3.24-3.21 (2H, m), 4.62-4.53 (1H, m), 5.44 (2H, s), 6.87-6.85 (1H, m), 7.08-7.06 (2H, m), 7.42-7.32 (1H, m), 7.50-7.47 (1H, m), 7.60-7.57 (1H, m), 7.77 (1H, s), 7.91-7.87 (1H, m), 8.17-8.14 (1H, m) |
| 729 | 1H-NMR | (CDCl3, ppm): 1.45 (3H, d), 2.29 (3H, s), 2.75 (3H, s), 3.34-3.12 (2H, m), 4.59-4.54 (1H, m), 5.38 (2H, s), 6.86 (1H, d), 7.09-7.06 (2H, m), 7.43-7.33 (1H, m), 7.52-7.46 (1H, m), 7.59 (1H, d), 7.84 (1H, s), 7.90 (1H, d), 8.15 (1H, s) |
| 730 | 1H-NMR | (CDCl3, ppm): 1.23 (3H, d), 1.96 (3H, s), 2.29 (3H, s), 2.5-2.7 (2H, m), 4.31 (1H, m), 5.34 (2H, s), 6.31 (1H, d), 6.4-7.2 (5H, s), 7.4-7.8 (3H, m), 8.06 (1H, d), 8.41 (1H, bs) |
| 741 | 1H-NMR | (CDCl3, ppm): 1.26 (3H, d), 1.95 (3H, s), 2.18 (3H, s), 2.30 (3H, s), 2.66-2.48 (2H, m), 4.39-4.20 (1H, m), 5.31 (2H, s), 6.25 (1H, d), 7.07-7.01 (2H, m), 7.44-7.41 (2H, m), 7.55-7.51 (2H, m), 7.71 (1H, d), 8.01 (1H, d), 8.32 (1H, s) |
| 778 | 1H-NMR | (CDCl3, ppm): 1.31 (3H, d), 1.95 (3H, s), 2.33 (3H, t), 2.61-2.56 (2H, m), 4.40-4.29 (1H, m), 5.28 (2H, s), 6.50-6.11 (2H, m), 7.15-7.12 (2H, m), 7.45-7.42 (1H, m), 7.55-7.52 (1H, m), 7.64 (1H, s), 7.72 (1H, d), 8.12 (1H, d), 8.50 (1H, s) |
| 799 | 1H-NMR | (CDCl3, ppm): 1.23 (3H, d), 1.93 (3H, s), 2.32 (3H, s), 2.56 (2H, m), 4.22 (1H, m), 5.52 (2H, s), 6.55-6.02 (3H, m), 7.21 (2H, m), 7.57-7.43 (2H, m), 7.76 (1H, d), 8.15 (1H, d), 8.39 (1H, s) |
| | 1H-NMR | (CDCl3, ppm): 1.24 (3H, d), 1.94 (3H, s), 2.28 (3H, s), 2.52 (1H, dd), 2.62 (1H, dd), 4.30 (1H, m), 5.38 (2H, s), 6.4-7.2 (7H, m), 7.72 (1H, d), 7.93 (1H, d), 8.06 (1H, d), 8.41 (1H, bs) |
| | 1H-NMR | (CDCl3, ppm): 1.40 (6H, s), 1.93 (3H, s), 2.77 (2H, s), 5.40 (2H, s), 5.93 (1H, bs), 6.87-7.23 (4H, m), 7.63-7.95 (2H, m), 8.35-8.65 (2H, m) |

Synthesis Example 6

Starting Material

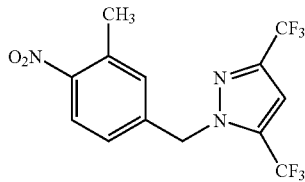

3-Methyl-4-nitrobenzyl chloride (1.81 g), 3,5-bis(trifluoromethyl)-1H-pyrazole (2.0 g) and potassium carbonate (1.63 g) were stirred in DMF (20 ml) at 60° C. for 1 hour. After finishing the reaction, water (100 ml) was added thereto and the mixture was extracted with ethyl acetate. The organic layer was washed with saturated aqueous solution of sodium chloride (100 ml) and dried with anhydrous sodium sulfate. After distilling off the solvent, the obtained residue was purified by silica gel column chromatography to obtain 1-(3-methyl-4-nitrobenzyl)-3,5-bis-(trifluoromethyl)-1H-pyrazole (3.3 g).

$^1$H-NMR (CDCl$_3$, ppm): 2.59 (3H, s), 5.50 (2H, s), 6.90 (1H, s), 7.1-7.2 (2H, m), 8.00 (1H, d).

Synthesis Example 7

Starting Material

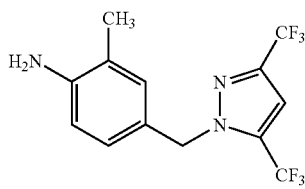

To a mixture of 1-(3-methyl-4-nitrobenzyl)-3,5-bis(trifluoromethyl)-1H-pyrazole (1.4 g), ammonium acetate (30.5 g), acetone (60 ml) and water (30 ml), 20% aqueous solution of titanium trichloride (27.5 g) was added at room temperature and the mixture was stirred at room temperature for 12 hours. After finishing the reaction, the mixture was extracted with ethyl acetate, washed with saturated aqueous solution of sodium chloride and dried with anhydrous sodium sulfate. After distilling off the solvent, the obtained residue was purified by silica gel column chromatography to obtain 1-(3-methyl-4-aminobenzyl)-3,5-bis(trifluoromethyl)-1H-pyrazole (1.19 g).

$^1$H-NMR (CDCl$_3$, ppm): 2.14 (3H, s), 3.66 (2H, m), 5.32 (2H, s), 6.62 (1H, d), 6.89 (1H, s), 6.8-7.1 (2H, m).

Synthesis Example 8

Starting Material

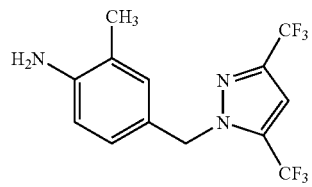

1-(3-Methyl-4-nitrobenzyl)-3,5-bis(trifluoromethyl)-1H-pyrazole (17.66 g) and iron powder (13.69 g) were heated and stirred in acetic acid (150 ml) at 40° C. for 5 hours. After finishing the reaction, an insoluble matter was filtered with Celite and the filtrate was concentrated under the reduced pressure. To the residue, 1N aqueous solution of sodium hydrate (200 ml) and ethyl acetate (200 ml) were added. The organic layer was separated, washed with water, and then, dried with anhydrous magnesium sulfate. After distilling off the solvent, 1-(3-methyl-4-aminobenzyl)-3,5-bis(trifluoromethyl)-1H-pyrazole (13.0 g), which was the same as that obtained in Synthesis Example 7, was obtained.

Synthesis Example 9

Starting Material

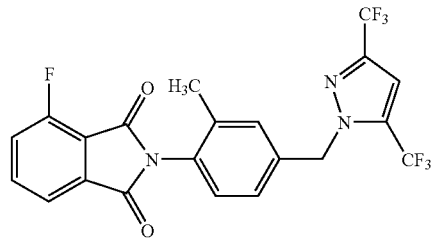

3-Fluorophthalic anhydride (4.98 g) and 1-(3-methyl-4-aminobenzyl)-3,5-bis(trifluoromethyl)-1H-pyrazole (9.70 g) were refluxed in acetic acid (43 ml) for 3 hours. After finishing the reaction, the acetic acid was distilled off under the reduced pressure and the obtained crude crystals were washed with t-butyl methyl ether to obtain the aimed 2-{4-

[3,5-bis(trifluoromethyl)-1H-pyrazol-1-yl-methyl]-2-methylphenyl}-4-fluoroisoindol-1,3-dione (10.80 g). mp. 158-159° C.

Synthesis Example 10

Starting Material

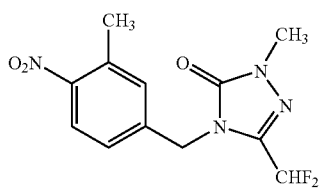

3-Methyl-4-nitrobenzyl chloride (0.56 g), 5-(difluoromethyl)-1,2-dihydro-2-methyl-3H-1,2,4-(triazol)-3-one (0.45 g) and potassium carbonate (0.61 g) were stirred in DMF (10 ml) at 50° C. for 5 hours. After finishing the reaction, the reaction mixture was poured into ice water and extracted with ethyl acetate. The organic layer was washed with saturated aqueous solution of sodium chloride and then dried with anhydrous magnesium sulfate, and the solvent was distilled off under the reduced pressure. The obtained residue was purified by silica gel column chromatography to obtain the aimed 5-difluoromethyl-2-methyl-4-(3-methyl-4-nitrobenzyl)-2,4-dihydro-[1,2,4]triazol-3-one (0.45 g).

$^1$H-NMR (CDCl$_3$, ppm): 2.5 (3H, s), 3.5 (3H, s), 4.9 (2H, s), 6.4 (1H, t), 7.2-7.3 (2H, m), 7.8-7.9 (1H, m).

Synthesis Example 11

Starting Material

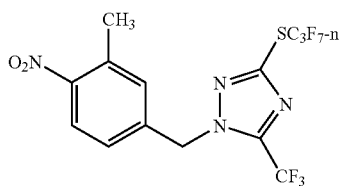

3-Methyl-4-nitrobenzyl chloride (0.43 g), 3-heptafluoropropylsulfanyl-5-trifluoromethyl-1H-(1,2,4)-triazole (0.70 g), tetrabutylammonium iodide (0.09 g), 18-crown-6 (0.06 g) and potassium carbonate (0.48 g) were refluxed in acetonitrile (10 ml) for 2 hours. After cooling, the reaction solution was diluted with ethyl acetate and washed with water and saturated aqueous solution of sodium chloride. After drying the organic layer with magnesium sulfate, the solvent was distilled off under the reduced pressure and the obtained residue was purified by silica gel column chromatography to obtain 3-heptafluoropropylsulfanyl-1-(3-methyl-4-nitrobenzyl)-5-trifluoromethyl-1H-(1,2,4)-triazole (0.30 g).

$^1$H-NMR (CDCl$_3$, ppm): 2.64 (3H, s), 5.62 (2H, s), 7.31-7.25 (2H, m), 8.05-7.86 (1H, m)

Synthesis Example 12

Starting Material

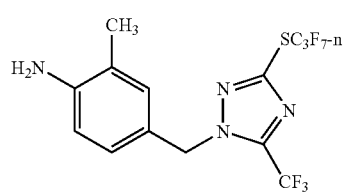

To a mixture of 3-heptafluoropropylsulfanyl-1-(3-methyl-4-nitrophenyl)-5-trifluoromethyl-1H-(1,2,4)-triazole (0.3 g), ammonium acetate (4.8 g), acetone (20 ml) and water (10 ml), 20% aqueous solution of titanium trichloride (4.3 g) was added at room temperature and the mixture was stirred at room temperature for 12 hours. After finishing the reaction, the mixture was extracted with ethyl acetate, washed with saturated aqueous solution of sodium chloride and dried with anhydrous sodium sulfate. After distilling off the solvent, the obtained residue was purified by silica gel column chromatography to obtain 4-(3-heptafluoropropylsulfanyl-5-trifluoromethyl-[1,2,4]triazol-1-ylmethyl)-2-methyl-phenylamine (0.28 g)

$^1$H-NMR (CDCl$_3$, ppm): 2.17 (3H, s), 4.16 (1H, brs), 5.40 (2H, s), 6.63-6.59 (2H, m), 7.13-6.99 (1H, m).

Synthesis Example 13

Starting Material

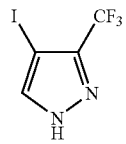

An acetonitrile solution (30 ml) of 3-trifluoromethyl-1H-pyrazole (5.0 g), dicerium ammonium nitrate (10.0 g) and iodine (5.6 g) was refluxed for 1 hour. After cooling, the reaction solution was washed with saturated aqueous solution of sodium thiosulfate and saturated aqueous solution of sodium chloride. After drying the organic layer with magnesium sulfate, the solvent was distilled off under the reduced pressure to obtain 4-iodo-3-trifluoromethyl-1H-pyrazole (9.3 g)

$^1$H-NMR (CDCl$_3$, ppm): 7.77 (1H, s). .

Synthesis Example 14

Starting Material

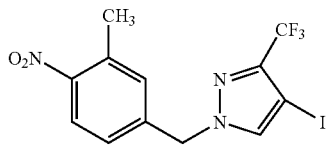

3-Methyl-4-nitrobenzyl chloride (0.77 g), 4-iodo-3-trifluoromethyl-1H-pyrazole (0.99 g) and potassium carbonate (0.63 g) were stirred in DMF (10 ml) at 60° C. for 1 hour. After cooling, the reaction solution was diluted with ethyl acetate and washed with water and saturated aqueous solution of sodium chloride. After drying the organic layer with magnesium sulfate, the solvent was distilled off under the reduced pressure and the obtained residue was purified by silica gel column chromatography to obtain 4-iodo-1-(3-methyl-4-nitrobenzyl)-3-trifluoromethyl-1H-pyrazole (1.0 g).

$^1$H-NMR (CDCl$_3$, ppm): 2.62 (3H, s), 5.36 (2H, s), 7.21-7.18 (2H, m), 7.52 (1H, s), 7.98 (1H, d).

Synthesis Example 15

Starting Material

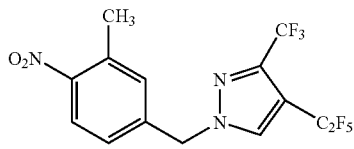

4-Iodo-1-(3-methyl-4-nitrobenzyl)-3-trifluoromethyl-1H-pyrazole (2.06 g), copper powder (0.95 g), iodopentafluoroethane (4.92 g) and DMF (13 ml) were set in an autoclave and heated and stirred for 8 hours, maintaining the inside temperature of 130-135° C. After cooling to room temperature, the reaction mixture was diluted with ethyl acetate (50 ml) and an insoluble matter was filtered with Celite and washed with ethyl acetate. The filtrate was concentrated under the reduced pressure and the obtained residue was purified by silica gel column chromatography to obtain 1-(3-methyl-4-nitrobenzyl)-4-pentafluoroethyl-3-trifluoromethyl-1H-pyrazole (1.39 g)

$^1$H-NMR (CDCl$_3$, ppm): 2.63 (3H, s), 5.38 (2H, s), 7.21-7.27 (2H, m), 7.74 (1H, s), 8.00 (1H, d).

Synthesis Example 16

Starting Material

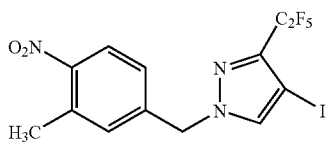

3-Methyl-4-nitrobenzyl chloride (8.57 g), 4-iodo-3-pentafluoroethyl-1H-pyrazole (16.00 g) and potassium carbonate (7.66 g) were stirred in DMF (70 ml) at 70° C. for 1 hour. After cooling, the reaction solution was poured into water and extracted with ethyl acetate. The organic phase was washed with water and saturated aqueous solution of sodium chloride. After drying the organic layer with sodium sulfate, the solvent was distilled off under the reduced pressure and the obtained residue was purified by silica gel column chromatography to obtain 4-iodo-1-(3-methyl-4-nitrobenzyl)-3-pentafluoroethyl-1H-pyrazole (4.60 g).

$^1$H-NMR (CDCl$_3$, ppm): 2.60 (3H, s), 5.38 (2H, s), 7.22-7.15 (2H, m), 7.53 (1H, s), 7.98 (1H, d).

Synthesis Example 17

Starting Material

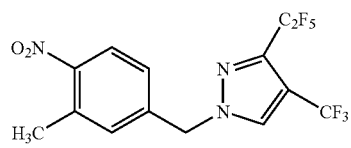

4-Iodo-1-(3-methyl-4-nitrobenzyl)-3-pentafluoroethyl-1H-pyrazole (1.84 g), (trifluoromethyl)trimethylsilane (1.14 g), copper(I) iodide (1.52 g), potassium fluoride (0.28 g) were stirred in DMF (8 ml) at 100° C. for 8 hours. After cooling, the mixture was poured into water and extracted with ethyl acetate. The combined organic phase was washed with saturated aqueous solution of sodium chloride. After drying the organic layer with sodium sulfate, the solvent was distilled off under the reduced pressure and the obtained residue was purified by silica gel column chromatography to obtain 1-(3-methyl-4-nitro-benzyl)-3-pentafluoroethyl-4-trifluoromethyl-1H-pyrazole (0.32 g).

$^1$H-NMR (CDCl$_3$, ppm): 2.61 (3H, s), 5.41 (2H, s), 7.31-7.18 (2H, m), 7.78 (1H, s), 8.00 (1H, d).

Synthesis Example 18

Starting Material

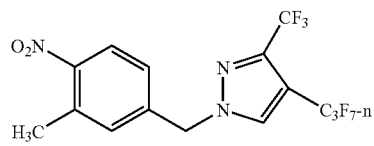

4-Iodo-1-(3-methyl-4-nitrobenzyl)-3-trifluoromethyl-1H-pyrazole (2.06 g), copper powder (0.95 g), heptafluoro-1-iodopropane (2.96 g) and DMF (14 ml) were set in an autoclave and heated and stirred for 8 hours, maintaining the inside temperature of 130-135° C. After cooling to room temperature, the reaction mixture was diluted with ethyl acetate (50 ml) and an insoluble matter was filtered with Celite and washed with ethyl acetate. The filtrate was concentrated under the reduced pressure and the obtained residue was purified by silica gel column chromatography to obtain 1-(3-methyl-4-nitrobenzyl)-4-pentafluoropropyl-3-trifluoromethyl-1H-pyrazole (0.80 g).

$^1$H-NMR (CDCl$_3$, ppm): 2.62 (3H, s), 5.42 (2H, s), 7.19-7.20 (2H, m), 7.74 (1H, s), 8.02 (1H, d).

Synthesis Example 19

Starting Material

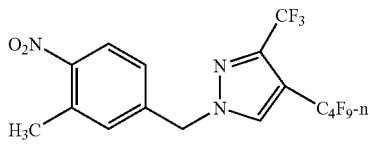

4-Iodo-1-(3-methyl-4-nitrobenzyl)-3-trifluoromethyl-1H-pyrazole (2.47 g), copper powder (1.14 g), nonafluoro-1-iodobutane (4.15 g) and DMF (16 ml) were set in an autoclave and heated and stirred for 8 hours, maintaining the inside temperature of 130-135° C. After cooling to room temperature, the reaction mixture was diluted with toluene (50 ml) and an insoluble matter was filtered with Celite and washed with toluene. The filtrate was concentrated under the reduced pressure and the obtained residue was purified by silica gel column chromatography to obtain 1-(3-methyl-4-nitrobenzyl)-4-nonafluorobutyl-3-trifluoromethyl-1H-pyrazole (1.50 g).

$^1$H-NMR (CDCl$_3$, ppm): 2.62 (3H, s), 5.42 (2H, s), 7.18-7.24 (2H, m), 7.74 (1H, s), 8.00 (1H, d).

Synthesis Example 20

Starting Material

An acetonitrile solution (20 ml) of 3-trifluoromethyl-1H-pyrazole (1.0 g), dicerium ammonium nitrate (2.0 g) and bromine (0.7 g) was refluxed for 2 hours. After cooling, the reaction solution was washed with saturated aqueous solution of sodium thiosulfate and saturated aqueous solution of sodium chloride. After drying the organic layer with magnesium sulfate, the solvent was distilled off under the reduced pressure to obtain 4-bromo-3-trifluoromethyl-1H-pyrazole (1.6 g).

$^1$H-NMR (CDCl$_3$, ppm): 7.73 (1H, s), 12.86 (1H, brs).

Synthesis Example 21

Starting Material

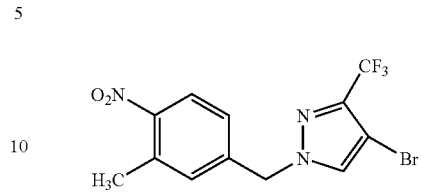

3-Methyl-4-nitrobenzyl chloride (0.77 g), 4-bromo-3-trifluoromethyl-1H-pyrazole (0.90 g) and potassium carbonate (0.57 g) were stirred in DMF (10 ml) at room temperature for 2 hours. The reaction solution was diluted with ethyl acetate and washed with water and saturated aqueous solution of sodium chloride. After drying the organic layer with magnesium sulfate, the solvent was distilled off under the reduced pressure and the obtained residue was purified by silica gel column chromatography to obtain 1-(3-methyl-4-nitrobenzyl)-4-bromo-3-trifluoromethyl-1H-pyrazole (0.9 g).

$^1$H-NMR (CDCl$_3$, ppm): 2.58 (3H, s), 5.35 (2H, s), 7.24-7.21 (2H, m), 7.49 (1H, s), 7.98 (1H, d).

Synthesis Example 22

Starting Material

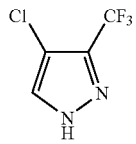

An acetonitrile solution (20 ml) of 3-trifluoromethyl-1H-pyrazole (0.5 g), dicerium ammonium nitrate (1.0 g) and N-chlorosuccinimide (0.7 g) was refluxed for 3 hours. After cooling, the reaction solution was washed with saturated aqueous solution of sodium thiosulfate and saturated aqueous solution of sodium chloride. After drying an organic layer with magnesium sulfate, the solvent was distilled off under the reduced pressure to obtain 4-chloro-3-trifluoromethyl-1H-pyrazole (0.9 g).

$^1$H-NMR (CDCl$_3$, ppm): 7.80 (1H, s).

Synthesis Example 23

Stating Material

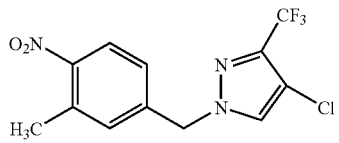

3-Methyl-4-nitrobenzyl chloride (0.82 g), 4-chloro-3-trifluoromethyl-1H-pyrazole (0.63 g) and potassium carbonate (0.61 g) were stirred in DMF (10 ml) at room temperature for 2 hours. The reaction solution was diluted with ethyl acetate and washed with water and saturated aqueous solution of sodium chloride. After drying the organic layer with magnesium sulfate, the solvent was distilled off under the reduced pressure and the obtained residue was purified by silica gel column chromatography to obtain 1-(3-methyl-4-nitrobenzyl)-4-chloro-3-trifluoromethyl-1H-pyrazole (0.98 g).

$^1$H-NMR (CDCl$_3$, ppm): 2.62 (3H, s), 5.33 (2H, s), 7.21-7.19 (2H, m), 7.46 (1H, s), 7.98 (1H, d).

Synthesis Example 24

Starting Material

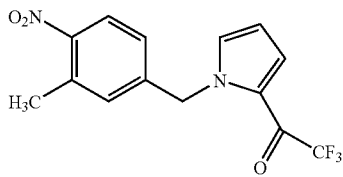

2-(Trifluoroacetyl)-1H-pyrrole (0.97 g) was added to DMF solution (10 ml) of 60% sodium hydride (0.16 g) and the mixture was stirred at room temperature for 30 minutes. 3-Methyl-4-nitrobenzyl chloride (1.0 g) was added thereto and the mixture was stirred at room temperature for 2 hours. The reaction solution was diluted with ethyl acetate and washed with water and saturated aqueous solution of sodium chloride. After drying the organic layer with magnesium sulfate, the solvent was distilled off under the reduced pressure and the obtained residue was purified by silica gel column chromatography to obtain 1-(3-methyl-4-nitrobenzyl)-2-(trifluoroacetyl)-1H-pyrrole (1.53 g).

$^1$H-NMR (CDCl$_3$, ppm): 2.55 (3H, s), 5.59 (2H, s), 6.44-6.41 (1H, m), 6.99 (1H, d), 7.04 (1H, s), 7.22-7.19 (1H, m), 7.35-7.32 (1H, m), 7.93 (1H, d).

Synthesis Example 25

Starting Material

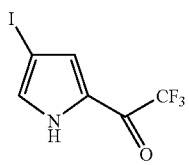

An acetonitrile solution (20 ml) of 2-(trifluoroacetyl)-1H-pyrrole (0.5 g), dicerium ammonium nitrate (0.84 g) and iodine (0.47 g) was refluxed for 2 hours. After cooling, the reaction solution was washed with saturated aqueous solution of sodium thiosulfate and saturated aqueous solution of sodium chloride. After drying the organic layer with magnesium sulfate, the solvent was distilled off under the reduced pressure to obtain 4-iodo-2-(trifluoroacetyl)-1H-pyrrole (0.6 g).

$^1$H-NMR (CDCl$_3$, ppm): 7.28-7.35 (2H, m), 9.52 (1H, brs).

Synthesis Example 26

Starting Material

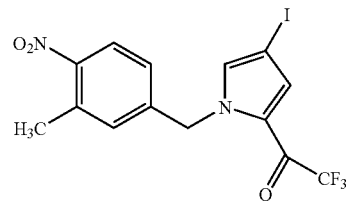

3-Methyl-4-nitrobenzyl chloride (0.63 g), 4-iodo-2-(trifluoroacetyl)pyrrole (0.89 g) and potassium carbonate (0.57 g) were stirred in DMF (10 ml) at room temperature for 2 hours. The reaction solution was diluted with ethyl acetate and washed with water and saturated aqueous solution of sodium chloride. After drying the organic layer with magnesium sulfate, the solvent was distilled off under the reduced pressure and the obtained residue was purified by silica gel column chromatography to obtain 4-iodo-1-(3-methyl-4-nitrobenzyl)-2-trifluoroacetyl-1H-pyrrole (0.45 g).

$^1$H-NMR (CDCl$_3$, ppm): 2.60 (3H, s), 5.56 (2H, s), 7.05-7.12 (2H, m), 7.21 (1H, d), 7.39 (1H, s), 7.94 (1H, d).

Synthesis Example 27

Starting Material

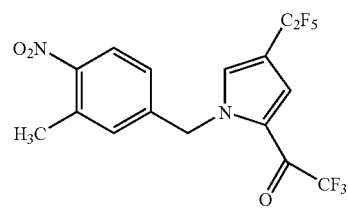

4-Iodo-1-(3-methyl-4-nitrobenzyl)-2-trifluoroacetyl-1H-pyrrole (1.75 g), copper powder (5.08 g), iodopentafluoroethane (5.92 g) and DMSO (6 ml) were set in an autoclave and heated and stirred for 8 hours, maintaining the inside temperature of 120° C. After finishing the reaction, the reaction mixture was poured into ice water and an insoluble matter was filtered with Celite, and then, it was extracted with ethyl acetate. The extracted solution was washed with water and then dried with anhydrous sodium sulfate. After distilling off the solvent, the obtained residue was purified by silica gel column chromatography to obtain 1-(3-methyl-4-nitrophenyl)-4-pentafluoroethyl-1H-pyrrole (1.35 g).

$^1$H-NMR (CDCl$_3$, ppm): 2.59 (3H, s), 5.62 (2H, s), 7.00-7.10 (2H, m), 7.43-7.50 (2H, m), 7.96 (1H, d).

Some specific examples of other processes to synthesize the compounds of the aforementioned formula (IX) are shown below.

Synthesis Example 28

Starting Material

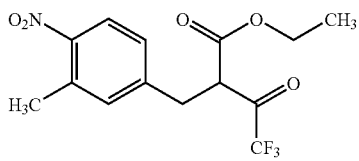

To a toluene suspension of ethyl 4,4,4-trifluoroacetoacetone (5.0 g), sodium hydride (1.1 g) was slowly added and the mixture was stirred for 1 hour. After adding 4-chloromethyl-2-methyl-1-nitro-benzene (5.5 g) and potassium iodide dissolved in acetone (0.5 g), the reaction solution was refluxed for 5 hours. After cooling, the solvent was distilled off under reduced pressure. The residue was suspended in ethyl acetate and washed with 1N aqueous solution of hydrochloric acid. After drying the organic layer with sodium sulfate, the solvent was distilled off and the obtained residue was purified by silica gel column chromatography to obtain ethyl 4,4,4-trifluoro-2-(3-methyl-4-nitro-benzyl)-3-oxo-butyrate (6.3 g). $n_D^{20}$ 1.4970

Synthesis Example 29

Starting Material

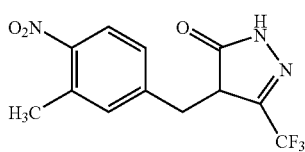

Ethyl 4,4,4-trifluoro-2-(3-methyl-4-nitro-benzyl)-3-oxo-butyrate (2.0 g), hydrazine monohydrate (0.5 g) and a small amount of p-toluenesulfonic acid were dissolved in toluene, and the mixture was refluxed for 4 hours. After cooling, the solvent was distilled off under reduced pressure. The residue was suspended in ethyl acetate and washed with 1N aqueous solution of hydrochloric acid. After drying the organic layer with sodium sulfate, the solvent was distilled off and the obtained residue was purified by silica gel column chromatography to obtain 4-(3-methyl-4-nitro-benzyl)-5-trifluoromethyl-2,4-dihydro-pyrazol-3-one (1.0 g).

$^1$H-NMR (DMSO-$d_6$, 90 MHz): δ 2.2 (3H, s), 3.8 (2H, s), 7.0 (1H, d, J=5.5 Hz), 7.2 (1H, s), 7.8 (1H, d, J=5.5 Hz), 11.2 (1H, brs).

Synthesis Example 30

Starting Material

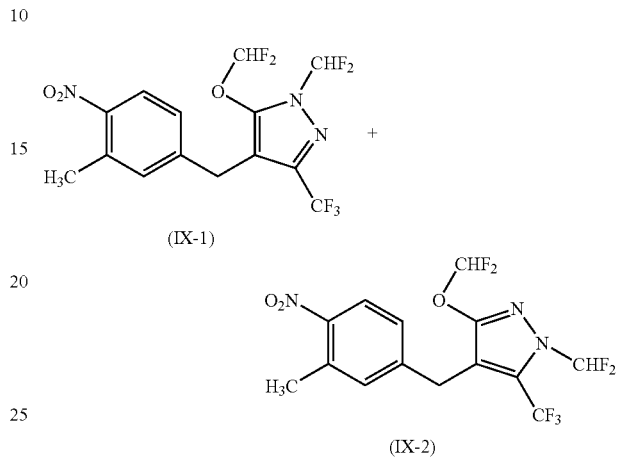

To a DMF suspension of 4-(3-methyl-4-nitro-benzyl)-5-trifluoromethyl-2,4-dihydro-pyrazol-3-one (1.0 g) and potassium carbonate (1.5 g), chlorodifluoromethane (5.7 g) was sealed in by using a balloon. After 5 hours, after the gas in the solution was saturated, the vessel was tightly closed and the mixture was stirred at 50° C. for 5 hours. After cooling, the solvent was distilled off and the obtained residue was dissolved in ethyl acetate and washed with water and saturated aqueous solution of sodium chloride. After drying the organic layer with sodium sulfate, the solvent was distilled off and the obtained residue was purified by silica gel column chromatography to obtain 5-difluoromethoxy-1-difluoromethyl-4-(3-methyl-4-nitro-benzyl)-3-trifluoromethyl-1H-pyrazole (IX-1) (0.5 g) and 3-difluoromethoxy-j-difluoromethyl-4-(3-ethyl-4-nitro-benzyl)-5-trifluoromethyl-1H-pyrazole (IX-2) (0.4 g) respectively.

(IX-1): $n_D^{20}$ 1.4780, (IX-2): $n_D^{20}$ 1.4855.

Synthesis Example 31

Starting Material

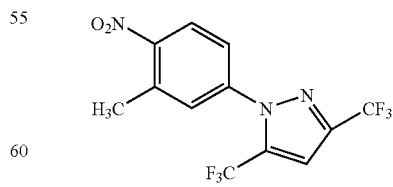

(3-Methyl-4-nitrophenyl)-hydrazine (3.0 g) and hexafluoroacetylacetone (3.7 g) were dissolved in toluene and the solution was refluxed for 6 hours. After cooling, the solvent was distilled off and the obtained residue was purified by silica gel column chromatography to obtain 1-(3-methyl-4-nitrophenyl)-3,5-bis(trifluoromethyl)-1H-pyrazole (5.6 g). $n_D^{20}$ 1.4890.

Synthesis Example 32

Starting Material

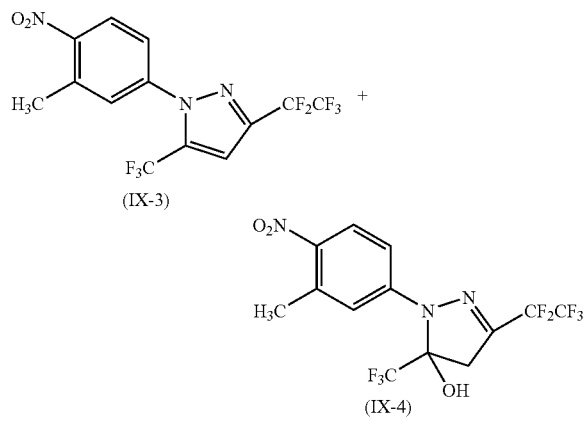

(IX-3)

(IX-4)

(3-Methyl-4-nitro-phenyl)-hydrazine (2.0 g) and 1,1,1,5,5,6,6,6-octafluoro-2,4-hexanedione (3.1 g) were dissolved in toluene and the solution was refluxed for 6 hours. After cooling, the solvent was distilled off and the obtained residue was purified by silica gel column chromatography to obtain 1-(3-methyl-4-nitro-phenyl)-3-pentafluoroethyl-5-trifluoromethyl-1H-pyrazole (IX-3) (3.0 g) and 2-(3-methyl-4-nitro-phenyl)-5-pentafluoroethyl-3-trifluoromethyl-3,4-dihydro-2H-pyrazol-3-ol (IX-4) (0.5 g), respectively.

(IX-3): $n_D^{20}$ 1.4690, (IX-4): $^1$H-NMR (CDCl$_3$, 90 MHz): δ 2.6 (3H, s), 3.3 (1H, br d, J=16 Hz), 3.7 (1H, br d, J=16 Hz), 4.1 (1H, s), 7.2 (2H, m), 7.8 (1H, d, J=7.8 Hz).

Synthesis Example 33

Starting Material

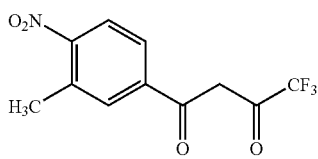

To a THF suspension of 1-(3-methyl-4-nitro-phenyl)-ethanone (2.0 g), sodium hydride (0.6 g) was slowly added and the mixture was stirred for 1 hour. After adding ethyl trifluoroacetate (1.6 g), the reaction mixture was refluxed for 5 hours. After cooling, the solvent was distilled off under reduced pressure. The residue was suspended in ethyl acetate and washed with 1N aqueous solution of hydrochloric acid. After drying the organic layer with sodium sulfate, the solvent was distilled off and the obtained residue was purified by silica gel column chromatography to obtain 4,4,4-trifluoro-1-(3-methyl-4-nitro-phenyl)-butane-1,3-dione (2.5 g).

$^1$H-NMR (CDCl$_3$, 90 MHz): δ 2.6 (3H, s), 6.5 (1H, s), 7.7-8.1 (3H, m).

Synthesis Example 34

Starting Material

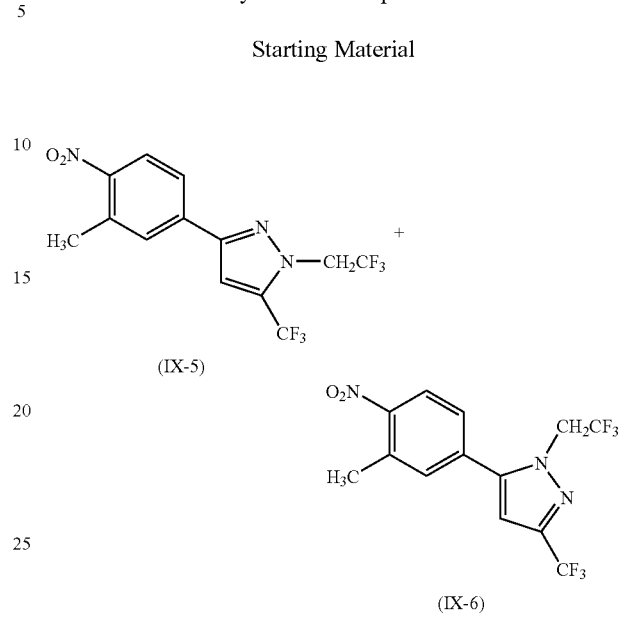

(IX-5)

(IX-6)

A toluene solution of 4,4,4-trifluoro-1-(3-methyl-4-nitrophenyl)-butane-1,3-dione (1.8 g), 2,2,2-trifluoroethylhydrazine (1.2 g) and a catalytic amount of p-toluenesulfonic acid were refluxed for 6 hours. After cooling, the solvent was distilled off and the obtained residue was purified by silica gel column chromatography to obtain 3-(3-methyl-4-nitro-phenyl)-1-(2,2,2-trifluoro-ethyl)-5-trifluoro-methyl-1H-pyrazole (IX-5) (1.1 g) and 5-(3-methyl-4-nitro-phenyl)-1-(2,2,2-trifluoro-ethyl)-3-trifluoromethyl-1H-pyrazole (1-6) (0.5 g), respectively.

(IX-5) mp; 98-104° C., (IX-6) mp; 50-53° C.

Synthesis Example 35

Starting Material

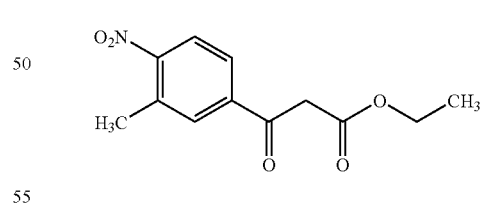

To a dichloromethane solution of 2,2-dimethyl-1,3-dioxane-4,6-dione (10 g) and dimethylaminopyridine (17 g), a dichloromethane solution of 3-methyl-4-nitro-benzoyl chloride (14 g) was added dropwise under ice cooling. After stirring at room temperature for 3 hours and then adding 100 ml of ethanol, the mixture was refluxed for 2 hours. After cooling, the solvent was distilled off under the reduced pressure. The residue was dissolved in ethyl acetate and washed with 1N aqueous solution of hydrochloric acid. After drying the organic layer with sodium sulfate, the solvent was distilled off and the obtained residue was purified by silica gel column chromatography to obtain ethyl 3-(3-methyl-4-nitrophenyl)-3-oxo-propionate (12.4 g). mp; 207-211° C.

Synthesis Example 36

Starting Material

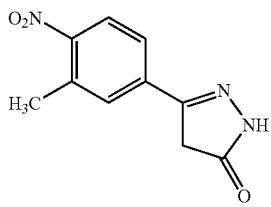

To an ethanol solution of ethyl 3-(3-methyl-4-nitro-phenyl)-3-oxo-propionate (3.0 g), hydrazine monohydrate (0.9 g) and a small amount of p-toluenesulfonic acid were added and the mixture was refluxed for 5 hours. After cooling, the solvent was distilled off under the reduced pressure and the obtained residue was purified by silica gel column chromatography to obtain 5-(3-methyl-4-nitro-phenyl)-2,4-dihydro-pyrazol-3-one (2.6 g). mp; 218-219° C.

Synthesis Example 37

Starting Material

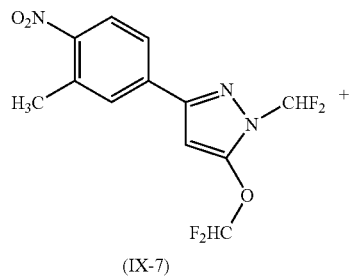

(IX-7)

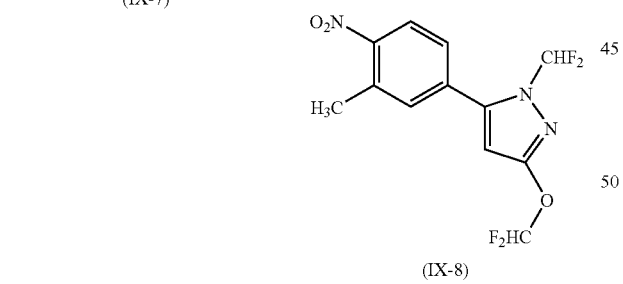

(IX-8)

To a DMF suspension of 5-(3-methyl-4-nitro-phenyl)-2,4-dihydro-1H-pyrazol-3-one (2.0 g) and potassium carbonate (6.3 g), chlorodifluoromethane (8.7 g) was sealed in by using a balloon. After 5 hours, after the gas in the solution was saturated, the vessel was tightly closed and the mixture was stirred at 50° C. for 5 hours. After cooling, the solvent was distilled off and the obtained residue was dissolved in ethyl acetate and washed with water and saturated aqueous solution of sodium chloride. After drying with sodium sulfate, the solvent was distilled off and the obtained residue was purified by silica gel column chromatography to obtain 5-difluoromethoxy-1-difluoromethyl-3-(3-methyl-4-nitro-phenyl)-1H-pyrazole (IX-7) (0.7 g) and 3-difluoromethoxy-1-difluoromethyl-5-(3-methyl-4-nitro-phenyl)-1H-pyrazole (IX-8) (0.5 g), respectively.

(IX-7) mp; 80-82° C., (IX-8) mp; 99-100° C.

Synthesis Example 38

Starting Material

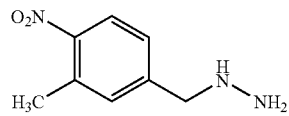

To an ethanol solution (60 ml) of hydrazine monohydrate (5.00 g), an ethanol solution (20 ml) of 3-methyl-4-nitrobenzyl chloride (3.71 g) was added dropwise while refluxing it, and the mixture was continuously refluxed for 6 hours. After finishing the reaction, the solvent was distilled off and (3-methyl-4-nitrobenzyl)-hydrazine (3.50 g) was obtained.

$^1$H-NMR (CDCl$_3$, ppm): 2.60 (3H, s), 2.65-3.35 (3H, m), 3.95 (2H, s), 7.20-7.40 (2H, m), 7.98 (1H, d).

Synthesis Example 39

Starting Material

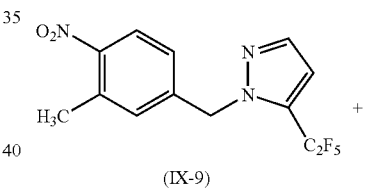

(IX-9)

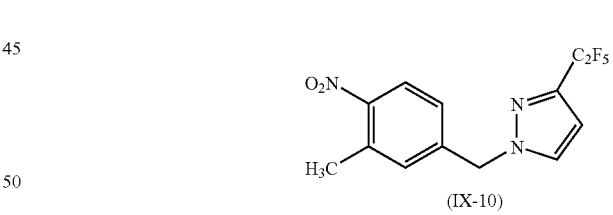

(IX-10)

(3-Methyl-4-nitrobenzyl)-hydrazine (1.81 g) and 5-ethoxy-1,1,1,2,2-pentafluoro-4-penten-3-one (2.18 g) were refluxed in ethanol (60 ml) for 8 hours, and p-toluenesulfonic acid (0.10 g) was added thereto and the mixture was further refluxed for 6 hours. After finishing the reaction, the solvent was distilled off and the obtained residue was purified by silica gel column chromatography (mixed solvent of n-hexane and ethyl acetate) to obtain 1-(3-methyl-4-nitrobenzyl)-5-pentafluoroethyl-1H-pyrazole (0.96 g) as the first elution portion and 1-(3-methyl-4-nitrobenzyl)-3-pentafluoroethyl-1H-pyrazole (0.50 g) as the second elution portion.

(IX-9): $^1$H-NMR (CDCl$_3$, ppm): 2.61 (3H, s), 5.49 (2H, s), 6.70 (1H, bs), 7.05-7.15 (2H, m), 7.66 (1H, bs), 7.94 (1H, d).

(IX-10): ¹H-NMR (CDCl$_3$, ppm): 2.64 (3H, s), 5.40 (2H, s), 6.63 (1H, d), 7.07-7.20 (2H, m), 7.52 (1H, d), 7.95 (1H, d).

Synthesis Example 40

Starting Material

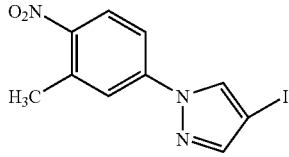

A mixture of 5-fluoro-2-nitrotoluene (2.33 g), 4-iodo-1H-pyrazole (2.91 g) and potassium carbonate (2.49 g) was heated and stirred in DMF (30 ml) at 140° C. for 4 hours. After cooling to room temperature, the reaction mixture was poured into ice water to separate out crystals. The obtained crystals were filtered, washed with water and dried, and 4-iodo-1-(3-methyl-4-nitrophenyl)-1H-pyrazole (4.60 g) was obtained.

¹H-NMR (CDCl$_3$, ppm): 2.70 (3H, s), 7.50-7.70 (3H, m), 7.95-8.15 (2H, m).

Synthesis Example 41

Starting Material

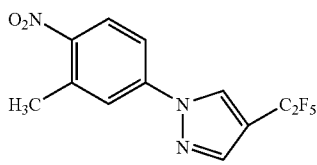

4-Iodo-1-(3-methyl-4-nitrophenyl)-1H-pyrazole (1.98 g), copper powder (1.14 g), iodopentafluoroethane (8.85 g) and DMSO (9 ml) were set in an autoclave and heated and stirred for 8 hours, maintaining the inside temperature of 100° C. After finishing the reaction, the reaction mixture was poured into ice water and an insoluble matter was filtered with Celite, and then, it was extracted with ethyl acetate. The extracted solution was washed with water and dried with anhydrous sodium sulfate. After distilling off the solvent, the obtained residue was purified by silica gel column chromatography to obtain 1-(3-methyl-4-nitrophenyl)-4-pentafluoroethyl-1H-pyrazole (0.72 g).

¹H-NMR (CDCl$_3$, ppm): 2.70 (3H, s), 7.60-7.73 (2H, m), 7.93 (1H, s), 8.13 (1H, d), 8.23 (1H, s).

Synthesis Example 42

Starting Material

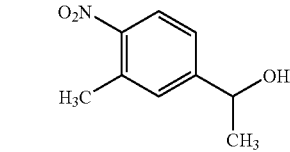

To a suspension of methanol (300 ml) of 3-methyl-4-nitroacetophenone (26.88 g), sodium borohydride (8.51 g) was added at 0° C. over a period of 1 hour. The mixture was further stirred at room temperature for 8 hours. After finishing the reaction, the reaction mixture was poured into ice water (1,000 ml) and extracted with ether. The organic layer was washed with saturated aqueous solution of sodium chloride and dried with anhydrous magnesium sulfate. After distilling off the solvent, the aimed 1-(3-methyl-4-nitrophenyl)-ethanol (23.33 g) was obtained.

¹H-NMR (CDCl$_3$, ppm): 1.51 (3H, d), 1.98 (1H, d), 2.62 (3H, s), 4.90-5.01 (1H, m), 7.28-7.35 (2H, m), 7.98 (1H, d).

Synthesis Example 43

Starting Material

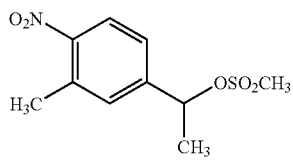

Into a THF solution (35 ml) of 1-(3-methyl-4-nitrophenyl)-ethanol (5.44 g) and triethylamine (3.95 g), a THF solution (10 ml) of methanesulfonyl chloride (3.48 g) was added dropwise at 5° C. over a period of 30 minutes. Further, the mixture was stirred at room temperature for 8 hours. After finishing the reaction, the solvent was distilled off and the residue was dissolved in ethyl acetate (100 ml). It was washed with 2N aqueous solution of hydrochloric acid and saturated aqueous solution of sodium bicarbonate and then dried with anhydrous magnesium sulfate. After distilling off the solvent, the aimed 1-(3-methyl-4-nitrophenyl)-ethyl methanesulfonate (5.80 g) was obtained.

¹H-NMR (CDCl₃, ppm): 1.74 (3H, d), 2.65 (3H, s), 2.95 (3H, s), 5.76 (1H, q), 7.35-7.45 (2H, m), 8.01 (1H, d).

Synthesis Example 44

Starting Material

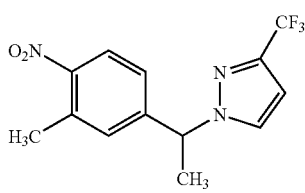

1-(3-Methyl-4-nitrophenyl)-ethyl methanesulfonate (2.59 g), 3-trifluoromethyl-1H-pyrazole (1.09 g), potassium carbonate (1.66 g) and 18-crown-6 (0.26 g) were refluxed in acetonitrile (100 ml) for 6 hours. After finishing the reaction, water (100 ml) was added to the mixture and extracted with ethyl acetate. The organic layer was washed with saturated aqueous solution of sodium bicarbonate and then dried with anhydrous sodium sulfate. After distilling off the solvent, the obtained residue was purified by silica gel column chromatography to obtain 1-[1-(3-methyl-4-nitrophenyl)-ethyl]-3-trifluoromethyl-1H-pyrazole (1.60 g).

¹H-NMR (CDCl₃, ppm): 1.95 (3H, d), 2.59 (3H, s), 5.59 (1H, q), 6.57 (1H, bs), 7.13-7.20 (2H, m), 7.47 (1H, bs), 8.00 (1H, d).

Synthesis Example 45

Starting Material

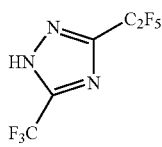

Ethyl pentafluoropropylenate (14.6 g) and hydrazine monohydrate (3.6 g) were refluxed in tetrahydrofuran (300 ml) for 1 hour. After cooling to room temperature, trifluoroacetamidine (10.0 g) was added dropwise to the mixture and it was refluxed for 3 hours. After finishing the reaction, saturated aqueous solution of sodium hydrogen carbonate was added thereto and the mixture was extracted with ethyl acetate. After drying the organic layer with anhydrous magnesium sulfate, the solvent was distilled off to obtain crude 3-pentafluoroethyl-5-trifluoromethyl-1H-(1,2,4)-triazole (7.9 g).

Synthesis Example 46

Starting Material

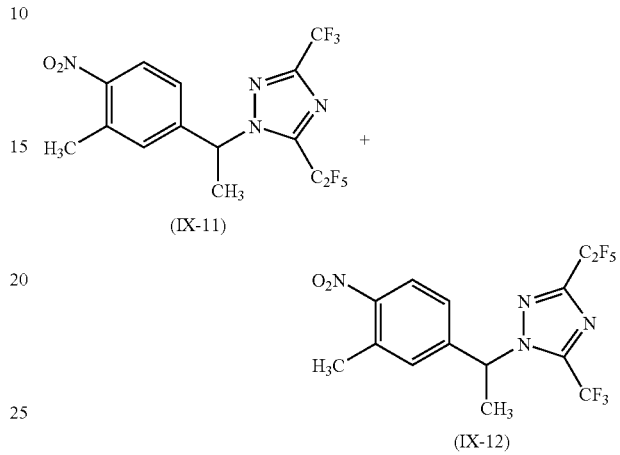

(IX-11)

(IX-12)

1-(3-Methyl-4-nitrophenyl)-ethyl methanesulfonate (2.5 g), 3-pentafluoroethyl-5-trifluoromethyl-1H-(1,2,4)-triazole (2.2 g), potassium carbonate (1.6 g) and 18-crown-6 (0.26 g) were refluxed in acetonitrile (100 ml) for 6 hours. After finishing the reaction, water (100 ml) was added thereto and the mixture was extracted with ethyl acetate. The organic layer was washed with saturated aqueous solution of sodium chloride (100 ml) and then dried with anhydrous sodium sulfate. After distilling off the solvent, the obtained residue was purified by silica gel column chromatography (mixed solvent of n-hexane and ethyl acetate) to obtain (IX-11) 1-([1-(3-methyl-4-nitro-phenyl)-ethyl]-5-pentafluoroethyl-3-trifluoromethyl-1H-(1,2,4)-triazole (0.95 g) as the first elution portion and (IX-12) 1-([1-(3-methyl-4-nitro-phenyl)-ethyl]-3-pentafluoroethyl-5-trifluoromethyl-1H-(1,2,4)-triazole (1.35 g) as the second elution portion.

(IX-11)

¹H-NMR (CDCl₃) δ: 8.03-7.97 (1H, m), 7.37 (2H, t, J=5.4 Hz), 5.86 (1H, q, J=7.0 Hz), 2.62 (3H, s), 2.00 (311, d, J=7.0 Hz).

(X-12)

¹H-NMR (CDCl₃) δ: 7.98 (1H, d; J=8.2 Hz), 7.34 (2H, t, J=7.1 Hz), 5.81 (1H, q, J=7.0 Hz), 2.63 (3H, s), 2.01 (3H, d, J=7.0 Hz).

Synthesis Example 47

Starting Material

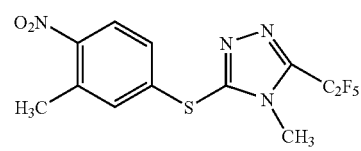

Sodium hydride (0.10 g) was added to a DMF solution (12 ml) of 4-methyl-5-pentafluoroethyl-4H-[1,2,4]triazol-3-thiol (0.70 g), and the mixture was stirred at room temperature until the generation of hydrogen gas stopped. Continuously, 5-fluoro-2-nitrotoluene (0.47 g) was added thereto and the mixture was further stirred at room temperature for 1 hour. After cooling to room temperature, the reaction mixture was poured into ice water and extracted with ethyl acetate. The organic layer was washed with saturated aqueous solution of sodium chloride and then dried with anhydrous sodium sulfate. After distilling off the solvent, the obtained residue was purified by silica gel column chromatography (mixed solvent of n-hexane and ethyl acetate) to obtain the aimed 4-methyl-3-(3-methyl-4-nitrophenyl sulfanyl)-5-pentafluoroethyl-4H-(1,2,4)-triazole (0.55 g).

$^1$H-NMR (CDCl$_3$, ppm): 2.70 (3H, s), 3.80 (3H, s), 8.10-8.30 (3H, m).

Synthesis Example 48

Starting Material

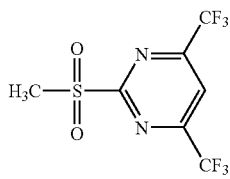

A mixture of 2-methylmelcapto-4,6-bistrifluoromethyl-pyrimidine (36 g), oxone (126 g), water (500 ml) and chloroform (110 ml) was refluxed for 2 days. After cooling to room temperature, the mixture was extracted with dichloromethane. The obtained organic layer was washed with water and then dried with anhydrous sodium sulfate. After distilling off the solvent, the obtained crude crystals were washed with petroleum ether to obtain 2-methanesulfonyl-4,6-bistrifluoromethyl-pyrimidine (7.5 g).

$^1$H-NMR (CDCl$_3$, ppm): 3.48 (3H, s), 8.19 (1H, s).

Synthesis Example 49

Starting Material

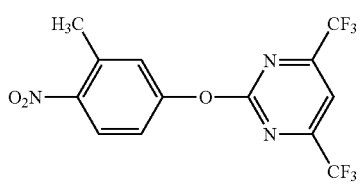

4-Nitro-m-cresol (0.77 g), 2-methanesulfonyl-4,6-bistrifluoromethyl-pyrimidine (1.77 g) and potassium carbonate (1.04 g) were refluxed in acetonitrile (15 ml) for 5 hours. After finishing the reaction, the reaction mixture was poured into ice to separate out crystals. The obtained crystals were filtered and dried to obtain 2-(3-methyl-4-nitrophenoxy)-4,6-bistrifluoromethyl-pyrimidine (1.03 g).

$^1$H-NMR (CDCl$_3$, ppm): 2.60 (3H, s), 7.1-7.3 (2H, m), 7.67 (1H, s), 8.10 (1H, d).

Synthesis Example 50

Starting Material

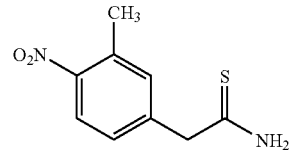

(3-Methyl-4-nitrophenyl)-acetonitrile (3.52 g) was dissolved in pyridine (30 ml), thereto excess H$_2$S was bubbled into at room temperature for 3 hours. Then the mixture was poured onto ice. The precipitate was collected by suction, washed with water and dried to obtain 2-(3-methyl-4-nitrophenyl)-thioacetamide (1.69 g).

$^1$H-NMR (CDCl$_3$, ppm): 2.60 (3H, s), 4.06 (2H, s), 6.40-8.00 (5H, m)

Synthesis Example 51

Starting Material

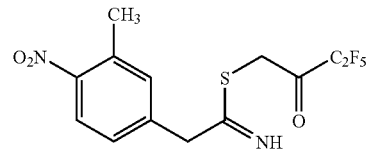

2-(3-Methyl-4-nitrophenyl)-thioacetamide (1.00 g), 1-bromo-3,3,4,4,4-pentafluoro-2-butanone (1.15 g) and potassium carbonate (0.79 g) were stirred in DMF (10 ml) at room temperature for 1 hour. The reaction solution was diluted with ethyl acetate and washed with water and saturated aqueous solution of sodium chloride. After drying the organic layer with magnesium sulfate, the solvent was distilled off under the reduced pressure and the obtained residue was purified by silica gel column chromatography to obtain 2-(3-Methyl-4-nitro-phenyl)-thioacetimidic acid 3,3,4,4,4-pentafluoro-2-oxo-butyl ester (1.30 g).

$^1$H-NMR (CDCl$_3$, ppm): 2.55 (3H, s), 3.57 (2H, dd), 3.90 (2H, d), 7.24-7.22 (2H, m), 7.91-7.89 (1H, m)

Synthesis Example 52

Starting Material

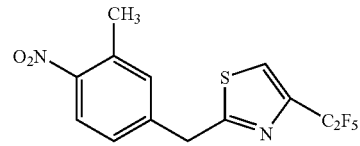

Trifluoroacetic anhydride (1.47 g) was added to 2-(3-Methyl-4-nitro-phenyl)-thioacetimidic acid 3,3,4,4,4-pentafluoro-2-oxo-butyl ester (1.30 g) and triethylamine (0.71 g) in dichloromethane (10 ml), and stirred at room temperature for 20 minutes. The reaction solution was washed with water, and the solvent was distilled off under the reduced pressure and the obtained residue was purified by silica gel column chromatography to obtain 2-(3-methyl-4-nitro-benzyl)-4-perfluoroethyl-thiazole (0.70 g).

$^1$H-NMR (CDCl$_3$, ppm): 2.63 (3H, s), 4.43 (2H, s), 7.30-7.28 (2H, m), 7.75 (1H, s), 7.98 (1H, d)

Synthesis Example 53

Starting Material

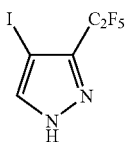

An acetonitrile solution (20 ml) of 3-pentafluoroethyl-1H-pyrazole (2.0 g), dicerium ammonium nitrate (3.0 g) and iodine (1.6 g) was refluxed for 3 hours. After cooling, the reaction solution was washed with saturated aqueous solution of sodium thiosulfate and saturated aqueous solution of sodium chloride. After drying the organic layer with magnesium sulfate, the solvent was distilled off under the reduced pressure to obtain 4-iodo-3-pentafluoroethyl-1H-pyrazole (3.2 g).

$^1$H-NMR (CDCl$_3$, ppm): 7.77 (1H, s), 11.11 (1H, m)

Synthesis Example 54

Starting Material

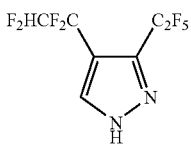

4-Iodo-3-pentafluoroethyl-1H-pyrazole (6.24 g), copper powder (3.81 g), Iodo-1,1,2,2-tetrafluoroethane (9.12 g) and DMF (30 ml) were set in an autoclave and heated and stirred for 8 hours, maintaining the inside temperature of 120-125° C. After cooling to room temperature, the insoluble material was filtered off through Celite and washed with diethyl ether. The filtrate was diluted with water and extracted with diethyl ether. The organic phase was washed with water and dried over sodium sulfate, and concentrated under the reduced pressure. The crude product was distilled under reduced pressure to obtain 3-pentafluoroethyl-4-(1,1,2,2-tetrafluoroethyl)-1H-pyrazole (0.60 g), bp. 125-135° C./20 mbar.

$^1$H-NMR (CDCl$_3$, ppm): 5.98 (1H, it), 7.96 (1H, s), 12.22 (1H, m)

Synthesis Example 55

Starting Material

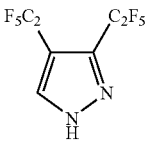

4-Iodo-3-pentafluoroethyl-1H-pyrazole (12.48 g), copper powder (7.63 g), iodopentafluoroethane (29.50 g) and DMF (60 ml) were set in an autoclave and heated and stirred for 8 hours, maintaining the inside temperature of 120-125° C. After cooling to room temperature, the insoluble material was filtered off through Celite and washed with diethyl ether. The filtrate was diluted with water and extracted with diethyl ether. The organic phase was washed with water and dried over sodium sulfate, and concentrated under the reduced pressure. The crude product was distilled under reduced pressure to obtain 3,4-bis-pentafluoroethyl-1H-pyrazole (1.20 g), bp. 110-115° C./20 mbar.

$^1$H-NMR (CDCl$_3$, ppm): 7.99 (1H, s), 12.31 (1H, m).

Synthesis Example 56

Starting Material

An acetonitrile solution (20 ml) of 4-methyl-1H-pyrazole (0.5 g), dicerium ammonium nitrate (1.7 g) and iodine (1.9 g) was refluxed for 3 hours. After cooling, the reaction solution was washed with saturated aqueous solution of sodium thiosulfate and saturated aqueous solution of sodium chloride. After drying the organic layer with magnesium sulfate, the solvent was distilled off under the reduced pressure to obtain 3,5-diiodo-4-methyl-1H-pyrazole (1.2 g).

$^1$H-NMR (CDCl$_3$, ppm): 2.03 (3H, s), 6.96 (1H, br s)

Synthesis Example 57

Starting Material

5-Trifluoromethyl-1H-(1,2,4)-triazole-3-thiol (11.0 g), heptafluoro-1-iodopropane (3.5 g) and triethylamine (0.90 g) were stirred in DMF (10 ml) at 90° C. for 24 hours. After cooling to room temperature, the reaction mixture was diluted with ethyl acetate and washed with water and saturated aqueous solution of sodium chloride. After drying the organic layer with magnesium sulfate, the solvent was distilled off under the reduced pressure to obtain 3-heptafluoropropylsulfanyl-5-trifluoromethyl-1H-(1,2,4)-triazole (0.70 g).

USE EXAMPLES

Biological Test Example 1

Test Against Larva of *Spodoptera litura*

Preparation of Test Solution:

| | |
|---|---|
| Solvent: | Dimethylformamide: 3 parts by weight |
| Emulsifier: | Polyoxyethylene alkyl phenyl ether: 1 part by weight |

In order to make an appropriate formulation of an active compound, 1 part by weight of the active compound was mixed with the above-mentioned amount of solvent containing the above-mentioned amount of emulsifier and the mixture was diluted with water to a prescribed concentration.

Test Method:

Leaves of sweet potato were soaked in the test solution diluted to a prescribed concentration with water, dried in the air and put in a dish of 9 cm diameter.

10 larvae of *Spodoptera litura* at the third instar were placed on the leaves and kept in a room at the constant temperature of 25° C. After 2 and 4 days further leaves of sweet potato were added and after 7 days the number of dead larvae was counted and the rate of death was calculated.

In this test the results of 2 dishes at 1 section were averaged.

Biological Test Example 2

Test Against Larva of *Cnaphalocrocis medinalis* Guenee

Test Method:

Paddy rice (variety: Tamanishiki) planted in a pot was treated by spraying 50 ml per pot of the diluted aqueous solution of the prescribed concentration of the active compound prepared in the same manner as in the above-mentioned Biological Test Example 1. After the treated rice plant was dried in the air, their foliage part was cut in 4-5 cm length, which were put in a dish with 9 cm diameter with a sheet of filter paper and 2 ml of water. Five larvae of *Cnaphalocrocis medinalis* Guenee at the second instar were put in the dish that was placed in a room at the constant temperature of 25° C. After 2 and 4 days, each rest (each ⅓ amount) of foliage parts of rice plant were cut in the same manner and added to the dish. After 7 days the number of dead larvae was counted and the rate of death was calculated. In this test the results of 2 dishes at 1 section were averaged.

Test Results:

In the above Biological Test Examples 1 and 2, as specific examples, the compounds of the aforementioned compound Nos. 8, 9, 10, 11, 12, 13, 14, 15, 16, 45, 47, 48, 49, 51, 52, 53, 81, 82, 83, 84, 85, 86, 87, 88, 89, 90, 91, 93, 103, 107, 116, 128, 132, 137, 138, 139, 140, 141, 142, 143, 144, 145, 146, 147, 148, 149, 150, 153, 155, 157, 174, 176, 177, 178, 180, 181, 182, 210, 211, 212, 213, 214, 215, 216, 217, 218, 219, 220, 221, 222, 226, 227, 229, 230, 231, 238, 239, 242, 243, 251, 253, 262, 264, 268, 270, 281, 299, 308, 310, 318, 322, 413, 414, 417, 422, 434, 446, 448, 473, 475, 492, 506, 508, 512, 518, 520, 539, 543, 544, 545, 546, 547, 548, 549, 552, 554, 559, 561, 562, 563, 564, 565, 566, 567, 568, 570, 571, 572, 573, 574, 578, 579, 580, 626, 637, 638, 639, 640, 641, 642, 643, 644, 645, 646, 647, 648, 649, 650, 655, 656, 657, 658, 659, 660, 661, 662, 663, 664, 665, 666, 667, 668, 669, 670, 671, 672, 681, 761, 762, 763, 804 and 920 showed controlling effect of 100% of rate of death at 20 ppm concentration of the active component.

Biological Test Example 3

Test Against *Myzus persicae* Resistant to Organophosphorous Agents and Carbamates Test Method:

About 30 bred *Myzus persicae* resistant to organophosphorous agents and carbamates were inoculated per 1 seedling of eggplant planted in a vinyl pot of 6 cm diameter. One day after the inoculation, a sufficient amount of a diluted aqueous solution of a prescribed concentration of an active compound prepared as mentioned above, was sprayed by using a spray gun. After spraying it was placed in a green house of 28° C. and the rate of death was calculated 7 days after the spraying. Test was repeated twice.

Test Results

The compounds of the aforementioned compound Nos. 140, 141, 144, 146, 147, 148, 174, 176, 177, 178, 180, 181, 211, 213, 214, 215, 218, 220, 222, 226, 239, 243, 569, 570, 572, 579, 761, 797 and 920 offered to the test as specific examples showed controlling effect of 100% of rate of death at 100 ppm concentration of the effective component.

Formulation Example 1

Granule

To a mixture of 10 parts of the compound of the present invention (No. 8), 30 parts of bentonite (montmorillonite), 58 parts of talc and 2 parts of ligninsulfonate salt, 25 parts of water are added, well kneaded, made into granules of 10-40 mesh by an extrusion granulator and dried at 40-50° C. to obtain granules.

Formulation Example 2

Granules

95 Parts of clay mineral particles having particle diameter distribution in the range of 0.2-2 mm are put in a rotary mixer. While rotating it, 5 parts of the compound of the present invention (No. 11) are sprayed together with a liquid diluent, wetted uniformly and dried at 40-50° C. to obtain granules.

Formulation Example 3

Emulsifiable Concentrate

30 Parts of the compound of the present invention (No. 12), 55 parts of xylene, 8 parts of polyoxyethylene alkyl phenyl ether and 7 parts of calcium alkylbenzenesulfonate are mixed and stirred to obtain an emulsifiable concentrate.

Formulation Example 4

Wettable Powder

Parts of the compound of the present invention (No. 15), 80 parts of a mixture of white carbon (hydrous amorphous silicon oxide fine powders) and powder clay (1:5), 2 parts of sodium alkylbenzenesulfonate and 3 parts of sodium alkylnaphthalenesulfonate-formalin-condensate are crushed and mixed to make a wettable powder.

Formulation Example 5

Water Dispersible Granule

Parts of the compound of the present invention (No. 16), 30 parts of sodium ligninsulfonate, 15 parts of bentonite and 35 parts of calcined diatomaceous earth powder are well mixed, added with water, extruded with 0.3 mm screen and dried to obtain water dispersible granules.

The invention claimed is:

1. A compound of formula (I)

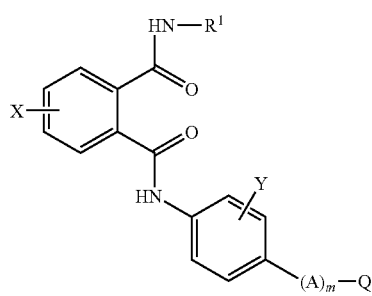

(I)

wherein

X represents hydrogen, fluorine, chlorine, bromine, iodine, nitro, $C_{1-4}$alkylsulfonyloxy, $C_{1-4}$alkylsulfinyl, $C_{1-4}$alkylsulfenyl or $C_{1-4}$alkylsulfonyl, $R^1$ represents $C_{1-4}$alkyl, $C_{1-4}$alkylthio-$C_{1-4}$alkyl, $C_{1-4}$alkylsulfinyl-$C_{1-4}$alkyl or $C_{1-4}$alkylsulfonyl-$_{1-4}$alkyl, Y represents fluorine, chlorine, bromine or $C_{1-4}$alkyl, m represents 1, A represents $CH_2$ or $CH(CH_3)$, and Q represents a 5-membered or 6-membered heterocyclic group that contains one to three N-atoms and which can be optionally substituted by at least one member selected from a group consisting of $C_{1-6}$alkyl, $C_{1-6}$alkoxy, $C_{1-6}$alkylthio, $C_{1-6}$alkylsulfinyl, $C_{1-6}$alkylsulfonyl, $C_{1-6}$haloalkyl, $C_{1-10}$haloalkoxy, $C_{1-6}$haloalkylthio, $C_{1-6}$haloalkylsulfinyl, $C_{1-6}$haloalkylsulfonyl, $C_{1-6}$haloalkylcarbonyl, halogen, oxo and hydroxy.

2. A compound according to claim 1 wherein

X represents hydrogen, fluorine, chlorine, bromine, iodine, nitro, methanesulfonyloxy, $C_{1-2}$alkylsulfinyl, $C_{1-2}$alkylsulfenyl or $C_{1-2}$alkylsulfonyl, $R^1$ represents isopropyl, $C_{1-2}$alkylthio-$C_{3-4}$alkyl, $C_{1-2}$alkylsulfinyl-$C_{3-4}$alkyl or $C_{1-2}$alkylsulfonyl-$C_{3-4}$alkyl, Y represents fluorine, chlorine or methyl, m represents 1, A represents $CH_2$ or $CH(CH_3)$, and Q represents a hetero cyclic group, selected from a group consisting of pyrazolyl, triazolyl, pyrazolinyl, imidazolyl, thiazolyl, pyrrolyl, and pyrimidinyl each of which may be optionally substituted by at least one member selected from the group consisting of $C_{1-4}$alkyl, $C_{1-4}$alkoxy, $C_{1-4}$alkylthio, $C_{1-4}$alkylsulfinyl, $C_{1-4}$alkylsulfonyl, $C_{1-8}$haloalkyl, $C_{1-4}$haloalkoxy, $C_{1-4}$haloalkylthio, $C_{1-4}$haloalkylsulfinyl, $C_{1-4}$haloalkylsulfonyl, $C_{1-4}$haloalkylcarbonyl, fluorine, chlorine, bromine, iodine, oxo and hydroxy.

3. A composition comprising a compound according to claim 1 and a diluent or a carrier.

4. A composition according to claim 3, further comprising at least one extender and/or surface active agent.

5. A compound of formula (VIII)

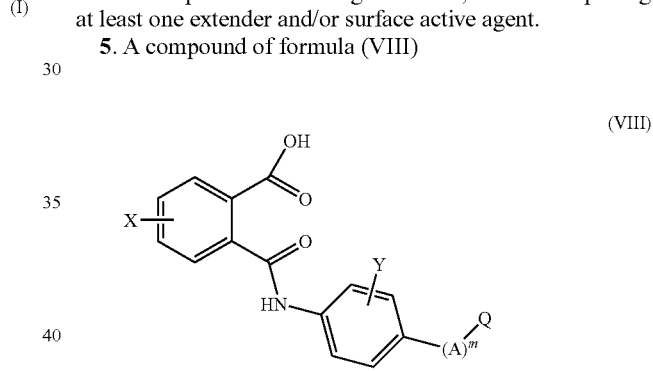

(VIII)

wherein

X represents hydrogen, halogen, nitro, $C_{1-6}$alkylsulfonyloxy, $C_{1-6}$alkylsulfinyl, $C_{1-6}$alkylsulfenyl or $C_{1-6}$alkylsulfonyl, Y represents halogen or $C_{1-6}$alkyl, A represents $CH_2$ or $CH(CH_3)$, and Q represents a 5-membered or 6-membered heterocyclic group that contains one to three N-atoms, or one O-atom or one S-atom and can be optionally substituted.

* * * * *